US008598202B2

(12) United States Patent
Apodaca et al.

(10) Patent No.: US 8,598,202 B2
(45) Date of Patent: Dec. 3, 2013

(54) ARYL-HYDROXYETHYLAMINO-PYRIMIDINES AND TRIAZINES AS MODULATORS OF FATTY ACID AMIDE HYDROLASE

(75) Inventors: Richard Apodaca, La Jolla, CA (US); J. Guy Breitenbucher, Escondido, CA (US); Alison L. Chambers, San Diego, CA (US); Xiaohu Deng, San Diego, CA (US); Natalie A. Hawryluk, San Diego, CA (US); John M. Keith, San Diego, CA (US); Neelakandha S. Mani, San Diego, CA (US); Jeffrey E. Merit, Stanford, CA (US); Joan M. Pierce, San Diego, CA (US); Mark Seierstad, Escondido, CA (US); Wei Xiao, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 878 days.

(21) Appl. No.: 12/378,734

(22) Filed: Feb. 18, 2009

(65) Prior Publication Data
US 2009/0264429 A1 Oct. 22, 2009

Related U.S. Application Data

(60) Provisional application No. 61/029,619, filed on Feb. 19, 2008, provisional application No. 61/086,353, filed on Aug. 5, 2008.

(51) Int. Cl.
*A01N 43/54* (2006.01)
*A61K 31/505* (2006.01)

(52) U.S. Cl.
USPC ........................ 514/311; 544/242; 514/275

(58) Field of Classification Search
USPC .................... 544/242, 311, 243; 514/275
See application file for complete search history.

(56) References Cited

U.S. PATENT DOCUMENTS

| | | | |
|---|---|---|---|
| 3,624,084 A | 11/1971 | Mathieu | |
| 5,594,141 A | 1/1997 | Yuan et al. | |
| 6,462,054 B1 | 10/2002 | Boger | |
| 6,881,740 B1 | 4/2005 | Jarrott et al. | |
| 6,891,043 B2 | 5/2005 | Boger | |
| 2003/0187026 A1 | 10/2003 | Li et al. | |
| 2005/0234030 A1 | 10/2005 | Bartolini et al. | |
| 2005/0239785 A1 | 10/2005 | Boger | |
| 2006/0025433 A1 | 2/2006 | Barbosa, Jr. et al. | |
| 2006/0058525 A1 | 3/2006 | Singh et al. | |
| 2006/0100212 A1 | 5/2006 | Boger | |
| 2006/0111359 A1 | 5/2006 | Boger | |
| 2006/0173184 A1 | 8/2006 | Apodaca et al. | |
| 2007/0004741 A1 | 1/2007 | Apodaca et al. | |
| 2007/0203156 A1 | 8/2007 | Boger | |

FOREIGN PATENT DOCUMENTS

| | | |
|---|---|---|
| WO | WO 2002 087569 A1 | 11/2002 |
| WO | WO 2004 033652 A2 | 4/2004 |
| WO | WO 2006 044617 A1 | 4/2006 |
| WO | WO 2006 044732 A2 | 4/2006 |
| WO | WO 2006 088840 A1 | 8/2006 |
| WO | WO 2007 014005 A1 | 2/2007 |
| WO | WO 2007 061862 A2 | 5/2007 |
| WO | WO 2007 098142 A2 | 8/2007 |
| WO | WO 2007 140005 A2 | 12/2007 |

OTHER PUBLICATIONS

International Search Report for Corresponding International Application No. PCT/US2009/01043 Mailed on Jul. 13, 2009.
Bork et al "The Combinatorial Synthesis of Purine Pyrimidine and Triazine Based Libraries" QSAR Comb Sci 2004 vol. 23 pp. 245-260.
Westhuyzen et al "Effect of Substituent Structure on Pyrimidine Electroliphic Substitution" Tetrahedron 2007 vol. 63 pp. 5394-5405.
Bagshawe et al. "Antibody-Directed Enzyme Prodrug Therapy: A Review" Drug Dev Res 1995 vol. 34 pp. 220-230.
Baker et al "Endocannabinoids Control Spasticity in a Multiple Sclerosis Model 1" FASEB J 2001 vol. 15(2) pp. 300-302.
Baker et al "Cannabinoids Control Spasticity and Tremor in a Multiple Sclerosis Model" Nature 2000 vol. 404 pp. 84-87.
Berge et al. "Pharmaceutical Salts". J. Pharm Sci 1977 vol. 66 pp. 1-19.
Bertolini et al."A New Rational Hypothesis for the Pharmacophore of the Active Metabolite of Leflunomide, a Potent Immunosuppressive Drug" J Med Chem 1997 vol. 40 pp. 2011-2016.
Bodor et al. "Novel Approaches to the Design of Safer Drugs: Soft Drugs and Site-Specific Chemical Delivery Systems" Adv Drug Res 1984 vol. 13 pp. 224-331.
Boger et al "Exceptionaly Potent Inhibitors of Fatty Acid Amide Hydrolase: The Enzyme Rsponsible for Degratation of Endogenous Oleamide and Anandamide" Proc Natl Acad Sci USA 2000 vol. 97(1) pp. 5044-5049.
Bouaboula et al "Anandamide Induced PPARγ Transcriptional Activation and 3TE-L1 Preadipocyte Differentation" E J Pharmacol 2005 vol. 517 pp. 174-181.
Bundgaard et al Design of Prodrugs H Bundgaard Ed. Elsevier 1985.

(Continued)

*Primary Examiner* — Paul V. Ward
(74) *Attorney, Agent, or Firm* — Michael J. Atkins

(57) ABSTRACT

Certain aryl-hydroxyethylamino-pyrimidine and triazine compounds are described, which are useful as FAAH inhibitors. Such compounds may be used in pharmaceutical compositions and methods for the treatment of disease states, disorders, and conditions mediated by fatty acid amide hydrolase (FAAH) activity, such as anxiety, pain, inflammation, sleep disorders, eating disorders, energy metabolism disorders, and movement disorders (e.g., multiple sclerosis). Methods of synthesizing such compounds are also disclosed.

36 Claims, No Drawings

(56) References Cited

OTHER PUBLICATIONS

Cravatt et al "Molecular Characterization of an Enzyme That Degrades Neuromodulatory Fatty-Acid Amides" Nature 1996 vol. 384 pp. 83-87.

Cravatt ET "Supersensitivity to Anandamide and Enhanced Endogenous Cannabinoid Signaling in Mice Lacking Fatty Acid Amide Hydrolase" AL Proc Natl Acad Sci USA 2001 vol. 98(16) pp. 9371-9376.

Cravatt et al "Chemical Characterization of a Family of Brain Lipids That Induce Sleep" Science 1995 vol. 268 pp. 1506-1509.

Croxford et al "Cannabinoid-Mediated Neuroportection, Not Immunosuppression, May Be More Relevant to Multiple Sclerosis" J Neuroimmunol 2008 vol. 193 pp. 120-129.

Devane et al "Isolation and Structure of a Brain Constituent That Binds to the Cannabinoid Receptor" Science 1992 vol. 258 pp. 1946-1949.

Fleisher et al "Improved Review Oral Drug Delivery: Solubility Limitations of Prodrugs Overcome by the Use" Adv Drug Delivery Rev 1996 vol. 19 pp. 115-130.

Gobbi et al "Antidepressant-Like Activity and Modulation of Brain Monoaminergic Transmission by Blockade of Anandamide Hydrolysis" Proc Natl Acad Sci USA 2005 vol. 102(51) pp. 18620-18625.

Goya et al "Recent Advances in Cannabinoid Receptor Agonist and Antagonist" Exp Opin Ther Patents 2000 vol. 10 pp. 1529-1538.

Holt et al "Inhibitors of Fatty Acid Amide Hydrolase Reduce Carrageenaninduced Hind Paw Inflammation in Pentobarbital-Treated Mice:Comparison With Indomethacin and Possible Involvement of Cannabinoid Receptors" Br J. Pharmacol 2005 vol. 146 pp. 467-476.

Karsak et al"Cannabinoid Receptor Type 2 Gene Is Associated With Human Osteoporosis" Hum Mol Genet 2005 vol. 14 pp. 3389-3396.

Kathuria et al "Modulation of Anxiety Through Blockade of Anandamide Hydrolysis" Nat Med 2003 vol. 9(1) pp. 76-81.

Kirkham et al "Endocannabinoid Levels in Rat Limbic Forebrain and Hypothalamus in Relation to Fasting, Feeding and Satiation: Stimulation of Eating by 2-Arachidonoyl Glycerol" Br J Pharmacol 2002 vol. 136 pp. 550-557.

Lamberti et al "The Palmitoylethanolamine Family: A New Class of Anti-Inflammatory Agents?" Curr Med Chem 2002 vol. 9(6) pp. 663-674.

Larsen et al Design and Application of Prodrugs Drug Design and Development Krogsgaard-Larsen et al Eds Harwood Academic Publishers 1991.

Mendelson et al "The Hypnotic Actions of the Fatty Acid Amide, Oleamide" Neuropsychopharmacology 2001 vol. 25 pp. S36-S39.

Ofek et al "Peripheral Cannabinoid Receptor CB2 Regulates Bone Mass" Proc Natl Acad Sci USA 2006 vol. 103 pp. 696-701.

Overton et al "GPR119 A Novel G Protein-Coupled Receptor Target for the Treatment of Type 2 Diabetes and Obesity" Br J Pharmacol 2008 vol. 153 pp. S76-S81.

Owton et al "Synthesis of Substituted 3-Trifluoromethyl-benzo[B]Thiophenes" Tetrahedron Lett 2003 vol. 44 pp. 7147-7149.

Piomelli et al "The Molecular Logic of Endocannabinoid Signalling" Nat Rev Neurosci 2003 vol. 4(11) pp. 873-884.

Plutzky et al "Preventing Type 2 Diabetes and Cardiovascular Disease in Metabolic Syndrome" Diab Vasc Dis Res 2007 vol. 4 Supp 3 pp. S12-S14.

Robinson "Discovery of the Hemifumarate and ($\alpha$-L-Alanyloxy)Methyl Ether as Prodrugs of an Antirheumatic Oxindole: Prodrugs for the Enolic OH Group" J Med Chem 1996 vol. 39 pp. 10-18.

Robson et al "Therapeutics Aspects of Cannabis and Cannabinoids" Br J. Psychiatry 2001 vol. 178 pp. 107-115.

Rodriguez De Fonesca "An Anorexic Lipid Mediator Regulated by Feeding" Nature 2001 vol. 414 pp. 209-212.

Shan et al "Prodrug Strategies Based on Intramolecular Cyclization Reactions" J Pharm Sci 1997 vol. 86(7) pp. 765-767.

Stahl et al Handbook of Pharmaceutical Salts, Properties, Selection and Use Stahl and Wermuth Eds Wiley VCH and VHCA Zurich 2002.

Steffens et al "Low Dose Oral Cannabinoid Therapy Reduces Progression of Atherosclerosis in Mice" Nature 2005 vol. 434 pp. 782-786.

Svendsen et al "Does the Cannabinoid Dronabinol Reduce Central Pain in Multiple Sclerosis? Randomised Double Blind Placebo Controlled Crossover Trial" Br Med J 2004 vol. 329 pp. 253.

Ueda et al "Purification and Characterization of an Acid Amidase Selective for N-Palmitoylethanolamine, A Putative Endogenous Anti-Inflammatory Substance" J Biol Chem 2001 vol. 276(38) pp. 35552-35557.

Varvel et al "Fatty Acid Amide Hydrolase (_/_) Mice Exhibit an Increasedsensitivity to the Disruptive Effects of Anandamide or Oleamide in a Working Memory Water Maze Task" J Pharmacol Exp Ther 2006 vol. 317(1) pp. 251-257.

Webb et al "Genetic Deletion of Fatty Acid Amide Hydrolase Results in Improved Long Term Outcome in Chronic Autoimmune Encephalitis"Neurosci Lett 2008 vol. 439 pp. 106-110.

ARYL-HYDROXYETHYLAMINO-PYRIMIDINES AND TRIAZINES AS MODULATORS OF FATTY ACID AMIDE HYDROLASE

This application claims the benefit of U.S. provisional patent application Ser. Nos. 61/029,619 filed Feb. 19, 2008 and 61/086,353 filed Aug. 5, 2008, which are hereby incorporated by reference.

FIELD OF THE INVENTION

Certain aryl-hydroxyethylamino-pyrimidine and triazine compounds, pharmaceutical compositions containing them, and methods of using them for the treatment of disease states, disorders, and conditions mediated by fatty acid amide hydrolase (FAAH) activity are provided. Certain methods of preparing the compounds are also disclosed.

BACKGROUND OF THE INVENTION

Medicinal benefits have been attributed to the cannabis plant for centuries. The primary bioactive constituent of cannabis is $\Delta^9$-tetrahydro-cannabinol (THC). The discovery of THC eventually led to the identification of two endogenous cannabinoid receptors responsible for its pharmacological actions, namely $CB_1$ and $CB_2$ (Goya, *Exp. Opin. Ther. Patents* 2000, 10, 1529). These discoveries not only established the site of action of THC, but also inspired inquiries into the endogenous agonists of these receptors, or "endocannabinoids". The first endocannabinoid identified was the fatty acid amide anandamide (AEA). AEA itself elicits many of the pharmacological effects of exogenous cannabinoids (Piomelli, *Nat. Rev. Neurosci.* 2003, 4(11), 873).

The catabolism of AEA is primarily attributable to the integral membrane bound protein fatty acid amide hydrolase (FAAH), which hydrolyzes AEA to arachidonic acid. FAAH was characterized in 1996 by Cravatt and co-workers (Cravatt, *Nature* 1996, 384, 83). It was subsequently determined that FAAH is additionally responsible for the catabolism of a large number of important lipid signaling fatty acid amides including: another major endocannabinoid, 2-arachidonoylglycerol (2-AG) (*Science* 1992, 258, 1946-1949); the sleep-inducing substance, oleamide (OEA) (*Science* 1995, 268, 1506); the appetite-suppressing agent, N-oleoylethanolamine (Rodriguez de Fonesca, *Nature* 2001, 414, 209); and the anti-inflammatory agent, palmitoylethanolamide (PEA) (Lambert, *Curr. Med. Chem.* 2002, 9(6), 663).

Small-molecule inhibitors of FAAH should elevate the concentrations of these endogenous signaling lipids and thereby produce their associated beneficial pharmacological effects. There have been some reports of the effects of various FAAH inhibitors in pre-clinical models.

In particular, two carbamate-based inhibitors of FAAH were reported to have analgesic properties in animal models. In rats, BMS-1 (see WO 02/087569), which has the structure shown below, was reported to have an analgesic effect in the Chung spinal nerve ligation model of neuropathic pain, and the Hargraves test of acute thermal nociception. URB-597 was reported to have efficacy in the zero plus maze model of anxiety in rats, as well as analgesic efficacy in the rat hot plate and formalin tests (Kathuria, *Nat. Med.* 2003, 9(1), 76). The sulfonylfluoride AM374 was also shown to significantly reduce spasticity in chronic relapsing experimental autoimmune encephalomyelitis (CREAE) mice, an animal model of multiple sclerosis (Baker, *FASEB J.* 2001, 15(2), 300).

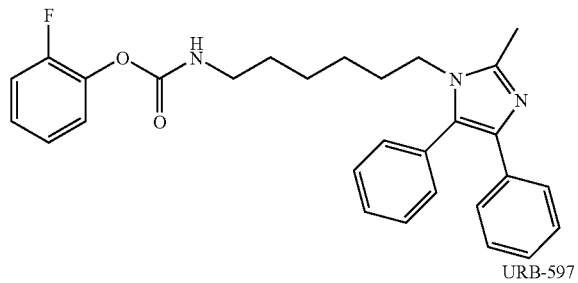

BMS-1

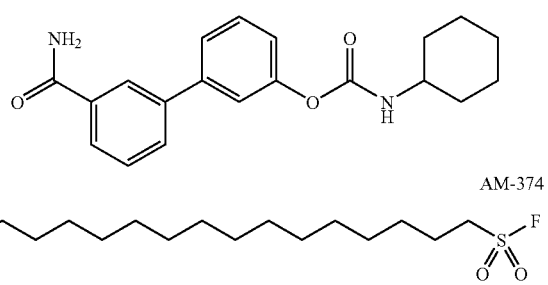

URB-597

AM-374

In addition, the oxazolopyridine ketone OL-135 is reported to be a potent inhibitor of FAAH, and has been reported to have analgesic activity in both the hot plate and tail emersion tests of thermal nociception in rats (WO 04/033652).

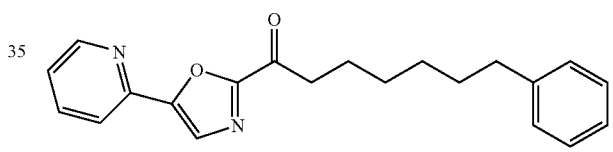

OL-135

Results of research on the effects of certain exogenous cannabinoids has elucidated that a FAAH inhibitor may be useful for treating various conditions, diseases, disorders, or symptoms. These include pain, nausea/emesis, anorexia, spasticity, movement disorders, epilepsy and glaucoma. To date, approved therapeutic uses for cannabinoids include the relief of chemotherapy-induced nausea and emesis among patients with cancer and appetite enhancement in patients with HIV/AIDs who experience anorexia as a result of wasting syndrome. Two products are commercially available in some countries for these indications, namely, dronabinol (Marinol®) and nabilone.

Apart from the approved indications, a therapeutic field that has received much attention for cannabinoid use is analgesia, i.e., the treatment of pain. Five small randomized controlled trials showed that THC is superior to placebo, producing dose-related analgesia (Robson, *Br. J. Psychiatry* 2001, 178, 107-115). Atlantic Pharmaceuticals is reported to be developing a synthetic cannabinoid, CT-3, a 1,1-dimethyl heptyl derivative of the carboxylic metabolite of tetrahydrocannabinol, as an orally active analgesic and anti-inflammatory agent. A pilot phase II trial in chronic neuropathic pain with CT-3 was reportedly initiated in Germany in May 2002.

A number of individuals with locomotor activity-related diseases, such as multiple sclerosis have claimed a benefit from cannabis for both disease-related pain and spasticity, with support from small controlled trials (Croxford et el., *J.*

*Neuroimmunol,* 2008, 193, 120-9; Svendsen, *Br. Med. J.* 2004, 329, 253). Likewise, various victims of spinal cord injuries, such as paraplegia, have reported that their painful spasms are alleviated after smoking marijuana. A report showing that cannabinoids appear to control spasticity and tremor in the CREAE model of multiple sclerosis demonstrated that these effects are mediated by $CB_1$ and $CB_2$ receptors (Baker, *Nature* 2000, 404, 84-87). Phase 3 clinical trials have been undertaken in multiple sclerosis and spinal cord injury patients with a narrow ratio mixture of tetrahydrocannabinol/cannabidiol (THC/CBD). It has been reported that FAAH knockout mice consistently recover to a better clinical score than wild type controls, and this improvement is not a result of anti-inflammatory activity, but rather may reflect some neuroprotection or remyelination promoting effect of lack of the enzyme (Webb et al, *Neurosci Lett.,* 2008, vol. 439, 106-110).

Reports of small-scale controlled trials to investigate other potential commercial uses of cannabinoids have been made. Trials in volunteers have been reported to have confirmed that oral, injected, and smoked cannabinoids produced dose-related reductions in intraocular pressure (IOP) and therefore may relieve glaucoma symptoms. Ophthalmologists have prescribed cannabis for patients with glaucoma in whom other drugs have failed to adequately control intraocular pressure (Robson, 2001, supra).

Inhibition of FAAH using a small-molecule inhibitor may be advantageous compared to treatment with a direct-acting $CB_1$ agonist. Administration of exogenous $CB_1$ agonists may produce a range of responses, including reduced nociception, catalepsy, hypothermia, and increased feeding behavior. These four in particular are termed the "cannabinoid tetrad." Experiments with FAAH –/– mice show reduced responses in tests of nociception, but did not show catalepsy, hypothermia, or increased feeding behavior (Cravatt, *Proc. Natl. Acad. Sci. USA* 2001, 98(16), 9371). Fasting caused levels of AEA to increase in rat limbic forebrain, but not in other brain areas, providing evidence that stimulation of AEA biosynthesis may be anatomically regionalized to targeted CNS pathways (Kirkham, *Br. J. Pharmacol.* 2002, 136, 550). The finding that AEA increases are localized within the brain, rather than systemic, suggests that FAAH inhibition with a small molecule could enhance the actions of AEA and other fatty acid amides in tissue regions where synthesis and release of these signaling molecules is occurring in a given pathophysiological condition (Piomelli, 2003, supra).

In addition to the effects of a FAAH inhibitor on AEA and other endocannabinoids, inhibitors of FAAH's catabolism of other lipid mediators may be used in treating certain other therapeutic indications. For example, PEA has demonstrated biological effects in animal models of inflammation (Holt, et al. *Br. J. Pharmacol.* 2005, 146, 467-476), immunosuppression, analgesia, and neuroprotection (Ueda, *J. Biol. Chem.* 2001, 276(38), 35552). Oleamide, another substrate of FAAH, induces sleep (Boger, *Proc. Natl. Acad. Sci. USA* 2000, 97(10), 5044; Mendelson, *Neuropsychopharmacology* 2001, 25, S36). Inhibition of FAAH has also been implicated in cognition (Varvel et al., *J. Pharmacol. Exp. Ther.* 2006, 317(1), 251-257) and depression (Gobbi et al., *Proc. Natl. Acad. Sci. USA* 2005, 102(51), 18620-18625).

Two additional indications for FMH are supported by recent data indicating that FAAH substrate activated receptors are important in energy metabolism, and in bone homeostasis (Overton et al., *Br. J. Pharmacol.* 2008, in press; and Plutzky, *Diab. Vasc. Dis. Res.* 2007, 4 Suppl 3, S12-4). It has been shown that the previously mentioned lipid signaling fatty acid amides catabolized by FAAH, oleoylethanolamide (OEA), is one of the most active agonists of the recently de-orphanised GPCR 119 (GPR119) (also termed glucose dependent insulinotropic receptor). This receptor is expressed predominantly in the pancreas in humans and activation improves glucose homeostasis via glucose-dependent insulin release in pancreatic beta-cells. GPR119 agonists can suppress glucose excursions when administered during oral glucose tolerance tests, and OEA has also been shown independently to regulate food intake and body weight gain when administered to rodents, indicating a probable benefit energy metabolism disorders, such as insulin resistance and diabetes. The FAAH substrate palmitoylethanolamide (PEA) is an agonist at the PPARα receptor. Evidence from surrogate markers in human studies with the PPARα agonist fenofibrate is supportive of the concept that PPARα agonism offers the potential for inducing a coordinated PPARα response that may improve dyslipidaemia, repress inflammation and limit atherosclerosis in patients with the metabolic syndrome or type 2 diabetes. The FAAH substrate anandamide (AEA) is an agonist at the PPARγ receptor. Anandamide treatment induces 3T3-L1 differentiation into adipocytes, as well as triglyceride droplet accumulation and expression of adiponectin (Bouaboula et al., *E. J. Pharmacol.* 2005, 517, 174-181). Low dose cannabinoid therapy has been shown to reduce atherosclerosis in mice, further suggesting a therapeutic benefit of FAAH inhibition in dyslipidemia, liver steatosis, steatohepatitis, obesity, and metabolic syndrome (Steffens et al., *Nature,* 2005, 434, 782-6).

Osteoporosis is one of the most common degenerative diseases. It is characterized by reduced bone mineral density (BMD) with an increased risk for bone fractures. $CB_2$-deficient mice have a markedly accelerated age-related trabecular bone loss and cortical expansion. A $CB_2$-selective agonism enhances endocortical osteoblast number and activity and restrains trabecular osteoclastogenesis and attenuates ovariectomy-induced bone loss (Ofek et al., *Proc. Natl. Acad. Sci. U.S.A.* 2006, 103, 696-701). There is a substantial genetic contribution to BMD, although the genetic factors involved in the pathogenesis of human osteoporosis are largely unknown. The applicability to human BMD is suggested by genetic studies in which a significant association of single polymorphisms and haplotypes was found encompassing the CNR2 gene on human chromosome 1p36, demonstrating a role for the peripherally expressed $CB_2$ receptor in the etiology of osteoporosis (Karsak et al., *Hum. Mol. Genet,* 2005, 14, 3389-96). Research also demonstrates a role in osteoarthritis.

Thus, small-molecule FAAH inhibitors should be useful in treating pain of various etiologies, anxiety, multiple sclerosis, Parkinson's disease and other movement disorders, nausea/emesis, eating disorders, epilepsy, glaucoma, inflammation, itch, immunosuppression, neuroprotection, depression, cognition enhancement, and sleep disorders, and potentially with fewer side effects than treatment with an exogenous cannabinoid.

Certain amino-substituted pyrimidine compounds have been described in the literature. Certain 2,6-substituted-4-monosubstituted pyrimidines were disclosed as prostaglandin D2 receptor antagonists (PCT Pat. Appl. Publ. No. WO 2006/044732). Certain 2,4-Pyrimidinediamine compounds appear in U.S. Pat. Appl. Publ. No. US 2006/0058525. U.S. Pat. Appl. Publ. No. US 2003/0187026 describes certain heterocyclic compounds as kinase inhibitors. Certain arylalkyl heterocyclic compounds are shown as pharmaceutical agents in U.S. Pat. No. 6,881,740. Certain piperazinyl and piperidinyl ureas, heteroaryl piperazinyl ureas, and heteroaryl-substituted ureas were disclosed as inhibitors of FAAH in U.S. Pat. Appl. Publ. No. US 2006/0173184, U.S. Pat. Appl. Publ.

No. US 2007/0004741, respectively. Certain α-keto-oxazole and oxazolyl piperidine compounds were disclosed as inhibitors of FAAH in PCT Pat. Appl. Publ. No. WO 2007/061862 and WO 2007/14005, respectively. Certain α-keto heterocyclic compounds were disclosed as inhibitors of FAAH in U.S. Pat. Nos. 6,462,054 and 6,891,043, U.S. Pat. Appl. Publ. Nos. US 2005/0239785 and US 2006/0111359, and PCT Pat. Appl. Publ. No. WO 2004/033652. Certain oxadiazole ketone compounds were disclosed as inhibitors of FAAH in U.S. Pat. Appl. Publ. No. US 2006/0100212, and PCT Pat. Appl. Publ. No. WO 2006/044617. Certain oxazole ketone compounds were disclosed as inhibitors of FAAH in U.S. Pat. Appl. Publ. No. US 2007/0203156, and PCT Pat. Appl. Publ. No. WO 2007/098142, and references cited therein for all of the publications referenced in this paragraph.

Still further, certain compounds were obtained from a third party. The compounds are identified herein as Examples 223-245 and Comparative Examples 1-8.

Despite the progress that has been achieved, there remains a desire for potent FAAH modulators with suitable pharmaceutical properties.

SUMMARY OF THE INVENTION

Certain aryl-hydroxyethylamino-pyrimidine and triazine derivatives are herein described, which have been found to have FAAH-modulating activity. The invention is directed to the general and preferred embodiments defined, respectively, by the independent and dependent claims appended hereto, which are incorporated by reference herein.

In one general aspect, the invention is directed to compounds of Formula (I-A):

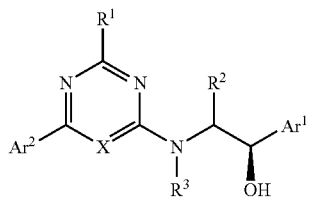

(I-A)

wherein:
$R^1$ is —H, —$C_{1-4}$alkyl, —$OC_{1-4}$alkyl, —$S(O)_{0-2}C_{1-4}$alkyl, —$CF_3$, —CN, —$N(R^a)R^b$, or a monocyclic cycloalkyl group,
  where $R^a$ and $R^b$ are each independently —H, —$C_{1-4}$alkyl optionally substituted with —OH, $N(R^m)R^n$, where $R^m$ and $R^n$ are —H, $C_{1-4}$alkyl; or taken together with the nitrogen of attachment $R^a$ and $R^b$ form a 4-7 membered heterocycloalkyl ring;
$Ar^1$ is a phenyl, napthyl, a 5 or 6 membered monocyclic heteroaryl group with carbon at the point of attachment, or a 9 or 10 membered bicyclic heteroaryl group with carbon at the point of attachment, each unsubstituted or substituted with;
  (i) one, two, or three $R^c$ moieties,
    where each $R^c$ moiety is independently —$C_{1-4}$alkyl, —$C_{1-4}$alkyl-OH, —$C_{1-4}$alkyl-CN, —$CF_3$, —OH, —$OC_{1-4}$alkyl, —$OCF_3$, —$OCHF_2$, —$OCH_2CF_3$, —$S(O)_{0-2}C_{1-4}$alkyl, —$SCF_3$, —$SO_2CF_3$, —CHO, —$COC_{1-4}$alkyl, —$CO_2C_{1-4}$alkyl, —$CO_2H$, —$N(R^d)R^e$, —$SO_2NR^dR^e$, —$NR^dSO_2R^e$, —$C(O)NR^dR^e$, —$NO_2$, —CN, -phenyl, pyridyl, or halo, where $R^d$ and $R^e$ are each independently —H or —$C_{1-4}$alkyl, or taken together $R^d$ and $R^e$ with the nitrogen of attachment form a 4-7 membered heterocycloalkyl ring; or
  (ii) two or three $R^c$ moieties where two $R^c$ moieties are adjacent to each other and together form —$O(CH_2)_{1-3}O$— unsubstituted or substituted with one or two fluoro groups, and the third $R^c$ moiety, when present, is —$C_{1-4}$alkyl, —$C_{1-4}$alkyl-OH, —$C_{1-4}$alkyl-CN, —$CF_3$, —OH, —$OC_{1-4}$alkyl, —$OCF_3$, —$OCHF_2$, —$OCH_2CF_3$, —$S(O)_{0-2}C_{1-4}$alkyl, —$SCF_3$, —$SO_2CF_3$, —CHO, —$COC_{1-4}$alkyl, —$CO_2C_{1-4}$alkyl, —$CO_2H$, —$N(R^d)R^e$, —$SO_2NR^dR^e$, —$NR^dSO_2R^e$, —$C(O)NR^dR^e$, —$NO_2$, —CN, or halo,
where $R^d$ and $R^e$ are each independently —H or —$C_{1-4}$alkyl;
X is N or $C(R^f)$,
  where $R^f$ is —H or methyl;
$Ar^2$ is:
  (i) a phenyl group substituted with: (a) one, two, or three $R^g$ moieties each at a meta or para position, and optionally with one or two additional $R^g$ moieties at an ortho position;
    where each $R^g$ moiety is independently —$C_{1-4}$alkyl, —$C_{1-4}$alkyl-OH, —$C_{1-4}$alkyl-CN, perhaloalkyl, perhaloalkoxy, —$OC_{1-4}$alkyl, —$OC_{1-4}$alkyl-(monocyclic cycloalkyl), —$S(O)_{0-2}C_{1-4}$alkyl, —$SCF_3$, —$SO_2CF_3$, —CHO, —$COC_{1-4}$alkyl, —$CO_2C_{1-4}$alkyl, —$CO_2H$, —$N(R^h)R^i$, —$SO_2NR^jR^k$, —$NR^hSO_2R^i$, —$C(O)NR^jR^k$, —$NO_2$, —CN, or halo; or a phenoxy, benzyl, phenethyl, or benzoyl group unsubstituted or substituted with —$C_{1-4}$alkyl, —$OC_{1-4}$alkyl, perhaloalkyl, perhaloalkoxy, —$NO_2$, —CN, or halo;
    where $R^h$ is —H or —$C_{1-4}$alkyl;
    $R^i$ is —$C_{1-4}$alkyl or monoyclic cycloalkyl group;
    or $R^h$ and $R^i$ taken together with the atoms to which they are attached form a monocyclic heterocycloalkyl ring;
    $R^j$ is —H or —$C_{1-4}$alkyl; and
    $R^k$ is —H, —$C_{1-4}$alkyl or monoyclic cycloalkyl group;
    or $R^j$ and $R^k$ taken together with the atoms to which they are attached form a monocyclic heterocycloalkyl ring; or
  (b) two adjacent $R^g$ moieties together form —$O(CH_2)_{1-2}O$— unsubstituted or substituted with one or two fluoro groups;
  (ii) a monocyclic heteroaryl group substituted with: one, two, or three $R^g$ moieties, where each $R^g$ moiety is independently or two adjacent $R^g$ moieties together form —$O(CH_2)_{1-2}O$— unsubstituted or substituted with one or two fluoro groups; or
  (iii) a naphthyl or bicyclic heteroaryl group unsubstituted or substituted with one, two, or three $R^l$ moieties,
    where each $R^l$ moiety is independently —$C_{1-4}$alkyl, —$OC_{1-4}$alkyl, perhaloalkyl, perhaloalkoxy, —$NO_2$, —CN, or halo;
$R^2$ is —H or methyl; and
$R^3$ is —H or methyl;
provided, however, that $Ar^2$ is not —CHO or para substituted —$OCF_3$ when $Ar^1$ is unsubstituted phenyl;
and pharmaceutically acceptable salts, pharmaceutically acceptable prodrugs, and pharmaceutically active metabolites of such compounds.

In another general aspect, the invention is directed to compounds of Formula (I-B):

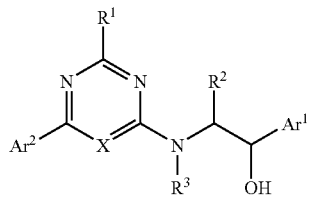

(I-B)

wherein:
$R^1$ is —$C_{1-4}$alkyl, —$OC_{1-4}$alkyl, —$S(O)_{0-2}C_{1-4}$alkyl, —CN, —$CF_3$, —$N(R^a)R^b$, or a monocyclic cycloalkyl group,
where $R^a$ and $R^b$ are each independently —H, —$C_{1-4}$alkyl optionally substituted with —OH, $N(R^m)R^n$, where $R^m$ and $R^n$ are —H, $C_{1-4}$alkyl; or taken together with the nitrogen of attachment $R^a$ and $R^b$ form a 4-7 membered heterocycloalkyl ring;
$Ar^1$ is a phenyl, napthyl, a 5 or 6 membered monocyclic heteroaryl group with carbon at the point of attachment, or a 9 or 10 membered bicyclic heteroaryl group with carbon at the point of attachment, each unsubstituted or substituted with;
(i) one, two, or three $R^c$ moieties,
where each $R^c$ moiety is independently —$C_{1-4}$alkyl, —$C_{1-4}$alkyl-OH, —$C_{1-4}$alkyl-CN, —$CF_3$, —OH, —$OC_{1-4}$alkyl, —$OCF_3$, —$OCHF_2$, —$OCH_2CF_3$, —$S(O)_{0-2}C_{1-4}$alkyl, —$SCF_3$, —$SO_2CF_3$, —CHO, —$COC_{1-4}$alkyl, —$CO_2C_{1-4}$alkyl, —$CO_2H$, —$N(R^d)R^e$, —$SO_2NR^dR^e$, —$NR^dSO_2R^e$, —$C(O)NR^dR^e$, —$NO_2$, —CN, phenyl, pyridyl, or halo,
where $R^d$ and $R^e$ are each independently —H or —$C_{1-4}$alkyl, or taken together $R^d$ and $R^e$ with the nitrogen of attachment form a 4-7 membered heterocycloalkyl ring; or
(ii) two or three $R^c$ moieties where two $R^c$ moieties are adjacent to each other and together form —$O(CH_2)_{1-3}O$— unsubstituted or substituted with one or two fluoro groups, and the third $R^c$ moiety, when present, is —$C_{1-4}$alkyl, —$C_{1-4}$alkyl-OH, —$C_{1-4}$alkyl-CN, —$CF_3$, —OH, —$OC_{1-4}$alkyl, —$OCF_3$, —$OCHF_2$, —$OCH_2CF_3$, —$S(O)_{0-2}C_{1-4}$alkyl, —$SCF_3$, —$SO_2CF_3$, —CHO, —$COC_{1-4}$alkyl, —$CO_2C_{1-4}$alkyl, —$CO_2H$, —$N(R^d)R^e$, —$SO_2NR^dR^e$, —$NR^dSO_2R^e$, —$C(O)NR^dR^e$, —$NO_2$, —CN, or halo, where $R^d$ and $R^e$ are each independently —H or —$C_{1-4}$alkyl;
X is N or $C(R^f)$,
where $R^f$ is —H or methyl;
$Ar^2$ is:
(i) a phenyl group substituted with: (a) one, two, or three $R^g$ moieties each at a meta or para position, and optionally with one or two additional $R^g$ moieties at an ortho position;
where each $R^g$ moiety is independently —$C_{1-4}$alkyl, —$C_{1-4}$alkyl-OH, —$C_{1-4}$alkyl-CN, perhaloalkyl, perhaloalkoxy, —$OC_{1-4}$alkyl, —$OC_{1-4}$alkyl-(monocyclic cycloalkyl), —$S(O)_{0-2}C_{1-4}$alkyl, —$SCF_3$, —$SO_2CF_3$, —CHO, —$COC_{1-4}$alkyl, —$CO_2C_{1-4}$alkyl, —$CO_2H$, —$N(R^h)R^i$, —$SO_2NR^jR^k$, —$NR^hSO_2R^i$, —$C(O)NR^jR^k$, —$NO_2$, —CN, or halo; or a phenoxy, benzyl, phenethyl, or benzoyl group unsubstituted or substituted with —$C_{1-4}$alkyl, —$OC_{1-4}$alkyl, perhaloalkyl, perhaloalkoxy, —$NO_2$, —CN, or halo;
where $R^h$ is —H or —$C_{1-4}$alkyl;
$R^i$ is —$C_{1-4}$alkyl or monocyclic cycloalkyl group;

or $R^h$ and $R^i$ taken together with the atoms to which they are attached form a monocyclic heterocycloalkyl ring;
$R^j$ is —H or —$C_{1-4}$alkyl; and
$R^k$ is —H, —$C_{1-4}$alkyl or monocyclic cycloalkyl group;
or $R^j$ and $R^k$ taken together with the atoms to which they are attached form a monocyclic heterocycloalkyl ring; or
(b) two adjacent $R^g$ moieties together form —$O(CH_2)_{1-2}O$— unsubstituted or substituted with one or two fluoro groups;
(ii) a monocyclic heteroaryl group substituted with one, two, or three $R^g$ moieties, where each $R^g$ moiety is independently or two adjacent $R^g$ moieties together form —$O(CH_2)_{1-2}O$— unsubstituted or substituted with one or two fluoro groups; or
(iii) a naphthyl or bicyclic heteroaryl group unsubstituted or substituted with one, two, or three $R^l$ moieties, where each $R^l$ moiety is independently —$C_{1-4}$alkyl, —$OC_{1-4}$alkyl, perhaloalkyl, perhaloalkoxy, —$NO_2$, —CN, or halo;
$R^2$ is —H or methyl; and
$R^3$ is —H or methyl;
and pharmaceutically acceptable salts, pharmaceutically acceptable prodrugs, and pharmaceutically active metabolites of such compounds.

In another general aspect, the invention is directed to compounds of Formula (I-C):

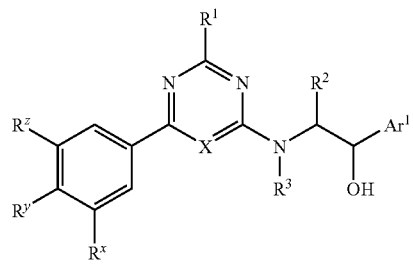

(I-C)

wherein:
$R^1$ is —H, —$C_{1-4}$alkyl, —$OC_{1-4}$alkyl, —$S(O)_{0-2}C_{1-4}$alkyl, —CN, —$CF_3$, —$N(R^a)R^b$, or a monocyclic cycloalkyl group,
where $R^a$ and $R^b$ are each independently —H, —$C_{1-4}$alkyl optionally substituted with —OH, $N(R^m)R^n$, where $R^m$ and $R^n$ are —H, $C_{1-4}$alkyl; or taken together with the nitrogen of attachment $R^a$ and $R^b$ form a 4-7 membered heterocycloalkyl;
$Ar^1$ is a phenyl, napthyl, a 5 or 6 membered monocyclic heteroaryl group with carbon at the point of attachment, or a 9 or 10 membered bicyclic heteroaryl group with carbon at the point of attachment, each unsubstituted or substituted with;
(i) one, two, or three $R^c$ moieties,
where each $R^c$ moiety is independently —$C_{1-4}$alkyl, —$C_{1-4}$alkyl-OH, —$C_{1-4}$alkyl-CN, —$CF_3$, —OH, —$OC_{1-4}$alkyl, —$OCF_3$, —$OCHF_2$, —$OCH_2CF_3$, —$S(O)_{0-2}C_{1-4}$alkyl, —$SCF_3$, —$SO_2CF_3$, —CHO, —$COC_{1-4}$alkyl, —$CO_2C_{1-4}$alkyl, —$CO_2H$, —$N(R^d)R^e$, —$SO_2NR^dR^e$, —$NR^dSO_2R^e$, —$C(O)NR^dR^e$, —$NO_2$, —CN, phenyl, pyridyl, or halo, where $R^d$ and $R^e$ are each independently —H or —$C_{1-4}$alkyl, or taken together $R^d$ and $R^e$ with the nitrogen of attachment form a 4-7 membered heterocycloalkyl; or (ii) two or three $R^c$ moieties where two $R^c$ moieties are adjacent to each other and together form —O(CH$_2$)$_{1-3}$O— unsubstituted or substituted with one or two fluoro groups, and the third $R^c$ moiety, when present, is —$C_{1-4}$alkyl, —$C_{1-4}$alkyl-OH, —$C_{1-4}$alkyl-CN, —CF$_3$, —OH, —OC$_{1-4}$alkyl, —OCF$_3$, —OCHF$_2$, —OCH$_2$CF$_3$, —S(O)$_{0-2}$C$_{1-4}$alkyl, —SCF$_3$, —SO$_2$CF$_3$, —CHO, —COC$_{1-4}$alkyl, —CO$_2$C$_{1-4}$alkyl, —CO$_2$H, —N(R$^d$)R$^e$, —SO$_2$NR$^d$R$^e$, —NR$^d$SO$_2$R$^e$, —C(O)NR$^d$R$^e$, —NO$_2$, —CN, or halo, where $R^d$ and $R^e$ are each independently —H or —$C_{1-4}$alkyl;

X is N or C(R$^f$),
where R$^f$ is —H or methyl;

$R^x$, $R^y$, and $R^z$ are each independently a)-c):
a) $R^x$ and $R^z$ are each —H, and $R^y$ is —NO$_2$, —C$_{2-3}$alkyl, —OC$_{2-4}$alkyl, or phenoxy;
b) $R^x$ and $R^z$ are each —H, $R^y$ is —OCF$_3$, and Ar$^1$ is a substituted phenyl group or an unsubstituted or substituted pyridyl group; or
c) one of $R^x$, $R^y$, and $R^z$ is —Cl, —F, or —CF$_3$, and the other two are: (i) independently —H or an R$^g$ moiety, provided that when $R^y$ is —H then $R^x$ and $R^z$ are not —CF$_3$;
where each R$^g$ moiety is —$C_{1-4}$alkyl, —$C_{1-4}$alkyl-OH, —$C_{1-4}$alkyl-CN, perhaloalkyl, perhaloalkoxy, —OC$_{1-4}$alkyl, —OC$_{1-4}$alkyl-(monocyclic cycloalkyl), —S(O)$_{0-2}$C$_{1-4}$alkyl, —SCF$_3$, —SO$_2$CF$_3$, —CHO, —COC$_{1-4}$alkyl, —CO$_2$C$_{1-4}$alkyl, —CO$_2$H, —N(R$^h$)R$^i$, —SO$_2$NR$^j$R$^k$, —NR$^h$SO$_2$R$^i$, —C(O)NR$^j$R$^k$, —NO$_2$, —CN, or halo; or a phenoxy, benzyl, phenethyl, or benzoyl group unsubstituted or substituted with —$C_{1-4}$ alkyl, —OC$_{1-4}$alkyl, perhaloalkyl, perhaloalkoxy, —NO$_2$, —CN, or halo;
where R$^h$ is —H or —$C_{1-4}$alkyl;
R$^i$ is —$C_{1-4}$alkyl or monocyclic cycloalkyl group;
or R$^h$ and R$^i$ taken together with the atoms to which they are attached form a monocyclic heterocycloalkyl ring;
R$^j$ is —H or —$C_{1-4}$alkyl; and
R$^k$ is —H, —$C_{1-4}$alkyl or monocyclic cycloalkyl group;
or R$^j$ and R$^k$ taken together with the atoms to which they are attached form a monocyclic heterocycloalkyl ring; or
(ii) two adjacent R$^g$ moieties that together form —O(CH$_2$)$_{1-2}$O— unsubstituted or substituted with one or two fluoro groups; or
(iii) a naphthyl or bicyclic heteroaryl group unsubstituted or substituted with one, two, or three R$^l$ moieties;
where each R$^l$ moiety is independently —$C_{1-4}$alkyl, —OC$_{1-4}$alkyl, perhaloalkyl, perhaloalkoxy, —NO$_2$, —CN, or halo;

$R^2$ is —H or methyl; and
$R^3$ is —H or methyl;

and pharmaceutically acceptable salts, pharmaceutically acceptable prodrugs, and pharmaceutically active metabolites of such compounds.

In especially preferred embodiments, the invention is directed to compounds described or exemplified in the detailed description below and their pharmaceutically acceptable salts.

In a further general aspect, the invention relates to pharmaceutical compositions each comprising: (a) an effective amount of at least one agent selected from compounds of Formula (I), pharmaceutically acceptable salts of compounds of Formula (I), pharmaceutically acceptable prodrugs of compounds of Formula (I), and pharmaceutically active metabolites of Formula (I):

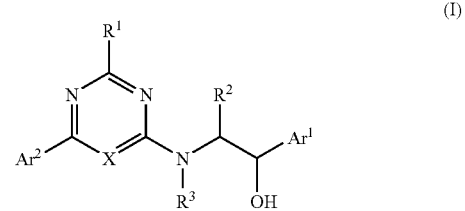

wherein:
$R^1$ is —H, —$C_{1-4}$alkyl, —OC$_{1-4}$alkyl, —S(O)$_{0-2}$C$_{1-4}$alkyl, —CN, —CF$_3$, —N(R$^a$)R$^b$, or a monocyclic cycloalkyl group,
where R$^a$ and R$^b$ are each independently —H, —$C_{1-4}$alkyl optionally substituted with —OH, N(R$^m$)R$^n$, where R$^m$ and R$^n$ are —H, $C_{1-4}$alkyl; or taken together with the nitrogen of attachment R$^a$ and R$^b$ form a 4-7 membered heterocycloalkyl ring;

Ar$^1$ is a phenyl, napthyl, a 5 or 6 membered monocyclic heteroaryl group with carbon at the point of attachment, or a 9 or 10 membered bicyclic heteroaryl group with carbon at the point of attachment, each unsubstituted or substituted with;

(i) one, two, or three R$^c$ moieties,
where each R$^c$ moiety is independently —$C_{1-4}$alkyl, —$C_{1-4}$alkyl-OH, —$C_{1-4}$alkyl-CN, —CF$_3$, —OH, —OC$_{1-4}$alkyl, —OCF$_3$, —OCHF$_2$, —OCH$_2$CF$_3$, —S(O)$_{0-2}$C$_{1-4}$alkyl, —SCF$_3$, —SO$_2$CF$_3$, —CHO, —COC$_{1-4}$alkyl, —CO$_2$C$_{1-4}$alkyl, —CO$_2$H, —N(R$^d$)R$^e$, —SO$_2$NR$^d$R$^e$, —NR$^d$SO$_2$R$^e$, —C(O)NR$^d$R$^e$, —NO$_2$, —CN, phenyl, pyridyl, or halo,
where R$^d$ and R$^e$ are each independently —H or —$C_{1-4}$alkyl, or taken together R$^d$ and R$^e$ with the nitrogen of attachment form a 4-7 membered heterocycloalkyl group; or (ii) two or three R$^c$ moieties where two Rc moieties are adjacent to each other and together form —O(CH$_2$)$_{1-3}$O— unsubstituted or substituted with one or two fluoro groups, and the third R$^c$ moiety, when present, is —$C_{1-4}$alkyl, —$C_{1-4}$alkyl-OH, —$C_{1-4}$alkyl-CN, —CF$_3$, —OH, —OC$_{1-4}$alkyl, —OCF$_3$, —OCHF$_2$, —OCH$_2$CF$_3$, —S(O)$_{0-2}$C$_{1-4}$alkyl, —SCF$_3$, —SO$_2$CF$_3$, —CHO, —COC$_{1-4}$alkyl, —CO$_2$C$_{1-4}$alkyl, —CO$_2$H, —N(R$^d$)R$^e$, —SO$_2$NR$^d$R$^e$, —NR$^d$SO$_2$R$^e$, —C(O)NR$^d$R$^e$, —NO$_2$, —CN, or halo,
where R$^d$ and R$^e$ are each independently —H or —$C_{1-4}$alkyl;

X is N or C(R$^f$),
where R$^f$ is —H or methyl;

Ar$^2$ is:
(i) a phenyl group substituted with: (a) one, two, or three R$^g$ moieties each at a meta or para position, and optionally with one or two additional. R$^g$ moieties at an ortho position;
where each R$^g$ moiety is independently —$C_{1-4}$alkyl, —$C_{1-4}$alkyl-OH, —$C_{1-4}$alkyl-CN, perhaloalkyl, perhaloalkoxy, —OC$_{1-4}$alkyl, —OC$_{1-4}$alkyl-(monocyclic cycloalkyl), —S(O)$_{0-2}$C$_{1-4}$alkyl, —SCF$_3$, —SO$_2$CF$_3$, —CHO, —COC$_{1-4}$alkyl, —CO$_2$C$_{1-4}$ alkyl, —CO$_2$H, —N(R$^h$)R$^i$, —SO$_2$NR$^j$R$^k$, —NR$^h$SO$_2$R$^i$, —C(O)NR$^j$R$^k$, —NO$_2$, —CN, or halo;

or a phenoxy, benzyl, phenethyl, or benzoyl group unsubstituted or substituted with —$C_{1-4}$alkyl, —$OC_{1-4}$alkyl, perhaloalkyl, perhaloalkoxy, —$NO_2$, —CN, or halo;

where $R^h$ is —H or —$C_{1-4}$alkyl;

$R^i$ is —$C_{1-4}$alkyl or monoyclic cycloalkyl group;

or $R^h$ and $R^k$ taken together with the atoms to which they are attached form a monocyclic heterocycloalkyl ring;

$R^j$ is —H or —$C_{1-4}$alkyl; and $R^k$ is —H, —$C_{1-4}$alkyl or monoyclic cycloalkyl group;

or $R^j$ and $R^k$ taken together with the atoms to which they are attached form a monocyclic heterocycloalkyl ring; or (b) two adjacent $R^g$ moieties together form —$O(CH_2)_{1-2}O$— unsubstituted or substituted with one or two fluoro groups;

(ii) a monocyclic heteroaryl group substituted with one, two, or three $R^g$ moieties, where each $R^g$ moiety is independently or two adjacent $R^g$ moieties together form —$O(CH_2)_{1-2}O$— unsubstituted or substituted with one or two fluoro groups; or (iii) a naphthyl or bicyclic heteroaryl group unsubstituted or substituted with one, two, or three $R^l$ moieties, where each $R^l$ moiety is independently —$C_{1-4}$alkyl, —$OC_{1-4}$alkyl, perhaloalkyl, perhaloalkoxy, —$NO_2$, —CN, or halo;

$R^2$ is —H or methyl; and $R^3$ is —H or methyl;

and (b) a pharmaceutically acceptable excipient.

In another general aspect, the invention is directed to a method of treating a subject suffering from or diagnosed with a disease, disorder, or medical condition mediated by FAAH activity, comprising administering to the subject in need of such treatment an effective amount of at least one agent selected from compounds of Formula (I) and their pharmaceutically acceptable salts, pharmaceutically active prodrugs, and pharmaceutically active metabolites. In preferred embodiments of the inventive method, the disease, disorder, or medical condition is selected from: anxiety, depression, pain, sleep disorders, eating disorders, inflammation, multiple sclerosis and other movement disorders, HIV wasting syndrome, closed head injury, stroke, learning and memory disorders, Alzheimer's disease, epilepsy, Tourette's syndrome, Niemann-Pick disease, Parkinson's disease, Huntington's chorea, optic neuritis, autoimmune uveitis, symptoms of drug or alcohol withdrawal, nausea, emesis, sexual dysfunction, post-traumatic stress disorder, cerebral vasospasm, glaucoma, irritable bowel syndrome, inflammatory bowel disease, immunosuppression, itch, gastroesophageal reflux disease, paralyticileus, secretory diarrhea, gastric ulcer, rheumatoid arthritis, unwanted pregnancy, hypertension, cancer, hepatitis, allergic airway disease, auto-immune diabetes, intractable pruritis, neuroinflammation, diabetes, metabolic syndrome, and osteoporosis.

Additional embodiments, features, and advantages of the invention will be apparent from the following detailed description and through practice of the invention.

DETAILED DESCRIPTION OF INVENTION AND ITS PREFERRED EMBODIMENTS

The invention may be more fully appreciated by reference to the following detailed description, including the following glossary of terms and the concluding examples. For the sake of brevity, the disclosures of the publications, including patents, cited in this specification are herein incorporated by reference.

As used herein, the terms "including", "containing" and "comprising" are used in their open, non-limiting sense.

The term "alkyl" refers to a straight- or branched-chain alkyl group having from 1 to 12 carbon atoms in the chain. Examples of alkyl groups include methyl (Me, which also may be structurally depicted by / symbol), ethyl (Et), n-propyl, isopropyl, butyl, isobutyl, sec-butyl, tert-butyl (tBu), pentyl, isopentyl, tert-pentyl, hexyl, isohexyl, and so on.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

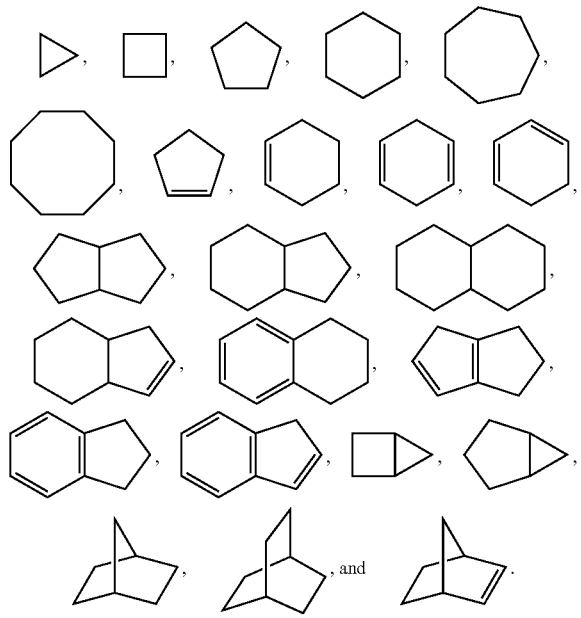

A "heterocycloalkyl" refers to a monocyclic, or fused, bridged, or spiro polycyclic ring structure that is saturated or partially saturated and has from 3 to 12 ring atoms per ring structure selected from carbon atoms and one, two, or three heteroatoms independently selected from nitrogen, oxygen, and sulfur. The ring structure may optionally contain up to two oxo groups on carbon or sulfur ring members. Illustrative examples of heterocycloalkyl groups include the following entities, in the form of properly bonded moieties:

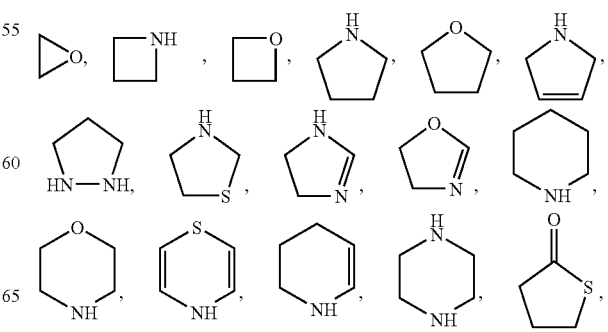

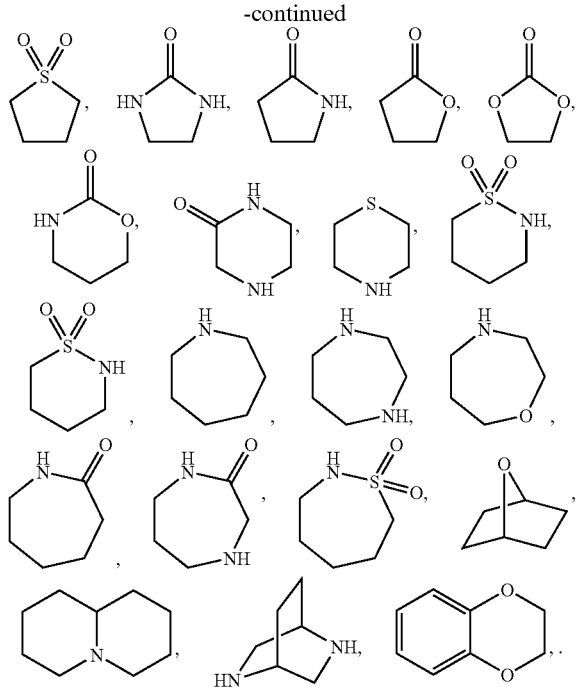

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

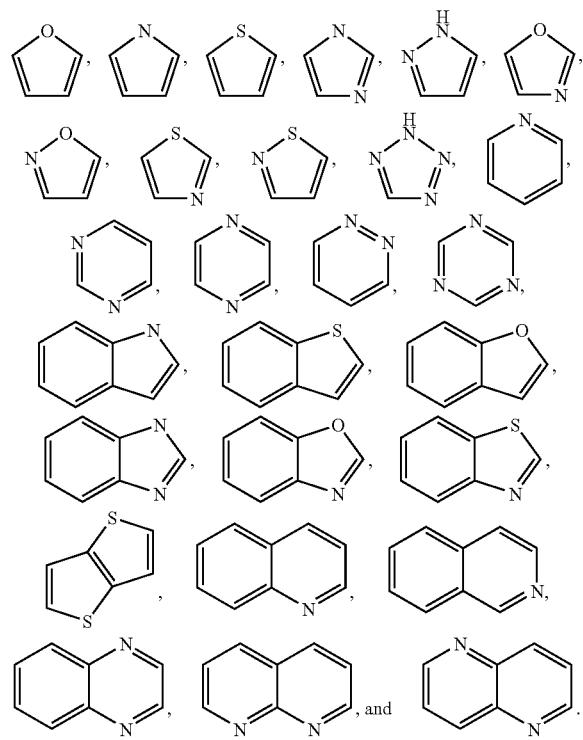

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (O) positions adjacent to the point of attachment of the phenyl ring, both "meta" (m) positions, and the one "para" (p) position across from the point of attachment as illustrated below.

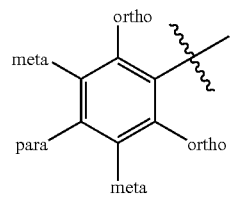

In one general embodiment, the invention relates to compounds that are encompassed by Formulae (I-A), (I-B), and (I-C) and pharmaceutically acceptable salts, pharmaceutically acceptable prodrugs, and pharmaceutically active metabolites of such compounds. In another general embodiment, the invention relates to pharmaceutical compositions each comprising a therapeutically effective amount of a FAAH-modulating agent selected from compounds of Formula (I) and pharmaceutically acceptable salts, pharmaceutically acceptable prodrugs, and pharmaceutically active metabolites of such compounds. Compounds encompassed by Formulae (I), (I-A), (I-B), and (I-C) having asymmetric or chiral centers may exist in different enantiomeric forms. All stereoisomers of the compounds of the general formula and racemates or mixtures of various combinations thereof, are intended to be represented by the formula. Thus, except where a stereocenter is shown as having a specific stereoisomeric form, a general formula shown herein is intended to represent all racemates, enantiomerically pure forms, diastereomeric forms, atropisomeric forms, and mixtures thereof. Furthermore, certain structures may exist as geometric isomers (i.e., cis and trans isomers), as tautomers, or as atropisomers, which are intended to be encompassed by a structural formula. Additionally, a formula given herein is intended to embrace hydrates, solvates, and polymorphs of such compounds, and mixtures thereof.

A structural formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{32}P$, $^{33}P$, $^{35}S$, $^{18}F$, $^{3}Cl$, and $^{125}I$, respectively. Such isotopically labeled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)], including drug or substrate tissue distribution assays, or in radioactive treatment of patients. In particular, an $^{18}F$- or $^{11}C$-labeled compound may be preferred for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a formula variable appears more than once, the choice of the species from a specified list is independent of the choice of the species for the same variable elsewhere in the formula.

In preferred embodiments of Formula (I), (I-A) or (I-C), $R^1$ is —H, methyl, isopropyl, trifluoromethyl, methylsulfanyl, methylsulfinyl, methanesulfonyl, amino, methylamino, dimethylamino, or cyclopropyl. In still other embodiments of Formula (I), (I-A) or (I-C), $R^1$ is amino. In still other embodiments of Formula (I), (I-A) or (I-C), $R^1$ is —H. In preferred embodiments of Formula (I-B), $R^1$ is methyl, isopropyl, trifluoromethyl, methylsulfanyl, methylsulfinyl, methanesulfonyl, amino, methylamino, dimethylamino, or cyclopropyl. In still other embodiments of Formula (I-B), $R^1$ is amino.

In preferred embodiments of Formula (I), (I-A), (I-B) or (I-C), $Ar^1$ is a phenyl group, each unsubstituted or substituted with one, two, or three $R^c$ moieties. In preferred embodiments of Formula (I), (I-A), (I-B), or (I-C), each $R^c$ moiety is independently fluoro, chloro, nitro, trifluoromethyl, methoxy, hydroxy, or trifluoromethoxy, or two adjacent $R^c$ moieties together form —O(CH$_2$)$_{1-2}$O— or —O(CF$_2$)O—. In some embodiments of Formula (I), (I-A), (I-B), or (I-C), $Ar^1$ is phenyl, 4-fluorophenyl, 4-nitrophenyl, 4-trifluoromethylphenyl, 4-chlorophenyl, 4-hydroxyphenyl, 4-methoxyphenyl, 4-hydroxy-3-methoxyphenyl, 3,4-dichlorophenyl, 3,4-difluorophenyl, 2-chlorophenyl, 3-chlorophenyl, 3-methoxyphenyl, 2-methoxyphenyl, 3,5-dichlorophenyl, 3-trifluoromethoxyphenyl, 3-fluorophenyl, 4-chloro-3-fluorophenyl, 3-chloro-4-fluorophenyl, 3-trifluoromethylphenyl, 2-pyridinyl, 3-pyridinyl, 4-pyridinyl, 1,3-benzodioxolyl, or 2,2-difluoro-1,3-benzodioxolyl. In still other embodiments of Formula (I), (I-A), (I-B), or (I-C), $Ar^1$ is unsubstituted phenyl, 4-fluorophenyl, or 4-trifluoromethoxyphenyl.

In preferred embodiments of Formula (I), (I-A), (I-B), or (I-C), X is C($R^f$). In further preferred embodiments of Formula (I), (I-A), (I-B), or (I-C), $R^f$ is —H.

In preferred embodiments of Formula (I), (I-A) or (I-B), $Ar^2$ is a phenyl substituted at either or both of the meta and para positions with one, two or three $R^g$ moieties. In some embodiments of Formula (I), (I-A) or (I-B), $Ar^2$ is a thiophenyl, pyridinyl, pyrimidinyl, or pyrazolyl group, each substituted with one, two, or three $R^g$ moieties. In some embodiments of Formula (I), (I-A) or (I-B), each $R^g$ moiety is independently methyl, ethyl, isopropyl, tert-butyl, hydroxymethyl, 1-hydroxyethyl, cyanomethyl, cyano-dimethyl-methyl, trifluoromethyl, methoxy, ethoxy, propoxy, isopropoxy, butoxy, isobutoxy, trifluoromethoxy, difluoromethoxy, trifluoroethoxy, cyclopropylmethoxy, methylsulfanyl, ethylsulfanyl, isopropylsulfanyl, methylsulfonyl, formyl, acetyl, dimethylamino, morpholin-4-yl, sulfamoyl, dimethylsulfamoyl, cyclopropylsulfamoyl, piperidine-1-sulfonyl, pyrrolidine-1-sulfonyl, nitro, cyano, chloro, fluoro, iodo, phenoxy, benzyl, benzoyl, or phenethyl, or two adjacent $R^g$ moieties together form —O(CH$_2$)$_{1-2}$O— or —O(CF$_2$)O—. In further preferred embodiments of Formula (I), (I-A) or (I-B), $Ar^2$ is 3,4-dimethylphenyl, 4-tert-butylphenyl, 4-cyanophenyl, 4-acetylphenyl, 4-methylphenyl, 4-chlorophenyl, 4-fluorophenyl, 4-trifluoromethylphenyl, 4-methoxyphenyl, 4-nitrophenyl, 3-methylphenyl, 3-trifluoromethoxyphenyl, 4-ethylphenyl, 4-isopropylphenyl, 3,4-dichlorophenyl, 3-chlorophenyl, 3-chloro-4-trifluoromethylphenyl, 4-ethoxyphenyl, 4-isopropoxyphenyl, 4-phenoxy-phenyl, 3-chloro-4-ethoxyphenyl, 3-chloro-4-isopropoxyphenyl, 3-fluoro-4-methylphenyl, 4-hydroxymethylphenyl, 4-formylphenyl, 3-formylphenyl, 4-trifluoroethoxyphenyl, 3-trifluoroethoxyphenyl, 4-chloro-3-methylphenyl, 4-chloro-3-fluorophenyl, 4-chloro-3-trifluoromethylphenyl, 3-fluoro-4-trifluoromethoxyphenyl, 4-ethoxy-3-fluorophenyl, 4-ethoxy-3-methylphenyl, 4-cyclopropylmethoxyphenyl, 4-butoxy-3-fluorophenyl, 4-butoxyphenyl, 3-fluoro-4-propoxyphenyl, 3-fluoro-4-isopropoxyphenyl, 4-isobutoxyphenyl, 4-methoxy-3-methylphenyl, 3-chloro-4-methylphenyl, 3,5-dimethylphenyl, 3-fluoro-4-trifluoromethylphenyl, 3-fluoro-5-trifluoromethylphenyl, 3-chloro-5-fluorophenyl, 4-propoxyphenyl, 4-isopropoxy-3-methylphenyl, 4-difluoromethoxy-3,5-difluorophenyl, 4-(cyano-dimethyl-methyl)phenyl, 4-acetyl-3-fluorophenyl, 3,5-dimethyl-4-isopropoxyphenyl, 3,4,5-trifluorophenyl, 4-benzoylphenyl, 3,5-difluorophenyl, 3,4-difluorophenyl, 4-dimethylaminophenyl, 4-methylsulfonylphenyl, 4-cyclopropylsulfamoylphenyl, 3-fluoro-4-methoxyphenyl, 1,4-benzodioxin-6-yl, 4-dimethylsulfamoylphenyl, 4-piperidine-1-sulfonylphenyl, 4-pyrrolidine-1-sulfonylphenyl, 3-chloro-4-fluorophenyl, 4-methylsulfanylphenyl, 4-cyano-3-fluorophenyl, 3-cyano-4-fluorophenyl, 4-isopropylsulfanylphenyl, 4-cyanomethylphenyl, 4-ethylsulfanylphenyl, 3-ethoxyphenyl, 3-propoxyphenyl, 3-butoxyphenyl, 4-trifluoromethoxyphenyl, 3-trifluoromethylphenyl, 4-(2-o-tolyl-ethyl)phenyl, 3-fluoro-4-(1-hydroxy-ethyl)phenyl, 4-iodophenyl, 4-ethoxy-3-trifluoromethylphenyl, 3,4-dimethoxyphenyl, 3-methoxyphenyl, 2,4-bis(trifluoromethyl)phenyl, 2-methoxy-4-(trifluoromethoxy)phenyl, 4-ethoxy-2-methylphenyl, 2,2-difluoro-1,3-benzodioxol-5-yl, 1,3-benzodioxol-5-yl, 5-acetyl-thiophen-2-yl, 6-methoxypyridin-3-yl, 6-ethoxypyridin-3-yl, 6-morpholin-4-ylpyridin-3-yl, 6-fluoro-5-methylpyridin-3-yl, 6-cyanopyridin-3-yl, 6-(dimethylamino)pyridine-3-yl, 2-morpholin-4-ylpyrimidin-5-yl, or 1-benzyl-1H-pyrazol-4-yl.

In other preferred embodiments of Formula (I), (I-A) or (I-B), $Ar^2$ is a naphthyl, benzoxadiazolyl, indolyl, benzothiophenyl, quinolinyl, or indazolyl, each unsubstituted or substituted with one, two, or three $R^i$ moieties. In some embodiments of Formula (I), (I-A) or (I-B), each $R^i$ moiety is independently methyl. In further preferred embodiments of Formula (I), (I-A) or (I-B), Ar is naphthyl, 2,1,3-benzoxadiazol-5-yl, 1H-indol-5-yl, 1H-indol-6-yl, 1-methyl-1H-indol-2-yl, 1-methyl-1H-indol-5-yl, 5-methyl-1-benzothiophen-2-yl, benzothiophen-3-yl, benzothiophen-5-yl, quinolin-3-yl, or 3-methyl-1H-indazol-6-yl.

In preferred embodiments of Formula (I—C), $R^x$ is —Cl or —F, $R^z$ is —H, and $R^y$ is —H or $R^g$. In further preferred embodiments of Formula (I—C), $R^x$ is —Cl or —F, $R^z$ is —H, and $R^y$ is —$C_{1-4}$alkyl, —$CF_3$, —$OC_{1-4}$alkyl, —$OCF_3$, or halo. In other embodiments of Formula (I-C), Ar is 4-nitrophenyl, 4-ethylphenyl, 4-isopropylphenyl, 4-ethoxyphenyl, 4-propoxyphenyl, 4-isopropxyphenyl, 4-butoxyphenyl, 4-isobutoxyphenyl, or 4-phenoxyphenyl. In other embodiments of Formula (I-C), $Ar^2$ is 4-trifluoromethoxyphenyl. In other embodiments of Formula (I-C), $Ar^2$ is 4-chlorophenyl, 4-fluorophenyl, 4-trifluorophenyl, 3,4-dichlorophenyl, 3-chlorophenyl, 3-chloro-4-trifluoromethylphenyl, 3-chloro-4-ethoxyphenyl, 3-chloro-4-isopropoxyphenyl, 3-fluoro-4-methylphenyl, 4-chloro-3-methylphenyl, 4-chloro-3-trifluoromethylphenyl, 3-fluoro-4-trifluoromethoxyphenyl, 4-butoxy-3-fluorophenyl, 3-fluoro-4-propoxyphenyl, 3-fluoro-4-isopropoxyphenyl, 3-chloro-4-methylphenyl, 3-fluoro-4-trifluoromethylphenyl, 3-fluoro-5-trifluoromethylphenyl, 3-chloro-5-fluorophenyl, 4-acetyl-3-fluorophenyl, 3,4,5-trifluorophenyl, 3,5-difluorophenyl, 3,4-difluorophenyl, 3-fluoro-4-methoxyphenyl, 3-chloro-4-fluorophenyl, 4-cyano-3-fluorophenyl, 3-cyano-4-fluorophenyl, 3-trifluoromethylphenyl, 3-fluoro-4-(1-hydroxy-ethyl)phenyl, or 4-ethoxy-3-trifluoromethylphenyl.

In preferred embodiments of Formula (I), (I-A), (I-B), or (I-C), $R^2$ is —H.

In preferred embodiments of Formula (I), (I-A), (I-B), or (I-C), $R^3$ is —H.

In certain embodiments of Formula (I), (I-A), (I-B), or (I-C), $R^g$ and/or $R^l$ is perhaloalkyl or perhaloalkoxy. The term "perhaloalkyl" refers to a straight- or branched-chain alkyl group having from 1 to 4 carbon atoms in the chain optionally substituting hydrogens with halogens. Examples of perhaloalkyl groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), trifluoroethyl ($CH_2CF_3$), tetrafluorotrifluoromethylethyl (—$CF(CF_3)_2$), and groups that in light of the ordinary skill in the art and the teachings provided herein would be considered equivalent to any one of the foregoing examples. The term "perhaloalkoxy" refers to a straight- or branched-chain alkoxy group having from 1 to 4 carbon atoms in the chain optionally substituting hydrogens with halogens. Examples of perhaloalkoxy groups include trifluoromethoxy ($OCF_3$), difluoromethoxy ($OCF_2H$), monofluoromethoxy ($OCH_2F$), pentafluoroethoxy ($OCF_2CF_3$), tetrafluoroethoxy ($OCHFCF_3$), trifluoroethoxy ($OCH_2CF_3$), tetrafluorotrifluoromethylethoxy (—$OCF(CF_3)_2$), and groups that in light of the ordinary skill in the art and the teachings provided herein would be considered equivalent to any one of the foregoing examples.

In preferred embodiments of Formulae (I), (I-B) or (I-C), the secondary hydroxyl group adjacent to $Ar^1$ is in the configuration as shown below:

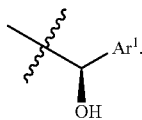

Further preferred embodiments of Formulae (I), (I-A), (I-B), or (I-C) encompass combinations of two or more of the preferred embodiments for each of $R^{1-3}$, X, $Ar^1$, $Ar^2$, $R^{a-l}$, and $R^{x-z}$ listed above.

The invention also relates to pharmaceutically acceptable salts of the free acids or bases represented by Formulae (I), (I-A), (I-B), or (I-C), preferably of the preferred embodiments described above and of the specific compounds exemplified herein. A "pharmaceutically acceptable salt" is intended to mean a salt of a free acid or base of a compound represented by Formulae (I), (I-A), (I-B), or (I-C) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002.

Preferred pharmaceutically acceptable salts are those that are pharmacologically effective and suitable for contact with the tissues of patients without undue toxicity, irritation, or allergic response. A compound of Formulae (I), (I-A), (I-B), or (I-C) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If a compound of Formulae (I), (I-A), (I-B), or (I-C) contains a basic nitrogen, the desired pharmaceutically acceptable salt may be prepared by any suitable method available in the art, for example, by treatment of the free base with an inorganic acid, such as hydrochloric acid, hydrobromic acid, sulfuric acid, sulfamic acid, nitric acid, boric acid, phosphoric acid, and the like; or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid; an amino acid, such as aspartic acid or glutamic acid; an aromatic acid, such as benzoic acid, 2-acetoxybenzoic acid, naphthoic acid, or cinnamic acid; a sulfonic acid, such as laurylsulfonic acid, p-toluenesulfonic acid, methanesulfonic acid, or ethanesulfonic acid; or any compatible mixture of acids such as those given as examples herein.

If a compound of Formulae (I), (I-A), (I-B), or (I-C) is an acid such as a carboxylic acid or sulfonic acid, the desired pharmaceutically acceptable salt may be prepared by any suitable method, for example, by treatment of the free acid with an inorganic or organic base, such as an amine (primary, secondary or tertiary), an alkali metal hydroxide, alkaline earth metal hydroxide, or any compatible mixture of bases such as those given as examples herein. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formulae (I), (I-A), (I-B), or (I-C). The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formulae (I), (I-A), (I-B), or (I-C)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formulae (I), (I-A), (I-B), or (I-C). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formulae (I), (I-A), (I-B), or (I-C) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

The present invention also relates to pharmaceutically active metabolites of compounds of Formulae (I), (I-A), (I-B), or (I-C). A "pharmaceutically active metabolite" means a pharmacologically active product of metabolism in the body of a compound of Formulae (I), (I-A), (I-B), or (I-C) or a salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

The compounds of Formulae (I), (I-A), (I-B), and (I-C), and their pharmaceutically acceptable salts, pharmaceutically acceptable prodrugs, and pharmaceutically active metabolites (collectively, "active agents") of the present invention are useful as FAAH inhibitors in the methods of the invention. The active agents may be used in the inventive methods for the treatment of medical conditions, diseases, or disorders mediated through inhibition or modulation of FAAH, such as those described herein. Active agents according to the invention may therefore be used as an analgesic, anti-depressant, cognition enhancer, neuroprotectant, sedative, appetite stimulant, or contraceptive.

Exemplary medical conditions, diseases, and disorders mediated by FAAH activity include anxiety, depression, pain, sleep disorders, eating disorders, inflammation, multiple sclerosis and other movement disorders, HIV wasting syndrome, closed head injury, stroke, learning and memory disorders, Alzheimer's disease, epilepsy, Tourette's syndrome, epilepsy, Niemann-Pick disease, Parkinson's disease, Huntington's chorea, optic neuritis, autoimmune uveitis, symptoms of drug or alcohol withdrawal, nausea, emesis, sexual dysfunction, post-traumatic stress disorder, cerebral vasospasm, diabetes, metabolic syndrome, osteoarthritis and osteoporosis.

Thus, the active agents may be used to treat subjects diagnosed with or suffering from such a disease, disorder, or condition. The term "treat" or "treating" as used herein is intended to refer to administration of an agent or composition of the invention to a subject for the purpose of effecting a therapeutic benefit through modulation of FAAH activity. Treating includes reversing, ameliorating, alleviating, inhibiting the progress of, lessening the severity of, reducing the incidence of, or preventing a disease, disorder, or condition, or one or more symptoms of such disease, disorder or condition mediated through modulation of FAAH activity. The term "subject" refers to a mammalian patient in need of such treatment, such as a human. "Modulators" include both inhibitors and activators, where "inhibitors" refer to compounds that decrease, prevent, inactivate, desensitize or down-regulate FAAH expression or activity, and "activators" are compounds that increase, activate, facilitate, sensitize, or up-regulate FAAH expression or activity.

Accordingly, the invention relates to methods of using the active agents described herein to treat subjects diagnosed with or suffering from a disease, disorder, or condition mediated through FAAH activity, such as: anxiety, pain, sleep disorders, eating disorders, inflammation, movement disorders (e.g., multiple sclerosis), glucose and lipid metabolism (e.g. diabetes) and bone homeostasis (e.g. osteoporosis).

Symptoms or disease states are intended to be included within the scope of "medical conditions, disorders, or diseases." For example, pain may be associated with various diseases, disorders, or conditions, and may include various etiologies. Illustrative types of pain treatable with a FAAH-modulating agent, in one example herein a FAAH-inhibiting agent, according to the invention include cancer pain, postoperative pain, GI tract pain, spinal cord injury pain, visceral hyperalgesia, thalamic pain, headache (including stress headache and migraine), low back pain, neck pain, musculoskeletal pain, peripheral neuropathic pain, central neuropathic pain, neurogenerative disorder related pain, and menstrual pain. HIV wasting syndrome includes associated symptoms such as appetite loss and nausea. Parkinson's disease includes, for example, levodopa-induced dyskinesia. Treatment of multiple sclerosis may include treatment of symptoms such as spasticity, neurogenic pain, central pain, or bladder dysfunction. Symptoms of drug withdrawal may be caused by, for example, addiction to opiates or nicotine. Nausea or emesis may be due to chemotherapy, postoperative, or opioid related causes. Treatment of sexual dysfunction may include improving libido or delaying ejaculation. Treatment of cancer may include treatment of glioma. Sleep disorders include, for example, sleep apnea, insomnia, and disorders calling for treatment with an agent having a sedative or narcotic-type effect. Eating disorders include, for example, anorexia or appetite loss associated with a disease such as cancer or HIV infection/AIDS.

In treatment methods according to the invention, an effective amount of at least one active agent according to the invention is administered to a subject suffering from or diagnosed as having such a disease, disorder, or condition. A "therapeutically effective amount" or "effective amount" means an amount or dose of a FAAH-modulating agent sufficient to generally bring about a desired therapeutic benefit in patients in need of treatment for a disease, disorder, or condition mediated by FAAH activity. Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary dose is in the range of from about 0.0001 to about 200 mg of active agent per kg of subject's body weight per day, preferably about 0.001 to 100 mg/kg/day, or about 0.01 to 35 mg/kg/day, or about 0.1 to 10 mg/kg daily in single or divided dosage units (e.g., BID, TID, QID). For a 70-kg human, an illustrative range for a suitable dosage amount is from about 0.05 to about 7 g/day, or about 0.2 to about 5 g/day. Once improvement of the patient's disease, disorder, or condition has occurred, the dose may be adjusted for maintenance treatment. For example, the dosage or the frequency of administration, or both, may be reduced as a function of the symptoms, to a level at which the desired therapeutic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be coadministered separately with an active agent of Formulae (I), (I-A), (I-B), and (I-C) or included with such an agent in a pharmaceutical composition according to the invention. In an exemplary embodiment, additional active ingredients are those that are known or discovered to be effective in the treatment of conditions, disorders, or diseases mediated by FAAH activity, such as another FAAH modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention. In one illustrative embodiment, a composition according to the invention may contain one or more additional active ingredients selected from opioids, NSAIDs (e.g., ibuprofen, cyclooxygenase-2 (COX-2) inhibitors, and naproxen), gabapentin, pregabalin, tramadol, acetaminophen, and aspirin.

The active agents of the invention are used, alone or in combination with one or more additional active ingredients, to formulate pharmaceutical compositions of the invention. A pharmaceutical composition of the invention comprises: (a) an effective amount of at least one active agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the active agents of the invention can be provided in the form of tablets or capsules, or as a solution, emulsion, or suspension. To prepare the oral compositions, the active agents may be formulated to yield a dosage of, e.g., from about 5 mg to 5 g daily, or from about 50 mg to 5 g daily, in single or divided doses. For example, a total daily dosage of about 5 mg to 5 g daily may be accomplished by dosing once, twice, three, or four times per day.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

Exemplary active agents useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formulae (I), (I-A), (I-B), and (I-C). For clarity, since compounds of Formulae (I-A), (I-B), and (I-C) are embodiments of compounds of Formula (I), compounds of Formulae (I-A), (I-B), and (I-C) are depicted in the following schemes collectively as compounds of Formula (I).

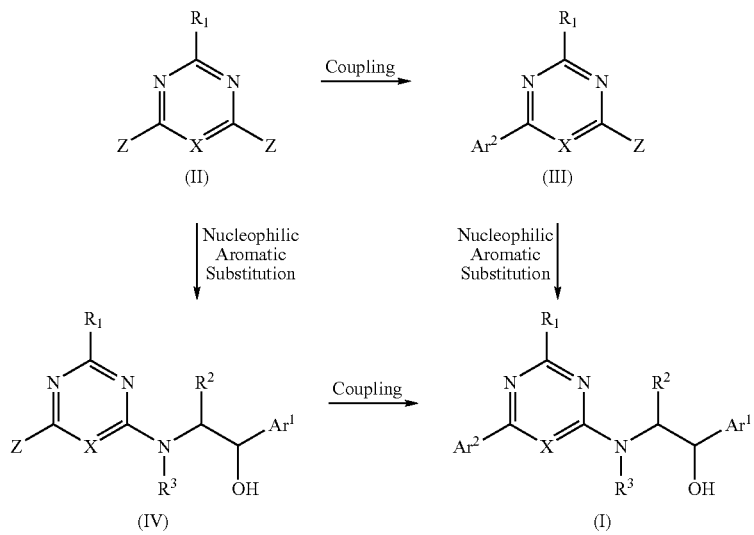

Scheme A

Referring to Scheme A, compounds of Formulae (I), (I-A), (I-B), and (I-C) are prepared from pyrimidines or triazines (II), where Z is halo or another suitable substituent. Various substituted pyrimidines and triazines are commercially available or are prepared using known methods. Pyrimidines of formula (III) are obtained via palladium-mediated cross-coupling of reagents (II) with suitable boronic acids. Preferably, pyrimidines of formula (II) are treated with the desired boronic acid in the presence of a base such as $K_3PO_4$ or KF, in a suitable polar solvent such as $CH_3CN$, 1,2-dimethoxyethane (DME), tetrahydrofuran (THF), water, or a mixture thereof, at a temperature from about 50° C. to about 180° C. using conventional heating or a microwave reactor. Pyrimidines (ill) are converted to compounds of Formulae (I-A), (I-B), and (I-C) via nucleophilic aromatic substitution ($S_NAr$) with aryl-substituted amino alcohols in the presence of a suitable base such as $NaHCO_3$, $(iPr)_2EtN$, $Et_3N$, or a mixture thereof, either neat or in a solvent such as 1,4-dioxane, THF, t-amyl alcohol, n-BuOH, or a mixture thereof, at a temperature from about 80° C. to about 150° C. Alternatively, pyrimidines or triazines of Formulae (I-A), (I-B), and (I-C) are obtained by $S_NAr$ displacement of compounds (II) with amino alcohols, followed by palladium-mediated cross-coupling using known procedures.

Compounds of Formulae (I), (I-A), (I-B), and (I-C) are additionally prepared in a one-pot fashion by nucleophilic aromatic substitution ($S_NAr$) displacement of compounds (II)

with amino alcohols in the presence of a suitable base such as NaHCO$_3$, in a suitable polar solvent such as CH$_3$CN at a temperature from about 50° C. to about 180° C.; followed by a palladium-mediated cross-coupling reaction with a suitable boronic acid in the presence of a base such as K$_3$PO$_4$, and palladium-mediated cross-coupling reagents such as Pd(dppf)Cl$_2$·CH$_2$Cl$_2$ and Pd(OAc)$_2$ at a temperature from about 50° C. to about 180° C.

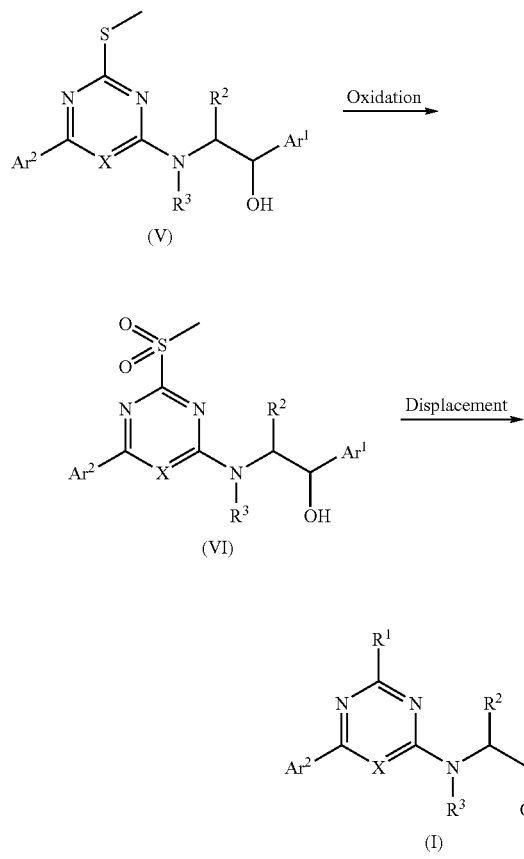

Referring to Scheme B, thioethers (V), obtained as described in Scheme A, are oxidized using generally known methods to provide sulfones (VI). Those skilled in the art will recognize that compounds (V) and (VI) are embodiments of Formulae (I), (I-A), (I-B), and (I-C). To prepare further embodiments of Formulae (I), (I-A), (I-B), and (I-C), the sulfone substituent is displaced by reaction with a suitable amine or alcohol in a solvent such as MeOH, EtOH, n-BuOH, t-amyl alcohol, THF, N,N-dimethylformamide (DMF), dimethylsulfoxide (DMSO), toluene, or a mixture thereof, with or without the presence of a base such as NaOMe, NaOEt, KOtBu, Et$_3$N, (iPr)$_2$EtN, pyridine, or a mixture thereof, at a temperature from about room temperature to the reflux temperature of the solvent. Preferably, displacement with a suitable amine is performed by heating a sulfone (VI) in t-amyl alcohol at 130° C. in a sealed tube.

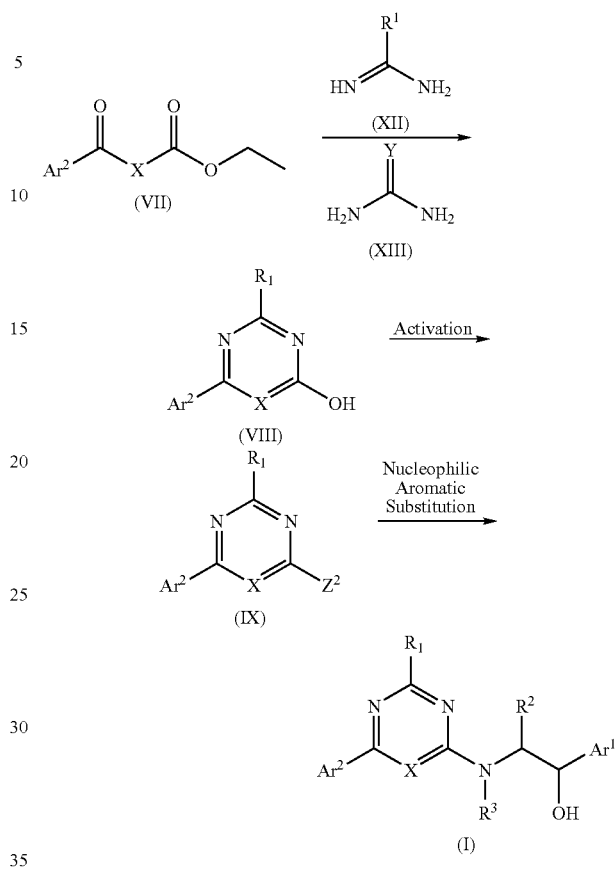

Referring to Scheme C, compounds of Formulae (I), (I-A), (I-B), and (I-C), where X is C(R$^f$), are prepared from β-ketoesters (VII), which are commercially available or are prepared according to general techniques known in the art. β-Ketoesters (VII) are reacted with amidines or carboximidamides (XII) or with ureas or thioureas (XIII) where Y is O, S, or NR$^a$, for example, in the presence of a base such as NaOEt or KOtBu, in a solvent such as EtOH, t-BuOH, or a mixture thereof, at a temperatures between about room temperature and the reflux temperature of the solvent, to form hydroxypyrimidines (VIII). Hydroxy-pyrimidines (VIII) are then activated for use in the S$_N$Ar displacement by general procedures known in the art. For example, treatment with POCl$_3$, PBr$_3$, or POBr$_3$ affords the corresponding halopyrimidines (IX) where Z$^2$ is a chloride or bromide. Alternatively, treatment of hydroxy-pyrimidines (VIII) with trifluoromethanesulfonic anhydride or N-phenyl-bis(trifluoromethanesulfonimide) in 1,2-dichloroethane, CH$_2$Cl$_2$, THF, or a mixture thereof, in the presence of a base such as pyridine, Et$_3$N, (iPr)$_2$EtN, KOtBu, or a mixture thereof, provides triflates where Z$^2$ is —OSO$_2$CF$_3$. Preferably, hydroxy-pyrimidines (VIII) are treated with POCl$_3$ in CH$_3$CN at a temperature from about 80° C. to about 100° C. Chloropyrimidines (IX) are processed to compounds of Formulae (I-A), (I-B), and (I-C) via S$_N$-aryl displacement as described in Scheme A.

Scheme D

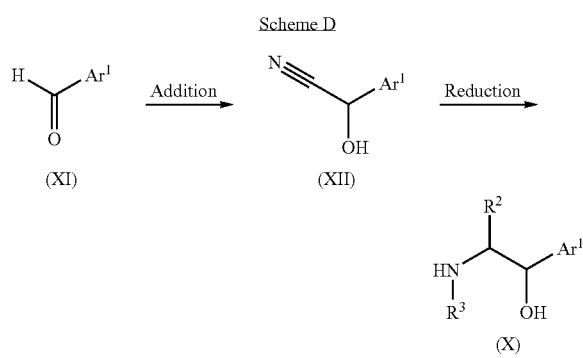

Racemic or enantio-enriched amino-alcohols (X) are commercially available or are prepared using generally known procedures. For example, in certain embodiments, amino-alcohols (X), where $R^2$ and $R^3$ are both —H, are prepared as shown in Scheme D. To form racemic amino-alcohols, aldehydes (XI) are treated with trimethylsilylcyanide (TMSCN) in the presence of a catalyst such as $ZnI_2$, neat or in a solvent such as diethyl ether ($Et_2O$), THF, 1,4-dioxane, or a mixture thereof, to provide cyanohydrins (XII). To form enantio-enriched amino-alcohols (X), reactions are are run in the presence of a chiral ligand, such as S-(−)-1,1'-bi-2-naphthol. Preferably, the resulting cyanohydrin is formed as the trimethylsilyl ether. Reduction of the nitrile using known general procedures, such as $LiAlH_4$, or a borane complex (such as borane complexed with THF ($BH_3$.THF), dimethylsulfide ($BH_3$.DMS), or N-ethyl-N-isopropylaniline (BACH.EI)), in solvent such as THF or $Et_2O$, provides amino-alcohols (X). Where a trimethylsilyl ether was formed, it is deprotected using standard acidic or basic conditions to give racemic or enantio-enriched amino-alcohols (X). Where racemic and non-racemic mixtures of enantiomers are obtained, single enantiomers may be isolated using known methods, such as chiral chromatography and recrystallization.

Alternatively, amino-alcohols (X) are accessed through the addition of azide anion to a suitable α-haloketone and subsequent reduction of the azido group and the ketone. In another embodiment, reduction of a suitable α-haloketone to the corresponding halohydrin and displacement with ammonia, methylamine, or dimethylamine, provides amino-alcohols (X).

Enantio-enriched amino-alcohols (X) are accessed through other stereoselective syntheses or chiral separation methods. For example, the reduction shown in Scheme D is optionally performed with a borane complex in the presence of a chiral catalyst such as (R)-2-methyl-CBS-oxazaborolidine (CBS) to generate chiral product. Stereoselective reductions of α-haloketones, α-azidoketones, or α-aminoketones, are also useful in preparing chiral reagents.

Scheme E

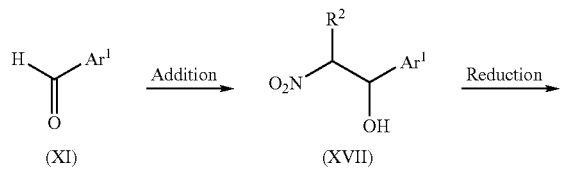

Alternatively, racemic amino-alcohols (X), where $R^2$ can be either —H or alkyl and $R^3$ is —H, are accessed via nitro-aldol addition as shown is Scheme E. Aldehydes (XI) are treated with nitromethane ($CH_3NO_2$) in the presence of base, such as NaOH, KOH, KOtBu, NaOtBu, TBAF, and NaH, in solvents such as THF and MeOH, at temperatures between 0° C. and the reflux temperature of the solvent, to form nitro-alcohols (XVII). Amino alcohols (X) are obtained by reduction of the nitro group using generally known methods such as Pd-catalyzed hydrogenation using a hydrogen source such as $H_2$, cyclohexadiene, or $NH_4HCO_2$ in the presence of Zn, in solvents such as MeOH and EtOH at temperatures between room temperature and the reflux temperature of the solvent. Where racemic and non-racemic mixtures of enantiomers are obtained, single enantiomers may be isolated using known methods, such as chiral chromatography and recrystallization.

Scheme F

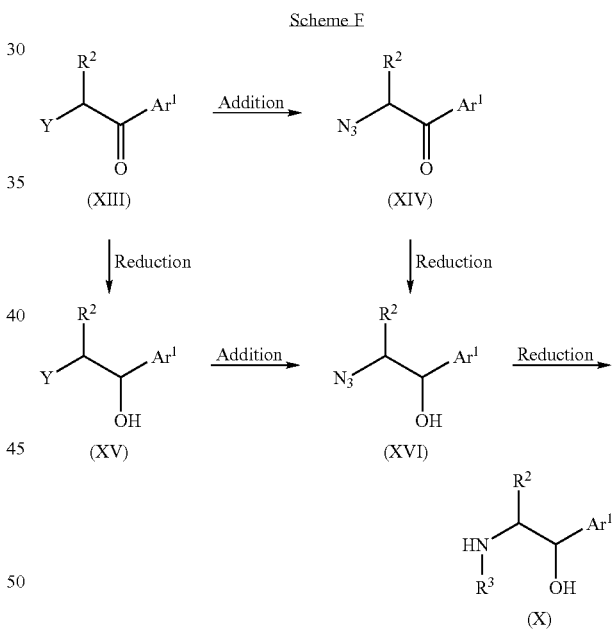

In certain embodiments, amino alcohols (X), where $R^2$ and $R^3$ are both —H may be prepared from α-halo ketones (XIII) shown in Scheme F. To prepared achiral amino-alcohols, α-halo ketones (XIII), where Y═Br or Cl, are treated with sodium azide ($NaN_3$) in solvents such as DMF, THF, MeOH, EtOH or a mixture thereof at temperatures between room temperature and the reflux temperature of the solvent to provide azido-ketones (XIV). Reduction of the azido-ketone using known methods, such as treatment with borane complex ($BH_3$.THF and $BH_3$.DMS) or $NaBH_4$, in solvent such as THF, MeOH and EtOH at temperatures between 0° C. and room temperature provide azido-alcohols (XVI). Alternatively, azido-alcohols (XVI) are prepared by reduction of the α-halo ketone (XIII) to give α-halo-alcohols (XV) which are converted to azido-alcohols (XVI) by addition of NaN₃. To form enantio-enriched amino-alcohols (X), α-halo ketones (XIII) or azido-ketones (XIV) are reduced using a borane complex in the presence of either (S) or (R)-2-methyl-CBS oxazaborolidine (CBS) in THF at temperatures between 0° C. and room temperature. Reduction of azido-alcohols (XVI) via known methods such as Pd-catalyzed hydrogenation using a hydrogen source such as $H_2$, and cyclohexadiene or $NH_4HCO_2$ in the presence of Zn, in solvents such as MeOH, EtOH or a mixture thereof, at temperatures between room temperature and the reflux temperature of the solvent, and at pressures ranging from 0-50 psi. provide amino-alcohols (X). Additionally, azido-alcohols (XVI) are reduced to amino-alcohols (X) using $NaBH_4$ in the presence of $CuSO_4 \cdot 5H_2O$ in solvents such as EtOH, MeOH, or a mixture thereof at temperatures between 0° C. and reflux temperature of the solvent. Preferably, α-halo ketones (XIII), where X=Br, are treated with $NaN_3$ in EtOH at room temperature followed by reduction using $NaBH_4$ in EtOH at 0° C. to provide azido-alcohols (XVI) which is subsequently reduced using a mixture of $NaBH_4$ and $CuSO_4 \cdot 5H_2O$ in MeOH at temperatures from about 0° C. to 80° C. to provide amino alcohols (X). Where racemic and non-racemic mixtures of enantiomers are obtained, single enantiomers may be isolated using known methods, such as chiral chromatography and recrystallization.

Compounds of Formulae (I), (I-A), (I-B), and (I-C) may be converted to their corresponding salts by applying general techniques described in the art. For example, a compound of Formulae (I), (I-A), (I-B), and (I-C) may be treated with trifluoroacetic acid, HCl, or citric acid in a solvent such as $Et_2O$, $CH_2Cl_2$, THF, or MeOH to provide the corresponding salt forms.

Compounds prepared according to the schemes described above may be obtained as single enantiomers, diastereomers, or regioisomers, by enantio-, diastero-, or regio-specific synthesis, or by resolution. Compounds prepared according to the schemes above may alternatively be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following specific examples are provided to further illustrate the invention and various preferred embodiments.

EXAMPLES

Chemistry

In obtaining the characterization data described in the examples below, the following analytical protocols were followed unless otherwise indicated.

Unless otherwise specified, reaction mixtures were stirred under a nitrogen atmosphere at room temperature (rt). Where solutions were "concentrated", they were concentrated using a rotary evaporator under reduced pressure. Where solutions are dried, they are typically dried over a drying agent such as $MgSO_4$ or $Na_2SO_4$.

Microwave reactions were carried out in either a CEM Discover® or a Biotage Initiator™ Microwave at specified temperatures.

Thin-layer chromatography was performed using Merck silica gel 60 $F_{254}$ 2.5 cm×7.5 cm 250 μm or 5.0 cm×10.0 cm 250 μm pre-coated silica gel plates. Preparative thin-layer chromatography was performed using EM Science silica gel 60 $F_{254}$ 20 cm×20 cm 0.5 mm pre-coated plates with a 20 cm×4 cm concentrating zone.

Normal phase purification was typically done by normal phase flash column chromatography (FCC) with RediSep® silica gel columns using EtOAc/hexanes or $CH_2Cl_2$/MeOH as eluent unless otherwise specified.

Reverse phase high performance liquid chromatography (HPLC) was performed under the following conditions: 1) Instrument, Shimadzu; Column, Phenomenex Gemini column 5 μm C18 (150×21.2 mm) or Waters Xterra RP18 OBD 5 μm (100×30 mm); Gradient, 95:5 to 0:100 water (0.05% trifluoroacetic acid (TFA))/$CH_3CN$ (0.05% TFA); Flow rate, 30-80 mL/min; Detection, UV at A=220-254 nM. 2) Instrument, Gilson; Column, Phenomenex LUNA column 5 μm C18 (250×50 mm) or Waters XBridge Prep C18 OBD 5 μm (30×150 mm); Gradient, 95:5 to 0:100 water (0.05% TFA)/$CH_3CN$ (0.05% TFA); Flow rate, 30-80 mL/min; Detection, UV at A=220-254 nM.

Analytical chiral HPLC was performed under the following conditions: Stationary phase, Chiralpak AS (250×4.6 mm) at 25° C.; Mobile Phase, 10% MeOH containing 0.2% triethylamine, 90% $CO_2$; Flow Rate, 2 mL/min; Back Pressure, 150 bar.

Preparative chiral HPLC was performed under the following conditions: Stationary Phase, Chiralpak AS-H SFC 250× 21 mm (L×I.D.); Mobile Phase, 10% MeOH containing 0.2% triethylamine, 90% $CO_2$; Flow Rate, 31.5 mL/min; Back Pressure, 150 bar.

Hydrochloride salts were obtained by treating the corresponding free bases with HCl (4 N in dioxane, 2 M in $Et_2O$, or 1.25 N in MeOH) at rt. The mixtures were either concentrated to obtain the HCl salt, or the resulting solid was isolated by filtration.

Trifluoroacetic acid salts were obtained by purification of the crude reaction product by preparative reverse phase HPLC.

Nuclear magnetic resonance (NMR) spectra were obtained on Bruker model DRX spectrometers. The format of $^1H$ NMR data below is: chemical shift in ppm downfield of the tetramethylsilane reference (multiplicity, coupling constant J in Hz, integration).

Mass spectra were obtained on an Agilent series 1100 MSD using electrospray ionization (ESI) in positive mode unless otherwise indicated. Calculated mass corresponds to the exact mass.

Chemical names were generated using ChemDraw Ultra 6.0.2 (CambridgeSoft Corp., Cambridge, Mass.) or ACD/Name Version 9 (Advanced Chemistry Development, Toronto, Ontario, Canada).

Intermediate A: (R)-2-Amino-1-(4-fluoro-phenyl)-ethanol hydrochloride

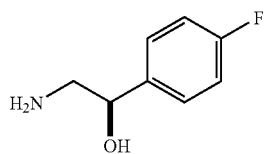 [SMILES: NC[C@H](O)c1ccc(F)cc1]

A mixture of (S)-(−)-1,1′-bi-2-naphthol ((S)-BINOL) (573 mg, 2.0 mmol) and lithium isopropoxide (132 mg, 2.0 mmol) was treated with toluene (40 mL). After 40 min, 4-fluorobenzaldehyde (2.15 mL, 20.0 mmol) was added. The resulting yellow solution was placed in a dry ice/acetone bath. After 10 min, trimethylsilyl cyanide (TMSCN; 2.5 mL, 20.0 mmol) was added. After 75 min, the resulting mixture was treated with methanolic HCl (10% by volume; 20 mL) and warmed to rt. The resulting mixture was poured onto a mixture of ethyl acetate (EtOAc) (200 mL) and water (200 mL). The aqueous phase was extracted with EtOAc (2×100 mL). The combined extracts were dried ($MgSO_4$), and concentrated, giving a mixture of green oil and a crystalline solid. The oil was decanted yielding 2.24 g of product (75%). A solution of this oil (1.0 g, 6.6 mmol) in THF (6.6 mL) was treated dropwise with $BH_3$·THF (1.0 M in THF; 13.2 mL, 13.2 mmol). The resulting mixture was heated to reflux for 1 h, stirred at rt for 16 h, and quenched by slow addition of MeOH (2.5 mL). Volatiles were removed in vacuo. MeOH (3 mL) was added, and the resulting solution was treated with HCl (2 M in $Et_2O$; 6 mL). $Et_2O$ (30 mL) was added, resulting in the formation of a solid, which was filtered and dried in vacuo, giving the title compound (564 mg, 45%).

Intermediate B: (R)-2-(6-Chloro-pyrimidin-4-ylamino)-1-(4-fluoro-phenyl)-ethanol

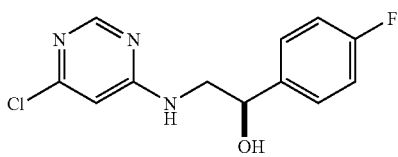 [SMILES: O[C@@H](CNc1cc(Cl)ncn1)c1ccc(F)cc1]

A suspension of (R)-2-amino-1-(4-fluoro-phenyl)-ethanol hydrochloride (500 mg, 2.61 mmol), 4,6-dichloropyrimidine (353 mg, 2.37 mmol), and $NaHCO_3$ (1.39 g, 16.6 mmol) in dioxane (10 mL) was heated in a 100° C. bath for 19 h and cooled to rt. Water (10 mL) was added, and the mixture, containing solid, was extracted with $CH_2Cl_2$ (3×10 mL). The combined organic extracts were dried ($MgSO_4$) and concentrated. The residue was purified (FCC) to give the title compound as a white solid (415 mg, 59%) in 90% enantiomeric excess (Chiralcel AD-H column, supercritical $CO_2$).

Intermediate C:
2-Amino-1-(3,4-dichloro-phenyl)-ethanol

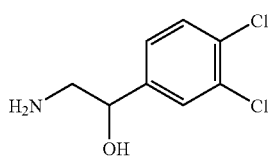 [SMILES: NCC(O)c1ccc(Cl)c(Cl)c1]

To a mixture of 3,4-dichlorobenzaldehyde (3.50 g, 20.2 mmol) and $ZnI_2$ (19 mg, 0.06 mmol) at 0° C. was added TMSCN (2.2 g, 2.2 mmol). The reaction mixture was stirred at 0° C. for 10 min and then warmed to rt and stirred for an additional 1 h. The mixture was concentrated to afford an orange-brown colored oil. The oil was dissolved in THF (20 mL) and $BH_3$·THF (1 M in THF; 25 mL, 25 mmol) was added at 0° C. The reaction mixture was warmed to rt and stirred overnight. The mixture was cooled to 0° C. and MeOH (6 mL) was added with continued stirring for 2 h. After being warmed to rt, the mixture was concentrated. The residue was dissolved in MeOH (10 mL) and HCl (2 M in $Et_2O$; 25 mL) was added at 0° C. After 30 min, $Et_2O$ (100 mL) was added and the resulting white solid was filtered and washed with $Et_2O$ (2×50 mL) to give a white solid (3.5 g, 72%).

Intermediate D: 4-Chloro-6-(3-chloro-4-trifluoromethyl-phenyl)-pyrimidine

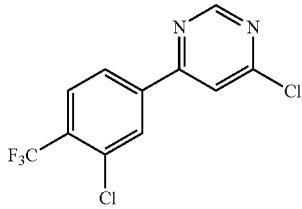 [SMILES: FC(F)(F)c1ccc(-c2cc(Cl)ncn2)cc1Cl]

To a solution of $CH_3CN$ and water (75:25 mL) that has been degassed by bubbling $N_2$ into the solvent were added 4,6-dichloro-pyrimidine (3.63 g, 22.7 mmol) and $Ph_3P$ (840 mg, 2.2 mmol). De-gassing was continued for an additional 15 min before adding 3-chloro-4-trifluoromethylphenyl boronic acid (5 g, 22 mmol), Pd(OAc)$_2$ (250 mg, 1.11 mmol) and $K_3PO_4$ (9.4 g, 44.3 mmol). The resulting mixture was stirred at rt for 2 h before diluting with water and extracting with EtOAc. The organic layer was dried ($Na_2SO_4$), and concentrated. The crude residue was purified (FCC) to give the title compound (2.3 g, 35%).

Intermediate E: 2,2-Difluoro-5-(4,4,5,5-tetramethyl-[1,3,2]dioxaborolan-2-yl)-benzo[1,3]dioxole

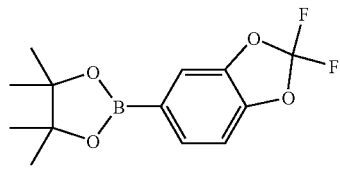 [SMILES: CC1(C)OB(c2ccc3c(c2)OC(F)(F)O3)OC1(C)C]

To an 80 mL microwave vessel were added 5-bromo-2,2-difluoro-benzo[1,3]dioxole (2.0 g, 8.44 mmol), bis(pinocolato)diboron (2.36 g, 9.28 mmol), potassium acetate (1.66 g, 16.9 mmol), Pd(dppf)Cl$_2$·CH$_2$Cl$_2$ (689 mg, 0.84 mmol) and 1,4-dioxane (25 mL). The vessel was purged with $N_2$ and then heated via microwave irradiation for 45 min at 140° C. The reaction mixture was diluted, filtered through a pad of celite and then filtered through a 0.45 μM nylon filter to remove residual palladium particulates, dried ($Na_2SO_4$) and concentrated. The crude material was purified (FCC) to yield the title compound as a green oil (1.41 g, 59%).

Intermediate F: 4,4,5,5-Tetramethyl-2-(5-trifluoromethyl-benzo[b]thiophen-2-yl)-[1,3,2]dioxaborolane

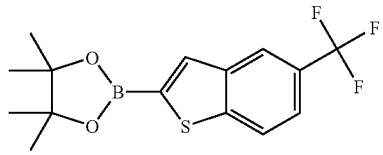 [SMILES: CC1(C)OB(c2cc3cc(C(F)(F)F)ccc3s2)OC1(C)C]

Step A: 5-Trifluoromethyl-benzo[b]thiophene. A mixture of 5-trifluoromethyl-benzo[b]thiophene-2-carboxylic acid (2.00 g, 8.12 mmol) and 1,8-diazabicyclo[5.4.0]undec-7-ene (DBU) (5.0 mL, 34 mmol) in DMA (13 mL) was heated via microwave irradiation at 200° C. for 1 h. The reaction was cooled to rt, diluted with HCl (1 N aq., 20 mL) and extracted with EtOAc (20 mL). The organic layer was washed with water (10 mL), dried ($Na_2SO_4$) and concentrated. The residue was taken up in $Et_2O$ (25 mL) and washed with water (25 mL). The aqueous layer was extracted with $Et_2O$ (10 mL×2). The combined $Et_2O$ layers were dried ($Na_2SO_4$) and concentrated. The crude material was purified (FCC) to yield the title compound (1.22 g, 74%).

Step B. To a 2-necked round bottom flask were added $[Ir(OMe)(COD)]_2$ (19 mg, 0.03 mmol) and 4,4'-di-tert-butyl-2,2'-bipyridine (dtbpy) (15.0 mg, 0.06 mmol) and the flask was evacuated and refilled with $N_2$. The flask was charged with a solution consisting of 5-trifluoromethyl-benzo[b]thiophene (380 mg, 1.88 mmol) in hexane (12 mL), followed by pinacolborane (0.35 mL, 2.44 mmol). The reaction mixture was allowed to stir at rt for 4 h before diluting with $CH_2Cl_2$ (20 mL) and washing with water (10 mL). The organic layer was dried ($Na_2SO_4$), concentrated, and purified (FCC) to yield the title compound (405 mg, 66%).

Intermediate G: 4-trifluoromethylsulfanyl-benzene boronic acid

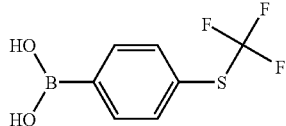 [SMILES: OB(O)c1ccc(SC(F)(F)F)cc1]

Step A: 4,4,5,5-Tetramethyl-2-(4-trifluoromethylsulfanyl-phenyl)-[1,3,2]dioxaborolane. Title compound was prepared analogously to Intermediate E.

Step B. To a round-bottomed flask were added 4,4,5,5-tetramethyl-2-(4-trifluoromethylsulfanyl-phenyl)-[1,3,2]dioxaborolane (960 mg, 3.16 mmol) and sodium periodate (2.03 g, 9.48 mmol) in THF and water (4:1, 26 mL). The resulting suspension was stirred at rt for 30 min. HCl (1 N aq., 2.21 mL) was added to the suspension and the reaction mixture was stirred at rt for 18 h. The resulting precipitate was removed by filtration and washed with hexanes. The filtrate was diluted with water (25 mL) and extracted with EtOAc (25 mL). The aqueous layer was extracted with EtOAc (10 mL×2), and the combined organic layers dried ($Na_2SO_4$) and concentrated to yield the title compound (512 mg, 73%).

Intermediate H. Route 1: 3-Trifluoromethyl-benzo[d]isoxazole-6-boronic acid

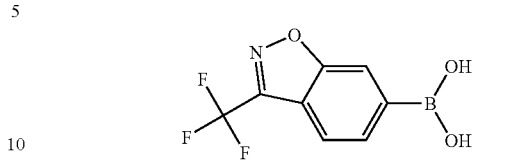

Step A: 1-(4-Bromo-2-hydroxy-phenyl)-2,2,2-trifluoro-ethanone. To a pre-cooled (0° C.) solution of 3-bromophenol (4.93 ml, 46.2 mmol) and dichloroethane (185 mL), was added trifluoroacetic anhydride (9.3 mL, 67 mmol) over 10 min. Aluminum chloride (20.1 g, 150.7 mmol) was then added portion-wise over 15 min. The reaction mixture was gradually warmed to rt over 2 h and then heated at 40° C. for 19 h. The reaction mixture was cooled to rt and poured over ice water. The resultant mixture was extracted with $CH_2Cl_2$ (50 mL×2) the combined organic layers were washed with a satd. $NaHCO_3$ solution (150 mL), followed by a brine solution (150 mL), dried ($Na_2SO_4$) and concentrated to dryness. The crude material was dissolved in $Et_2O$ (100 mL) and extracted with $NaHCO_3$ (10% aq., 100 mL×4). The pH of the combined aqueous extracts was lowered to 7 by careful addition of HCl (6 N aq.) and the resultant mixture extracted with $Et_2O$ (200 mL). The $Et_2O$ layer was dried ($Na_2SO_4$) and concentrated. The residue, containing 95% product and 5% 3-bromophenol by NMR analysis, was purified (FCC) to yield the title compound (5.55 g, 45%).

Step B: 1-(4-Bromo-2-hydroxy-phenyl)-2,2,2-trifluoro-ethanone oxime. To a round bottom flask were added sodium acetate (9.46 g, 115 mmol), hydroxylamine hydrochloride (7.09 g, 102 mmol) and MeOH (10 mL). To this mixture was added a solution consisting of 1-(4-bromo-2-hydroxy-phenyl)-2,2,2-trifluoro-ethanone (2.5 g, 9.3 mmol) and MeOH (62 mL). The reaction vessel was heated at 64° C. for 7 h before cooling to rt and pouring the reaction mixture into ice water (100 mL). The aqueous solution was then extracted with EtOAc (75 mL×2) and the organic layers dried ($Na_2SO_4$) and concentrated to yield the title compound as a mixture of the two possible oxime isomers (2.64 g, 100%).

Step C: 6-Bromo-3-trifluoromethyl-benzo[d]isoxazole. To a flask containing 1-(4-bromo-2-hydroxy-phenyl)-2,2,2-trifluoro-ethanone oxime (2.64 g, 9.29 mmol) was added acetic anhydride (14 mL) and the reaction mixture stirred for 18 h at rt. The reaction mixture was concentrated and taken up in toluene and again concentrated to yield the acylated intermediate. This intermediate was dissolved in pyridine (15 mL) and triethylamine (3.2 mL) and heated at 112° C. for 4.5 h. The reaction mixture was concentrated and the residue was taken up in toluene and again concentrated the residue was then partitioned between EtOAc (25 mL) and HCl (1 N aq., 25 mL). The layers were separated and the organic layer washed with HCl (1 N aq., 25 mL). The combined water layers were then extracted with EtOAc (25 mL×2) and the combined organic layers were washed with brine (15 mL), dried ($Na_2SO_4$) and concentrated. The crude material was purified (FCC) to yield the title compound (44 mg, 17%).

Step D. Title compound was prepared using methods similar to those described in Intermediate G.

Intermediate H, Route 2:
3-Trifluoromethyl-benzo[d]isoxazole-6-boronic acid

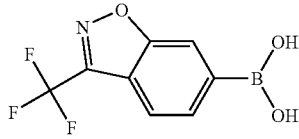 [SMILES: OB(O)c1ccc2c(C(F)(F)F)noc2c1]

Step A: 1-(4-Bromo-2-fluoro-phenyl)-2,2,2-trifluoro-ethanol. A mixture of 4-bromo-2-fluoro-benzaldehyde (8.12 g, 40.0 mmol) and (trifluoromethyl)trimethylsilane (7.50 mL, 48.0 mmol) in THF (40 mL) was cooled to 0° C. before treating with TBAF (1 M in THF, 0.6 mL) and warming to rt. After 3 h, an additional portion of TBAF (1 M in THF, 8.0 mL) was added. The resultant mixture was allowed to stir for 10 min before adding HCl (1 N aq., 40 mL) and extracting with Et$_2$O (40 mL). The Et$_2$O layer was dried (MgSO$_4$) and concentrated to yield the title compound (10.7 g, 98%).

Step B: 1-(4-Bromo-2-fluoro-phenyl)-2,2,2-trifluoro-ethanone. Dess-Martin periodinane (16.57 g, 39.06 mmol) was added to a solution consisting of 1-(4-bromo-2-fluoro-phenyl)-2,2,2-trifluoro-ethanol (10.66 g, 39.06 mmol) and DCM (100 mL) and the resultant mixture was stirred at rt for 1.5 h. Na$_2$S$_2$O$_3$ (10% aq., 100 mL) was added and the resulting mixture extracted with CH$_2$Cl$_2$ (100 mL). The organic layer was washed with Na$_2$S$_2$O$_3$ (50 mL×2), NaHCO$_3$ (satd. aq., 100 mL×2), and brine (100 mL×2). The organic layer was dried (Na$_2$SO$_4$) and concentrated. The crude material was purified (FCC) to yield the title compound (3.20 g, 30%).

Step C: 1-(4-Bromo-2-fluoro-phenyl)-2,2,2-trifluoro-ethanone oxime. To a solution consisting of 1-(4-bromo-2-fluoro-phenyl)-2,2,2-trifluoro-ethanone (3.12 g, 11.5 mmol) and MeOH (50 mL) were added hydroxylamine hydrochloride (4.00 g, 57.5 mmol) and sodium acetate (5.90 g, 71.9 mmol). The resulting mixture was heated at 64° C. for 19 h, at which time additional hydroxylamine hydrochloride (2.40 g, 34.5 mmol) and sodium acetate (3.54 g, 43.1 mmol) were added. Heating was continued for 24 h and the mixture was cool to rt and the mixture was filtered to remove solids. The filtrate was diluted with EtOAc (150 mL), washed with water (150 mL), dried (Na$_2$SO$_4$) and concentrated. The title compound was obtained as a 70:30 ratio of the E and Z oxime isomers (3.28 g, 100%).

Step D: 6-Bromo-3-trifluoromethyl-benzo[d]isoxazole. A solution consisting of 1-(4-bromo-2-fluoro-phenyl)-2,2,2-trifluoro-ethanone oxime (3.2 g, 11.2 mmol) 1,8-diazabicyclo[5.4.0]undec-7-ene (DBU) (1.1 mL, 7.4 mmol) and THF (42 mL) was heated at 150° C. via microwave irradiation for 30 min. The reaction mixture was diluted with CH$_2$Cl$_2$ (25 mL) and washed with HCl (1 N aq., 25 mL). The organic layer was then dried (Na$_2$SO$_4$), concentrated, and purified (FCC) to yield the title compound (1.97 g, 66%).

Step E. Title compound was prepared using methods analogous to those described in Intermediate G.

Intermediate I: 3-Chloro-4-trifluoromethoxy-benzene boronic acid

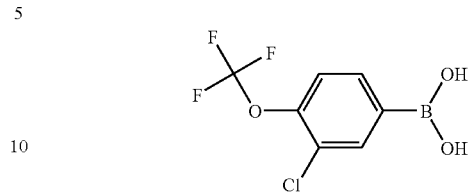

Step A: 4-Bromo-2-chloro-1-trifluoromethoxy-benzene. To a 0° C. solution consisting of 3-chloro-4-trifluoromethoxy-aniline (2.12 g, 10.0 mmol) and HBr (48% aq, 50 mL) was added NaNO$_2$ (2 M aq., 917.7 mg, 13.3 mmol) dropwise at a rate such that the reaction temperature remained below 5° C. After stirring for 1.75 h, urea (330 mg, 5.5 mmol) was added and the mixture stirred for 20 min. A solution consisting of Cu(I)Br (2.96 g, 20.6 mmol) and HBr (48% aq., 13.1 mL) was then added while keeping the reaction temperature in the range of 0-5° C. Upon complete addition, the reaction mixture was heated to 85° C. for 2.5 h. After cooling to rt, the reaction mixture was poured into ice water (150 mL) and extracted with hexanes (100 mL). The aqueous layer was washed with CH$_2$Cl$_2$ (100 mL) and the combined organic phases washed with satd. aq. NaHCO$_3$ (150 mL×2), dried (Na$_2$SO$_4$) and concentrated. The crude material was purified (FCC) to yield the title compound (806 mg, 29%).

Step B. Title compound was prepared using methods similar to those described in Intermediate G.

Intermediate J:
3-Pentafluoroethyl-benzo[d]isoxazole-6-boronic acid

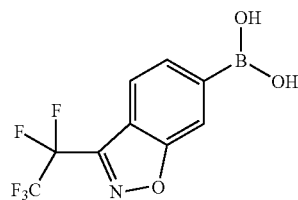 [SMILES: OB(O)c1ccc2c(C(F)(F)C(F)(F)F)noc2c1]

Title compound was prepared using methods similar to those described in Intermediate H, Route 2.

Intermediate K: (1R)-2-Amino-1-(4-fluoro-phenyl)-ethanol hydrochloride salt

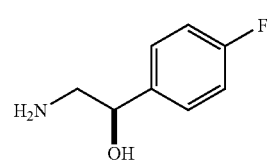 [SMILES: NC[C@H](O)c1ccc(F)cc1]

Step A: (1R)-2-Chloro-1-(4-fluoro-phenyl)-ethanol. To a solution consisting of BH$_3$.THF (1 M, 150 mL) and (R)-(+)-2-methyl-CBS-oxazaborolidine (1 M in THF) (2.14 mL) was added a second solution consisting of 2-chloro-4'-fluoro-acetophenone (37.0 g, 214 mmol) and THF (100 ml) over 1 h at rt. The resultant colorless reaction mixture was stirred for 45 min and then quenched with MeOH (75 mL). The solvent was removed in vacuo leaving the title compound as pale yellow oil, which was used without further purification (37 g, 100%)

Step B: (1R)-2-Azido-1-(4-fluoro-phenyl)-ethanol. Sodium azide (41.8 g, 642 mmol) was added to a solution consisting of (1R)-2-chloro-1-(4-fluoro-phenyl)-ethanol (37.4 g, 214 mmol) and DMF (214 mL) at rt. The reaction mixture was heated to 100° C. for 3 h, diluted with water (500 mL), and extracted with EtOAc (700 mL). The organic layer was washed with brine (500 mL), and the organic layer dried ($MgSO_4$), filtered, and concentrated, giving the title compound as a yellow liquid, which was used without further purification (39 g, 100%).

Step C: To a solution consisting of (1R)-2-azido-1-(4-fluoro-phenyl)-ethanol (38.8 g, 214. mmol) and EtOH (250 mL) was added 5% Pd/C (60% water, 38 g). The reaction mixture was subjected to 50 psi of hydrogen at rt for 1 h. The reaction mixture was filtered through a 0.45 μM nylon filter giving a black filtrate. HPLC analysis showed that the reaction was incomplete. Fresh Pd/C was added (38 g) and the reaction mixture re-subjected to hydrogenation at 50 psi and rt for 2 h. The reaction mixture was filtered again through a 0.45 μM nylon filter giving a black filtrate. The solvent was removed under vacuum and the residue dissolved in EtOH (215 mL). The ethanolic solution was then treated with HCl (2 M in $Et_2O$, 107 mL), followed by $Et_2O$ (250 ml). The precipitated title compound was isolated via vacuum filtration (20.8 g, 51%).

A solution consisting of (R)-(−)-2-amino-1-(4-fluoro-phenyl)-ethanol (22.3 g, 116 mmol) was dissolved and ethanol (225 mL) was heated at 70° C. to give a homogeneous solution. Heptane (115 mL) was slowly added and the solution was allowed to stir for 10 min before allowing the solution to slowly cool to rt. Upon cooling, crystals formed. After cooling to rt, the solution was placed at −20° C. for 18 h. The mother liquor in the flask was decanted and the remaining crystals were washed twice with heptane (~50 ml) and dried under vacuum leaving the title compound (18.29 g, 81%). The ee of the recrystallized material and the crude material were determined by preparing [2-(4-fluoro-phenyl)-2-hydroxy-ethyl]-carbamic acid tert-butyl ester using known methods. HPLC conditions: OD-H column, 95% hexanes/5% EtOH (0.1% DEA), 0.8 ml/min flow. The ee of the crude material and recrystallized material was 94% and 97-98% respectfully.

Intermediate M: (R)-2-(6-Chloro-pyrimidin-4-ylamino)-1-(4-fluoro-phenyl)-ethanol

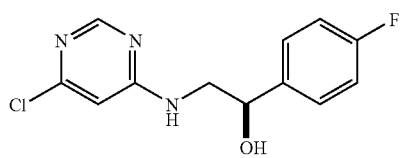 [SMILES: O[C@@H](CNc1cc(Cl)ncn1)c1ccc(F)cc1]

Title compound was prepared analogously to the methods described in Example 1, Step A.

Intermediate N: 4-(1,2,2,2-Tetrafluoro-1-trifluoromethyl-ethyl)-benzene boronic acid and 2-[3-(1,2,2,2-tetrafluoro-1-trifluoromethyl-ethyl)-benzene boronic acid

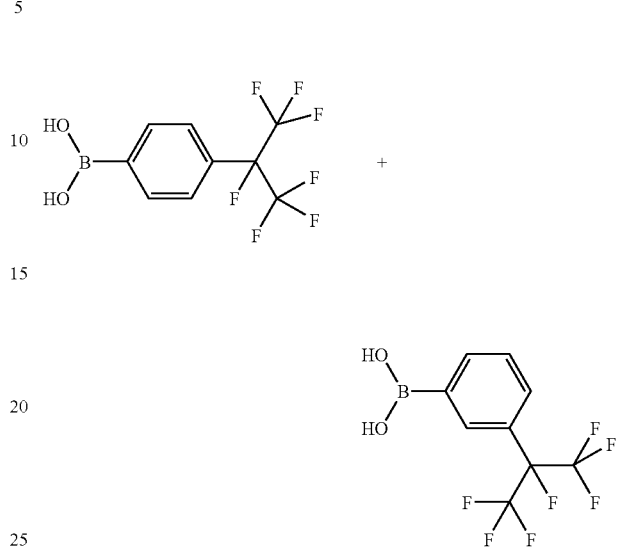

Step A: 4,4,5,5-Tetramethyl-2-[4-(1,2,2,2-tetrafluoro-1-trifluoromethyl-ethyl)-Phenyl]-[1,3,2]dioxaborolane and 4,4,5,5-Tetramethyl-2-[3-(1,2,2,2-tetrafluoro-1-trifluoromethyl-ethyl)-phenyl]-[1,3,2]dioxaborolane. Title compounds was obtained as a mixture using methods analogous to those described in Intermediate F.

Step B: Title compounds were obtained as a mixture using methods analogous to those described in Intermediate G.

Intermediate O:
3-Trifluoromethyl-benzo[b]thiophen-6-yl-benzene boronic acid

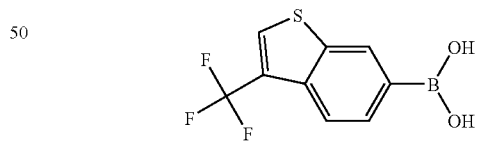

Step A: 4,4,5,5-Tetramethyl-2-(3-trifluoromethyl-benzo[b]thiophen-6-yl)-[1,3,2]dioxaborolane. Title compound was prepared using methods analogous to those described in Intermediate E. (6-bromo-3-trifluoromethyl-benzo[b]thiophene was prepared as described in Tet. Lett., 2003, 44, 7147).

Step B: Title compound was prepared using methods analogous to those described in Intermediate G.

Example 1

(1R)-2-([6-[4-(Ethyloxy)-3-(trifluoromethyl)phenyl]pyrimidin-4-yl]amino)-1-Phenylethanol

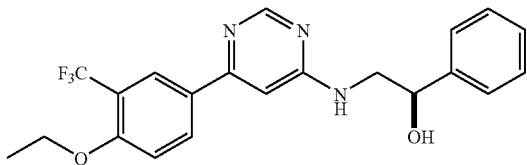 [SMILES: CCOc1ccc(-c2cc(NC[C@H](O)c3ccccc3)ncn2)cc1C(F)(F)F]

Step A: (1R)-2-[(6-Chloropyrimidin-4-yl)amino]-1-phenylethanol. To a solution consisting of (R)-(−)-2-amino-1-phenylethanol (4.80 g, 35.0 mmol) in and 1,4-dioxane (150 mL) at rt was added dropwise a solution consisting of 4,6-dichloropyrimidine (5.21 g, 35.0 mmol) and 1,4-dioxane (75 mL). Upon complete addition, NaHCO$_3$ (17.6 g, 0.210 mol) was added and the mixture was heated to reflux (100° C.) for 17 h. The reaction mixture was cooled, diluted with water (60 mL) and the pH was adjusted to 12 by the addition of a 1 N NaOH (25 mL). The solution was extracted with CH$_2$Cl$_2$ (75 mL), washed with satd. aq. NaCl (50 mL), and the organic extract was dried (Na$_2$SO$_4$) and concentrated. The crude material (8.2 g) was suspended in CH$_2$Cl$_2$ (40 mL) and warmed to 50° C. to give a homogeneous solution. The solution was cooled to rt and treated with a few drops of hexanes to give the title compound as a pale yellow solid (7.0 g, 81%). MS (ESI): mass calcd. for C$_{21}$H$_{20}$F$_3$N$_3$O$_2$, 403.2; m/z found, 404.2 [M+H]$^+$. $^1$H NMR (CD$_3$OD): 8.44 (s, 1H), 8.15 (s, 1H), 8.09 (dd, J=8.8, 2.2 Hz, 1H), 7.43 (d, J=7.7 Hz, 2H), 7.34 (t, J=7.7 Hz, 2H), 7.27-7.25 (m, 2H), 6.86 (s, 1H), 4.91-4.88 (m, 1H), 4.21 (q, J=7.1 Hz, 2H), 3.76-3.68 (m, 1H), 3.58 (dd, J=13.7, 7.7 Hz, 1H), 1.45 (t, J=7.1 Hz, 3H).

Step B. 2-[(6-Chloropyrimidin-4-yl)amino]-1-phenylethanol (62.4 mg, 0.25 mmol), 3-chloro-4-ethoxyphenyl boronic acid (100 mg, 0.5 mmol), Pd(PPh$_3$)$_4$ (14.4 mg, 0.0125 mmol), and K$_3$PO$_4$ (106 mg, 0.50 mmol) were placed in a two-necked round bottom flask and the flask evacuated. The flask was backfilled with N$_2$ and then charged with DME (2.0 mL) and degassed water (0.5 mL). The reaction mixture was heated at reflux (85° C.) for 17 h. The reaction mixture was then cooled, diluted with water (10 mL×2), extracted with EtOAc (10 mL×2), and the organic layer dried (Na$_2$SO$_4$) and concentrated. The crude residue was purified (FCC followed by reverse-phase HPLC) to yield the desired product (90.1 mg, 97%). MS (ESI): mass calcd. for C$_{20}$H$_{20}$ClN$_3$O$_2$, 369.1; m/z found, 370.2 [M+H]$^+$. $^1$H NMR (CD$_3$OD): 8.42 (s, 1H), 7.94 (d, J=2.3 Hz, 1H), 7.81 (dd, J=8.6, 2.3 Hz, 1H), 7.43 (d, J=7.1 Hz, 2H), 7.36-7.32 (m, 2H), 7.27-7.24 (m, 1H), 7.14 (d, J=8.6 Hz, 1H), 6.82 (s, 1H), 4.92-4.89 (m, 1H), 4.19 (q, J=6.8 Hz, 2H), 3.75-3.67 (m, 1H), 3.58 (dd, J=13.9, 7.8 Hz, 1H), 1.46 (t, J=6.8 Hz, 3H).

The compounds in Examples 2-19 were prepared using methods analogous to those described in Example 1, using either enantiomerically pure or racemic amino alcohols in Step A and substituting the appropriate boronic acids or esters in Step B. Final compounds were purified by FCC.

Example 2

2-{[6-(4-Chlorophenyl)pyrimidin-4-yl]amino}-1-phenylethanol

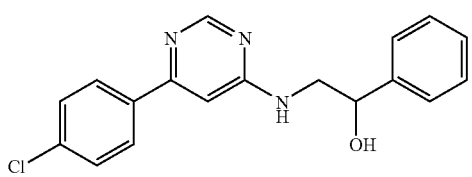 [SMILES: OC(CNc1cc(-c2ccc(Cl)cc2)ncn1)c1ccccc1]

MS (ESI): mass calcd. for C$_{18}$H$_{16}$ClN$_3$O, 325.1; m/z found, 326.2 [M+H]$^+$. $^1$H NMR (CD$_3$OD): 8.45 (s, 1H), 7.88 (d, J=8.2 Hz, 2H), 7.48 (d, J=8.7 Hz, 2H), 7.43 (d, J=7.7 Hz, 2H), 7.35-7.32 (m, 2H), 7.27-7.24 (m, 1H), 6.88 (s, 1H), 4.89 (dd, J=7.7, 4.9 Hz, 1H), 3.77-3.67 (m, 1H), 3.59 (dd, J=13.7, 7.7 Hz, 1H).

Example 3

2-{[6-(4-Fluorophenyl)pyrimidin-4-yl]amino}-1-phenylethanol

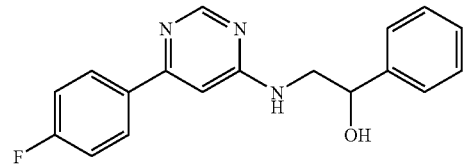 [SMILES: OC(CNc1cc(-c2ccc(F)cc2)ncn1)c1ccccc1]

MS (ESI): mass calcd. for C$_{18}$H$_{16}$FN$_3$O, 309.1; m/z found, 310.2 [M+H]$^+$. $^1$H NMR (CD$_3$OD): 8.45 (s, 1H), 7.94 (dd, J=8.8, 5.5 Hz, 2H), 7.42 (d, J=7.1 Hz, 2H), 7.34 (t, J=7.7 Hz, 2H), 7.26 (t, J=7.1 Hz, 1H), 7.22-7.19 (m, 2H), 6.86 (s, 1H), 4.89 (dd, J=7.1, 4.9 Hz, 1H), 3.78-3.67 (m, 1H), 3.58 (dd, J=13.7, 7.7 Hz, 1H).

Example 4

1-Phenyl-2-([6-[4-(trifluoromethyl)phenyl]pyrimidin-4-yl]amino)ethanol trifluoroacetic acid salt

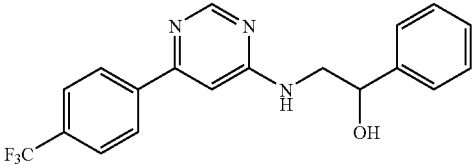 [SMILES: OC(CNc1cc(-c2ccc(C(F)(F)F)cc2)ncn1)c1ccccc1]

MS (ESI): mass calcd. for C$_{19}$H$_{16}$F$_3$N$_3$O, 359.1; m/z found, 360.2 [M+H]$^+$. $^1$H NMR (CD$_3$OD): 8.68 (s, 1H), 7.99 (d, J=8.2 Hz, 2H), 7.92 (d, J=8.8 Hz, 2H), 7.45 (d, J=7.1 Hz, 2H), 7.37-7.34 (m, 2H), 7.29-7.27 (m, 1H), 7.04 (s, 1H), 4.94 (dd, J=7.1, 4.9 Hz, 1H), 3.95-3.88 (m, 1H), 3.78 (dd, J=13.7, 7.7 Hz, 1H).

Example 5

2-{[6-(4-Nitrophenyl)pyrimidin-4-yl]amino}-1-phenylethanol trifluoroacetic acid salt

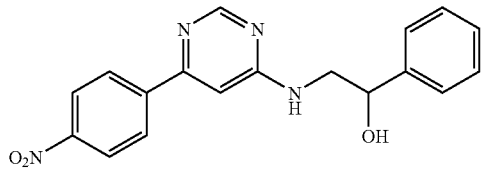 [SMILES: O=[N+]([O-])c1ccc(-c2cc(NCC(O)c3ccccc3)ncn2)cc1]

MS (ESI): mass calcd. for $C_{18}H_{16}N_4O_3$, 336.1; m/z found, 337.2 [M+H]$^+$. $^1$H NMR (CD$_3$OD): 8.68 (s, 1H), 8.44 (d, J=9.1 Hz, 2H), 8.05 (d, J=8.8 Hz, 2H), 7.45 (d, J=7.3 Hz, 2H), 7.38-7.34 (m, 2H), 7.30-7.26 (m, 1H), 7.06 (s, 1H), 4.96-4.92 (m, 1H), 3.95-3.86 (m, 1H), 3.77 (dd, J=13.6, 7.8 Hz, 1H).

Example 6

2-{[6-(4-Ethylphenyl)pyrimidin-4-yl]amino}-1-phenylethanol

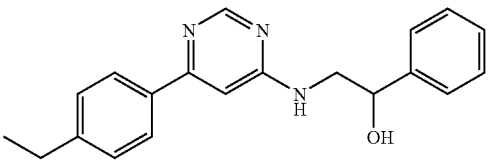 [SMILES: CCc1ccc(-c2cc(NCC(O)c3ccccc3)ncn2)cc1]

MS (ESI): mass calcd. for $C_{20}H_{21}N_3O$, 319.2; m/z found, 320.2 [M+H]$^+$. $^1$H NMR (CD$_3$OD): 8.44 (s, 1H), 7.80 (d, J=8.3 Hz, 2H), 7.43 (d, J=7.6 Hz, 2H), 7.37-7.31 (m, 4H), 7.28-7.24 (m, 1H), 6.86 (s, 1H), 4.91-4.90 (m, 1H), 3.77-3.67 (m, 1H), 3.58 (dd, J=13.9, 7.8 Hz, 1H), 2.70 (q, J=7.6 Hz, 2H), 1.26 (t, J=7.6 Hz, 3H).

Example 7

2-({6-[4-(1-Methylethyl)phenyl]pyrimidin-4-yl}amino)-1-phenylethanol

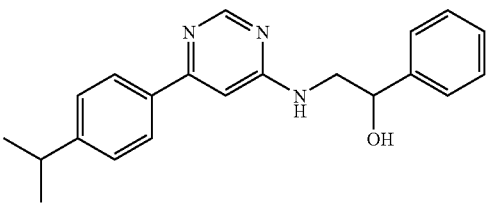 [SMILES: CC(C)c1ccc(-c2cc(NCC(O)c3ccccc3)ncn2)cc1]

MS (ESI): mass calcd. for $C_{21}H_{23}N_3O$, 333.2; m/z found, 334.2 [M+H]$^+$. $^1$H NMR (CD$_3$OD): 8.44 (s, 1H), 7.82-7.80 (m, 2H), 7.44-7.43 (m, 2H), 7.36-7.33 (m, 4H), 7.28-7.24 (m, 1H), 6.86 (m, 1H), 4.91-4.90 (m, 1H), 3.76-3.68 (m, 1H), 3.58 (dd, J=13.9, 7.8 Hz, 1H), 2.97 (septet, J=6.8 Hz, 1H), 1.28 (d, J=6.8 Hz, 6H).

Example 8

2-{[6-(3,4-Dichlorophenyl)pyrimidin-4-yl]amino}-1-phenylethanol

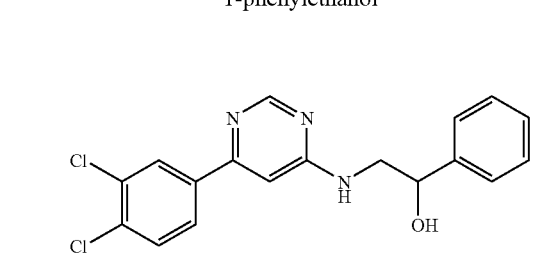

MS (ESI): mass calcd. for $C_{18}H_{15}Cl_2N_3O$, 359.1; m/z found, 360.1 [M+H]$^+$. $^1$H NMR (CD$_3$OD): 8.46 (s, 1H), 8.09-8.08 (m, 1H), 7.82 (dd, J=8.2, 2.2 Hz, 1H), 7.63 (d, J=8.2 Hz, 1H), 7.43 (d, J=7.7 Hz, 2H), 7.35-7.32 (m, 2H), 7.27-7.24 (m, 1H), 6.89 (s, 1H), 4.89 (dd, J=7.1, 4.9 Hz, 1H), 3.78-3.67 (m, 1H), 3.58 (dd, J=13.7, 7.7 Hz, 1H).

Example 9

2-{[6-(3-Chlorophenyl)pyrimidin-4-yl]amino}-1-Phenylethanol

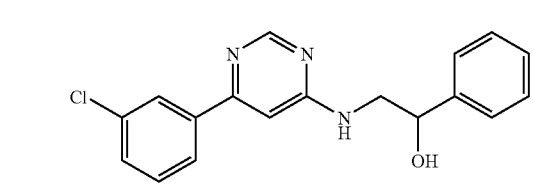 [SMILES: OC(CNc1cc(-c2cccc(Cl)c2)ncn1)c1ccccc1]

MS (ESI): mass calcl. for $C_{18}H_{16}ClN_3O$, 325.1; m/z found, 326.1 [M+H]$^+$. $^1$H NMR (CD$_3$OD): 8.46 (s, 1H), 7.92 (s, 1H), 7.82-7.81 (m, 1H), 7.47-7.46 (m, 2H), 7.43 (d, J=7.7 Hz, 2H), 7.34 (t, J=7.7 Hz, 2H), 7.27-7.24 (m, 1H), 6.89 (s, 1H), 4.91-4.88 (m, 1H), 3.78-3.68 (m, 1H), 3.59 (dd, J=13.7, 7.7 Hz, 1H).

Example 10

2-({6-[3-Chloro-4-(trifluoromethyl)phenyl]pyrimidin-4-yl}amino)-1-Phenylethanol

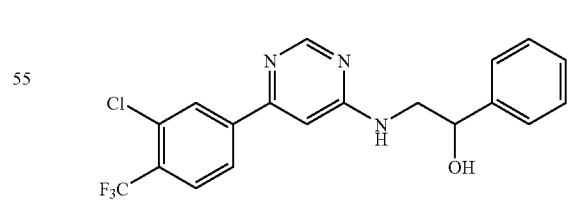

MS (ESI): mass calcd. for $C_{19}H_{15}ClF_3N_3O$, 393.1; m/z found, 394.1 [M+H]$^+$. $^1$H NMR (CD$_3$OD): 8.50 (s, 1H), 8.16 (s, 1H), 8.00 (d, J=8.2 Hz, 1H), 7.89 (d, J=8.2 Hz, 1H), 7.44 (d, J=7.7 Hz, 2H), 7.36-7.33 (m, 2H), 7.26 (t, J=7.1 Hz, 1H), 6.97 (s, 1H), 4.91-4.89 (m, 1H), 3.79-3.70 (m, 1H), 3.60 (dd, J=13.7, 7.7 Hz, 1H).

Example 11

2-({6-[4-(Ethyloxy)phenyl]pyrimidin-4-yl}amino)-1-phenylethanol

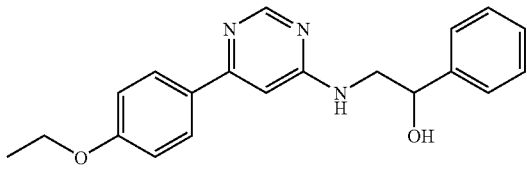 [SMILES: CCOc1ccc(-c2cc(NCC(O)c3ccccc3)ncn2)cc1]

MS (ESI): mass calcd. for $C_{20}H_{21}N_3O_2$, 335.2; m/z found, 336.2 [M+H]$^+$. $^1$H NMR (CD$_3$OD): 8.41 (s, 1H), 7.84 (d, J=8.8 Hz, 2H), 7.43 (d, J=7.7 Hz, 2H), 7.36-7.33 (m, 2H), 7.27-7.25 (m, 1H), 7.00 (d, J=8.8 Hz, 2H), 6.81 (s, 1H), 4.91-4.88 (m, 1H), 4.09 (q, J=7.1 Hz, 2H), 3.75-3.67 (m, 1H), 3.57 (dd, J=13.7, 7.7 Hz, 1H), 1.41 (t, J=7.1 Hz, 3H).

Example 12

2-[(6-{4-[(1-Methylethyl)oxy]phenyl}pyrimidin-4-yl)amino]-1-phenylethanol

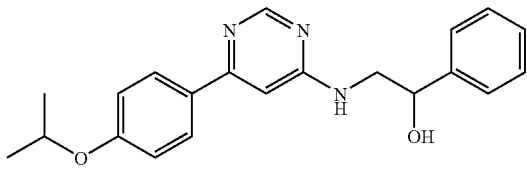 [SMILES: CC(C)Oc1ccc(-c2cc(NCC(O)c3ccccc3)ncn2)cc1]

MS (ESI): mass calcd. for $C_{21}H_{23}N_3O_2$, 349.2; m/z found, 350.2 [M+H]$^+$. $^1$H NMR (CD$_3$OD): 8.40 (s, 1H), 7.83 (d, J=9.3 Hz, 2H), 7.43 (d, J=7.7 Hz, 2H), 7.34 (t, J=7.7 Hz, 2H), 7.26 (t, J=7.1 Hz, 1H), 6.98 (d, J=8.8 Hz, 2H), 6.81 (s, 1H), 4.89 (dd, J=7.7, 4.4 Hz, 1H), 4.68 (septet, J=6.0 Hz, 1H), 3.75-3.67 (m, 1H), 3.57 (dd, J=13.7, 7.7 Hz, 1H), 1.33 (d, J=6.0 Hz, 6H).

Example 13

1-Phenyl-2-({6-[4-(phenyloxy)phenyl]pyrimidin-4-yl}amino)ethanol

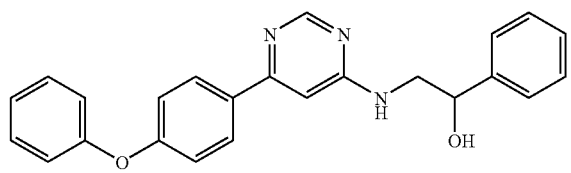 [SMILES: OC(CNc1cc(-c2ccc(Oc3ccccc3)cc2)ncn1)c1ccccc1]

MS (ESI): mass calcd. for $C_{24}H_{21}N_3O_2$, 383.2; m/z found, 384.2 [M+H]$^+$. $^1$H NMR (CD$_3$OD): 8.43 (s, 1H), 7.90-7.88 (m, 2H), 7.44-7.38 (m, 4H), 7.36-7.32 (m, 2H), 7.27-7.24 (m, 1H), 7.19-7.15 (m, 1H), 7.07-7.03 (m, 4H), 6.85 (s, 1H), 4.91-4.89 (m, 1H), 3.75-3.67 (m, 1H), 3.59 (dd, J=13.9, 7.8 Hz, 1H).

Example 14

2-({6-[3-Chloro-4-(ethyloxy)phenyl]pyrimidin-4-yl}amino)-1-phenylethanol

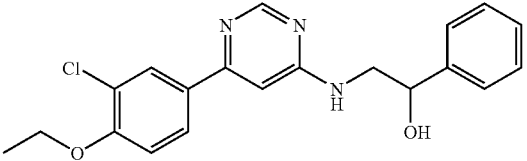 [SMILES: CCOc1ccc(-c2cc(NCC(O)c3ccccc3)ncn2)cc1Cl]

MS (ESI): mass calcd. for $C_{12}H_{12}ClN_3O$, 249.1; m/z found, 250.2 [M+H]$^+$. $^1$H NMR (CD$_3$OD): 8.21 (s, 1H), 7.40 (d, J=7.1 Hz, 2H), 7.35-7.32 (m, 2H), 7.27-7.24 (m, 1H), 6.52 (s, 1H), 4.84 (dd, J=7.7, 4.9 Hz, 1H), 3.74-3.66 (m, 1H), 3.56-3.54 (m, 1H).

Example 15

(1R)-1-Phenyl-2-({6-[4-(trifluoromethyl)phenyl]pyrimidin-4-yl}amino)ethanol

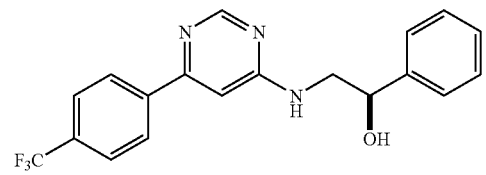 [SMILES: O[C@@H](CNc1cc(-c2ccc(C(F)(F)F)cc2)ncn1)c1ccccc1]

MS (ESI): mass calcd. for $C_{19}H_{16}F_3N_3O$, 359.1; m/z found, 360.2 [M+H]$^+$. $^1$H NMR (CD$_3$OD): 8.50 (s, 1H), 8.08 (d, J=8.1 Hz, 2H), 7.78 (d, J=8.3 Hz, 2H), 7.43 (d, J=7.3 Hz, 2H), 7.36-7.32 (m, 2H), 7.28-7.24 (m, 1H), 6.96 (s, 1H), 4.92-4.90 (m, 1H), 3.80-3.70 (m, 1H), 3.61 (dd, J=13.6, 7.8 Hz, 1H).

Example 16

(1R)-2-([6-[3-Chloro-4-(trifluoromethyl)phenyl]pyrimidin-4-yl]amino)-1-phenylethanol

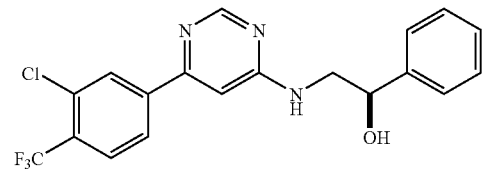 [SMILES: O[C@@H](CNc1cc(-c2ccc(C(F)(F)F)c(Cl)c2)ncn1)c1ccccc1]

MS (ESI): mass calcd. for $C_{19}H_{15}ClF_3N_3O$, 393.1; m/z found, 394.1 [M+H]$^+$. $^1$H NMR (CD$_3$OD): 8.50 (s, 1H), 8.16 (s, 1H), 8.01-7.98 (m, 1H), 7.88 (d, J=8.3 Hz, 1H), 7.44 (d, J=7.3 Hz, 2H), 7.37-7.34 (m, 2H), 7.27-7.24 (m, 1H), 6.97 (s, 1H), 4.93-4.90 (m, 1H), 3.79-3.71 (m, 1H), 3.60 (dd, J=13.6, 7.6 Hz, 1H).

The title compound was also prepared in a manner similar to Example 1, with modifications to combine steps A and B as follows:

To a solution of 4,6-dichloropyrimidine (50 g, 0.34 mol, 1.0 equiv) in CH$_3$CN (1.2 L), was added NaHCO$_3$ (34 g, 0.40 mol, 1.2 equiv) and (R)-(−)-2-amino-1-phenyl-ethanol (48.3 g, 0.35 mol, 1.05 equiv) sequentially. The reaction mixture was stirred at reflux temperature under N$_2$ for 3 hours then cooled to rt. HPLC analysis of the crude reaction mixture indicated that the reaction was complete, to afford the intermediate (1R)-2-[(6-chloropyrimidin-4-yl)amino]-1-phenylethanol. In the same flask, without purification or workup, was added a solution of K$_3$PO$_4$ (85 g, 0.40 mol, 1.2 equiv) in H$_2$O (750 mL), 3-chloro-4-(trifluoromethyl)phenylboronic acid (79.4 g, 0.35 mol, 1.05 equiv), Pd(dppf)Cl$_2$·CH$_2$Cl$_2$ (2.4 g, 2.9 mmol, 0.009 equiv) and Pd(OAc)$_2$ (68 mg, 0.29 mmol, 0.0009 equiv) sequentially under N$_2$ at rt. The reaction solution was degassed with N$_2$ (3×) and was stirred at reflux temperature for 16 hours then cooled to rt. The layers were separated and the CH$_3$CN phase was dried (MgSO$_4$) and filtered. The filtrate solution was stirred with Si-Thiol (8.8 g, 1.5 mmol/g loading, 4 equiv of Pd added) at rt for 1 hour. Si-Thiol is commercially available through SiliCycle (230-400 mesh, 40-63 μm). The Si-Thiol was removed by filtration and washed with EtOAc. The organics were combined and concentrated under reduced pressure. The crude residue was recrystallized from hot EtOH (~250 mL) with stirring to afford the title compound (83 g). Further concentration of the mother liquor followed by a second recrystallization from hot EtOH with stirring provided an additional crop of the title compound (23 g). The combined recrystallized yield of the title compound was 80% (106 g, >99% ee). MS (ESI): mass calcd. for C$_{19}$H$_{15}$ClF$_3$N$_3$O, 393.1; m/z found, 394.1 [M+H]$^+$. $^1$H NMR (CDCl$_3$, 500 MHz): 8.69 (s, 1H), 8.12 (s, 1H), 7.93 (d, J=8.2 Hz, 1H), 7.79 (d, J=8.2 Hz, 1H), 7.52-7.28 (m, 5H), 6.74 (s, 1H), 5.42 (brs, 1H), 5.10-4.98 (m, 1H), 3.92 (brs, 1H), 3.70-3.58 (m, 1H).

Example 16A (1R)-2-({6-[3-Chloro-4-(trifluoromethyl)phenyl]pyrimidin-4-yl}amino)-1-Phenylethanol hydrochloride salt $^1$H NMR (CD$_3$OD): 8.72 (s, 1H), 8.11 (s, 1H), 8.04 (d, J=8.3, 1H), 7.92 (d, J=8.1 Hz, 1H), 7.48-7.44 (m, 2H), 7.37-7.34 (m, 2H), 7.30-7.27 (m, 1H), 7.11 (s, 1H), 4.95 (dd, J=4.1, 7.8, 1H), 3.94 (dd, J=4.2, 13.6 Hz, 1H), 3.60 (dd, J=13.6, 7.6 Hz, 1H).

Example 17

1-[4-(6-{[(2R)-2-Hydroxy-2-phenylethyl]amino}pyrimidin-4-yl)phenyl]ethanone

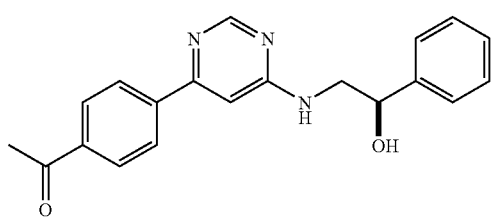 [SMILES: CC(=O)c1ccc(-c2cc(NC[C@H](O)c3ccccc3)ncn2)cc1]

MS (ESI): mass calcd. for C$_{20}$H$_{19}$N$_3$O$_2$, 333.2; m/z found, 334.2 [M+H]$^+$. $^1$H NMR (CD$_3$OD): 8.49 (s, 1H), 8.10 (d, J=8.6, 2H), 8.02 (d, J=8.8 Hz, 2H), 7.43 (d, J=7.3 Hz, 2H), 7.36-7.32 (m, 2H), 7.27-7.24 (m, 1H), 6.96 (s, 1H), 4.92-4.89 (m, 1H), 3.79-3.69 (m, 1H), 3.60 (dd, J=13.6, 7.8 Hz, 1H), 2.64 (s, 3H).

Example 18

(1R)-2-({6-[4-(1-Methylethyl)phenyl]pyrimidin-4-yl}amino)-1-Phenylethanol

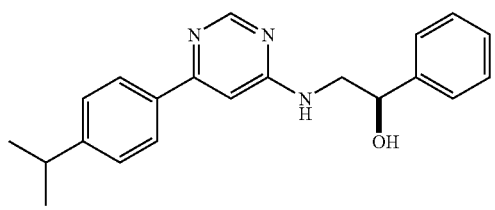 [SMILES: CC(C)c1ccc(-c2cc(NC[C@H](O)c3ccccc3)ncn2)cc1]

MS (ESI): mass calcd. for C$_{21}$H$_{23}$N$_3$O, 333.2; m/z found, 334.2 [M+H]$^+$. $^1$H NMR (CD$_3$OD): 8.44 (s, 1H), 7.82-7.80 (m, 2H), 7.44-7.42 (m, 2H), 7.36-7.32 (m, 4H), 7.27-7.24 (m, 1H), 6.86 (s, 1H), 4.91-4.89 (m, 1H), 3.77-3.68 (m, 1H), 3.59 (dd, J=13.6, 7.6 Hz, 1H), 2.96 (septet, J=6.8 Hz, 1H), 1.28 (d, J=6.8 Hz, 6H).

Example 19

(1R)-2-[(6-{3-Chloro-4-[(1-methylethyl)oxy]phenyl}pyrimidin-4-yl)amino]-1-phenylethanol

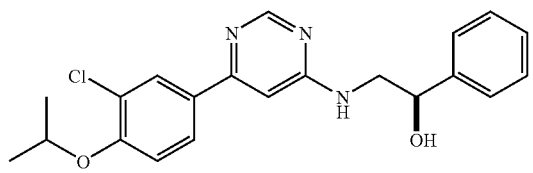

MS (ESI): mass calcd. for C$_{21}$H$_{22}$ClN$_3$O$_2$, 383.1; m/z found, 384.2 [M+H]$^+$. $^1$H NMR (CD$_3$OD): 8.42 (s, 1H), 7.94 (d, J=2.3 Hz, 1H), 7.80 (dd, J=8.6, 2.3 Hz, 1H), 7.44-7.42 (m, 2H), 7.36-7.32 (m, 2H), 7.27-7.24 (m, 1H), 7.16 (d, J=8.8 Hz, 1H), 6.82 (s, 1H), 4.91-4.89 (m, 1H), 4.73 (septet, J=6.1 Hz, 1H), 3.75-3.66 (m, 1H), 3.58 (dd, J=13.6, 7.6 Hz, 1H), 1.37 (d, J=6.1 Hz, 6H).

Example 20

(1R)-2-{[6-(3-Fluoro-4-methylphenyl)pyrimidin-4-yl]amino}-1-phenylethanol trifluoroacetic acid salt

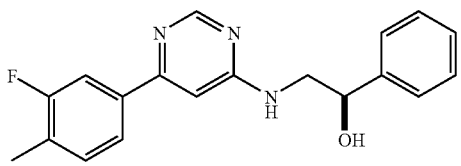 [SMILES: Cc1ccc(-c2cc(NC[C@H](O)c3ccccc3)ncn2)cc1F]

The title compound was synthesized in a manner similar to Example 1 with modifications to Step B as follows:

Step B. (1R)-2-[(6-Chloropyrimidin-4-yl)amino]-1-phenylethanol (62.4 mg, 0.3 mmol), 3-fluoro-4-methyl-phenyl boronic acid (42 mg, 0.30 mmol), Pd(PPh$_3$)$_4$ (2.9 mg, 0.0025 mmol), and K$_3$PO$_4$ (106 mg, 0.50 mmol) were placed in a microwave vial and the vial evacuated. The vial was then backfilled with N$_2$ and charged with DME (2.0 mL) and degassed water (0.5 mL). The reaction mixture was heated in the microwave for 21 min at 180° C. The crude reaction mixture was diluted with CH$_2$Cl$_2$ and filtered through a plug of MgSO$_4$. The filtrate was concentrated and the residue purified using reverse phase chromatography (Gilson) to yield the title compound (87.4 mg, 80%). MS (ESI): mass calcd. for C$_{19}$H$_{18}$FN$_3$O, 323.1; m/z found, 324.2 [M+H]$^+$. $^1$H NMR (CD$_3$OD): 8.62 (s, 1H), 7.55-7.48 (m, 3H), 7.43 (d, J=7.1 Hz, 2H), 7.37-7.34 (m, 2H), 7.29-7.27 (m, 1H), 6.98 (s, 1H), 4.95-4.92 (m, 1H), 3.93-3.87 (m, 1H), 3.79 (dd, J=13.7, 7.7 Hz, 1H), 2.38 (s, 3H).

The compounds in Examples 21-102 were prepared using methods analogous to those described in Example 20, using either enantiomerically pure or racemic amino alcohols and appropriately substituted 4,6-dichloropyrimidines in Step A and substituting the appropriate boronic acids or esters in Step B.

Example 21

(1R)-2-([6-[4-(Hydroxymethyl)phenyl]pyrimidin-4-yl]amino)-1-Phenylethanol

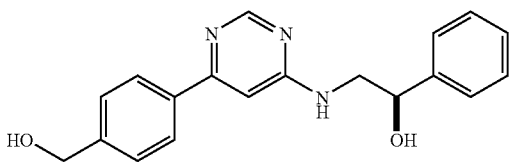 [SMILES: OCc1ccc(-c2cc(NC[C@H](O)c3ccccc3)ncn2)cc1]

MS (ESI): mass calcd. for C$_{19}$H$_{19}$N$_3$O$_2$, 321.2; m/z found, 322.2 [M+H]$^+$. $^1$H NMR (CD$_3$OD): 8.45 (s, 1H), 7.87 (d, J=8.2 Hz, 2H), 7.47 (d, J=8.2 Hz, 2H), 7.43 (d, J=7.7 Hz, 2H), 7.36-7.33 (m, 2H), 7.27-7.24 (m, 1H), 6.88 (s, 1H), 4.90 (dd, J=7.7, 4.4 Hz, 1H), 4.67 (s, 2H), 3.76-3.68 (m, 1H), 3.60 (dd, J=13.7, 7.7 Hz, 1H).

Example 22

4-(6-{[(2R)-2-Hydroxy-2-phenylethyl]amino}pyrimidin-4-yl)benzaldehyde

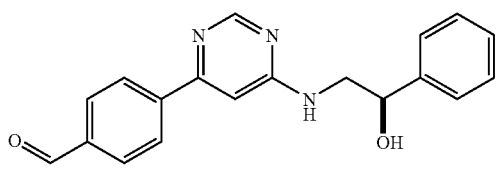 [SMILES: O=Cc1ccc(-c2cc(NC[C@H](O)c3ccccc3)ncn2)cc1]

MS (ESI): mass calcd. for C$_{19}$H$_{17}$N$_3$O$_2$, 319.1; m/z found, 320.2 [M+H]$^+$. $^1$H NMR (CDCl$_3$): 10.09 (s, 1H), 8.70 (s, 1H), 8.12 (d, J=8.8 Hz, 2H), 7.98 (d, J=8.8 Hz, 2H), 7.43-7.42 (m, 2H), 7.40-7.37 (m, 2H), 7.33-7.30 (m, 1H), 6.79 (s, 1H), 5.33 (br s, 1H), 5.01-4.99 (m, 1H), 3.94-3.87 (m, 1H), 3.65-3.60 (m, 1H).

Example 23

3-(6-{[(2R)-2-Hydroxy-2-phenylethyl]amino}pyrimidin-4-yl)benzaldehyde

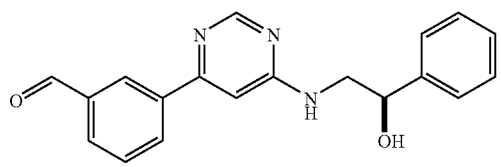 [SMILES: O=Cc1cccc(-c2cc(NC[C@H](O)c3ccccc3)ncn2)c1]

MS (ESI): mass calcd. for C$_{19}$H$_{17}$N$_3$O$_2$, 319.1; m/z found, 320.2 [M+H]$^+$. $^1$H NMR (CDCl$_3$): 10.10 (s, 1H), 8.69 (s, 1H), 8.45-8.44 (m, 1H), 8.20-8.25 (m, 1H), 7.99-7.97 (m, 1H), 7.66-7.63 (m, 1H), 7.44-7.37 (m, 4H), 7.34-7.30 (m, 1H), 6.80 (s, 1H), 5.33 (br s, 1H), 5.01 (dd, J=7.3, 3.3 Hz, 1H), 3.93-3.85 (m, 1H), 3.66-3.60 (m, 1H).

Example 24

(1R)-1-Phenyl-2-[(6-{4-[(2,2,2-trifluoroethyl)oxy]phenyl}pyrimidin-4-yl)amino]ethanol

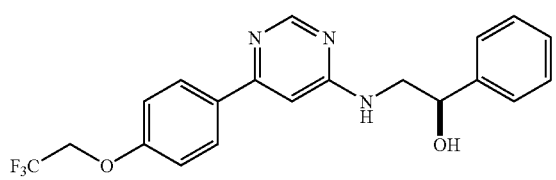 [SMILES: O[C@@H](CNc1cc(-c2ccc(OCC(F)(F)F)cc2)ncn1)c1ccccc1]

MS (ESI): mass calcd. for C$_{20}$H$_{18}$F$_3$N$_3$O$_2$, 389.1; m/z found, 390.2 [M+H]$^+$. $^1$H NMR (CD$_3$OD): 8.43 (s, 1H), 7.90 (d, J=8.8 Hz, 2H), 7.43 (d, J=7.7 Hz, 2H), 7.36-7.33 (m, 2H), 7.27-7.24 (m, 1H), 7.12 (d, J=8.8 Hz, 2H), 6.84 (s, 1H), 4.91-4.87 (m, 1H), 4.61 (q, J=8.2 Hz, 2H), 3.73-3.69 (m, 1H), 3.59 (dd, J=14.3 8.2 Hz, 1H).

Example 25

(1R)-1-Phenyl-2-[(6-{3-[(2,2,2-trifluoroethyl)oxy]phenyl}pyrimidin-4-yl)amino]ethanol

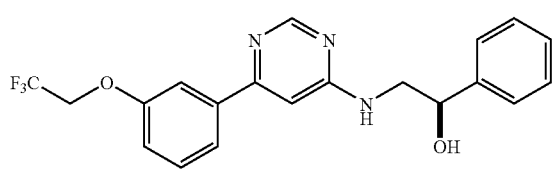 [SMILES: O[C@@H](CNc1cc(-c2cccc(OCC(F)(F)F)c2)ncn1)c1ccccc1]

MS (ESI): mass calcd. for C$_{20}$H$_{18}$F$_3$N$_3$O$_2$, 389.1; m/z found, 390.2 [M+H]$^+$. $^1$H NMR (CD$_3$OD): 8.46 (s, 1H), 7.57-7.54 (m, 2H), 7.46-7.42 (m, 3H), 7.36-7.32 (m, 2H), 7.27-7.23 (m, 1H), 7.14-7.11 (m, 1H), 6.89 (s, 1H), 4.91-4.88 (m, 1H), 4.63-4.57 (m, 2H), 3.77-3.69 (m, 1H), 3.62-3.58 (m, 1H).

Example 26

(1R)-2-{[6-(4-Chloro-3-methylphenyl)pyrimidin-4-yl]amino}-1-phenylethanol trifluoroacetic acid salt

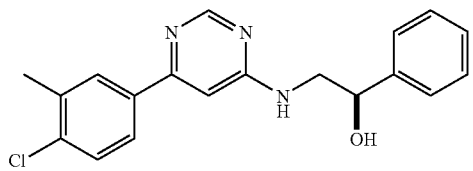

MS (ESI): mass calcd. for $C_{19}H_{18}ClN_3O$, 339.1; m/z found, 340.1 [M+H]⁺. ¹H NMR (CD₃OD): 8.64 (s, 1H), 7.74 (s, 1H), 7.61-7.59 (m, 2H), 7.45-7.44 (m, 2H), 7.37-7.34 (m, 2H), 7.29-7.27 (m, 1H), 6.98 (s, 1H), 4.95-4.93 (m, 1H), 3.94-3.89 (m, 1H), 3.82-3.78 (m, 1H), 2.49 (s, 3H).

Example 27

(1R)-2-{[6-(4-Chloro-3-fluorophenyl)pyrimidin-4-yl]amino}-1-phenylethanol trifluoroacetic acid salt

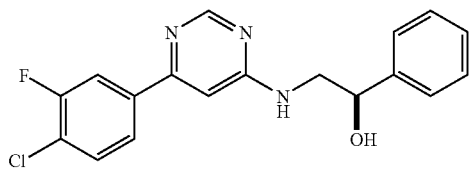

MS (ESI): mass calcd. for $C_{18}H_{15}ClFN_3O$, 343.1 m/z found, 344.1 [M+H]⁺. ¹H NMR (CD₃OD): 8.65 (s, 1H), 7.77-7.22 (m, 2H), 7.64-7.62 (m, 1H), 7.45-7.44 (m, 2H), 7.36-7.34 (m, 2H), 7.29-7.28 (m, 1H), 7.01 (s, 1H), 4.95-4.93 (m, 1H), 3.93-3.90 (m, 1H), 3.79 (dd, J=13.7, 8.2 Hz, 1H).

Example 28

(1R)-2-({6-[4-Chloro-3-(trifluoromethyl)phenyl]pyrimidin-4-yl}amino)-1-phenylethanol trifluoroacetic acid salt

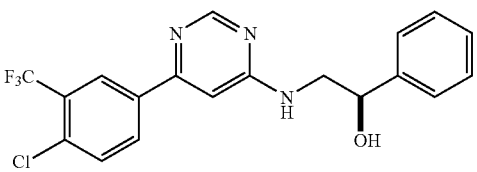 [SMILES: O[C@@H](CNc1cc(-c2ccc(Cl)c(C(F)(F)F)c2)ncn1)c1ccccc1]

MS (ESI): mass calcd. for $C_{19}H_{15}ClF_3N_3O$, 393.1; m/z found, 394.1 [M+H]⁺. ¹H NMR (CD₃OD): 8.65 (s, 1H), 8.24 (s, 1H), 8.04 (dd, J=8.2, 2.2 Hz, 1H), 7.86 (d, J=8.8 Hz, 1H), 7.44 (d, J=7.1 Hz, 2H), 7.36 (t, J=7.7 Hz, 2H), 7.29-7.26 (m, 1H), 7.03 (s, 1H), 4.95-4.93 (m, 1H), 3.93-3.87 (m, 1H), 3.78 (dd, J=13.2, 7.7 Hz, 1H).

Example 29

(1R)-2-({6-[3-Fluoro-4-(trifluoromethoxy)phenyl]pyrimidin-4-yl}amino)-1-phenylethanol trifluoroacetic acid salt

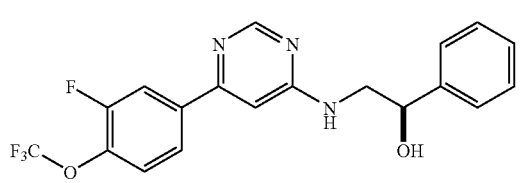 [SMILES: O[C@@H](CNc1cc(-c2ccc(OC(F)(F)F)c(F)c2)ncn1)c1ccccc1]

MS (ESI): mass calcd. for $C_{19}H_{15}F_4N_3O_2$, 393.1; m/z found, 394.1 [M+H]⁺. ¹H NMR (CD₃OD): 8.64 (s, 1H), 7.88-7.85 (m, 1H), 7.75-7.73 (m, 1H), 7.69-7.65 (m, 1H), 7.44 (d, J=7.7 Hz, 2H), 7.36 (t, J=7.7 Hz, 2H), 7.29-7.27 (m, 1H), 7.00 (s, 1H), 4.95-4.92 (m, 1H), 3.93-3.84 (m, 1H), 3.77 (dd, J=13.7, 7.7 Hz, 1H).

Example 30

(1R)-2-{[6-(4-Ethoxy-3-fluorophenyl)pyrimidin-4-yl]amino}-1-phenylethanol trifluoroacetic acid salt

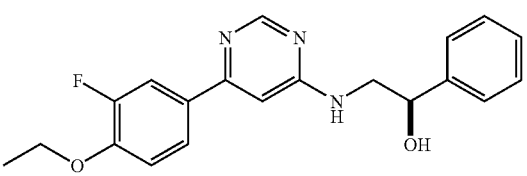

MS (ESI): mass calcd. for $C_{20}H_{20}FN_3O_2$, 353.2; m/z found, 354.2 [M+H]⁺. ¹H NMR (CD₃OD): 8.60 (s, 1H), 7.63-7.59 (m, 2H), 7.45-7.43 (m, 2H), 7.37-7.34 (m, 2H), 7.33-7.27 (m, 2H), 6.94 (s, 1H), 4.94-4.92 (m, 1H), 4.23 (q, J=7.1 Hz, 2H), 3.93-3.88 (m, 1H), 3.79 (dd, J=13.7, 8.2 Hz, 1H), 1.47 (t, J=7.1 Hz, 3H).

Example 31

(1R)-2-{[6-(4-Ethoxy-3-methylphenyl)pyrimidin-4-yl]amino}-1-Phenylethanol trifluoroacetic acid salt

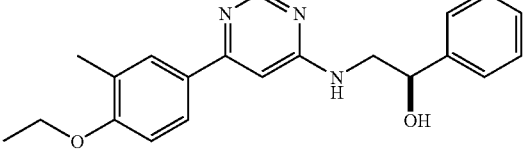

MS (ESI): mass calcd. for $C_{21}H_{23}N_3O_2$, 349.2; m/z found, 350.2 [M+H]⁺. ¹H NMR (CD₃OD): 8.58 (s, 1H), 7.64-7.62 (m, 1H), 7.60 (s, 1H), 7.44-7.43 (m, 2H), 7.37-7.34 (m, 2H), 7.30-7.27 (m, 1H), 7.11-7.10 (m, 1H), 6.93 (s, 1H), 4.94-4.92 (m, 1H), 4.17 (q, J=7.1 Hz, 2H), 3.91 (dd, J=13.2, 4.4 Hz, 1H), 3.79 (dd, J=13.7, 7.7 Hz, 1H), 2.30 (s, 3H), 1.46 (t, J=7.1 Hz, 3H).

Example 32

(1R)-2-({6-[4-(Cyclopropylmethoxy)phenyl]pyrimidin-4-yl}amino)-1-phenylethanol trifluoroacetic acid salt

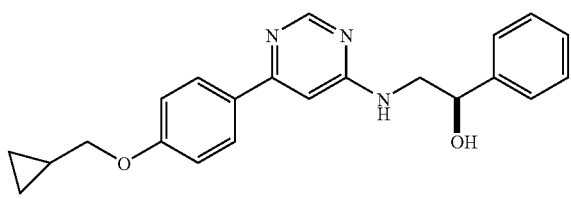 [SMILES: O[C@@H](CNc1cc(-c2ccc(OCC3CC3)cc2)ncn1)c1ccccc1]

MS (ESI): mass calcd. for C$_{22}$H$_{23}$N$_3$O$_2$, 361.2; m/z found, 362.2 [M+H]$^+$. $^1$H NMR (CD$_3$OD): 8.58 (s, 1H), 7.74 (d, J=8.8 Hz, 2H), 7.45 (d, J=7.7 Hz, 2H), 7.37-7.34 (m, 2H), 7.30-7.26 (m, 1H), 7.14 (d, J=8.8 Hz, 2H), 6.92 (s, 1H), 4.94-4.92 (m, 1H), 3.95 (d, J=7.1 Hz, 2H), 3.91-3.87 (m, 1H), 3.80-3.76 (m, 1H), 1.32-1.26 (m, 1H), 0.67-0.63 (m, 2H), 0.40-0.37 (m, 2H).

Example 33

(1R)-2-{[6-(4-Butoxy-3-fluorophenyl)pyrimidin-4-yl]amino}-1-phenylethanol trifluoroacetic acid salt

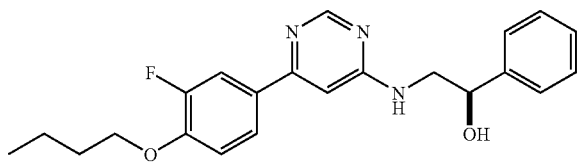 [SMILES: CCCCOc1ccc(-c2cc(NC[C@H](O)c3ccccc3)ncn2)cc1F]

MS (ESI): mass calcd. for C$_{22}$H$_{24}$FN$_3$O$_2$, 381.2; m/z found, 382.2 [M+H]$^+$. $^1$H NMR (CD$_3$OD): 8.59 (s, 1H), 7.63-7.59 (m, 2H), 7.43 (d, J=7.7 Hz, 2H), 7.37-7.34 (m, 2H), 7.31 (t, J=8.8 Hz, 1H), 7.29-7.28 (m, 1H), 6.93 (s, 1H), 4.94-4.92 (m, 1H), 4.17 (t, J=6.6 Hz, 2H), 3.94-3.86 (m, 1H), 3.78 (dd, J=13.7, 7.7 Hz, 1H), 1.86-1.81 (m, 2H), 1.54 (sextet, J=7.7 Hz, 2H), 1.01 (t, J=7.7 Hz, 3H).

Example 34

(1R)-2-{[6-(4-Butoxyphenyl)pyrimidin-4-yl]amino}-1-phenylethanol trifluoroacetic acid salt

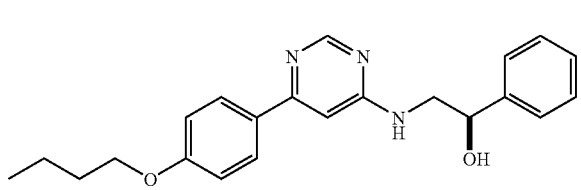 [SMILES: CCCCOc1ccc(-c2cc(NC[C@H](O)c3ccccc3)ncn2)cc1]

MS (ESI): mass calcd. for C$_{22}$H$_{25}$N$_3$O$_2$, 363.2; m/z found, 364.2 [M+H]$^+$. $^1$H NMR (CD$_3$OD): 8.59 (s, 1H), 7.75 (d, J=8.8 Hz, 2H), 7.45 (d, J=7.7 Hz, 2H), 7.37-7.34 (m, 2H), 7.29-7.27 (m, 1H), 7.14 (d, J=8.8 Hz, 2H), 6.93 (s, 1H), 4.94-4.92 (m, 1H), 4.10 (t, J=6.6 Hz, 2H), 3.95-3.88 (m, 1H), 3.80-3.76 (m, 1H), 1.83-1.78 (m, 2H), 1.54 (sextet, J=7.7 Hz, 2H), 1.00 (t, J=7.7 Hz, 3H).

Example 35

(1R)-2-{[6-(3-Fluoro-4-propoxyphenyl)pyrimidin-4-yl]amino}-1-Phenylethanol trifluoroacetic acid salt

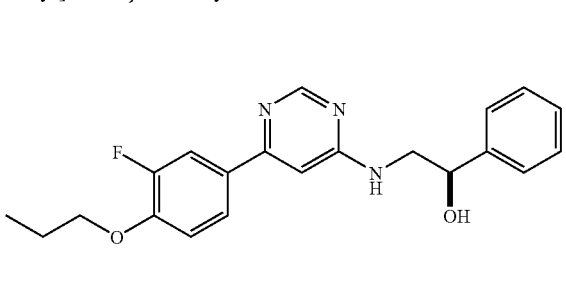

MS (ESI): mass calcd. for C$_{21}$H$_{22}$FN$_3$O$_2$, 367.2; m/z found, 368.2 [M+H]$^+$. $^1$H NMR (CD$_3$OD): 8.61 (s, 1H), 7.63-7.59 (m, 2H), 7.45-7.43 (m, 2H), 7.37-7.26 (m, 4H), 6.94 (m, 1H), 4.94-4.92 (m, 1H), 4.13 (t, J=6.6 Hz, 2H), 3.93-3.90 (m, 1H), 3.82-3.77 (m, 1H), 1.87 (sextet, J=7.1 Hz, 2H), 1.08 (t, J=7.1 Hz, 3H).

Example 36

(1R)-2-({6-[3-Fluoro-4-(1-methylethoxy)phenyl]pyrimidin-4-yl}amino)-1-phenylethanol trifluoroacetic acid salt

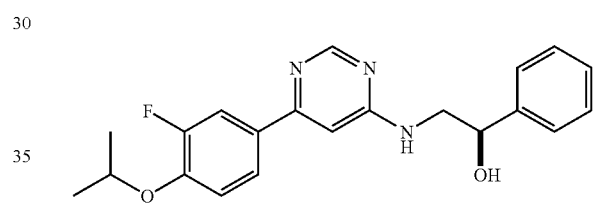

MS (ESI): mass calcd. for C$_{21}$H$_{22}$FN$_3$O$_2$, 367.2; m/z found, 368.2 [M+H]$^+$. $^1$H NMR (CD$_3$OD): 8.60 (s, 1H), 7.63-7.58 (m, 2H), 7.45-7.43 (m, 2H), 7.37-7.27 (m, 4H), 6.93 (s, 1H), 4.94-4.92 (m, 1H), 4.81-4.74 (m, 1H), 3.94-3.88 (m, 1H), 3.81-3.77 (m, 1H), 1.39 (d, J=6.0 Hz, 6H).

Example 37

(1R)-2-({6-[4-(2-Methylpropoxy)phenyl]pyrimidin-4-yl}amino)-1-phenylethanol trifluoroacetic acid salt

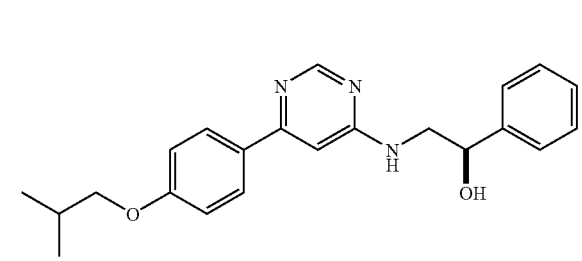 [SMILES: CC(C)COc1ccc(-c2cc(NC[C@H](O)c3ccccc3)ncn2)cc1]

MS (ESI): mass calcd. for C$_{22}$H$_{25}$N$_3$O$_2$, 363.2; m/z found, 364.2 [M+H]$^+$. $^1$H NMR (CD$_3$OD): 8.60 (s, 1H), 7.74 (d, J=8.8 Hz, 2H), 7.43 (d, J=7.7 Hz, 2H), 7.36 (t, J=7.7 Hz, 2H), 7.30-7.27 (m, 1H), 7.16 (d, J=8.8 Hz, 2H), 6.94 (s, 1H), 4.93 (dd, J=8.2, 4.4 Hz, 1H), 3.94-3.90 (m, 1H), 3.86 (d, J=6.6 Hz, 2H), 3.80 (dd, J=13.7, 7.7 Hz, 1H), 2.11 (heptet, J=6.6 Hz, 1H), 1.05 (d, J=7.1 Hz, 6H).

Example 38

(1R)-2-{[6-(4-Methoxy-3-methylphenyl)pyrimidin-4-yl]amino}-1-phenylethanol trifluoroacetic acid salt

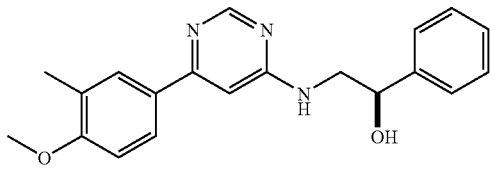 [SMILES: COc1ccc(-c2cc(NC[C@H](O)c3ccccc3)ncn2)cc1C]

MS (ESI): mass calcd. for C$_{20}$H$_{21}$N$_3$O$_2$, 335.2; m/z found, 336.2 [M+H]$^+$. $^1$H NMR (CD$_3$OD): 8.58 (s, 1H), 7.66 (dd, J=8.8, 2.7 Hz, 1H), 7.60-7.59 (m, 1H), 7.44 (d, J=7.7 Hz, 2H), 7.36 (t, J=7.1 Hz, 2H), 7.30-7.27 (m, 1H), 7.13 (d, J=8.8 Hz, 1H), 6.93 (s, 1H), 4.94-4.92 (m, 1H), 3.94 (s, 3H), 3.94-3.90 (m, 1H), 3.79 (dd, J=13.7, 7.7 Hz, 1H), 2.29 (s, 3H).

Example 39

(1R)-2-{[6-(3-Chloro-4-methylphenyl)pyrimidin-4-yl]amino}-1-phenylethanol trifluoroacetic acid salt

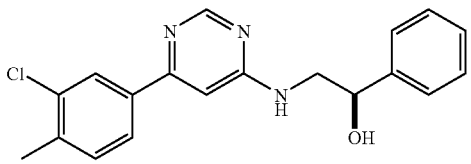 [SMILES: Cc1ccc(-c2cc(NC[C@H](O)c3ccccc3)ncn2)cc1Cl]

MS (ESI): mass calcd. for C$_{19}$H$_{18}$ClN$_3$O, 339.1; m/z found, 340.1 [M+H]$^+$. $^1$H NMR (CD$_3$OD): 8.62 (s, 1H), 7.85-7.84 (m, 1H), 7.63 (dd, J=8.2, 1.7 Hz, 1H), 7.54 (d, J=8.2 Hz, 1H), 7.44 (d, J=7.1 Hz, 2H), 7.37-7.34 (m, 2H), 7.30-7.26 (m, 1H), 6.98 (s, 1H), 4.95-4.92 (m, 1H), 3.94-3.89 (m, 1H), 3.80 (dd, J=13.7, 7.7 Hz, 1H), 2.48 (s, 3H).

Example 40

(1R)-2-{[6-(3,5-Dimethylphenyl)pyrimidin-4-yl]amino}-1-phenylethanol trifluoroacetic acid salt

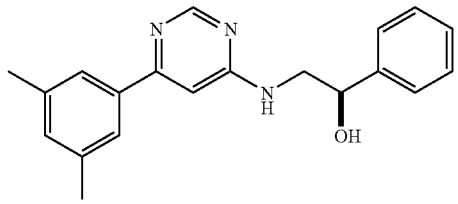 [SMILES: Cc1cc(C)cc(-c2cc(NC[C@H](O)c3ccccc3)ncn2)c1]

MS (ESI): mass calcd. for C$_{20}$H$_{21}$N$_3$O, 319.2; m/z found, 320.2 [M+H]$^+$. $^1$H NMR (CD$_3$OD): 8.61 (s, 1H), 7.45-7.43 (m, 2H), 7.39 (s, 2H), 7.38-7.33 (m, 3H), 7.30-7.27 (m, 1H), 6.96 (s, 1H), 4.95-4.93 (m, 1H), 3.94-3.91 (m, 1H), 3.80 (dd, J=13.2, 7.7 Hz, 1H), 2.42 (s, 6H).

Example 41

(1R)-2-({6-[3-Fluoro-4-(trifluoromethyl)phenyl]pyrimidin-4-yl}amino)-1-phenylethanol trifluoroacetic acid salt

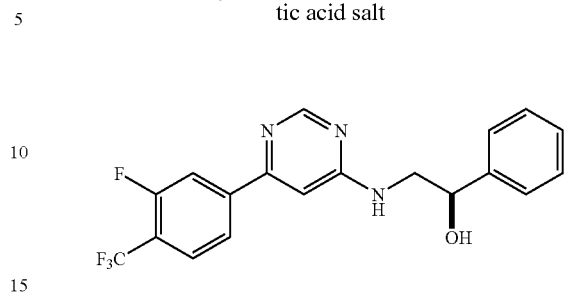

MS (ESI): mass calcd. for C$_{19}$H$_{15}$F$_4$N$_3$O, 377.1; m/z found, 378.1 [M+H]$^+$. $^1$H NMR (CD$_3$OD): 8.63 (s, 1H), 7.93-7.90 (m, 1H), 7.86-7.81 (m, 2H), 7.45-7.44 (m, 2H), 7.37-7.34 (m, 2H), 7.29-7.26 (m, 1H), 7.04 (s, 1H), 4.95-4.92 (m, 1H), 3.90-3.83 (m, 1H), 3.78-3.73 (m, 1H).

Example 42

(1R)-2-({6-[3-Fluoro-5-(trifluoromethyl)phenyl]pyrimidin-4-yl}amino)-1-phenylethanol trifluoroacetic acid salt

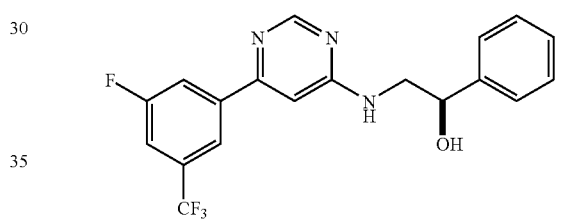

MS (ESI): mass calcd. for C$_{19}$H$_{15}$F$_4$N$_3$O, 377.1; m/z found, 378.1 [M+H]$^+$. $^1$H NMR (CD$_3$OD): 8.64 (s, 1H), 8.01 (s, 1H), 7.93-7.91 (m, 1H), 7.76-7.74 (m, 1H), 7.44 (d, J=7.1 Hz, 2H), 7.36 (t, J=7.7 Hz, 2H), 7.29-7.26 (m, 1H), 7.04 (s, 1H), 4.95-4.93 (m, 1H), 3.92-3.84 (m, 1H), 3.77 (dd, J=13.7, 7.7 Hz, 1H).

Example 43

(1R)-2-{[6-(3-Chloro-5-fluorophenyl)pyrimidin-4-yl]amino}-1-phenylethanol trifluoroacetic acid salt

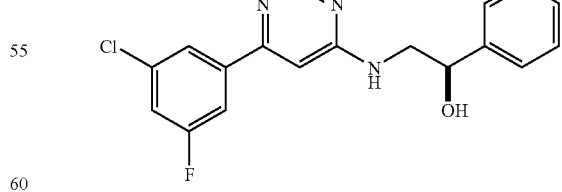

MS (ESI): mass calcd. for C$_{18}$H$_{15}$ClFN$_3$O, 343.1; m/z found, 344.2 [M+H]$^+$. $^1$H NMR (CD$_3$OD): 8.63 (s, 1H), 7.72 (s, 1H), 7.59-7.57 (m, 1H), 7.53-7.50 (m, 1H), 7.45 (d, J=7.1 Hz, 2H), 7.37-7.34 (m, 2H), 7.29-7.26 (m, 1H), 7.00 (s, 1H), 4.95-4.92 (m, 1H), 3.93-3.86 (m, 1H), 3.77 (dd, J=13.7, 7.7 Hz, 1H).

Example 44

(1R)-1-Phenyl-2-{[6-(4-propoxyphenyl)pyrimidin-4-yl]amino}ethanol trifluoroacetic acid salt

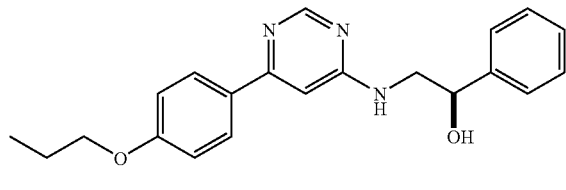 [SMILES: CCCOc1ccc(-c2cc(NC[C@H](O)c3ccccc3)ncn2)cc1]

MS (ESI): mass calcd. for $C_{21}H_{23}N_3O_2$, 349.2; m/z found, 350.2 [M+H]$^+$. $^1$H NMR (CD$_3$OD): 8.58 (s, 1H), 7.76-7.74 (m, 2H), 7.43 (d, J=7.1 Hz, 2H), 7.37-7.34 (m, 2H), 7.30-7.25 (m, 1H), 7.15-7.13 (m, 2H), 6.93 (s, 1H), 4.94-4.92 (m, 1H), 4.05 (t, J=6.6 Hz, 2H), 3.94-3.86 (m, 1H), 3.80-3.75 (m, 1H), 1.88-1.81 (m, 2H), 1.07 (t, J=7.7 Hz, 3H).

Example 45

(1R)-2-{[6-(2,1,3-Benzoxadiazol-5-yl)pyrimidin-4-yl]amino}-1-Phenylethanol trifluoroacetic acid salt

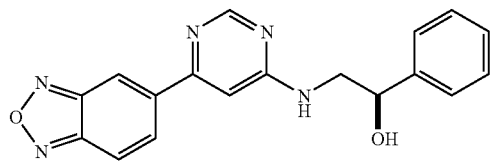 [SMILES: O[C@@H](CNc1cc(-c2ccc3nonc3c2)ncn1)c1ccccc1]

MS (ESI): mass calcd. for $C_{18}H_{15}N_5O_2$, 333.1; m/z found, 334.2 [M+H]$^+$. $^1$H NMR (CD$_3$OD): 8.70 (s, 1H), 8.49-8.48 (m, 1H), 8.14 (d, J=9.3 Hz, 1H), 7.88 (dd, J=9.3 Hz, 1.7 Hz, 1H), 7.45 (d, J=7.7 Hz, 2H), 7.36 (t, J=7.7 Hz, 2H), 7.30-7.27 (m, 1H), 7.13 (s, 1H), 4.97-4.94 (m, 1H), 3.96-3.90 (m, 1H), 3.79 (dd, J=13.7, 8.2 Hz, 1H).

Example 46

(1R)-2-({6-[3-Methyl-4-(1-methylethoxy)phenyl]pyrimidin-4-yl}amino)-1-phenylethanol

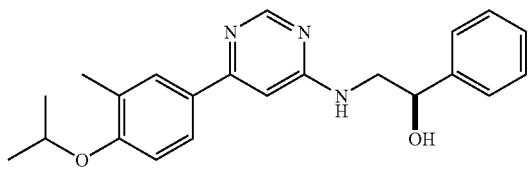 [SMILES: Cc1cc(-c2cc(NC[C@H](O)c3ccccc3)ncn2)ccc1OC(C)C]

MS (ESI): mass calcd. for $C_{22}H_{25}N_3O_2$, 363.2; m/z found, 364.2 [M+H]$^+$. $^1$H NMR (CD$_3$OD): 8.40 (s, 1H), 7.70-7.69 (m, 2H), 7.42 (d, J=7.7 Hz, 2H), 7.36-7.33 (m, 2H), 7.27-7.24 (m, 1H), 6.98 (d, J=9.3 Hz, 1H), 6.80 (s, 1H), 4.91-4.88 (m, 1H), 4.68 (septet, J=6.0 Hz, 1H), 3.74-3.68 (m, 1H), 3.57 (dd, J=13.7, 7.7 Hz, 1H), 2.24 (s, 3H), 1.35 (d, J=6.0 Hz, 6H).

Example 47

(1R)-2-({6-[3-Chloro-4-(trifluoromethyl)phenyl]-5-methylpyrimidin-4-yl}amino)-1-phenylethanol trifluoroacetic acid salt

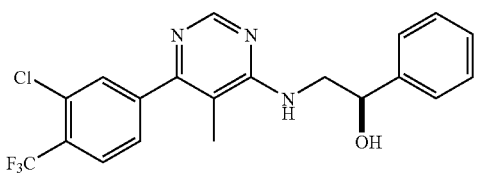

MS (ESI): mass calcd. for $C_{20}H_{17}ClF_3N_3O$, 407.1; m/z found, 408.1 [M+H]$^+$. $^1$H NMR (CD$_3$OD): 8.66 (s, 1H), 8.04 (d, J=8.2 Hz, 1H), 7.89 (s, 1H), 7.69 (d, J=7.7 Hz, 1H), 7.49 (d, J=7.7 Hz, 2H), 7.37 (t, J=7.7 Hz, 2H), 7.31-7.28 (m, 1H), 5.02 (dd, J=7.7, 4.9 Hz, 1H), 3.97-3.88 (m, 2H), 2.09 (s, 3H).

Example 48

(1R)-2-({6-[3-Fluoro-4-(trifluoromethyl)phenyl]-5-methylpyrimidin-4-yl}amino)-1-phenylethanol trifluoroacetic acid salt

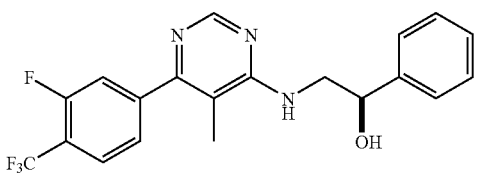 [SMILES: Cc1c(NC[C@H](O)c2ccccc2)ncnc1-c1ccc(C(F)(F)F)c(F)c1]

MS (ESI): mass calcd. for $C_{20}H_{17}F_4N_3O$, 391.1; m/z found, 392.1 [M+H]$^+$. $^1$H NMR (CD$_3$OD): 8.66 (s, 1H), 7.97 (t, J=7.7 Hz, 1H), 7.65 (d, J=10.4 Hz, 1H), 7.56 (d, J=7.7 Hz, 1H), 7.44 (d, J=7.7 Hz, 2H), 7.38-7.35 (m, 2H), 7.31-7.28 (m, 1H), 5.03-5.01 (m, 1H), 3.97-3.89 (m, 2H), 2.09 (s, 3H).

Example 49

(1R)-2-({6-[4-(Difluoromethoxy)-3,5-difluorophenyl]pyrimidin-4-yl}amino)-1-phenylethanol trifluoroacetic acid salt

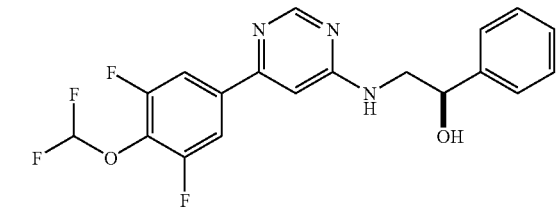 [SMILES: O[C@@H](CNc1cc(-c2cc(F)c(OC(F)F)c(F)c2)ncn1)c1ccccc1]

MS (ESI): mass calcd. for $C_{19}H_{15}F_4N_3O_2$, 393.1; m/z found, 394.1 [M+H]$^+$. $^1$H NMR (CD$_3$OD): 8.65 (s, 1H), 7.68 (d, J=8.3 Hz, 2H), 7.45 (d, J=7.6 Hz, 2H), 7.37-7.34 (m, 2H), 7.30-7.26 (m, 1H), 6.99 (t, $J_{H-F}$=72.0 Hz, 1H), 7.00 (s, 1H), 4.94-4.91 (m, 1H), 3.92-3.85 (m, 1H), 3.79-3.74 (m, 1H).

Example 50

2-[4-(6-{[(2R)-2-Hydroxy-2-phenylethyl]amino}pyrimidin-4-yl)phenyl]-2-methylpropanenitrile trifluoroacetic acid salt

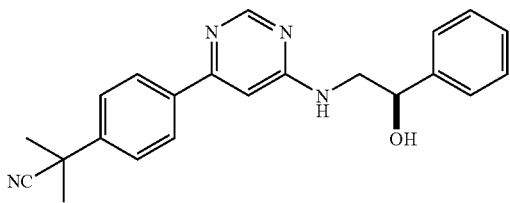

MS (ESI): mass calcd. for $C_{22}H_{22}N_4O$, 358.2; m/z found, 359.2 [M+H]$^+$. $^1$H NMR (CD$_3$OD): 8.67 (s, 1H), 7.86-7.84 (m, 2H), 7.81-7.79 (m, 2H), 7.43 (d, J=7.1 Hz, 2H), 7.38-7.34 (m, 2H), 7.31-7.27 (m, 1H), 7.02 (s, 1H), 4.93 (dd, J=7.3, 4.3 Hz, 1H), 3.94 (dd, J=13.6, 4.3 Hz, 1H), 3.80 (dd, J=13.9, 7.8 Hz, 1H), 1.78 (s, 6H).

Example 51

1-[2-Fluoro-4-(6-{[(2R)-2-hydroxy-2-phenylethyl]amino}pyrimidin-4-yl)phenyl]ethanone trifluoroacetic acid salt

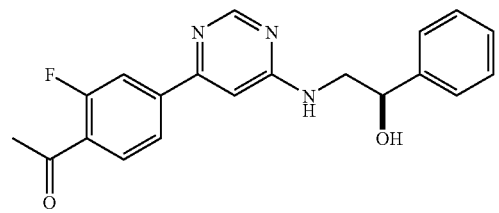 [SMILES: CC(=O)c1ccc(-c2cc(NC[C@H](O)c3ccccc3)ncn2)cc1F]

MS (ESI): mass calcd. for $C_{20}H_{18}FN_3O_2$, 351.1; m/z found, 352.2 [M+H]$^+$. $^1$H NMR (CD$_3$OD): 8.69 (s, 1H), 8.07-8.04 (m, 1H), 7.76-7.73 (m, 1H), 7.72-7.71 (m, 1H), 7.44 (d, J=7.2 Hz, 2H), 7.36 (t, J=7.2 Hz, 2H), 7.30-7.28 (m, 1H), 7.06 (s, 1H), 4.95-4.93 (m, 1H), 3.92 (dd, J=13.5, 3.6 Hz, 1H), 3.79 (dd, J=13.8, 7.9 Hz, 1H), 2.67 (d, J=4.3 Hz, 3H).

Example 52

(1R)-2-({6-[3,5-Dimethyl-4-(1-methylethoxy)phenyl]pyrimidin-4-yl}amino)-1-phenylethanol trifluoroacetic acid salt

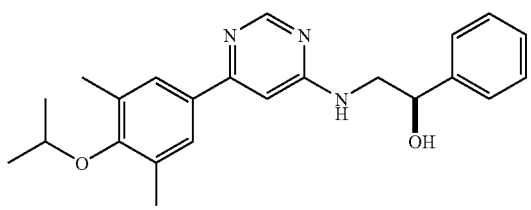 [SMILES: Cc1cc(-c2cc(NC[C@H](O)c3ccccc3)ncn2)cc(C)c1OC(C)C]

MS (ESI): mass calcd. for $C_{23}H_{27}N_3O_2$, 377.2; m/z found, 378.2 [M+H]$^+$. $^1$H NMR (CD$_3$OD): 8.60 (s, 1H), 7.48 (s, 2H), 7.43 (d, J=7.2 Hz, 2H), 7.37-7.35 (m, 2H), 7.30-7.27 (m, 1H), 6.93 (s, 1H), 4.94-4.92 (m, 1H), 4.37 (septet, J=6.3 Hz, 1H), 3.91 (dd, J=13.5, 4.3 Hz, 1H), 3.78 (dd, J=13.8, 8.2 Hz, 1H), 2.36 (s, 6H), 1.31 (d, J=6.3 Hz, 6H).

Example 53

(1R)-2-{[6-(1H-Indol-6-yl)pyrimidin-4-yl]amino}-1-phenylethanol trifluoroacetic acid salt

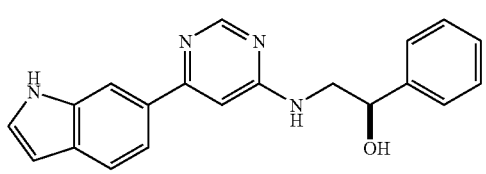 [SMILES: O[C@@H](CNc1cc(-c2ccc3cc[nH]c3c2)ncn1)c1ccccc1]

MS (ESI): mass calcd. for $C_{20}H_{18}N_4O$, 330.2; m/z found, 331.2 [M+H]$^+$. $^1$H NMR (CD$_3$OD): 8.60 (s, 1H), 7.88 (s, 1H), 7.77 (d, J=8.2 Hz, 1H), 7.50 (d, J=2.7 Hz, 1H), 7.46-7.44 (m, 2H), 7.43 (dd, J=8.2, 1.7 Hz, 1H), 7.36 (t, J=7.7 Hz, 2H), 7.30-7.27 (m, 1H), 7.03 (s, 1H), 6.59 (d, J=3.3 Hz, 1H), 4.95-4.93 (m, 1H), 3.94-3.91 (m, 1H), 3.82-3.78 (m, 1H).

Example 54

(1R)-1-Phenyl-2-{[6-(3,4,5-trifluorophenyl)pyrimidin-4-yl]amino}ethanol trifluoroacetic acid salt

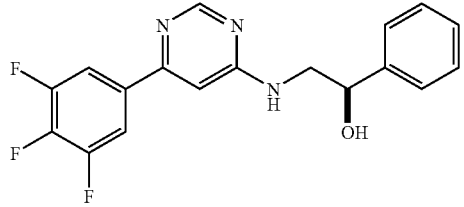 [SMILES: O[C@@H](CNc1cc(-c2cc(F)c(F)c(F)c2)ncn1)c1ccccc1]

MS (ESI): mass calcd. for $C_{18}H_{14}F_3N_3O$, 345.1; m/z found, 346.1 [M+H]$^+$. $^1$H NMR (CD$_3$OD): 8.61 (s, 1H), 7.70-7.68 (m, 2H), 7.43 (d, J=7.7 Hz, 2H), 7.37-7.33 (m, 2H), 7.28-7.26 (m, 1H), 6.97 (s, 1H), 4.94-4.92 (m, 1H), 3.91-3.83 (m, 1H), 3.77 (dd, J=13.7, 7.7 Hz, 1H).

Example 55

(1R)-2-{[6-(1-Methyl-1H-indol-2-yl)pyrimidin-4-yl]amino}-1-phenylethanol trifluoroacetic acid salt

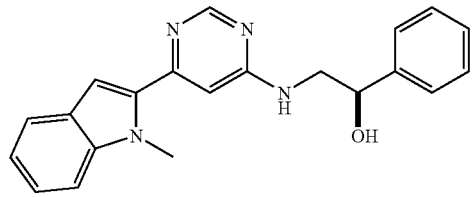 [SMILES: Cn1c(-c2cc(NC[C@H](O)c3ccccc3)ncn2)cc2ccccc21]

MS (ESI): mass calcd. for $C_{21}H_{20}N_4O$, 344.2; m/z found, 345.2 [M+H]$^+$. $^1$H NMR (CD$_3$OD): 8.65 (s, 1H), 7.68 (d, J=7.7 Hz, 1H), 7.54 (d, J=8.2 Hz, 1H), 7.45 (d, J=7.1 Hz, 2H), 7.41-7.35 (m, 3H), 7.31-7.28 (m, 1H), 7.20-7.17 (m, 1H), 7.09 (s, 1H), 6.96 (s, 1H), 4.96-4.90 (m, 1H), 3.98-3.88 (m, 1H), 3.91 (s, 3H), 3.83-3.77 (m, 1H).

Example 56

(1R)-2-{[6-(5-Methyl-1-benzothiophen-2-yl)pyrimidin-4-yl]amino}-1-phenylethanol

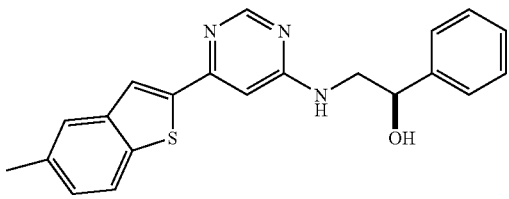 [SMILES: Cc1ccc2sc(-c3cc(NC[C@H](O)c4ccccc4)ncn3)cc2c1]

MS (ESI): mass calcd. for $C_{21}H_{19}N_3OS$, 361.1; m/z found, 362.2 [M+H]$^+$. $^1$H NMR (CD$_3$OD): 8.39 (s, 1H), 7.92 (s, 1H), 7.75 (d, J=8.2 Hz, 1H), 7.66 (s, 1H), 7.43 (d, J=7.1 Hz, 2H), 7.35 (t, J=7.7 Hz, 2H), 7.27-7.23 (m, 2H), 6.94 (s, 1H), 4.92-4.89 (m, 1H), 3.76-3.71 (m, 1H), 3.59 (dd, J=13.7, 7.7 Hz, 1H), 2.46 (s, 3H).

Example 57

[4-(6-{[(2R)-2-Hydroxy-2-phenylethyl]amino}pyrimidin-4-yl)phenyl](phenyl)methanone trifluoroacetic acid salt

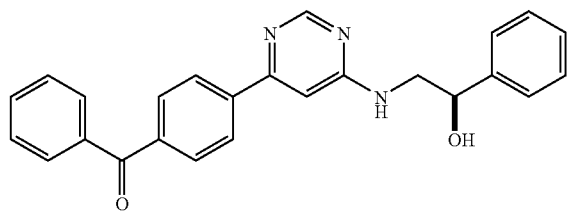 [SMILES: O=C(c1ccccc1)c1ccc(-c2cc(NC[C@H](O)c3ccccc3)ncn2)cc1]

MS (ESI): mass calcd. for $C_{25}H_{21}N_3O_2$, 395.2; m/z found, 396.3 [M+H]$^+$. $^1$H NMR (CD$_3$OD): 8.69 (s, 1H), 7.98-7.94 (m, 4H), 7.82-7.81 (m, 2H), 7.71-7.68 (m, 1H), 7.57 (t, J=7.7 Hz, 2H), 7.44 (d, J=7.1 Hz, 2H), 7.36 (t, J=7.1 Hz, 2H), 7.30-7.27 (m, 1H), 7.08 (s, 1H), 4.96-4.94 (m, 1H), 3.96-3.90 (m, 1H), 3.82 (dd, J=13.7, 8.2 Hz, 1H).

Example 58

(1R)-2-{[6-(3,5-Difluorophenyl)pyrimidin-4-yl]amino}-1-phenylethanol trifluoroacetic acid salt

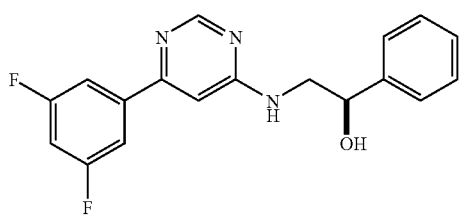 [SMILES: O[C@@H](CNc1cc(-c2cc(F)cc(F)c2)ncn1)c1ccccc1]

MS (ESI): mass calcd. for $C_{18}H_{15}F_2N_3O$, 327.1; m/z found, 328.3 [M+H]$^+$. $^1$H NMR (CD$_3$OD): 8.64 (s, 1H), 7.49-7.43 (m, 4H), 7.37-7.34 (m, 2H), 7.31-7.27 (m, 2H), 7.00 (s, 1H), 4.95-4.92 (m, 1H), 3.93-3.85 (m, 1H), 3.78 (dd, J=13.7, 7.7 Hz, 1H).

Example 59

(1R)-2-{[6-(3,4-Difluorophenyl)pyrimidin-4-yl]amino}-1-phenylethanol trifluoroacetic acid salt

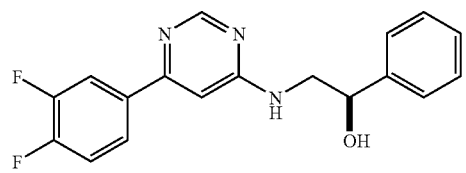 [SMILES: O[C@@H](CNc1cc(-c2ccc(F)c(F)c2)ncn1)c1ccccc1]

MS (ESI): mass calcd. for $C_{18}H_{15}F_2N_3O$, 327.1; m/z found, 328.3 [M+H]$^+$. $^1$H NMR (CD$_3$OD): 8.64 (s, 1H), 7.82-7.78 (m, 1H), 7.67-7.63 (m, 1H), 7.56-7.51 (m, 1H), 7.43 (d, J=7.7 Hz, 2H), 7.37-7.34 (m, 2H), 7.30-7.24 (m, 1H), 6.97 (s, 1H), 4.95-4.92 (m, 1H), 3.94-3.87 (m, 1H), 3.78 (dd, J=13.7, 7.7 Hz, 1H).

Example 60

(1R)-2-({6-[3-Chloro-4-(trifluoromethyl)phenyl]-2-(methylsulfanyl)pyrimidin-4-yl}amino)-1-phenylethanol trifluoroacetic acid salt

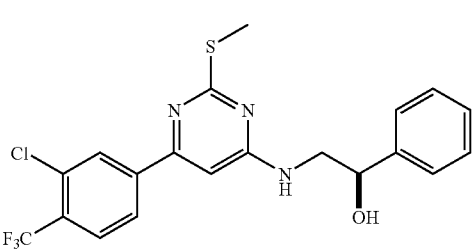

MS (ESI): mass calcd. for $C_{20}H_{17}ClF_3N_3OS$, 439.1; m/z found, 440.1 [M+H]$^+$. $^1$H NMR (CD$_3$OD): 8.09 (s, 1H), 7.95 (d, J=8.1 Hz, 1H), 7.90 (d, J=8.1 Hz, 1H), 7.44 (d, J=7.6 Hz, 2H), 7.37-7.33 (m, 2H), 7.29-7.25 (m, 1H), 6.69 (s, 1H), 4.96-4.93 (m, 1H), 3.91-3.85 (m, 1H), 3.78-3.73 (m, 1H), 2.65 (s, 3H).

Example 61

(1R)-2-({2-Amino-6-[3-chloro-4-(trifluoromethyl)phenyl]pyrimidin-4-yl}amino)-1-phenylethanol trifluoroacetic acid salt

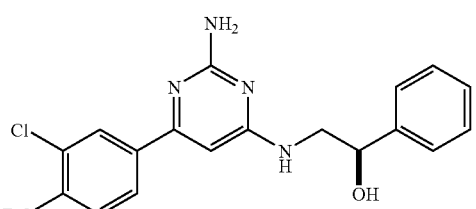

MS (ESI): mass calcd. for $C_{19}H_{16}ClF_3N_4O$, 408.1; m/z found, 409.1 [M+H]$^+$. $^1$H NMR (CD$_3$OD): 8.00-7.98 (m, 2H), 7.83-7.80 (m, 1H), 7.45-7.43 (m, 2H), 7.38-7.34 (m, 2H), 7.30-7.26 (m, 1H), 6.44 (s, 1H), 4.92-4.89 (m, 1H), 3.84 (dd, J=13.6, 4.5 Hz, 1H), 3.65 (dd, J=13.6, 8.3 Hz, 1H).

Example 62

(1R)-2-({6-[3-Chloro-4-(trifluoromethyl)phenyl]ivrimidin-4-yl}amino)-1-(4-fluorophenyl)ethanol

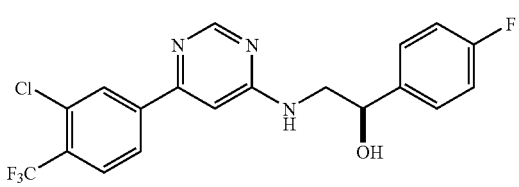

MS (ESI): mass calcd. for $C_{19}H_{14}ClF_4N_3O$, 411.1; m/z found, 412.1 [M+H]$^+$. $^1$H NMR (CD$_3$OD): 8.50 (s, 1H), 8.17 (s, 1H), 8.00 (d, J=8.3 Hz, 1H), 7.88 (d, J=8.1 Hz, 1H), 7.47-7.43 (m, 2H), 7.09-7.04 (m, 2H), 6.97 (s, 1H), 4.92-4.89 (m, 1H), 3.76-3.70 (m, 1H), 3.63-3.57 (m, 1H).

Example 63

(1R)-2-{[6-(6-Methoxypyridin-3-yl)pyrimidin-4-yl]amino}-1-phenylethanol

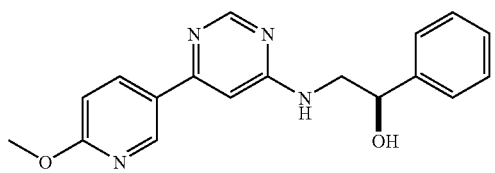 [SMILES: COc1ccc(-c2cc(NC[C@H](O)c3ccccc3)ncn2)cn1]

MS (ESI): mass calcd. for $C_{18}H_{18}N_4O_2$, 322.1; m/z found, 323.2 [M+H]$^+$. $^1$H NMR (CD$_3$OD): 8.90-8.83 (m, 1H), 8.62 (s, 1H), 8.35 (dd, J=2.5, 8.7 Hz, 1H), 7.65-7.57 (m, 2H), 7.55-7.49 (m, 2H), 7.46-7.40 (m, 1H), 7.09-6.99 (m, 2H), 5.10-5.05 (m, 1H), 4.15 (s, 3H), 3.96-3.85 (m, 1H), 3.76 (dd, J=7.7, 13.7 Hz, 1H).

Example 64

(1R)-2-{[6-(6-Ethoxypyridin-3-yl)pyrimidin-4-yl]amino}-1-phenylethanol

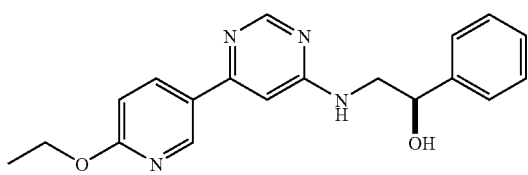 [SMILES: CCOc1ccc(-c2cc(NC[C@H](O)c3ccccc3)ncn2)cn1]

MS (ESI): mass calcd. for $C_{19}H_{20}N_4O_2$, 336.2; m/z found, 337.2 [M+H]$^+$. $^1$H NMR (CD$_3$OD): 8.43 (d, J=2.5 Hz, 1H), 8.21 (s, 1H), 7.93 (dd, J=2.5, 8.7 Hz, 1H), 7.23-7.17 (m, 2H), 7.14-7.08 (m, 2H), 7.05-6.99 (m, 1H), 6.64-6.59 (m, 2H), 4.68-4.65 (m, 1H), 4.15 (q, J=7.1 Hz, 2H), 3.54-3.43 (m, 1H), 3.35 (dd, J=7.7, 13.7 Hz, 1H), 1.17 (t, J=7.1 Hz, 3H).

Example 65

(1R)-2-({6-[4-(Dimethylamino)phenyl]pyrimidin-4-yl}amino)-1-phenylethanol

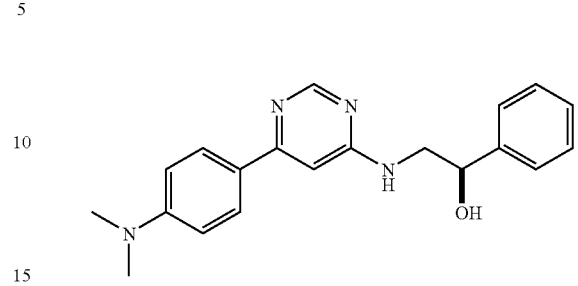

MS (ESI): mass calcd. for $C_{20}H_{22}N_4O$, 334.2; m/z found, 335.2 [M+H]$^+$. $^1$H NMR (CD$_3$OD): 8.38 (s, 1H), 7.83-7.78 (m, 2H), 7.48-7.41 (m, 2H), 7.39-7.33 (m, 2H), 7.30-7.24 (m, 1H), 6.85-6.79 (m, 2H), 6.79-6.76 (m, 1H), 4.95-4.87 (m, 1H), 3.78-3.65 (m, 1H), 3.58 (dd, J=13.7, 7.6 Hz, 1H), 3.03 (s, 6H).

Example 66

(1R)-2-({6-[4-(Methylsulfonyl)phenyl]pyrimidin-4-yl}amino)-1-phenylethanol

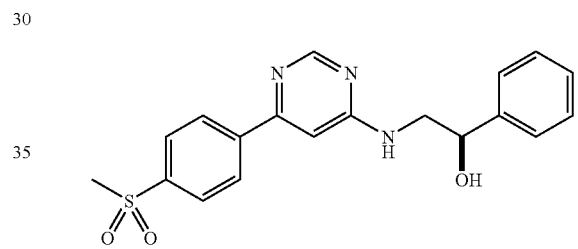

MS (ESI): mass calcd. for $C_{19}H_{19}N_3O_3S$, 369.1; m/z found, 370.1 [M+H]$^+$. $^1$H NMR (CD$_3$OD): 8.53 (s, 1H), 8.19-8.12 (m, 2H), 8.10-8.04 (m, 2H), 7.52-7.39 (m, 2H), 7.39-7.30 (m, 2H), 7.30-7.23 (m, 1H), 7.03-6.95 (m, 1H), 4.98-4.87 (m, 1H), 3.87-3.68 (m, 1H), 3.68-3.58 (m, 1H), 3.18 (s, 3H).

Example 67

N-Cyclopropyl-4-(6-{[(2R)-2-hydroxy-2-phenyl-ethyl]amino}pyrimidin-4-yl)benzenesulfonamide

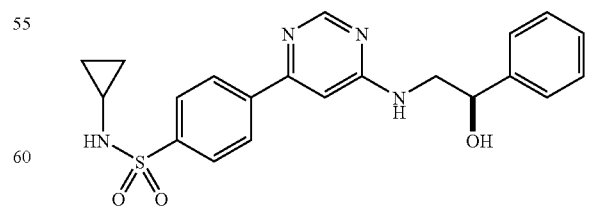

MS (ESI): mass calcd. for $C_{21}H_{22}N_4O_3S$, 410.1; m/z found, 411.2 [M+H]$^+$. $^1$H NMR (CD$_3$OD): 8.52 (s, 1H), 8.18-8.03 (m, 2H), 8.02-7.95 (m, 2H), 7.50-7.39 (m, 2H), 7.38-7.33 (m, 2H), 7.31-7.24 (m, 1H), 7.03-6.93 (m, 1H), 4.97-4.86 (m, 1H), 3.86-3.67 (m, 1H), 3.63 (dd, J=13.7, 7.7 Hz, 1H), 2.30-2.12 (m, 1H), 0.63-0.41 (m, 4H).

Example 68

(1R)-2-{[6-(3-Chloro-4-ethoxyphenyl)pyrimidin-4-yl]amino}-1-phenylethanol

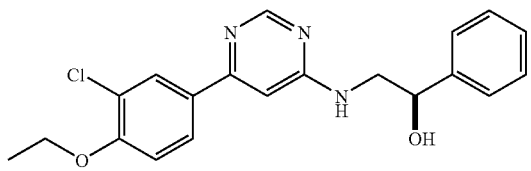 [SMILES: CCOc1ccc(-c2cc(NC[C@H](O)c3ccccc3)ncn2)cc1Cl]

MS (ESI): mass calcd. for $C_{20}H_{20}ClN_3O_2$, 369.1; m/z found, 370.2 [M+H]$^+$. $^1$H NMR (CD$_3$OD): 8.43 (s, 1H), 7.96 (d, J=2.2 Hz, 1H), 7.83 (dd, J=8.7, 2.2 Hz, 1H), 7.45 (d, J=7.6 Hz, 2H), 7.38-7.32 (m, 2H), 7.30-7.25 (m, 1H), 7.15 (d, J=8.7 Hz, 1H), 6.83 (s, 1H), 4.96-4.86 (m, 1H), 4.20 (q, J=7.0 Hz, 2H), 3.79-3.66 (m, 1H), 3.60 (dd, J=13.8, 7.7 Hz, 1H), 1.47 (t, J=7.0 Hz, 3H).

Example 69

(1R)-2-[(2'-Morpholin-4-yl-4,5'-bipyrimidin-6-yl)amino]-1-phenylethanol

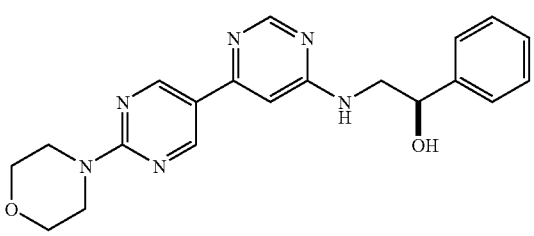 [SMILES: O[C@@H](CNc1cc(-c2cnc(N3CCOCC3)nc2)ncn1)c1ccccc1]

MS (ESI): mass calcd. for $C_{20}H_{22}N_6O_2$, 378.2; m/z found, 379.2 [M+H]$^+$. $^1$H NMR (CD$_3$OD): 8.87 (d, J=2.9 Hz, 2H), 8.43 (s, 1H), 7.51-7.38 (m, 2H), 7.38-7.32 (m, 2H), 7.30-7.24 (m, 1H), 6.86-6.75 (m, 1H), 4.90 (dd, J=7.6, 4.7 Hz, 1H), 3.95-3.83 (m, 4H), 3.79-3.73 (m, 4H), 3.74-3.69 (m, 1H), 3.60 (dd, J=13.8, 7.7 Hz, 1H).

Example 70

(1R)-2-{[6-(6-Morpholin-4-ylpyridin-3-yl)pyrimidin-4-yl]amino}-1-Phenylethanol

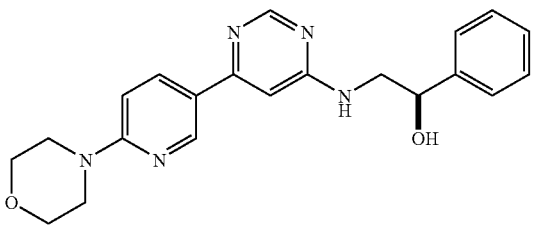 [SMILES: O[C@@H](CNc1cc(-c2ccc(N3CCOCC3)nc2)ncn1)c1ccccc1]

MS (ESI): mass calcd. for $C_{21}H_{23}N_5O_2$, 377.2; m/z found, 378.2 [M+H]$^+$. $^1$H NMR (CD$_3$OD): 8.74-8.64 (m, 1H), 8.42 (s, 1H), 8.09 (dd, J=9.0, 2.5 Hz, 1H), 7.50-7.39 (m, 2H), 7.38-7.33 (m, 2H), 7.30-7.24 (m, 1H), 6.93-6.85 (m, 1H), 6.83-6.80 (m, 1H), 4.94-4.87 (m, 1H), 3.86-3.76 (m, 4H), 3.76-3.68 (m, 1H), 3.64-3.56 (m, 5H).

Example 71

(1R)-2-{[6-(3-Fluoro-4-methoxyphenyl)pyrimidin-4-yl]amino}-1-pPhenylethanol

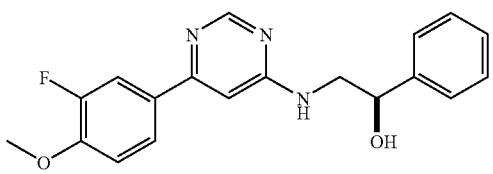 [SMILES: COc1ccc(-c2cc(NC[C@H](O)c3ccccc3)ncn2)cc1F]

MS (ESI): mass calcd. for $C_{19}H_{18}FN_3O_2$, 339.1; m/z found, 340.2 [M+H]$^+$. $^1$H NMR (CD$_3$OD): 8.33 (s, 1H), 7.65-7.52 (m, 2H), 7.37-7.29 (m, 2H), 7.27-7.22 (m, 2H), 7.19-7.13 (m, 1H), 7.13-7.06 (m, 1H), 6.73 (s, 1H), 4.83-4.78 (m, 1H), 3.84 (s, 3H), 3.69-3.55 (m, 1H), 3.48 (dd, J=13.8, 7.7 Hz, 1H).

Example 72

(1R)-2-{[6-(2,3-Dihydro-1,4-benzodioxin-6-yl)pyrimidin-4-yl]amino}-1-phenylethanol

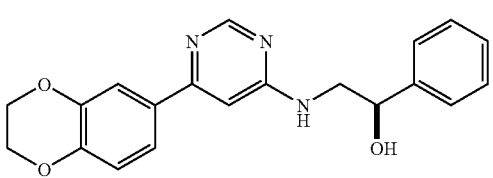 [SMILES: O[C@@H](CNc1cc(-c2ccc3c(c2)OCCO3)ncn1)c1ccccc1]

MS (ESI): mass calcd. for $C_{20}H_{19}N_3O_3$, 349.1; m/z found, 350.2 [M+H]$^+$. $^1$H NMR (CD$_3$OD): 8.41 (s, 1H), 7.47-7.42 (m, 3H), 7.42-7.37 (m, 1H), 7.37-7.33 (m, 2H), 7.30-7.24 (m, 1H), 6.97-6.86 (m, 1H), 6.82-6.78 (m, 1H), 4.95-4.85 (m, 1H), 4.34-4.22 (m, 4H), 3.79-3.63 (m, 1H), 3.63-3.54 (m, 1H).

Example 73

(1R)-2-({6-[3-Chloro-4-(trifluoromethyl)phenyl]-2-methylpyrimidin-4-yl}amino)-1-phenylethanol

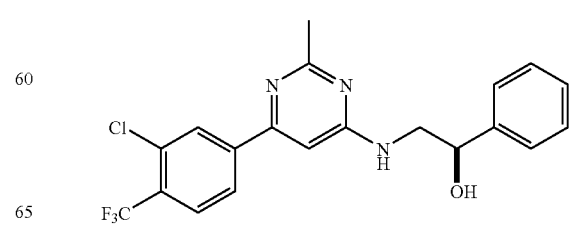

MS (ESI): mass calcd. for $C_{20}H_{17}ClF_3N_3O$, 407.1; m/z found, 408.1 [M+H]$^+$. $^1$H NMR (CD$_3$OD): 8.15 (s, 1H), 8.00-7.94 (m, 1H), 7.89-7.85 (m, 1H), 7.48-7.39 (m, 2H), 7.39-7.32 (m, 2H), 7.29-7.24 (m, 1H), 6.81-6.70 (m, 1H), 4.97-4.85 (m, 1H), 3.87-3.67 (m, 1H), 3.66-3.58 (m, 1H), 2.52 (s, 3H).

Example 74

(1R)-2-{[6-(1-Benzyl-1H-pyrazol-4-yl)pyrimidin-4-yl]amino}-1-phenylethanol

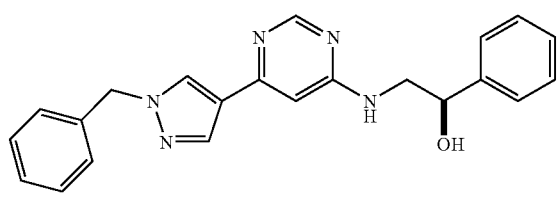 [SMILES: O[C@@H](CNc1cc(-c2cnn(Cc3ccccc3)c2)ncn1)c1ccccc1]

MS (ESI): mass calcd. for $C_{22}H_{21}N_5O$, 371.2; m/z found, 372.2 [M+H]$^+$. $^1$H NMR (CD$_3$OD): 8.34 (s, 1H), 8.20 (s, 1H), 8.02 (s, 1H), 7.45-7.41 (m, 2H), 7.40-7.22 (m, 8H), 6.68 (s, 1H), 5.39 (s, 2H), 4.93-4.84 (m, 1H), 3.77-3.61 (m, 1H), 3.62-3.52 (m, 1H).

Example 75

(1R)-2-{[6-(6-Fluoro-5-methylpyridin-3-yl)pyrimidin-4-yl]amino}-1-phenylethanol

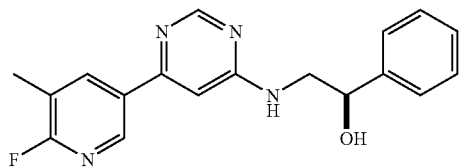 [SMILES: Cc1cc(-c2cc(NC[C@H](O)c3ccccc3)ncn2)cnc1F]

MS (ESI): mass calcd. for $C_{18}H_{17}FN_4O$, 324.1; m/z found, 325.2 [M+H]$^+$. $^1$H NMR (CD$_3$OD): 8.48 (s, 1H), 8.12 (s, 1H), 7.50-7.39 (m, 2H), 7.38-7.32 (m, 2H), 7.30-7.24 (m, 1H), 7.07-7.01 (m, 1H), 6.60 (s, 1H), 5.04-4.84 (m, 1H), 3.86-3.67 (m, 1H), 3.67-3.56 (m, 1H), 2.43 (s, 3H).

Example 76

4-(6-{[(2R)-2-Hydroxy-2-phenylethyl]amino}pyrimidin-4-yl)-N,N-dimethylbenzenesulfonamide

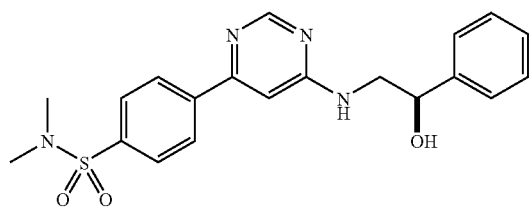 [SMILES: CN(C)S(=O)(=O)c1ccc(-c2cc(NC[C@H](O)c3ccccc3)ncn2)cc1]

MS (ESI): mass calcd. for $C_{20}H_{22}N_4O_3S$, 398.1; m/z found, 399.2 [M+H]$^+$. $^1$H NMR (CD$_3$OD): 8.57-8.46 (m, 1H), 8.19-8.11 (m, 2H), 7.93-7.88 (m, 2H), 7.49-7.42 (m, 2H), 7.39-7.33 (m, 2H), 7.30-7.24 (m, 1H), 7.03-6.94 (m, 1H), 5.00-4.84 (m, 1H), 3.84-3.68 (m, 1H), 3.67-3.57 (m, 1H), 2.82-2.61 (m, 6H).

Example 77

5-(6-{[(2R)-2-Hydroxy-2-phenylethyl]amino}pyrimidin-4-yl)pyridine-2-carbonitrile

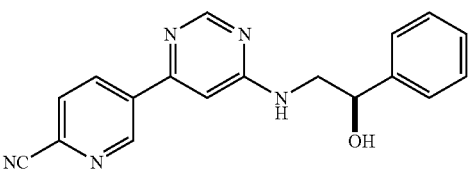

MS (ESI): mass calcd. for $C_{18}H_{15}N_5O$, 317.1; m/z found, 318.2 [M+H]$^+$. $^1$H NMR (CD$_3$OD): 9.32-9.12 (m, 1H), 8.60-8.43 (m, 2H), 8.04-7.93 (m, 1H), 7.49-7.41 (m, 2H), 7.39-7.33 (m, 2H), 7.30-7.25 (m, 1H), 7.08-7.00 (m, 1H), 5.00-4.84 (m, 1H), 3.86-3.68 (m, 1H), 3.68-3.58 (m, 1H).

Example 78

(1R)-2-({6-[6-(Dimethylamino)pyridin-3-yl]pyrimidin-4-yl}amino)-1-phenylethanol

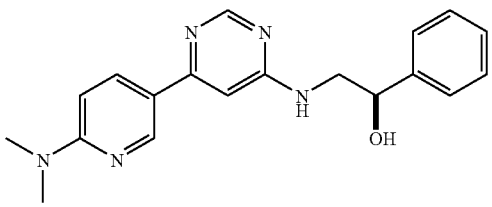

MS (ESI): mass calcd. for $C_{19}H_{21}N_5O$, 335.2; m/z found, 336.2 [M+H]$^+$. $^1$H NMR (CD$_3$OD): 8.78-8.67 (m, 1H), 8.52-8.46 (m, 1H), 8.14 (dd, J=9.1, 2.5 Hz, 1H), 7.58-7.49 (m, 2H), 7.48-7.41 (m, 2H), 7.40-7.33 (m, 1H), 6.94-6.77 (m, 2H), 4.94-4.86 (m, 1H), 3.92-3.73 (m, 1H), 3.72-3.62 (m, 1H), 3.25 (s, 6H).

Example 79

(1R)-1-Phenyl-2-({6-[4-(piperidin-1-ylsulfonyl)phenyl]pyrimidin-4-yl}amino)ethanol

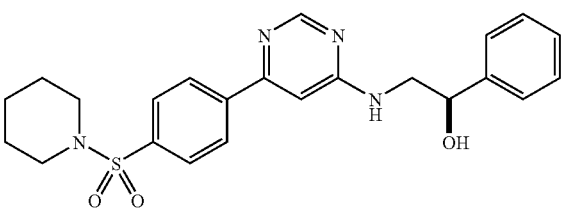 [SMILES: O=S(=O)(c1ccc(-c2cc(NC[C@H](O)c3ccccc3)ncn2)cc1)N1CCCCC1]

MS (ESI): mass calcd. for $C_{23}H_{26}N_4O_3S$, 438.2; m/z found, 439.2 [M+H]$^+$. $^1$H NMR (CD$_3$OD): 8.52 (s, 1H), 8.17-8.09 (m, 2H), 7.90-7.85 (m, 2H), 7.48-7.41 (m, 2H), 7.39-7.33 (m, 2H), 7.30-7.23 (m, 1H), 7.02-6.93 (m, 1H), 5.04-4.87 (m, 1H), 3.87-3.66 (m, 1H), 3.66-3.59 (m, 1H), 3.10-2.96 (m, 4H), 1.72-1.53 (m, 4H), 1.53-1.40 (m, 2H).

Example 80

(1R)-1-Phenyl-2-({6-[4-(Pyrrolidin-1-ylsulfonyl)phenyl]pyrimidin-4-yl}amino)ethanol

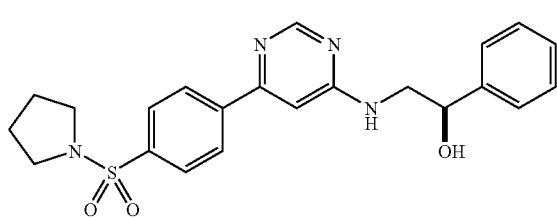 [SMILES: O=S(=O)(c1ccc(-c2cc(NC[C@H](O)c3ccccc3)ncn2)cc1)N1CCCC1]

MS (ESI): mass calcd. for $C_{22}H_{24}N_4O_3S$, 424.2; m/z found, 425.2 [M+H]$^+$. $^1$H NMR (CD$_3$OD): 8.57-8.45 (m, 1H), 8.19-8.07 (m, 2H), 7.98-7.91 (m, 2H), 7.49-7.39 (m, 2H), 7.39-7.32 (m, 2H), 7.30-7.24 (m, 1H), 7.04-6.90 (m, 1H), 5.01-4.85 (m, 1H), 3.87-3.69 (m, 1H), 3.67-3.59 (m, 1H), 3.28-3.19 (m, 4H), 1.91-1.61 (m, 4H).

Example 81

4-(6-{[(2R)-2-Hydroxy-2-phenylethyl]amino}pyrimidin-4-yl)benzenesulfonamide

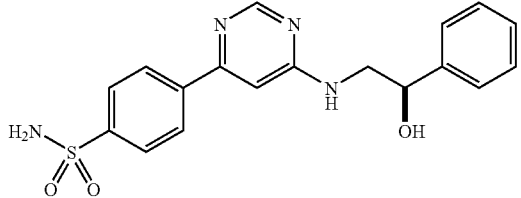 [SMILES: NS(=O)(=O)c1ccc(-c2cc(NC[C@H](O)c3ccccc3)ncn2)cc1]

MS (ESI): mass calcd. for $C_{18}H_{18}N_4O_3S$, 370.1; m/z found, 373.2 [M+H]$^+$. $^1$H NMR (CD$_3$OD): 8.33 (s, 1H), 7.93-7.86 (m, 2H), 7.85-7.82 (m, 2H), 7.32-7.22 (m, 2H), 7.22-7.14 (m, 2H), 7.13-7.07 (m, 1H), 6.84-6.75 (m, 1H), 4.88-4.67 (m, 1H), 3.66-3.49 (m, 1H), 3.49-3.40 (m, 1H).

Example 82

(1R)-2-{[6-(4-Fluorophenyl)pyrimidin-4-yl]amino}-1-phenylethanol trifluoroacetic acid salt

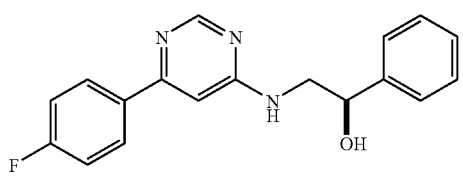 [SMILES: O[C@@H](CNc1cc(-c2ccc(F)cc2)ncn1)c1ccccc1]

MS (ESI): mass calcd. for $C_{18}H_{16}FN_3O$, 309.1; m/z found, 310.2 [M+H]$^+$. $^1$H NMR ((CD$_3$)$_2$CO): 8.89 (br hump, 4H), 8.06 (br s, 2H), 7.49 (d, J=7.0 Hz, 2H), 7.37-7.34 (m, 4H), 7.30-7.26 (m, 2H), 5.05 (br s, 1H), 3.98 (br s, 1H), 3.75 (br s, 1H).

Example 83

(1R)-2-{[6-(3-Chloro-4-fluorophenyl)pyrimidin-4-yl]amino}-1-Phenylethanol trifluoroacetic acid salt

MS (ESI): mass calcd. for $C_{18}H_{15}ClFN_3O$, 343.1; m/z found, 344.1 [M+H]$^+$. $^1$H NMR ((CD$_3$)$_2$CO): 10.06 (br hump, 2H), 9.20-8.6 (br m, 2H), 8.13-7.98 (m, 2H), 7.51-7.47 (m, 2H), 7.36-7.33 (m, 2H), 7.28-7.25 (m, 1H), 5.04 (br s, 1H), 3.96 (br s, 1H), 3.73 (br s, 1H).

Example 84

(1R)-2-({6-[3-(Methylsulfanyl)phenyl]pyrimidin-4-yl}amino)-1-phenylethanol trifluoroacetic acid salt

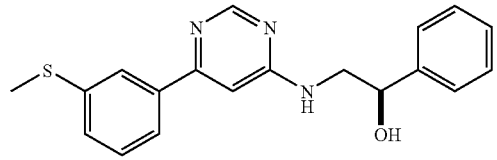 [SMILES: CSc1cccc(-c2cc(NC[C@H](O)c3ccccc3)ncn2)c1]

MS (ESI): mass calcd. for $C_{19}H_{19}N_3OS$, 337.1; m/z found, 338.1 [M+H]$^+$. $^1$H NMR ((CD$_3$)$_2$CO): 11.25 (br hump, 2H), 8.88 (s, 1H), 7.71 (s, 1H), 7.59 (br s, 1H), 7.48-7.45 (m, 4H), 7.36-7.32 (m, 3H), 7.27 (t, J=6.5 Hz, 1H), 5.10-5.00 (br m, 1H), 4.00-3.68 (br m, 2H), 2.55 (s, 3H).

Example 85

(1R)-2-{[6-(1H-Indol-5-yl)pyrimidin-4-yl]amino}-1-phenylethanol trifluoroacetic acid salt

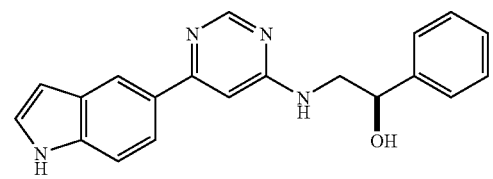 [SMILES: O[C@@H](CNc1cc(-c2ccc3[nH]ccc3c2)ncn1)c1ccccc1]

MS (ESI): mass calcd. for $C_{20}H_{18}N_4O$, 330.2; m/z found, 331.2 [M+H]$^+$. $^1$H NMR ((CD$_3$)$_2$CO): 10.85 (s, 1H), 9.02 (br s, 1H), 8.68 (s, 1H), 8.10 (s, 1H), 7.55-7.50 (m, 5H), 7.35 (t, J=7.0 Hz, 2H), 7.26 (t, J=7.0 Hz, 1H), 6.56 (s, 1H), 5.10-5.01 (br m, 1H), 3.95-3.92 (m, 1H), 3.70-3.65 (m, 1H).

Example 86

(1R)-1-Phenyl-2-[(6-quinolin-3-ylpyrimidin-4-yl) amino]ethanol trifluoroacetic acid salt

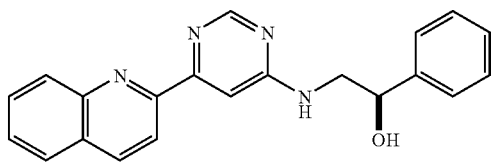 [SMILES: O[C@@H](CNc1cc(-c2ccc3ccccc3n2)ncn1)c1ccccc1]

MS (ESI): mass calcd. for $C_{21}H_{18}N_4O$, 342.2; m/z found, 343.2 [M+H]$^+$. $^1$H NMR ((CD$_3$)$_2$CO): 12.63 (br s, 3H), 9.59-8.81 (m, 3H), 8.26-8.14 (m, 2H), 8.00 (br s, 1H), 7.81 (br s, 1H), 7.57-7.48 (m, 2H), 7.36 (t, J=7.5 Hz, 2H), 7.29-7.26 (br t, J=7.0 Hz, 1H), 5.12-5.07 (br m, 1H), 4.04-3.81 (br m, 2H).

Example 87

(1R)-2-{[6-(1-Benzothiophen-3-yl)pyrimidin-4-yl] amino}-1-phenylethanol trifluoroacetic acid salt

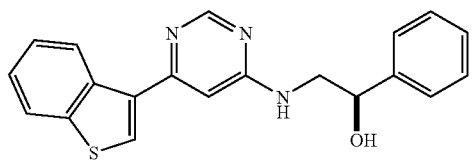 [SMILES: O[C@@H](CNc1cc(-c2csc3ccccc23)ncn1)c1ccccc1]

MS (ESI): mass calcd. for $C_{20}H_{17}N_3OS$, 347.1; m/z found, 348.1 [M+H]$^+$. $^1$H NMR ((CD$_3$)$_2$CO): 10.13 (br hump, 2H), 9.19 (br s, 1H), 8.81 (br s, 1H), 8.45 (s, 1H), 8.11 (s, 1H), 8.04-8.03 (dd, J=1.5, 7.0 Hz, 1H), 7.51-7.46 (m, 4H), 7.36-7.32 (m, 3H), 7.27 (t, J=7.0 Hz, 1H), 5.06 (br s, 1H), 3.98 (br s, 1H), 3.71 (br s, 1H).

Example 88

2-Fluoro-4-(6-{[(2R)-2-hydroxy-2-phenylethyl] amino}pyrimidin-4-yl)benzonitrile trifluoroacetic acid salt

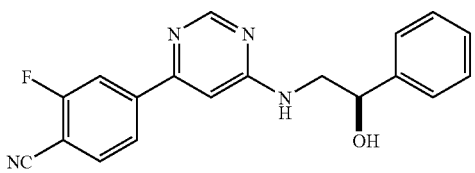

MS (ESI): mass calcd. for $C_{19}H_{15}FN_4O$, 334.1; m/z found, 335.2 [M+H]$^+$. $^1$H NMR ((CD$_3$)$_2$CO): 8.34 (br s, 1H), 8.03-8.00 (m, 2H), 7.73 (br hump, 3H), 7.47 (br s, 2H), 7.34 (t, J=7.2 Hz, 2H), 7.27 (t, J=7.8 Hz, 1H), 5.02 (br hump, 1H), 3.95-3.68 (br m, 2H).

Example 89

2-Fluoro-5-(6-{[(2R)-2-hydroxy-2-phenylethyl] amino}pyrimidin-4-yl)benzonitrile trifluoroacetic acid salt

MS (ESI): mass calcd. for $C_{19}H_{15}FN_4O$, 334.1; m/z found, 335.2 [M+H]$^+$. $^1$H NMR ((CD$_3$)$_2$CO): 8.83 (br hump, 1H), 8.55-8.35 (br m, 3H), 7.76 (br hump, 2H), 7.62 (t, J=9.0 Hz, 1H), 7.47 (br s, 2H), 7.34 (t, J=7.2 Hz, 2H), 7.26 (t, J=7.2 Hz, 1H), 5.02 (br hump, 1H), 3.95-3.68 (br m, 2H).

Example 90

(1R)-2-{[6-(1-Methyl-1H-indol-5-yl)pyrimidin-4-yl] amino}-1-phenylethanol trifluoroacetic acid salt

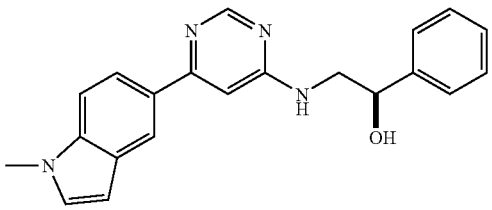 [SMILES: Cn1ccc2cc(-c3cc(NC[C@H](O)c4ccccc4)ncn3)ccc21]

MS (ESI): mass calcd. for $C_{21}H_{20}N_4O$, 344.2; m/z found, 345.2 [M+H]$^+$. $^1$H NMR ((CD$_3$)$_2$CO): 9.11 (s, 1H), 8.66 (s, 1H), 8.04 (s, 1H), 7.54-7.44 (m, 4H), 7.36-7.33 (m, 4H), 7.27 (t, J=7.2 Hz, 1H), 7.14 (s, 1H), 6.52 (s, 1H), 5.10-4.99 (m, 1H), 3.92-3.61 (br m, 2H), 3.81 (s, 3H).

Example 91

(1R)-2-[(6-{4-[(1-Methylethyl)sulfanyl] phenyl}pyrimidin-4-yl)amino]-1-phenylethanol trifluoroacetic acid salt

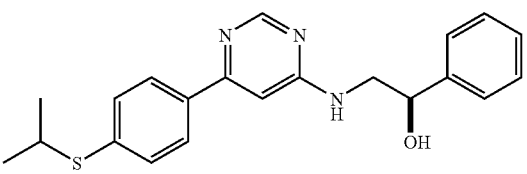

MS (ESI): mass calcd. for $C_{21}H_{23}N_3OS$, 365.2; m/z found, 366.2 [M+H]$^+$. $^1$H NMR ((CD$_3$)$_2$CO): 9.31 (br s, 1H), 8.83 (s, 1H), 7.80 (br d, J=8.4 Hz, 2H), 7.47-7.41 (m, 4H), 7.33 (t, J=7.8 Hz, 2H), 7.26 (br s, 2H), 5.09-5.02 (br m, 1H), 3.97-3.62 (br m, 3H), 1.32 (d, J=6.6 Hz, 6H).

Example 92

[4-(6-{[(2R)-2-Hydroxy-2-phenylethyl]amino}pyrimidin-4-yl)phenyl]acetonitrile trifluoroacetic acid salt

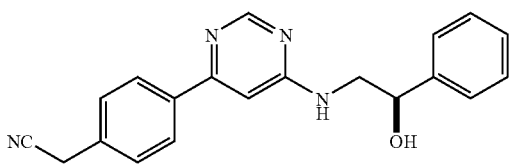

MS (ESI): mass calcd. for $C_{20}H_{18}N_4O$, 330.2; m/z found, 331.2 [M+H]$^+$. $^1$H NMR ((CD$_3$)$_2$CO): 9.30 (s, 1H), 8.88 (s, 1H), 7.92 (d, J=8.6 Hz, 2H), 7.79 (br hump, 1H), 7.58 (d, J=7.8 Hz, 2H), 7.49-7.46 (m, 2H), 7.35-7.25 (m, 4H), 5.10-5.02 (br m, 1H), 4.08 (s, 2H), 3.98-3.69 (m, 2H).

Example 93

(1R)-2-({6-[3-Chloro-4-(trifluoromethyl)phenyl]-2-(trifluoromethyl)pyrimidin-4-yl}amino)-1-phenylethanol trifluoroacetic acid salt

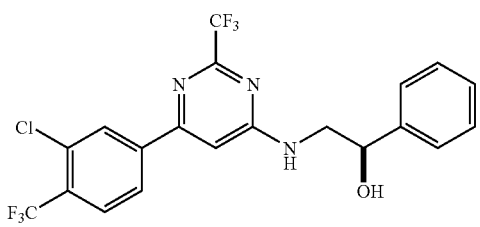 [SMILES: O[C@@H](CNc1cc(-c2ccc(C(F)(F)F)c(Cl)c2)nc(C(F)(F)F)n1)c1ccccc1]

MS (ESI): mass calcd. for $C_{20}H_{14}ClF_6N_3O$, 461.1; m/z found, 462.1 [M+H]$^+$. $^1$H NMR ((CD$_3$)$_2$CO): 8.38-8.19 (br m, 2H), 7.99 (d, J=8.4 Hz, 1H), 7.49-7.45 (m, 3H), 7.35 (t, J=7.8 Hz, 2H), 7.26 (t, J=7.2 Hz, 1H), 5.00 (br s, 1H), 3.97-3.54 (br m, 2H).

Example 94

(1R)-2-{[6-(3,4-Dichlorophenyl)-2-methylpyrimidin-4-yl]amino}-1-phenylethanol

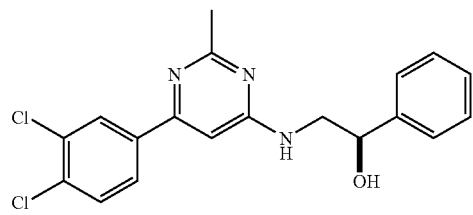 [SMILES: Cc1nc(NC[C@H](O)c2ccccc2)cc(-c2ccc(Cl)c(Cl)c2)n1]

MS (ESI): mass calcd. for $C_{19}H_{17}Cl_2N_3O$, 373.1; m/z found, 374.1 [M+H]$^+$. $^1$H NMR (CD$_3$OD): 8.06 (d, J=2.1 Hz, 1H), 7.79 (dd, J=2.1, 8.4 Hz, 1H), 7.61 (d, J=8.4 Hz, 1H), 7.45-7.39 (m, 2H), 7.37-7.30 (m, 2H), 7.28-7.22 (m, 1H), 6.67 (s, 1H), 4.91-4.88 (m, 1H), 3.80-3.67 (m, 1H), 3.59 (dd, J=7.4, 13.8 Hz, 1H), 2.49 (s, 3H).

Example 95

(1R)-2-{[6-(3,4-Dichlorophenyl)-pyrimidin-4-yl]amino}-1-phenylethanol

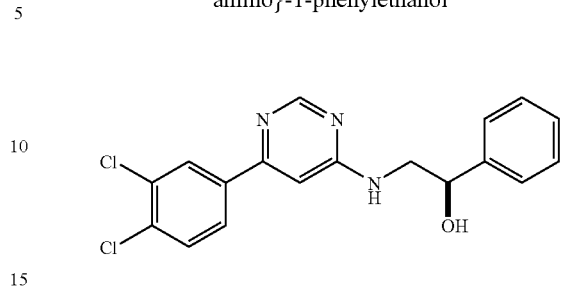

MS (ESI): mass calcd. for $C_{18}H_{15}Cl_2N_3O$, 359.1; m/z found, 360.1 [M+H]$^+$. $^1$H NMR (CD$_3$OD): 8.46 (s, 1H), 8.10 (d, J=2.1 Hz, 1H), 7.83 (dd, J=2.1, 8.4 Hz, 1H), 7.63 (d, J=8.4 Hz, 1H), 7.45-7.40 (m, 2H), 7.37-7.31 (m, 2H), 7.28-7.23 (m, 1H), 6.90 (s, 1H), 4.92-4.88 (m, 1H), 3.80-3.67 (m, 1H), 3.59 (dd, J=7.7, 13.7 Hz, 1H).

Example 96

(1R)-2-({6-[4-(Ethylsulfanyl)phenyl]pyrimidin-4-yl}amino)-1-Phenylethanol

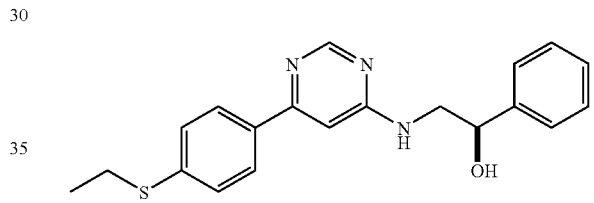

MS (ESI): mass calcd. for $C_{20}H_{21}N_3OS$, 351.1 m/z found, 352.2 [M+H]$^+$. $^1$H NMR (CD$_3$OD): 8.44 (s, 1H), 7.82 (d, J=8.8 Hz, 2H), 7.44-7.42 (m, 2H), 7.39 (d, J=8.8 Hz, 2H), 7.35-7.32 (m, 2H), 7.27-7.24 (m, 1H), 6.86 (s, 1H), 4.89 (dd, J=7.7, 4.4 Hz, 1H), 3.75-3.69 (m, 1H), 3.58 (dd, J=13.7, 7.7 Hz, 1H), 3.02 (q, J=7.1 Hz, 2H), 1.33 (t, J=7.1 Hz, 3H).

Example 97

(1R)-2-{[6-(3-Ethoxyphenyl)pyrimidin-4-yl]amino}-1-phenylethanol

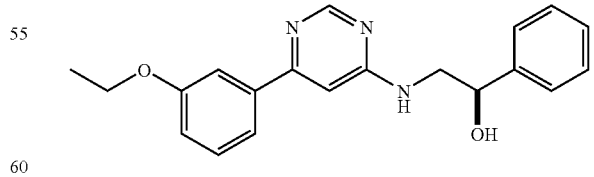

MS (ESI): mass calcd. for $C_{20}H_{21}N_3O_2$, 335.2; m/z found, 336.2 [M+H]$^+$. $^1$H NMR (CD$_3$OD): 8.44 (s, 1H), 7.44-7.41 (m, 4H), 7.38-7.32 (m, 3H), 7.28-7.24 (m, 1H), 7.01 (ddd, J=8.1, 2.5, 1.3 Hz, 1H), 6.87 (s, 1H), 4.91-4.89 (m, 1H), 4.10 (q, J=7.1 Hz, 2H), 3.76-3.68 (m, 1H), 3.61-3.55 (m, 1H), 1.41 (t, J=7.1 Hz, 3H).

Example 98

(1R)-1-Phenyl-2-{[6-(3-propoxyphenyl)pyrimidin-4-yl]amino}ethanol

MS (ESI): mass calcd. for $C_{21}H_{23}N_3O_2$, 349.2; m/z found, 350.2 [M+H]$^+$. $^1$H NMR (CD$_3$OD): 8.44 (s, 1H), 7.44-7.41 (m, 4H), 7.38-7.32 (m, 3H), 7.28-7.24 (m, 1H), 7.03-7.00 (m, 1H), 6.87 (s, 1H), 4.93-4.89 (m, 1H), 4.00 (t, J=6.6 Hz, 2H), 3.76-3.68 (m, 1H), 3.61-3.55 (m, 1H), 1.87-1.78 (m, 2H), 1.07 (t, J=7.3 Hz, 3H).

Example 99

(1R)-2-{[6-(3-Butoxyphenyl)pyrimidin-4-yl]amino}-1-phenylethanol

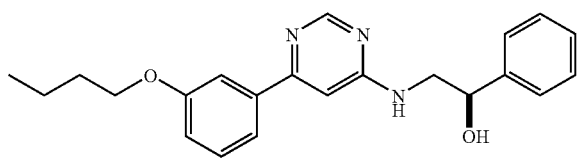 [SMILES: CCCCOc1cccc(-c2cc(NC[C@H](O)c3ccccc3)ncn2)c1]

MS (ESI): mass calcd. for $C_{22}H_{25}N_3O_2$, 363.2; m/z found, 364.1 [M+H]$^+$. $^1$H NMR (CD$_3$OD): 8.44 (s, 1H), 7.44-7.40 (m, 4H), 7.38-7.32 (m, 3H), 7.28-7.24 (m, 1H), 7.02 (ddd, J=8.1, 2.5, 1.0 Hz, 1H), 6.87 (s, 1H), 4.91-4.89 (m, 1H), 4.05 (t, J=6.6 Hz, 2H), 3.76-3.68 (m, 1H), 3.61-3.56 (m, 1H), 1.82-1.75 (m, 2H), 1.58-1.49 (m, 2H), 1.00 (t, J=7.6 Hz, 3H).

Example 100

(1R)-2-{[6-(1-Benzothiophen-5-yl)pyrimidin-4-yl]amino}-1-phenylethanol trifluoroacetic acid salt

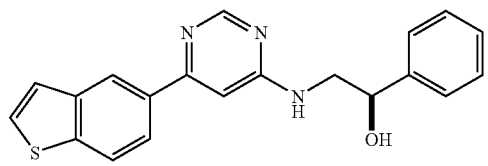 [SMILES: O[C@@H](CNc1cc(-c2ccc3sccc3c2)ncn1)c1ccccc1]

MS (ESI): mass calcd. for $C_{20}H_{17}N_3OS$, 347.1; m/z found, 348.1 [M+H]$^+$. $^1$H NMR (CD$_3$OD): 8.67 (s, 1H), 8.31 (d, J=1.6 Hz, 1H), 8.17 (d, J=8.2 Hz, 1H), 7.79 (d, J=5.5 Hz, 1H), 7.72 (dd, J=8.2, 1.7 Hz, 1H), 7.55 (d, J=5.5 Hz, 1H), 7.46-7.44 (m, 2H), 7.38-7.35 (m, 2H), 7.30-7.28 (m, 1H), 7.07 (s, 1H), 4.97-4.94 (m, 1H), 3.97-3.91 (m, 1H), 3.82 (dd, J=13.7, 7.7 Hz, 1H).

Example 101

(1R)-2-({6-[3-Chloro-4-(trifluoromethyl)phenyl]-2-(dimethylamino)pyrimidin-4-yl}amino)-1-phenylethanol trifluoroacetic acid salt

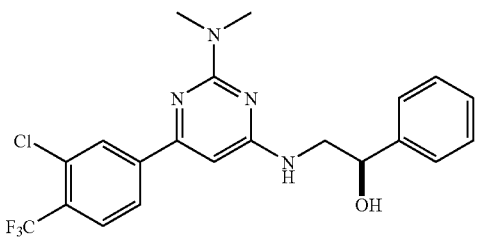

MS (ESI): mass calcd. for $C_{21}H_{20}ClF_3N_4O$, 436.1; m/z found, 437.1 [M+H]$^+$. $^1$H NMR (CD$_3$OD): 8.01 (s, 1H), 7.95 (d, J=8.2 Hz, 1H), 7.80 (d, J=7.7 Hz, 1H), 7.43-7.41 (m, 2H), 7.36-7.33 (m, 2H), 7.29-7.26 (m, 1H), 6.32 (s, 1H), 4.94-4.93 (m, 1H), 3.85-3.81 (m, 1H), 3.71 (dd, J=13.7, 7.7 Hz, 1H), 3.28 (s, 6H).

Example 102

(1R)-2-({6-[3-Fluoro-4-(trifluoromethyl)phenyl]-2-(methylsulfanyl)pyrimidin-4-yl}amino)-1-phenylethanol trifluoroacetic acid salt

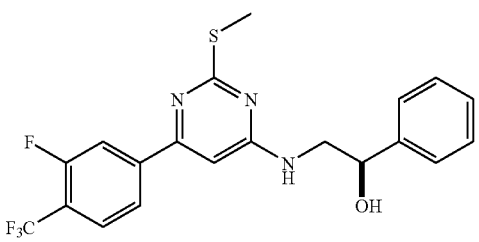

MS (ESI): mass calcd. for $C_{20}H_{17}F_4N_3OS$, 423.1; m/z found, 424.1 [M+H]$^+$. $^1$H NMR (CD$_3$OD): 7.86-7.83 (m, 3H), 7.43-7.42 (m, 2H), 7.36-7.33 (m, 2H), 7.28-7.25 (m, 1H), 6.68 (s, 1H), 4.95-4.92 (m, 1H), 3.87-3.78 (m, 1H), 3.73-3.69 (m, 1H), 2.62 (s, 3H).

The compounds in Examples 103-104 were prepared using methods analogous to those in Example 20, substituting the appropriate triazine in Step A, and the appropriate boronic acid in Step B.

Example 103

(1R)-1-Phenyl-2-({4-[4-(trifluoromethyl)phenyl]-1,3,5-triazin-2-yl}amino)ethanol trifluoroacetic acid salt

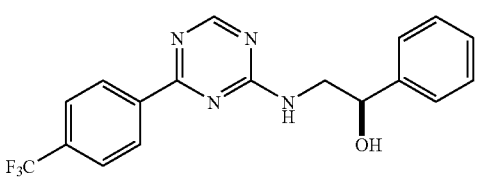

MS (ESI): mass calcd. for $C_{18}H_{15}F_3N_4O$, 360.3; m/z found, 361.2 [M+H]$^+$. $^1$H NMR (CD$_3$OD, TFA salt): 8.54-

8.53 (m, 2H), 7.83-7.79 (m, 2H), 7.49-7.43 (m, 2H), 7.36-7.21 (m, 3H), 4.97-4.95 (m, 1H), 3.88-3.60 (m, 2H).

Example 104

(1R)-2-({4-[3-Chloro-4-(trifluoromethyl)phenyl]-1,3,5-triazin-2-yl}amino)-1-phenylethanol trifluoroacetic acid salt

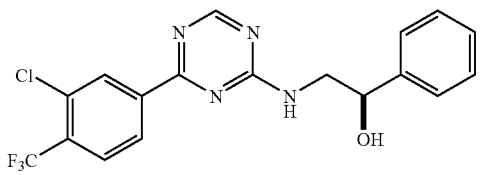

MS (ESI): mass calcd. for $C_{18}H_{14}ClF_3N_4O$, 394.8; m/z found, 395.1 [M+H]$^+$. $^1$H NMR (CD$_3$OD, TFA salt): 8.53 (m, 1H), 8.44-8.41 (m, 1H), 7.93-7.90 (dd, J=8.4, 12.0 Hz, 1H), 7.44 (t, J=9.0 Hz, 2H), 7.36-7.20 (m, 3H), 4.96-4.94 (m, 1H), 3.87-3.62 (m, 2H).

Example 105

(1R)-1-Phenyl-2-({6-[3-(trifluoromethyl)phenyl]pyrimidin-4-yl}amino)ethanol

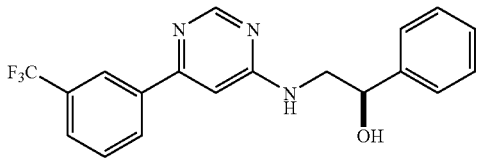 [SMILES: O[C@@H](CNc1cc(-c2cccc(C(F)(F)F)c2)ncn1)c1ccccc1]

The title compound was prepared in a manner similar to Example 1, with modifications to Step B as follows:

To a round bottomed flask were added 2-[(6-chloropyrimidin-4-yl)amino]-1-phenylethanol (62.4 mg, 0.25 mmol), 3-trifluoromethylphenyl boronic acid (71.2 mg, 0.38 mmol), K$_3$PO$_4$ (106.1 mg, 0.5 mmol), Pd(OAc)$_2$ (8.4 mg, 0.013 mmol) and 1,1'-bis(di-tert-butylphosphino)-ferrocene (5.9 mg, 0.013 mmol). The flask was then evacuated, backfilled with N$_2$, and charged with 1,4-dioxane (2.5 mL). The reaction mixture was heated at reflux for 2.5 h, before cooling to rt, diluting with EtOAc (15 mL), washing with water (2×10 mL), drying, and concentrating to dryness. The crude residue was purified (FCC) to yield the title compound (35.7 mg, 40%). MS (ESI): mass calcd. for $C_{19}H_{16}F_3N_3O$, 359.1; m/z found, 360.2 [M+H]$^+$. $^1$H NMR (CD$_3$OD): 8.50 (s, 1H), 8.23 (s, 1H), 8.15 (d, J=7.8 Hz, 1H), 7.78 (d, J=8.1 Hz, 1H), 7.69 (t, J=7.8 Hz, 1H), 7.44 (d, J=7.3 Hz, 2H), 7.37-7.33 (m, 2H), 7.28-7.24 (m, 1H), 6.96 (s, 1H), 4.93-4.90 (m, 1H), 3.79-3.69 (m, 1H), 3.61 (dd, J=13.6, 7.8 Hz, 1H).

Example 106

(1R)-1-Phenyl-2-[(6-{4-[(trifluoromethyl)oxy]phenyl}pyrimidin-4-yl)amino]ethanol

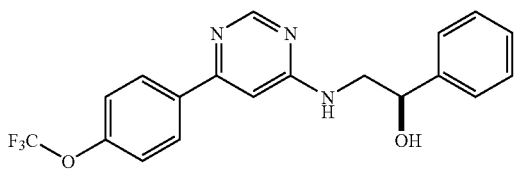

Step A. 4-Chloro-6-(4-trifluoromethoxy-phenyl)-pyrimidine. To a suspension of 4,6-dichloropyrimidine (2.18 g, 14.7 mmol) and 4-trifluoromethoxyphenyl boronic acid (3.32 g, 16.1 mmol) in DME (72 mL) and water (18 mL) were added K$_3$PO$_4$ (6.24 g, 29.4 mmol) and Pd(PPh$_3$)$_4$ (0.51 g, 0.44 mmol). The reaction mixture was heated at 85° C. under N$_2$ for 16 h. The reaction mixture was cooled to rt and the organic layer separated, dried (MgSO$_4$), and concentrated. The residue was purified (FCC) to give the title compound as a yellow solid (2.20 g, 54%).

Step B. To a solution consisting of 4-chloro-6-(4-trifluoromethoxy)phenylpyrimidine (0.137 g, 0.5 mmol) and (R)-2-amino-1-phenylethanol (75 mg, 0.55 mmol) and dioxane (2 mL) was added NaHCO$_3$ (252 mg, 3.0 mmol) at rt. The reaction mixture was heated at reflux for 18 h. The reaction mixture was cooled to rt and the precipitate was isolated via filtration. The precipitate was purified (FCC) to give a white solid (63 mg, 34%). MS (ESI): mass calcd. for $C_{19}H_{16}F_3N_3O_2$, 375.1; m/z found, 376.1 [M+H]$^+$. $^1$H NMR (CDCl$_3$): 8.67 (s, 1H), 8.01-7.97 (m, 2H), 7.46-7.21 (m, 7H), 6.70 (s, 1H), 5.38-5.18 (m, 1H), 5.05-4.95 (m, 1H), 4.00-3.77 (m, 1H), 3.68-3.54 (m, 1H).

The compounds in Examples 107-130 were synthesized in a similar manner to those described in Example 106, substituting the appropriate boronic acids and esters in Step A and amino alcohols (prepared analogously to Intermediate B or C) in Step B.

Example 107

1-(4-Nitrophenyl)-2-[(6-{4-[(trifluoromethyl)oxy]phenyl}pyrimidin-4-yl)amino]ethanol

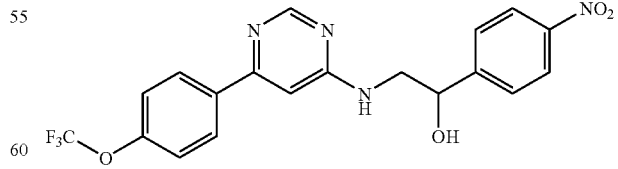

MS (ESI): mass calcd. for $C_{19}H_{15}F_3N_4O_4$, 420.1; m/z found, 421.1 [M+H]$^+$. $^1$H NMR (CDCl$_3$): 8.71 (s, 1H), 8.32-8.14 (m, 2H), 8.02-7.98 (m, 2H), 7.66-7.55 (m, 2H), 7.34-7.24 (m, 2H), 6.74 (d, J=1.1 Hz, 1H), 5.30-4.94 (m, 2H), 4.05-3.89 (m, 1H), 3.74-3.56 (m, 1H).

Example 108

2-[(6-{4-[(Trifluoromethyl)oxy]phenyl}pyrimidin-4-yl)amino]-1-[4-(trifluoromethyl)phenyl]ethanol

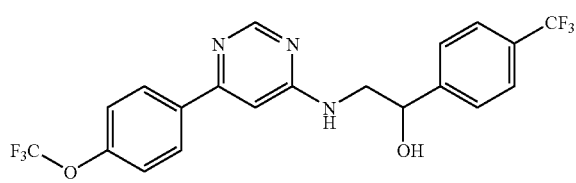 [SMILES: OC(CNc1cc(-c2ccc(OC(F)(F)F)cc2)ncn1)c1ccc(C(F)(F)F)cc1]

MS (ESI): mass calcd. for $C_{20}H_{15}F_6N_3O_2$, 443.1; m/z found, 444.1 [M+H]$^+$. $^1$H NMR (CDCl$_3$): 8.69 (s, 1H), 8.04-7.96 (m, 2H), 7.64 (d, J=8.2 Hz, 2H), 7.54 (d, J=8.4 Hz, 2H), 7.31 (d, J=8.0 Hz, 2H), 6.72 (d, J=1.2 Hz, 1H), 5.20 (m, 1H), 5.13-5.04 (m, 1H), 4.03-3.79 (m, 1H), 3.74-3.56 (m, 1H).

Example 109

1-(4-Chlorophenyl)-2-[(6-{4-[(trifluoromethyl)oxy]phenyl}pyrimidin-4-yl)amino]ethanol

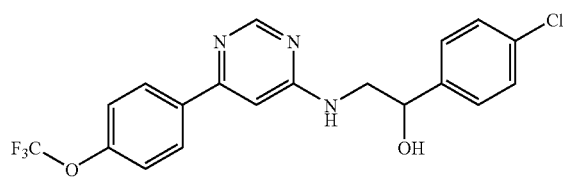 [SMILES: OC(CNc1cc(-c2ccc(OC(F)(F)F)cc2)ncn1)c1ccc(Cl)cc1]

MS (ESI): mass calcd. for $C_{19}H_{15}ClF_3N_3O_2$, 409.1; m/z found, 410.1 [M+H]$^+$. $^1$H NMR (CDCl$_3$): 8.67 (s, 1H), 8.04-7.96 (m, 2H), 7.35 (s, 4H), 7.31 (d, J=8.0 Hz, 2H), 6.71 (d, J=1.1 Hz, 1H), 5.25-5.16 (m, 1H), 5.05-4.93 (m, 1H), 4.05-3.78 (m, 1H), 3.68-3.50 (m, 1H).

Example 110

4-{1-Hydroxy-2-[(6-{4-[(trifluoromethyl)oxy]phenyl}pyrimidin-4-yl)amino]ethyl}phenol

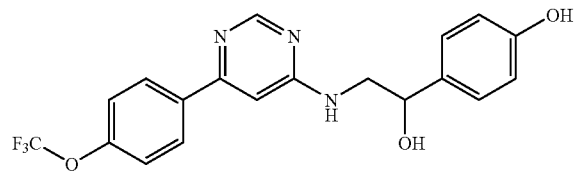 [SMILES: Oc1ccc(C(O)CNc2cc(-c3ccc(OC(F)(F)F)cc3)ncn2)cc1]

MS (ESI): mass calcd. for $C_{19}H_{16}F_3N_3O_3$, 391.1; m/z found, 392.2 [M+H]$^+$. $^1$H NMR (CDCl$_3$): 8.66 (s, 1H), 8.07-7.89 (m, 2H), 7.34-7.27 (m, 4H), 6.91-6.76 (m, 2H), 6.70 (d, J=1.1 Hz, 1H), 5.37-5.19 (m, 1H), 5.08-4.85 (m, 1H), 3.90-3.74 (m, 1H), 3.66-3.51 (m, 1H).

Example 111

1-[4-(Methyloxy)phenyl]-2-[(6-{4-[(trifluoromethyl)oxy]phenyl}-pyrimidin-4-yl)amino]ethanol

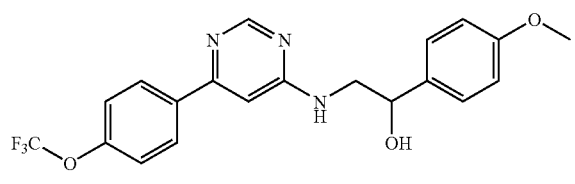 [SMILES: COc1ccc(C(O)CNc2cc(-c3ccc(OC(F)(F)F)cc3)ncn2)cc1]

MS (ESI): mass calcd. for $C_{20}H_{18}F_3N_3O_3$, 405.1; m/z found, 406.2 [M+H]$^+$. $^1$H NMR (CDCl$_3$): 8.66 (s, 1H), 8.03-7.96 (m, 2H), 7.32 (m, 4H), 6.97-6.83 (m, 2H), 6.69 (d, J=1.0 Hz, 1H), 5.43-5.12 (m, 1H), 5.00-4.83 (m, 1H), 3.93-3.73 (m, 4H), 3.66-3.53 (m, 1H).

Example 112

4-{1-Hydroxy-2-[(6-{4-[(trifluoromethyl)oxy]phenyl}pyrimidin-4-yl)amino]ethyl}-2-(methyloxy)phenol

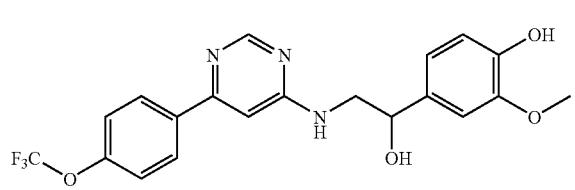 [SMILES: COc1cc(C(O)CNc2cc(-c3ccc(OC(F)(F)F)cc3)ncn2)ccc1O]

MS (ESI): mass calcd. for $C_{20}H_{18}F_3N_3O_4$, 421.1; m/z found, 422.2 [M+H]$^+$. $^1$H NMR (CDCl$_3$): 8.66 (s, 1H), 8.10-7.85 (m, 2H), 7.31 (d, J=8.2 Hz, 2H), 7.00-6.84 (m, 3H), 6.70 (s, 1H), 5.63 (s, 1H), 5.39-5.17 (m, 1H), 4.99-4.83 (m, 1H), 3.90 (s, 3H), 3.87-3.75 (m, 1H), 3.68-3.54 (m, 1H).

Example 113

1-(4-Fluorophenyl)-2-[(6-{4-[(trifluoromethyl)oxy]phenyl}pyrimidin-4-yl)amino]ethanol

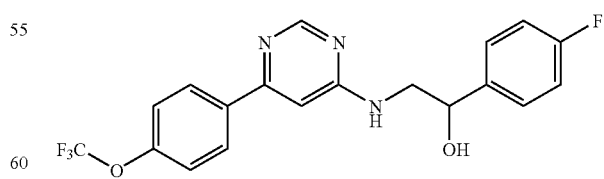

MS (ESI): mass calcd. for $C_{19}H_{15}F_4N_3O_2$, 393.1; m/z found, 394.1 [M+H]$^+$. $^1$H NMR (CDCl$_3$): 8.67 (s, 1H), 8.08-7.92 (m, 2H), 7.45-7.35 (m, 2H), 7.33-7.29 (m, 2H), 7.12-7.01 (m, 2H), 6.78-6.64 (m, 1H), 5.36-5.16 (m, 1H), 5.08-4.91 (m, 1H), 3.95-3.76 (m, 1H), 3.67-3.52 (m, 1H).

Example 114

1-(3,4-Dichlorophenyl)-2-[(6-{4-[(trifluoromethyl)oxy]phenyl}-pyrimidin-4-yl)amino]ethanol

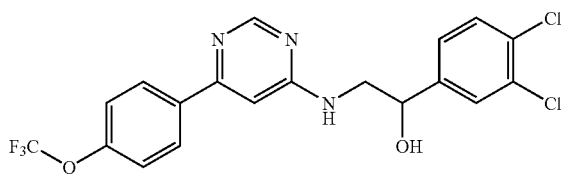 [SMILES: OC(CNc1cc(-c2ccc(OC(F)(F)F)cc2)ncn1)c1ccc(Cl)c(Cl)c1]

MS (ESI): mass calcd. for $C_{19}H_{14}Cl_2F_3N_3O_2$, 443.0; m/z found, 444.1 [M+H]$^+$. $^1$H NMR (CDCl$_3$): 8.68 (s, 1H), 8.09-7.85 (m, 2H), 7.53 (d, J=2.0 Hz, 1H), 7.44 (d, J=8.3 Hz, 1H), 7.31 (d, J=8.0 Hz, 2H), 7.24 (d, J=2.0 Hz, 1H), 6.73 (d, J=1.1 Hz, 1H), 5.22-5.16 (m, 1H), 5.02-4.93 (m, 1H), 3.96-3.83 (m, 1H), 3.66-3.51 (m, 1H).

Example 115

1-(2-Chlorophenyl)-2-[(6-{4-[(trifluoromethyl)oxy]phenyl}pyrimidin-4-yl)amino]ethanol

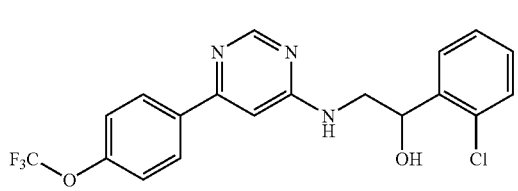 [SMILES: OC(CNc1cc(-c2ccc(OC(F)(F)F)cc2)ncn1)c1ccccc1Cl]

MS (ESI): mass calcd. for $C_{19}H_{15}ClF_3N_3O_2$, 409.1; m/z found, 410.1 [M+H]$^+$. $^1$H NMR (CDCl$_3$): 8.68 (s, 1H), 8.09-7.88 (m, 2H), 7.65 (dd, J=7.6, 1.7 Hz, 1H), 7.39-7.20 (m, 5H), 6.75 (s, 1H), 5.40-5.34 (m, 1H), 5.33-5.22 (m, 1H), 3.98-3.84 (m, 1H), 3.77-3.62 (m, 1H).

Example 116

1-(3-Chlorophenyl)-2-[(6-{4-[(trifluoromethyl)oxy]phenyl}pyrimidin-4-yl)amino]ethanol

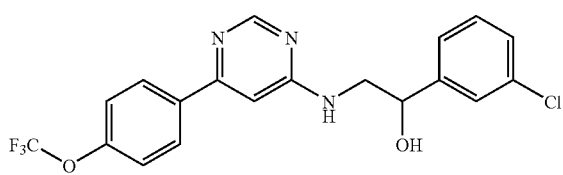 [SMILES: OC(CNc1cc(-c2ccc(OC(F)(F)F)cc2)ncn1)c1cccc(Cl)c1]

MS (ESI): mass calcd. for $C_{19}H_{15}ClF_3N_3O_2$, 409.1; m/z found, 410.1 [M+H]$^+$. $^1$H NMR (CDCl$_3$): 8.68 (s, 1H), 8.03-7.97 (m, 2H), 7.46-7.40 (m, 1H), 7.34-7.28 (m, 5H), 6.72 (d, J=1.1 Hz, 1H), 5.29-5.18 (m, 1H), 5.03-4.92 (m, 1H), 4.02-3.82 (m, 1H), 3.70-3.53 (m, 1H).

Example 117

1-[3-(Methyloxy)phenyl]-2-[(6-{4-[(trifluoromethyl)oxy]phenyl}-pyrimidin-4-yl)amino]ethanol

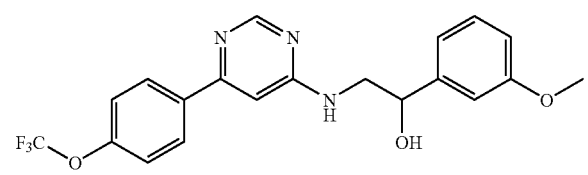 [SMILES: COc1cccc(C(O)CNc2cc(-c3ccc(OC(F)(F)F)cc3)ncn2)c1]

MS (ESI): mass calcd. for $C_{20}H_{18}F_3N_3O_3$, 405.1; m/z found, 406.2 [M+H]$^+$. $^1$H NMR (CDCl$_3$): 8.67 (s, 1H), 8.07-7.91 (m, 2H), 7.34-7.27 (m, 3H), 7.06-6.94 (m, 2H), 6.90-6.80 (m, 1H), 6.70 (d, J=1.0 Hz, 1H), 5.36-5.17 (m, 1H), 5.04-4.92 (m, 1H), 3.96-3.76 (m, 4H), 3.70-3.56 (m, 1H).

Example 118

1-[2-(Methyloxy)phenyl]-2-[(6-{4-[(trifluoromethyl)oxy]phenyl}-pyrimidin-4-yl)amino]ethanol

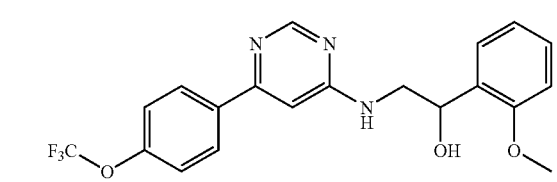 [SMILES: COc1ccccc1C(O)CNc1cc(-c2ccc(OC(F)(F)F)cc2)ncn1]

MS (ESI): mass calcd. for $C_{20}H_{18}F_3N_3O_3$, 405.13; m/z found, 406.2 [M+H]$^+$. $^1$H NMR (CDCl$_3$): 8.67 (s, 1H), 8.09-7.89 (m, 2H), 7.47 (dd, J=7.5, 1.4 Hz, 1H), 7.35-7.29 (m, 3H), 7.01-6.98 (m, 1H), 6.93 (d, J=8.3 Hz, 1H), 6.74 (s, 1H), 5.50-5.30 (m, 1H), 5.26-5.18 (m, 1H), 3.97-3.81 (m, 4H), 3.73-3.58 (m, 1H).

Example 119

(1R,2S)-1-Phenyl-2-[(6-{4-[(trifluoromethyl)oxy]phenyl}pyrimidin-4-yl)amino]propan-1-ol

MS (ESI): mass calcd. for $C_{20}H_{18}F_3N_3O_2$, 389.1; m/z found, 390.2 [M+H]$^+$. $^1$H NMR (CDCl$_3$): 8.60 (s, 1H), 7.95 (d, J=8.8 Hz, 2H), 7.38-7.35 (m, 4H), 7.32-7.27 (m, 3H), 6.65 (d, J=1.0 Hz, 1H), 5.11 (br s, 1H), 4.93 (d, J=2.8 Hz, 1H), 4.67 (br s, 1H), 4.43 (brs, 1H), 1.13 (d, J=7.1 Hz, 3H).

Example 120

(1R,2R)-2-[Methyl(6-{4-[(trifluoromethyl)oxy]phenyl}pyrimidin-4-yl)amino]-1-phenylpropan-1-ol

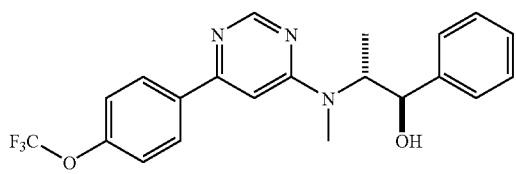

MS (ESI): mass calcd. for $C_{21}H_{20}F_3N_3O_2$, 403.2; m/z found, 404.2 [M+H]$^+$. $^1$H NMR (CDCl$_3$): 8.70 (s, 1H), 8.05-7.99 (m, 2H), 7.45-7.29 (m, 7H), 6.77 (s, 1H), 4.97-4.81 (m, 1H), 4.78-4.70 (m, 2H), 2.98 (s, 3H), 1.18 (d, J=7.2 Hz, 3H).

Example 121

(1R,2S)-2-[Methyl(6-{4-[(trifluoromethyl)oxy]phenyl}pyrimidin-4-yl)amino]-1-phenylpropan-1-ol

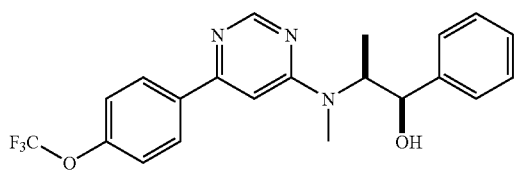 [SMILES: C[C@H](Nc1cc(-c2ccc(OC(F)(F)F)cc2)ncn1)[C@H](O)c1ccccc1]

MS (ESI): mass calcd. for $C_{21}H_{20}F_3N_3O_2$, 403.2; m/z found, 404.2 [M+H]$^+$. $^1$H NMR (CDCl$_3$): 8.67 (d, J=1.0 Hz, 1H), 8.10-7.88 (m, 2H), 7.41-7.27 (m, 7H), 6.70 (d, J=1.1 Hz, 1H), 4.99-4.84 (m, 3H), 2.74 (s, 3H), 1.33 (d, J=7.1 Hz, 3H).

Example 122

1-(2,2-Difluoro-1,3-benzodioxol-5-yl)-2-[(6-{4-[(trifluoromethyl)oxy]phenyl}pyrimidin-4-yl)amino]ethanol

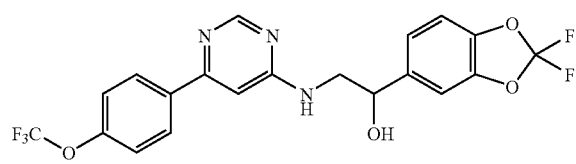 [SMILES: OC(CNc1cc(-c2ccc(OC(F)(F)F)cc2)ncn1)c1ccc2c(c1)OC(F)(F)O2]

MS (ESI): mass calcd. for $C_{20}H_{14}F_5N_3O_4$, 455.1; m/z found, 456.1 [M+H]$^+$. $^1$H NMR (CDCl$_3$): 8.68 (s, 1H), 8.09-7.91 (m, 2H), 7.37-7.00 (m, 5H), 6.73 (s, 1H), 5.30-5.18 (m, 1H), 5.06-4.93 (m, 1H), 3.93-3.79 (m, 1H), 3.68-3.48 (m, 1H).

Example 123

1-Pyridin-2-yl-2-[(6-{4-[(trifluoromethyl)oxy]phenyl}pyrimidin-4-yl)amino]ethanol

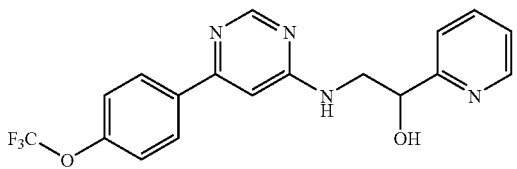 [SMILES: OC(CNc1cc(-c2ccc(OC(F)(F)F)cc2)ncn1)c1ccccn1]

MS (ESI): mass calcd. for $C_{18}H_{15}F_3N_4O_2$, 376.1; m/z found, 377.2 [M+H]$^+$. $^1$H NMR (CDCl$_3$): 8.64 (s, 1H), 8.59-8.54 (m, 1H), 8.01-7.96 (m, 2H), 7.75-7.71 (m, 1H), 7.51-7.44 (m, 1H), 7.34-7.20 (m, 3H), 6.70 (d, J=1.1 Hz, 1H), 5.48-5.37 (m, 1H), 5.04-5.00 (m, 1H), 4.15-3.95 (m, 1H), 3.80-3.60 (m, 1H).

Example 124

1-Pyridin-3-yl-2-[(6-{4-[(trifluoromethyl)oxy]phenyl}pyrimidin-4-yl)amino]ethanol

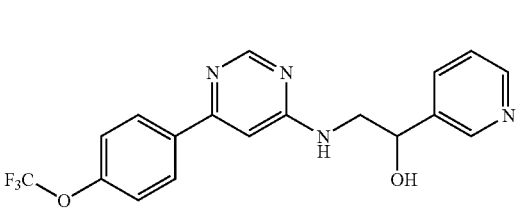 [SMILES: OC(CNc1cc(-c2ccc(OC(F)(F)F)cc2)ncn1)c1cccnc1]

MS (ESI): mass calcd. for $C_{18}H_{15}F_3N_4O_2$, 376.1; m/z found, 377.1 [M+H]$^+$. $^1$H NMR (CDCl$_3$): 8.71-8.50 (m, 3H), 8.11-7.91 (m, 2H), 7.82-7.75 (m, 1H), 7.35-7.28 (m, 3H), 6.73 (s, 1H), 5.49-5.36 (m, 1H), 5.11-5.00 (m, 1H), 3.99-3.85 (m, 1H), 3.73-3.56 (m, 1H).

Example 125

1-Pyridin-4-yl-2-[(6-{4-[(trifluoromethyl)oxy]phenyl}pyrimidin-4-yl)amino]ethanol MS (ESI): mass calcd. for $C_{18}H_{15}F_3N_4O_2$, 376.1; m/z found, 377.1 [M+H]$^+$. $^1$H NMR (CDCl$_3$): 8.68 (s, 1H), 8.60-8.53 (m, 2H), 8.05-7.89 (m, 2H), 7.38-7.28 (m, 4H), 6.73 (s, 1H), 5.46-5.35 (m, 1H), 5.08-4.92 (m, 1H), 4.02-3.90 (m, 1H), 3.70-3.53 (m, 1H).

Example 126

1-(3,5-Dichlorophenyl)-2-[(6-{4-[(trifluoromethyl)oxy]phenyl}-pyrimidin-4-yl)amino]ethanol

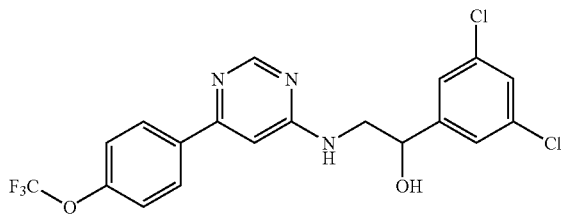 [SMILES: OC(CNc1cc(-c2ccc(OC(F)(F)F)cc2)ncn1)c1cc(Cl)cc(Cl)c1]

MS (ESI): mass calcd. for $C_{19}H_{14}Cl_2F_3N_3O_2$, 443.0; m/z found, 444.1 [M+H]$^+$. $^1$H NMR (CDCl$_3$): 8.69 (s, 1H), 8.04-7.97 (m, 2H), 7.35-7.28 (m, 5H), 6.74 (d, J=1.1 Hz, 1H), 5.25-5.18 (m, 1H), 5.00-4.92 (m, 1H), 3.96-3.82 (m, 1H), 3.66-3.53 (m, 1H).

Example 127

1-(1,3-Benzodioxol-5-yl)-2-[(6-{4-[(trifluoromethyl)oxy]phenyl}-pyrimidin-4-yl)amino]ethanol

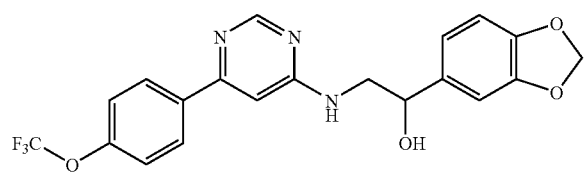 [SMILES: OC(CNc1cc(-c2ccc(OC(F)(F)F)cc2)ncn1)c1ccc2c(c1)OCO2]

MS (ESI): mass calcd. for $C_{20}H_{16}F_3N_3O_4$, 419.1; m/z found, 420.1 [M+H]$^+$. $^1$H NMR (CDCl$_3$): 8.66 (s, 1H), 8.08-7.89 (m, 2H), 7.33-7.29 (m, 2H), 6.93 (d, J=1.6 Hz, 1H), 6.86 (dd, J=8.0, 1.3 Hz, 1H), 6.80 (d, J=7.9 Hz, 1H), 6.71 (d, J=1.1 Hz, 1H), 5.96 (s, 2H), 5.28-5.21 (m, 1H), 4.98-4.86 (m, 1H), 3.87-3.75 (m, 1H), 3.65-3.52 (m, 1H).

Example 128

(1S)-2-({6-[3-Chloro-4-(trifluoromethyl)phenyl]pyrimidin-4-yl}amino)-1-phenylethanol

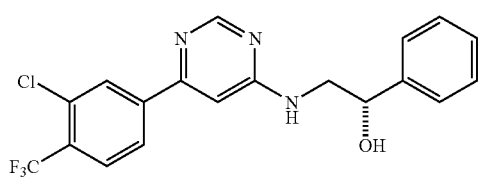

MS (ESI): mass calcd. for $C_{19}H_{15}ClF_3N_3O$, 393.1; m/z found, 394.1 [M+H]$^+$. $^1$H NMR (CD$_3$OD): 8.50 (s, 1H), 8.16 (s, 1H), 8.01-7.98 (m, 1H), 7.88 (d, J=8.3 Hz, 1H), 7.44 (d, J=7.3 Hz, 2H), 7.37-7.34 (m, 2H), 7.27-7.24 (m, 1H), 6.97 (s, 1H), 4.93-4.90 (m, 1H), 3.79-3.71 (m, 1H), 3.60 (dd, J=13.6, 7.6 Hz, 1H).

Example 129

(1R)-2-({6-[3-Fluoro-4-(1-hydroxyethyl)phenyl]pyrimidin-4-yl}amino)-1-phenylethanol trifluoroacetic acid salt

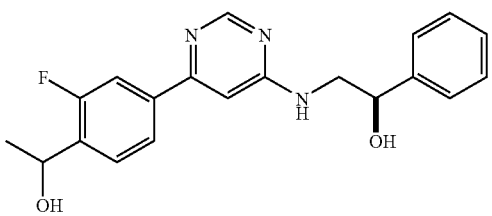 [SMILES: CC(O)c1ccc(-c2cc(NC[C@H](O)c3ccccc3)ncn2)cc1F]

To a solution consisting of 1-[2-fluoro-4-(6-{[(2R)-2-hydroxy-2-phenylethyl]amino}pyrimidin-4-yl)phenyl]ethanone (46.5 mg, 0.10 mmol) in ethanol (1 mL) at 0° C. was added NaBH$_4$ (5.7 mg, 0.15 mmol). The reaction mixture was allowed to warm to rt and stirred for 10 min. Additional NaBH$_4$ (5.7 mg, 0.15 mmol) was added and the reaction mixture was allowed to stir at rt for 15 min. An additional amount of NaBH$_4$ (5.7 mg, 0.15 mmol) was added and stirring was continued at rt for an additional hour. The reaction mixture was then diluted with water (2 mL) and extracted with CH$_2$Cl$_2$ (10 mL). The organic extract was dried (Na$_2$SO$_4$) and concentrated. The crude material was purified by reverse phase chromatography to yield the title compound (32.2 mg, 69%). MS (ESI): mass calcd. for $C_{20}H_{20}FN_3O_2$, 353.2; m/z found, 354.2 [M+H]$^+$. $^1$H NMR (CD$_3$OD): 8.66 (s, 1H), 7.80 (t, J=7.8 Hz, 1H), 7.64 (dd, J=8.1, 1.8 Hz, 1H), 7.55 (m, 1H), 7.43 (d, J=7.1 Hz, 2H), 7.38-7.34 (m, 2H), 7.30-7.27 (m, 1H), 5.18 (q, J=6.6 Hz, 1H), 4.95-4.92 (m, 1H), 3.92 (dd, J=13.6, 4.3 Hz, 1H), 3.80 (dd, J=13.6, 7.6 Hz, 1H), 1.48 (d, J=6.6 Hz, 3H).

Example 130

2-({6-[3-Chloro-4-(trifluoromethyl)phenyl]pyrimidin-4-yl}amino)-1-[3-(trifluoromethoxy)phenyl]ethanol trifluoroacetic acid salt

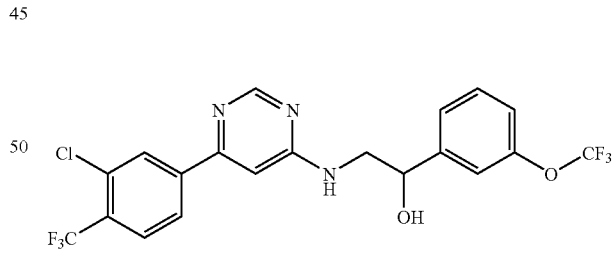

Step A: 2-Amino-1-(3,4-difluoro-phenyl)-ethanol. To a solution consisting of 3,4-difluorobenzaldehyde (3.85 g, 27.1 mmol), zinc iodide (104.9 mg, 0.329 mmol) and THF (5 mL) at 0° C. under nitrogen was added TMSCN (4.60 mL, 33.9 mmol). The resultant mixture was stirred for 3.5 h at 0° C. and then cannulated into a 0° C. suspension of LiAlH$_4$ (1.41 g, 67.7 mmol) in THF (80 mL). The resultant mixture was allowed to gradually warm to rt with stirring for 21 h. The reaction mixture was then re-cooled to 0° C. and carefully treated with water (2.57 mL) followed by 15% aq. NaOH (2.57 mL) and lastly with water (7.7 mL). The resultant mixture was stirred for 1 h, the solids removed by vacuum filtration and the filtrate concentrated. The resulting crude product was purified by FCC(CH₂Cl₂/MeOH/NH₃) to give the desired product.

Step B. A vial containing a solution of 4-chloro-6-(3-chloro-4-trifluoromethyl-phenyl)-pyrimidine (59.9 mg, 0.204 mmol), 2-amino-1-(3-trifluoromethoxy-phenyl)-ethanol (72.4 mg, 0.327 mmol), n-BuOH (2 mL) and DIPEA (0.15 mL, 0.86 mmol) was flushed with N₂, capped and heated at 100° C. for 20 h. The reaction mixture was purified directly by reverse-phase HPLC. MS (ESI): mass calcd. for $C_{20}H_{14}ClF_6N_3O_2$, 477.8; m/z found, 334.1 [M+H]⁺. ¹H NMR ((CD₃)₂CO): 10.06 (br hump, 2H), 8.92-8.77 (m, 1H), 8.35-8.23 (m, 1H), 8.10-8.00 (m, 2H), 7.67-7.34 (m, 4H), 7.24 (d, J=6.6 Hz, 1H), 5.20-5.01 (br m, 1H), 4.29-3.82 (br m, 2H).

The compounds in Examples 131-135 were prepared using methods analogous to those described in Example 130, using the appropriate aldehydes in Step A.

Example 131

2-({6-[3-Chloro-4-(trifluoromethyl)phenyl]pyrimidin-4-yl}amino)-1-(3-fluorophenyl)ethanol trifluoroacetic acid salt

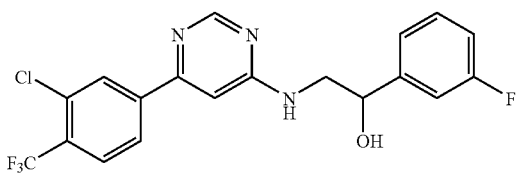 [SMILES: OC(CNc1cc(-c2ccc(C(F)(F)F)c(Cl)c2)ncn1)c1cccc(F)c1]

MS (ESI): mass calcd. for $C_{19}H_{14}ClF_4N_3O$, 411.8; m/z found, 412.1 [M+H]⁺. ¹H NMR ((CD₃)₂CO): 10.52 (br hump, 2H), 8.95-8.81 (m, 1H), 8.34-8.21 (m, 1H), 8.07-8.03 (m, 1H), 7.44-7.25 (m, 3H), 7.05-7.02 (m, 1H), 5.15-4.98 (br m, 1H), 4.05-3.53 (br m, 2H).

Example 132

2-[6-(3-Chloro-4-trifluoromethyl-phenyl)-pyrimidin-4-ylamino]-1-(3,4-difluoro-phenyl)-ethanol trifluoroacetic acid salt

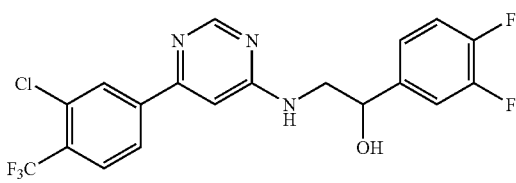 [SMILES: OC(CNc1cc(-c2ccc(C(F)(F)F)c(Cl)c2)ncn1)c1ccc(F)c(F)c1]

MS (ESI): mass calcd. for $C_{19}H_{13}ClF_5N_3O$, 429.8; m/z found, 430.1 [M+H]⁺. ¹H NMR ((CD₃)₂CO): 9.65 (br hump, 2H), 8.92-8.71 (m, 1H), 8.36-8.22 (m 1H), 8.08-8.03 (m, 1H), 7.44-7.19 (m, 3H), 5.13-4.96 (br m, 1H), 4.01-3.53 (br m, 2H).

Example 133

1-(4-Chloro-3-fluoro-Phenyl)-2-[6-(3-chloro-4-trifluoromethyl-phenyl)-pyrimidin-4-ylamino]-ethanol trifluoroacetic acid salt

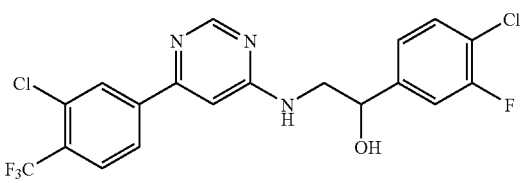 [SMILES: OC(CNc1cc(-c2ccc(C(F)(F)F)c(Cl)c2)ncn1)c1ccc(Cl)c(F)c1]

MS (ESI): mass calcd. for $C_{19}H_{13}Cl_2F_4N_3O$, 446.2; m/z found, 446.1 [M+H]⁺. ¹H NMR ((CD₃)₂CO): 10.06 (br hump, 2H), 8.91-8.62 (m, 1H), 8.34-8.02 (m, 2H), 7.66-7.34 (m, 3H), 5.15-5.10 (br m, 1H), 4.01-3.80 (br m, 2H).

Example 134

1-(3-Chloro-4-fluorophenyl)-2-({6-[3-chloro-4-(trifluoromethyl)phenyl]pyrimidin-4-yl}amino)ethanol trifluoroacetic acid salt

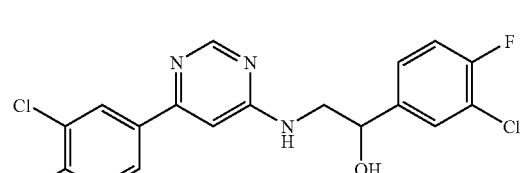

MS (ESI): mass calcd. for $C_{19}H_{13}Cl_2F_4N_3O$, 446.2; m/z found, 446.1 [M+H]⁺. ¹H NMR ((CD₃)₂CO): 10.14 (br hump, 2H), 8.92-8.80 (m, 1H), 8.34-8.20 (m, 1H), 8.07-7.99 (m, 1H), 7.67-7.57 (m, 1H), 7.48-7.41 (m, 1H), 7.29-7.21 (m, 1H), 5.14-4.96 (br m, 1H), 4.01-3.55 (br m, 2H).

Example 135

2-({6-[3-Chloro-4-(trifluoromethyl)phenyl]pyrimidin-4-yl}amino)-1-[3-(trifluoromethyl)phenyl]ethanol trifluoroacetic acid salt

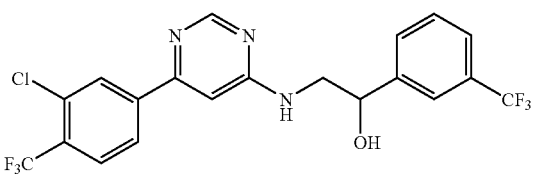 [SMILES: OC(CNc1cc(-c2ccc(C(F)(F)F)c(Cl)c2)ncn1)c1cccc(C(F)(F)F)c1]

MS (ESI): mass calcd. for $C_{20}H_{14}ClF_6N_3O$, 461.8; m/z found, 462.1 [M+H]⁺. ¹H NMR ((CD₃)₂CO): 10.35 (br hump, 2H), 8.92-8.81 (m, 1H), 8.34-8.21 (m, 1H), 8.09-8.02 (m, 1H), 7.84-7.72 (m, 2H), 7.65-7.20 (m, 2H), 5.25-5.08 (br m, 1H), 4.07-3.59 (br m, 2H).

Example 136

(1R)-2-{[2-Cyclopropyl-6-(3,4-dichlorophenyl)pyrimidin-4-yl]amino}-1-phenylethanol

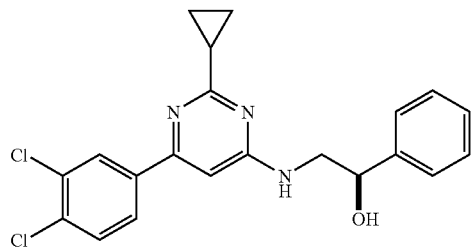 [SMILES: O[C@@H](CNc1cc(-c2ccc(Cl)c(Cl)c2)nc(C2CC2)n1)c1ccccc1]

Step A: 2-Cyclopropyl-6-(3,4-dichloro-phenyl)-pyrimidin-4-ol. To a solution consisting of 3-(3,4-dichlorophenyl)-3-oxo-propionic acid ethyl ester (252 mg, 0.967 mmol) and MeOH were added cyclopropylcarbamidine hydrochloride (140 mg, 1.16 mmol) and potassium tert-butoxide (266 mg, 2.37 mmol). The reaction mixture was stirred at rt overnight, then concentrated. Water and $CH_2Cl_2$ were added, and the mixture was adjusted to pH 7 with glacial acetic acid. The layers were separated, and the aqueous phase was extracted with EtOAc. The organics were combined, dried ($Na_2SO_4$), and concentrated. The crude residue was purified (FCC) to give the title compound as a white solid (133 mg, 49%).

Step B. 4-Chloro-2-cyclopropyl-6-(3,4-dichloro-phenyl)-Pyrimidine. To a suspension of 2-cyclopropyl-6-(3,4-dichloro-phenyl)-pyrimidin-4-ol (131 mg, 0.467 mmol) in acetonitrile was added $POCl_3$ (0.13 mL, 1.42 mmol). The reaction mixture was heated at 80° C. for 105 min, cooled to rt, quenched with satd. aq. $NaHCO_3$, and extracted with EtOAc. The organic layer was dried ($Na_2SO_4$) and concentrated. The crude residue was purified (FCC) to give the title compound (113 mg, 81%).

Step C. A mixture of 4-chloro-2-cyclopropyl-6-(3,4-dichloro-phenyl)-pyrimidine (108 mg, 0.364 mmol), (R)-(−)-2-amino-1-phenylethanol (67.2 mg, 0.490 mmol), and $NaHCO_3$ (190.1 mg, 2.26 mmol) and 1,4-dioxane was refluxed for 48 h. The mixture was poured into water and extracted with $CH_2Cl_2$. The organic layer was dried ($Na_2SO_4$) and concentrated. The crude residue was purified (FCC) to give the title compound as a white solid (119.4 mg, 82%). MS (ESI): mass calcd. for $C_{21}H_{19}Cl_2N_3O$, 399.09; m/z found, 400.1 [M+H]$^+$. $^1$H NMR ($CD_3OD$): 8.13-8.05 (m, 1H), 7.85-7.79 (m, 1H), 7.64-7.58 (m, 1H), 7.45-7.31 (m, 4H), 7.30-7.23 (m, 1H), 6.68-6.59 (m, 1H), 4.93-4.85 (m, 1H), 3.81-3.65 (m, 1H), 3.56-3.48 (m, 1H), 2.16-2.01 (m, 1H), 1.16-1.09 (m, 2H), 1.02-0.94 (m, 2H).

Example 137

(1R)-2-{[6-(3,4-Dichlorophenyl)-2-(1-methylethyl)pyrimidin-4-yl]amino}-1-phenylethanol

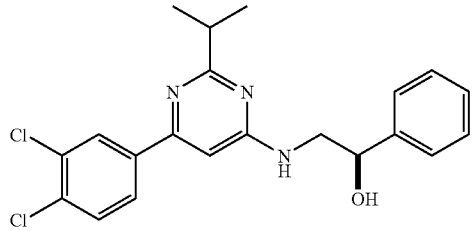 [SMILES: CC(C)c1nc(NC[C@H](O)c2ccccc2)cc(-c2ccc(Cl)c(Cl)c2)n1]

The title compound was prepared in a similar manner to that in Example 136, substituting isobutyramidine in Step A. MS (ESI): mass calcd. for $C_{21}H_{21}Cl_2N_3O$, 401.11; m/z found, 402.1 [M+H]$^+$. $^1$H NMR ($CD_3OD$): 8.14-8.08 (m, 1H), 7.87-7.80 (m, 1H), 7.63-7.57 (m, 1H), 7.44-7.38 (m, 2H), 7.36-7.29 (m, 2H), 7.27-7.22 (m, 1H), 6.71-6.64 (m, 1H), 4.96-4.90 (m, 1H), 3.84-3.70 (m, 1H), 3.61-3.53 (m, 1H), 3.06-2.95 (m, 1H), 1.36-1.27 (m, 6H).

Example 138

(1R)-2-({6-[3-Chloro-4-(trifluoromethyl)phenyl]-2-(methylsulfonyl)pyrimidin-4-yl}amino)-1-phenylethanol

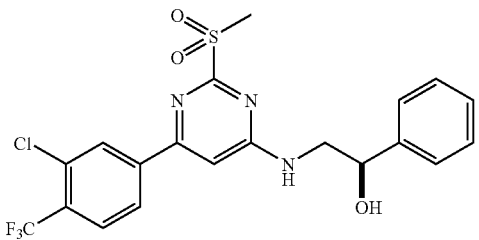 [SMILES: CS(=O)(=O)c1nc(NC[C@H](O)c2ccccc2)cc(-c2ccc(C(F)(F)F)c(Cl)c2)n1]

To a solution consisting of (1R)-2-({6-[3-chloro-4-(trifluoromethyl)phenyl]-2-(methylsulfanyl)pyrimidin-4-yl}amino)-1-phenylethanol (55.4 mg, 0.10 mmol) and $CH_2Cl_2$ (2 mL) was slowly added 3-chloroperoxybenzoic acid (45 mg, 0.20 mmol). The reaction mixture was stirred at rt for 3 h and then washed with aq. $Na_2SO_3$ (4 mL×2) followed by a satd. aq. $NaHCO_3$ (5 mL×2). The layers were separated and extracted with $CH_2Cl_2$ (15 mL), dried ($Na_2SO_4$) and concentrated. The crude material was purified by reverse phase chromatography to yield the final product (20 mg, 43%). MS (ESI): mass calcd. for $C_{20}H_{17}ClF_3N_3O_3S$, 471.1; m/z found, 472.1 [M+H]$^+$. $^1$H NMR ($CD_3OD$): 8.30 (s, 1H), 8.14 (d, J=8.2 Hz, 1H), 7.90 (d, J=8.2 Hz, 1H), 7.45-7.44 (m, 2H), 7.36-7.32 (m, 2H), 7.27-7.21 (m, 1H), 7.15 (s, 1H), 4.95-4.91 (m, 1H), 3.87-3.80 (m, 1H), 3.70-3.65 (m, 1H), 3.34 (s, 3H).

Example 139

(1R)-2-({6-[3-Chloro-4-(trifluoromethyl)phenyl]-2-(methylsulfinyl)pyrimidin-4-yl}amino)-1-phenylethanol

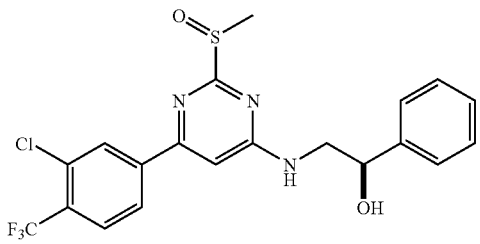

The title compound was prepared analogously to Example 138 using 1 molar equivalent of 3-chloroperoxybenzoic acid. MS (ESI): mass calcd. for $C_{20}H_{17}ClF_3N_3O_2S$, 455.1; m/z found, 456.1 [M+H]$^+$. $^1$H NMR (CD$_3$OD): 8.35 (s, 1H), 8.13 (d, J=8.8 Hz, 1H), 7.89 (d, J=8.2 Hz, 1H), 7.44-7.43 (m, 2H), 7.35-7.32 (m, 2H), 7.26-7.23 (m, 1H), 7.05 (s, 1H), 4.92-4.90 (m, 1H), 3.87-3.79 (m, 1H), 3.74-3.67 (m, 1H), 2.94 (s, 0.34H), 2.93 (s, 0.66H).

Example 140

(1R)-2-{[6-(3-Methyl-1H-indazol-6-yl)pyrimidin-4-yl]amino}-1-phenylethanol trifluoroacetic acid salt

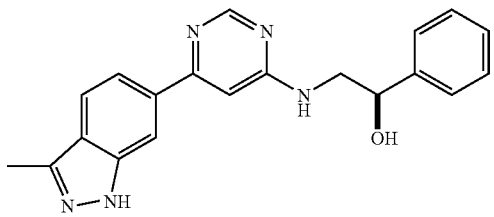 [SMILES: Cc1n[nH]c2cc(-c3cc(NC[C@H](O)c4ccccc4)ncn3)ccc12]

A solution consisting of 1-[2-fluoro-4-(6-{[(2R)-2-hydroxy-2-phenylethyl]amino}pyrimidin-4-yl)phenyl]ethanone (68 mg, 0.15 mmol) and hydrazine monohydrate (1.5 mL) was heated to reflux in a sealed tube for 10 h. The reaction mixture was poured over ice and the precipitate was filtered and washed with hexanes (15 mL). Reverse phase chromatography yielded the title compound (19 mg, 29%). MS (ESI): mass calcd. for $C_{20}H_{19}N_5O$, 345.2; m/z found, 346.2 [M+H]$^+$. $^1$H NMR (CD$_3$OD): 8.65 (s, 1H), 7.96-7.93 (m, 2H), 7.48-7.44 (m, 3H), 7.38-7.35 (m, 2H), 7.30-7.26 (m, 1H), 7.06 (s, 1H), 4.96-4.94 (m, 1H), 3.96-3.91 (m, 1H), 3.83-3.79 (m, 1H), 2.61 (s, 3H).

Example 141

(1R)-2-({6-[3-Chloro-4-(trifluoromethyl)phenyl]-2-(methylamino)pyrimidin-4-yl}amino)-1-phenylethanol trifluoroacetic acid salt

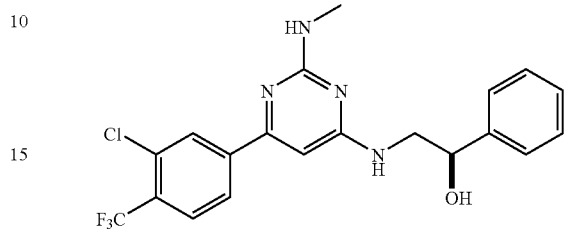

To a solution consisting of (1R)-2-({6-[3-chloro-4-(trifluoromethyl)phenyl]-2-(methylsulfonyl)pyrimidin-4-yl}amino)-1-phenylethanol (47.2 mg, 0.10 mmol) and t-amyl alcohol (1 mL) in a sealed tube was added methylamine (0.2 M in THF; 0.15 mL). The reaction mixture was heated at 130° C. for 18 h. The crude material was filtered through a syringe tip filter eluting with t-amyl alcohol (0.5 mL) and directly purified by reverse phase chromatography to yield the final product (36 mg, 67%)). MS (ESI): mass calcd. for $C_{20}H_{18}ClF_3N_4O$, 422.1; m/z found, 423.1 [M+H]$^+$. $^1$H NMR (CD$_3$OD): 7.99-7.97 (m, 2H), 7.80 (d, J=7.7 Hz, 1H), 7.44-7.43 (m, 2H), 7.37-7.34 (m, 2H), 7.29-7.26 (m, 1H), 6.39 (s, 1H), 4.96-4.94 (m, 1H), 3.89-3.85 (m, 1H), 3.75-3.70 (m, 1H), 3.05 (s, 3H).

Example 142

(1R)-2-{[6-(4-Iodophenyl)pyrimidin-4-yl]amino}-1-phenylethanol

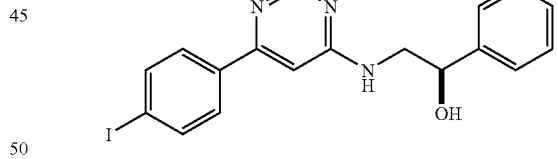

Step A: [4-(6-Chloro-pyrimidin-4-yl)-phenyl]-carbamic acid tert-butyl ester. The title compound was prepared analogously to that described in Example 20, Step B.

Step B: 4-(6-Chloro-pyrimidin-4-yl)-phenylamine. A mixture of [4-(6-chloro-pyrimidin-4-yl)-phenyl]-carbamic acid tert-butyl ester (918 mg, 3.00 mmol), CH$_2$Cl$_2$ (30 mL) and HCl (4 N in dioxane; 3.80 mL) was stirred overnight at rt and the solid isolated by filtration. The resultant solid was taken up in water, treated with satd. aq. NaHCO$_3$ and extracted with CH$_2$Cl$_2$. The extract was dried, filtered, and concentrated. The material was used directly in Step C.

Step C: 4-Chloro-6-(4-iodo-phenyl)-pyrimidine. A solution consisting of 4-(6-chloro-pyrimidin-4-yl)-phenylamine (399 mg, 1.94 mmol) and CH$_3$CN (40 mL) was cooled to 0° C. under N$_2$ and treated with tert-butyl nitrite (0.39 mL, 3.24 mmol) to give a dark brown mixture. After 30 min, CuI (1.50 g, 7.88 mmol) was added. After 30 min at 0° C., the mixture was heated to 75° C. for 30 min. The mixture was cooled to rt, diluted with EtOAc, and washed with water followed by satd. aq. NaHCO$_3$. The organic layer was dried (MgSO$_4$), filtered and concentrated. Purification of the residue by FCC (CH$_2$Cl$_2$/hexanes) gave 218.1 mg (36%) of the pure product. MS (ESI): mass calcd. for C$_{10}$H$_6$ClIN$_2$, 315.93; m/z found, 317.0 [M+H]$^+$. $^1$H NMR ((CD$_3$)$_2$CO): 9.04 (br s, 1H), 8.18 (d, J=1.2 Hz, 1H), 8.08-8.06 (m, 2H), 7.98-7.97 (m, 2H).

Step D. The title compound was prepared analogously to that described in Example 1, Step A. MS (ESI): mass calcd. for C$_{18}$H$_{16}$IN$_3$O, 417.3; m/z found, 418 [M+H]$^+$. $^1$H NMR ((CD$_3$)$_2$CO): 8.53 (s, 1H), 7.84 (s, 4H), 7.46 (d, J=7.8 Hz, 2H), 7.35-7.33 (m, 2H), 7.27-7.24 (m, 1H), 6.81 (br s, 1H), 5.05 (br s, 1H), 4.97 (br t, J=3.6 Hz, 1H), 3.84 (br s, 1H), 3.56-3.52 (m, 1H).

The compounds in Examples 143-146 were prepared using methods analogous to those described for the preceding examples.

Example 143

(1S)-2-[6-(3-Chloro-4-trifluoromethyl-phenyl)-Pyrimidin-4-ylamino]-1-(3,4-difluoro-phenyl)-ethanol

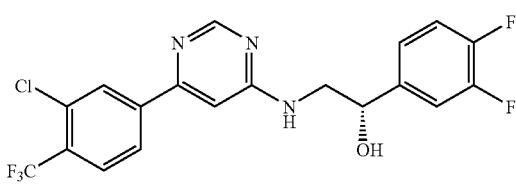 [SMILES: O[C@H](CNc1cc(-c2ccc(C(F)(F)F)c(Cl)c2)ncn1)c1ccc(F)c(F)c1]

Analytical data obtained for this compound compared favorably with that obtained for Example 132.

Example 144

(1R)-2-[6-(3-Chloro-4-trifluoromethyl-phenyl)-pyrimidin-4-ylamino]-1-(3,4-difluoro-phenyl)-ethanol

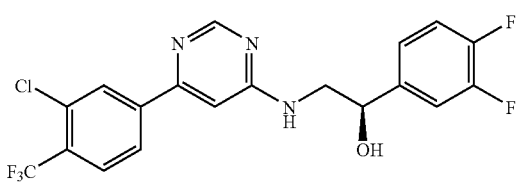 [SMILES: O[C@@H](CNc1cc(-c2ccc(C(F)(F)F)c(Cl)c2)ncn1)c1ccc(F)c(F)c1]

Analytical data obtained for this compound compared favorably with that obtained for Example 132.

Example 145

(1S)-1-(4-Chloro-3-fluoro-phenyl)-2-[6-(3-chloro-4-trifluoromethyl-phenyl)-pyrimidin-4-ylamino]-ethanol

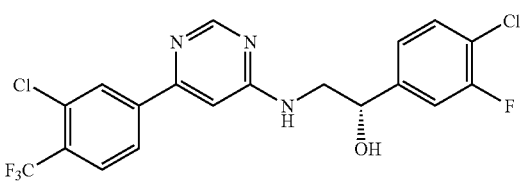 [SMILES: O[C@H](CNc1cc(-c2ccc(C(F)(F)F)c(Cl)c2)ncn1)c1ccc(Cl)c(F)c1]

Analytical data obtained for this compound compared favorably with that obtained for Example 133.

Example 146

(1R)-1-(4-Chloro-3-fluoro-phenyl)-2-[6-(3-chloro-4-trifluoromethyl-Phenyl)-pyrimidin-4-ylamino]-ethanol

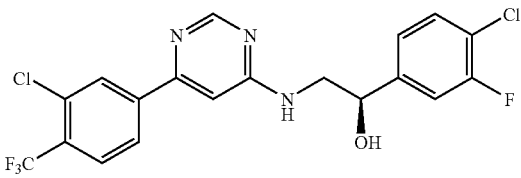 [SMILES: O[C@@H](CNc1cc(-c2ccc(C(F)(F)F)c(Cl)c2)ncn1)c1ccc(Cl)c(F)c1]

Analytical data obtained for this compound compared favorably with that obtained for Example 133.

The compounds in Examples 147-154 were prepared using methods analogous to those described for the preceding examples.

Example 147

2-({6-[4-(Methyloxy)phenyl]pyrimidin-4-yl}amino)-1-phenylethanol

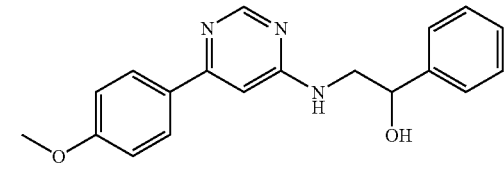

MS (ESI): mass calcd. for C$_{19}$H$_{19}$N$_3$O$_2$, 321.2; m/z found, 322.2 [M+H]$^+$. $^1$H NMR (CD$_3$OD): 8.41 (s, 1H), 7.85 (d, J=9.3 Hz, 2H), 7.43 (d, J=7.7 Hz, 2H), 7.35 (t, J=7.7 Hz, 2H), 7.28-7.25 (m, 1H), 7.02 (d, J=8.8 Hz, 2H), 6.82 (s, 1H), 4.91-4.88 (m, 1H), 3.85 (s, 3H), 3.76-3.67 (m, 1H), 3.57 (dd, J=13.7, 7.7 Hz, 1H).

Example 148

2-{[6-(3-Methylphenyl)pyrimidin-4-yl]amino}-1-phenylethanol

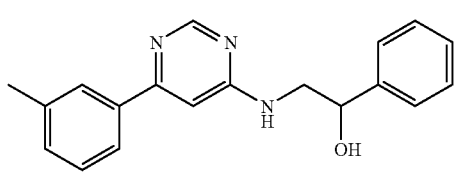 [SMILES: Cc1cccc(-c2cc(NCC(O)c3ccccc3)ncn2)c1]

MS (ESI): mass calcd. for C$_{19}$H$_{19}$N$_3$O, 305.2; m/z found, 306.2 [M+H]$^+$. $^1$H NMR (CD$_3$OD): 8.45 (s, 1H), 7.70 (s, 1H), 7.65 (d, J=7.6 Hz, 1H), 7.44-7.43 (m, 2H), 7.37-7.33 (m, 3H), 7.30-7.24 (m, 2H), 6.86 (s, 1H), 4.92-4.90 (m, 1H), 3.77-3.66 (m, 1H), 3.58 (dd, J=13.9, 7.8 Hz, 1H), 2.42 (s, 3H).

Example 149

1-Phenyl-2-[(6-{3-[(trifluoromethyl)oxy]phenyl}pyrimidin-4-yl)amino]ethanol

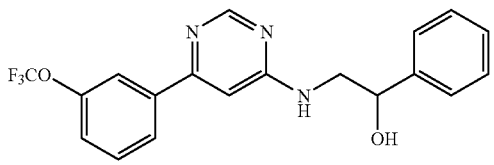 [SMILES: OC(CNc1cc(-c2cccc(OC(F)(F)F)c2)ncn1)c1ccccc1]

MS (ESI): mass calcd. for C$_{19}$H$_{16}$F$_3$N$_3$O$_2$, 375.1; m/z found, 376.2 [M+H]$^+$. $^1$H NMR (CD$_3$OD): 8.48 (s, 1H), 7.91-7.89 (m, 1H), 7.84 (s, 1H), 7.59 (t, J=8.1 Hz, 1H), 7.44 (d, J=7.1 Hz, 2H), 7.40-7.38 (m, 1H), 7.36-7.33 (m, 2H), 7.28-7.24 (m, 1H), 6.93 (s, 1H), 4.93-4.90 (m, 1H), 3.79-3.68 (m, 1H), 3.59 (dd, J=13.6, 7.6 Hz, 1H).

Example 150

(1S,2R)-1-Phenyl-2-[(6-{4-[(trifluoromethyl)oxy]phenyl}pyrimidin-4-yl)amino]propan-1-ol

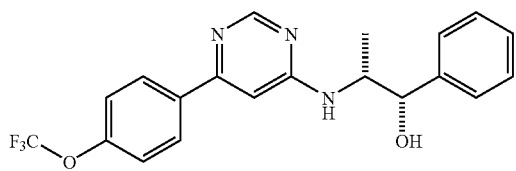 [SMILES: C[C@@H](Nc1cc(-c2ccc(OC(F)(F)F)cc2)ncn1)[C@@H](O)c1ccccc1]

MS (ESI): mass calcd. for C$_{20}$H$_{18}$F$_3$N$_3$O$_2$, 389.1; m/z found, 390.2 [M+H]$^+$. $^1$H NMR (CDCl$_3$): 8.58 (s, 1H), 7.93 (d, J=8.8 Hz, 2H), 7.35-7.34 (m, 4H), 7.32-7.26 (m, 3H), 6.63 (d, J=1.0 Hz, 1H), 5.20 (br s, 1H), 4.92 (d, J=2.5 Hz, 1H), 4.86 (br s, 1H), 4.41 (br s, 1H), 1.12 (d, J=7.1 Hz, 3H).

Example 151

(1S)-1-Phenyl-2-[(6-{4-[(trifluoromethyl)oxy]phenyl}pyrimidin-4-yl)amino]ethanol

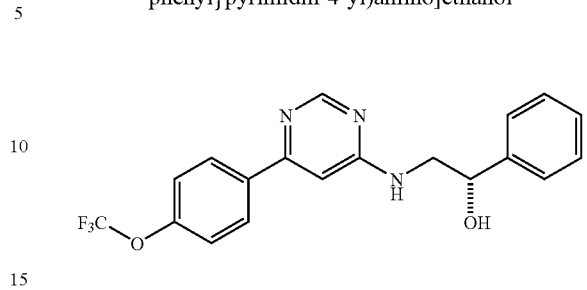

MS (ESI): mass calcd. for C$_{19}$H$_{16}$F$_3$N$_3$O$_2$, 375.1; m/z found, 376.2 [M+H]$^+$. $^1$H NMR (CDCl$_3$): 8.62 (s, 1H), 7.97 (d, J=8.8 Hz, 2H), 7.43-7.36 (m, 4H), 7.33-7.28 (m, 3H), 6.67 (d, J=1.0 Hz, 1H), 5.41 (br s, 1H), 4.99-4.96 (m, 1H), 4.25 (br s, 1H), 3.89-3.83 (m, 1H), 3.62-3.55 (m, 1H).

Example 152

(1R)-2-({6-[2,4-Bis(trifluoromethyl)phenyl]pyrimidin-4-yl}amino)-1-phenylethanol trifluoroacetic acid salt

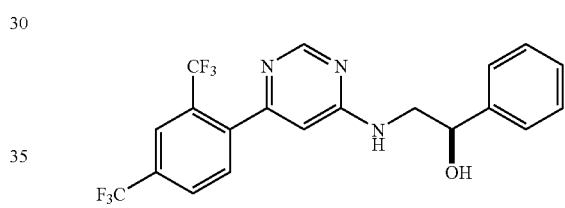

MS (ESI): mass calcd. for C$_{20}$H$_{15}$F$_6$N$_3$O, 427.1; m/z found, 428.1 [M+H]$^+$. $^1$H NMR (CD$_3$OD): 8.67 (s, 1H), 8.22 (s, 1H), 8.18 (d, J=7.7 Hz, 1H), 7.87-7.85 (m, 1H), 7.44-7.43 (m, 2H), 7.37-7.34 (m, 2H), 7.30-7.27 (m, 1H), 6.80 (s, 1H), 4.95-4.94 (m, 1H), 3.94-3.90 (m, 1H), 3.83-3.79 (m, 1H).

Example 153

(1R)-2-({6-[2-Methoxy-4-(trifluoromethoxy)phenyl]pyrimidin-4-yl}amino)-1-phenylethanol trifluoroacetic acid salt

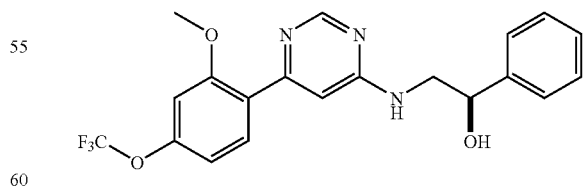

MS (ESI): mass calcd. for C$_{20}$H$_{18}$F$_3$N$_3$O$_3$, 405.1; m/z found, 406.2 [M+H]$^+$. $^1$H NMR (CD$_3$OD): 8.63 (s, 1H), 7.66-7.63 (m, 1H), 7.45-7.43 (m, 2H), 7.38-7.34 (m, 2H), 7.30-7.28 (m, 1H), 7.16 (s, 1H), 7.11-7.09 (m, 1H), 6.94 (s, 1H), 4.95-4.92 (m, 1H), 3.96 (s, 3H), 3.95-3.91 (m, 1H), 3.80 (dd, J=13.7, 7.7 Hz, 1H).

Example 154

(1R)-2-{[6-(4-Ethoxy-2-methylphenyl)pyrimidin-4-yl]amino}-1-phenylethanol trifluoroacetic acid salt

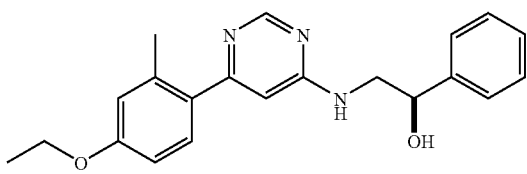 [SMILES: CCOc1ccc(-c2cc(NC[C@H](O)c3ccccc3)ncn2)c(C)c1]

MS (ESI): mass calcd. for $C_{21}H_{23}N_3O_2$, 349.2; m/z found, 350.2 [M+H]$^+$. $^1$H NMR (CD$_3$OD): 8.61 (s, 1H), 7.43 (d, J=7.7 Hz, 2H), 7.38-7.31 (m, 3H), 7.30-7.27 (m, 1H), 6.95 (s, 1H), 6.92 (dd, J=8.8, 2.2 Hz, 1H), 6.71 (s, 1H), 4.94 (dd, J=7.7, 4.4 Hz, 1H), 4.10 (q, J=7.1 Hz, 2H), 3.95-3.91 (m, 1H), 3.81 (dd, J=13.7, 7.7 Hz, 1H), 2.36 (s, 3H), 1.41 (t, J=7.1 Hz, 3H).

The compounds in Examples 155-156 were prepared using methods analogous to those described in Example 136.

Example 155

(1R)-2-{[6-(3,4-Dichlorophenyl)-2-methylpyrimidin-4-yl]amino}-1-phenylethanol

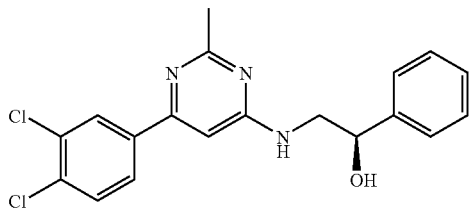 [SMILES: Cc1nc(NC[C@H](O)c2ccccc2)cc(-c2ccc(Cl)c(Cl)c2)n1]

MS (ESI): mass calcd. for $C_{19}H_{17}Cl_2N_3O$, 373.07; m/z found, 374.1 [M+H]$^+$. $^1$H NMR (CD$_3$OD): 8.06 (d, J=2.1 Hz, 1H), 7.79 (dd, J=2.1, 8.4 Hz, 1H), 7.61 (d, J=8.4 Hz, 1H), 7.45-7.39 (m, 2H), 7.37-7.30 (m, 2H), 7.28-7.22 (m, 1H), 6.67 (s, 1H), 4.91-4.88 (m, 1H), 3.80-3.67 (m, 1H), 3.59 (dd, J=7.4, 13.8 Hz, 1H), 2.49 (s, 3H).

Example 156

(1R)-2-{[6-(3,4-Dichlorophenyl)-pyrimidin-4-yl]amino}-1-phenylethanol

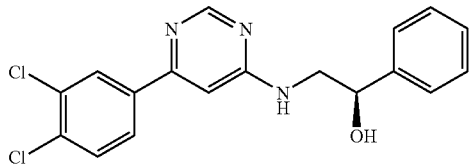 [SMILES: O[C@@H](CNc1cc(-c2ccc(Cl)c(Cl)c2)ncn1)c1ccccc1]

MS (ESI): mass calcd. for $C_{18}H_{15}Cl_2N_3O$, 359.06; m/z found, 360.1 [M+H]$^+$. $^1$H NMR (CD$_3$OD): 8.46 (s, 1H), 8.10 (d, J=2.1 Hz, 1H), 7.83 (dd, J=2.1, 8.4 Hz, 1H), 7.63 (d, J=8.4 Hz, 1H), 7.45-7.40 (m, 2H), 7.37-7.31 (m, 2H), 7.28-7.23 (m, 1H), 6.90 (s, 1H), 4.92-4.88 (m, 1H), 3.80-3.67 (m, 1H), 3.59 (dd, J=7.7, 13.7 Hz, 1H).

The compounds prepared in Example 157-162 were prepared using methods analogous to those described in Example 141.

Example 157

(1R)-2-({2-[(2-Aminoethyl)amino]-6-[3-chloro-4-(trifluoromethyl)phenyl]pyrimidin-4-yl}amino)-1-phenylethanol trifluoroacetic acid salt

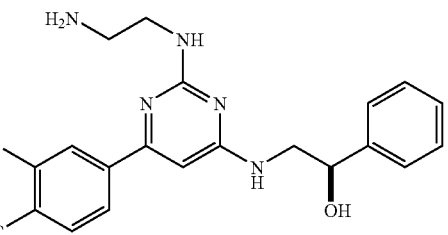

MS (ESI): mass calcd. for $C_{21}H_{21}ClF_3N_5O$, 451.14; m/z found, 452.2 [M+H]$^+$. $^1$H NMR (CD$_3$OD): 8.02 (s, 1H), 7.95 (d, J=8.4 Hz, 1H), 7.86 (d, J=9.3 Hz, 1H), 7.45-7.43 (m, 2H), 7.38-7.35 (m, 2H), 7.30-7.27 (m, 1H), 6.46 (s, 1H), 4.93-4.90 (m, 1H), 3.81-3.76 (m, 4H), 3.26-3.23 (m, 2H).

Example 158

(1R)-2-[(6-[3-Chloro-4-(trifluoromethyl)phenyl]-2-{[2-(dimethylamino)ethyl]amino}pyrimidin-4-yl)amino]-1-phenylethanol trifluoroacetic acid salt

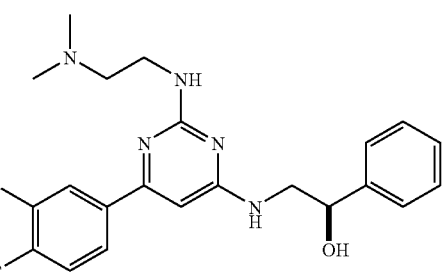

MS (ESI): mass calcd. for $C_{23}H_{25}ClF_3N_5O$, 479.17; m/z found, 480.2 [M+H]$^+$. $^1$H NMR (CD$_3$OD): 8.02 (s, 1H), 7.96 (d, J=8.1 Hz, 1H), 7.85 (d, J=8.8 Hz, 1H), 7.44 (d, J=7.8 Hz, 2H), 7.39-7.35 (m, 2H), 7.31-7.27 (m, 1H), 6.47 (s, 1H), 4.93-4.90 (m, 1H), 3.92-3.87 (m, 2H), 3.82-3.77 (m, 2H), 3.49-3.44 (m, 2H), 2.97 (s, 6H).

Example 159

(1R)-2-({6-[3-Chloro-4-(trifluoromethyl)phenyl]-2-(ethylamino)pyrimidin-4-yl}amino)-1-phenylethanol trifluoroacetic acid salt

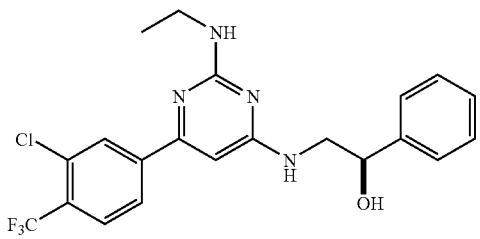 [SMILES: CCNc1nc(NC[C@H](O)c2ccccc2)cc(-c2ccc(C(F)(F)F)c(Cl)c2)n1]

MS (ESI): mass calcd. for $C_{21}H_{20}ClF_3N_4O$, 436.13; m/z found, 437.2 [M+H]$^+$. $^1$H NMR (CD$_3$OD): 7.99-7.97 (m, 2H), 7.80 (d, J=8.6 Hz, 1H), 7.44-7.42 (m, 2H), 7.37-7.34 (m, 2H), 7.30-7.26 (m, 1H), 6.39 (s, 1H), 4.96-4.92 (m, 1H), 3.88-3.82 (m, 1H), 3.71 (dd, J=13.4, 7.6 Hz, 1H), 3.53 (q, J=7.1 Hz, 2H), 1.28 (t, J=7.3 Hz, 3H).

Example 160

(1R)-2-({6-[3-Chloro-4-(trifluoromethyl)phenyl]-2-[(2-hydroxyethyl)amino]pyrimidin-4-yl}amino)-1-phenylethanol trifluoroacetic acid salt

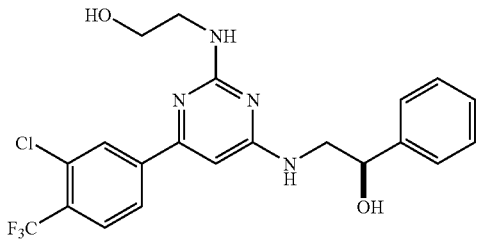 [SMILES: OCCNc1nc(NC[C@H](O)c2ccccc2)cc(-c2ccc(C(F)(F)F)c(Cl)c2)n1]

MS (ESI): mass calcd. for $C_{21}H_{20}ClF_3N_4O_2$, 452.12; m/z found, 453.1 [M+H]$^+$. $^1$H NMR (CD$_3$OD): 8.00-7.98 (m, 2H), 7.81 (d, J=8.8 Hz, 1H), 7.43 (d, J=7.6 Hz, 2H), 7.37-7.34 (m, 2H), 7.30-7.26 (m, 1H), 6.42 (s, 1H), 4.95-4.92 (m, 1H), 3.86-3.81 (m, 1H), 3.78-3.69 (m, 3H), 3.64-3.62 (m, 2H).

Example 161

(1R)-2-({2-Azetidin-1-yl-6-[3-chloro-4-(trifluoromethyl)phenyl]pyrimidin-4-yl}amino)-1-Phenylethanol trifluoroacetic acid salt

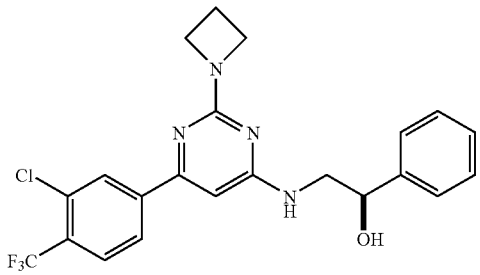 [SMILES: O[C@@H](CNc1cc(-c2ccc(C(F)(F)F)c(Cl)c2)nc(N2CCC2)n1)c1ccccc1]

MS (ESI): mass calcd. for $C_{22}H_{20}ClF_3N_4O$, 448.13; m/z found, 449.2 [M+H]$^+$. $^1$H NMR (CD$_3$OD): 7.98 (s, 1H), 7.96 (d, J=8.3 Hz, 1H), 7.78-7.76 (m, 1H), 7.43-7.41 (m, 2H), 7.37-7.34 (m, 2H), 7.30-7.26 (m, 1H), 6.29 (s, 1H), 4.93 (dd, J=8.1, 4.5 Hz, 1H), 4.35 (t, J=7.8 Hz, 4H), 3.80 (dd, J=13.6, 4.3 Hz, 1H), 3.64 (dd, J=13.6, 7.8 Hz, 1H), 2.50 (pentet, J=7.8 Hz, 2H).

Example 162

(1R)-2-({6-[3-Chloro-4-(trifluoromethyl)phenyl]-2-(cyclopropylamino)pyrimidin-4-yl}amino)-1-phenylethanol trifluoroacetic acid salt

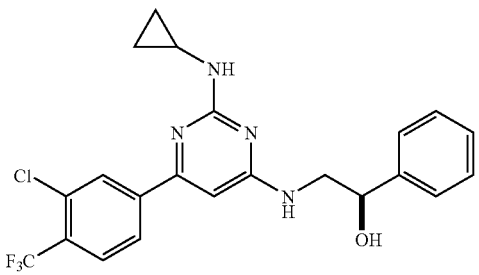 [SMILES: O[C@@H](CNc1cc(-c2ccc(C(F)(F)F)c(Cl)c2)nc(NC2CC2)n1)c1ccccc1]

MS (ESI): mass calcd. for $C_{22}H_{20}ClF_3N_4O$, 448.13; m/z found, 449.1 [M+H]$^+$. $^1$H NMR (CD$_3$OD): 7.99-7.98 (m, 2H), 7.80 (d, J=8.1 Hz, 1H), 7.44 (d, J=7.3 Hz, 2H), 7.37-7.33 (m, 2H), 7.30-7.26 (m, 1H), 6.41 (s, 1H), 4.98-4.92 (br hump, 1H), 3.91-3.84 (m, 1H), 3.72-3.67 (m, 1H), 2.88-2.80 (br hump, 1H), 0.92 (d, J=5.8 Hz, 2H), 0.74-0.68 (br hump, 2H).

Example 163

(1R)-2-[(6-[3-Chloro-4-(trifluoromethyl)phenyl]-2-{[2-(methylamino)ethyl]amino}pyrimidin-4-yl)amino]-1-phenylethanol hydrochloride salt

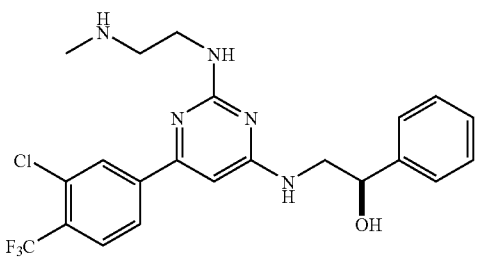 [SMILES: CNCCNc1nc(NC[C@H](O)c2ccccc2)cc(-c2ccc(C(F)(F)F)c(Cl)c2)n1]

Step A: (1R)-{2-[4-(3-Chloro-4-trifluoromethyl-phenyl)-6-(2-hydroxy-2-phenyl-ethylamino)-pyrimidin-2-ylamino]-ethyl}-methyl-carbamic acid tert-butyl ester. The title compound was prepared using methods analogous to those described in Example 141.

Step B: To a solution consisting of (1R)-{2-[4-(3-chloro-4-trifluoromethyl-phenyl)-6-(2-hydroxy-2-phenyl-ethylamino)-pyrimidin-2-ylamino]-ethyl}-methyl-carbamic acid tert-butyl ester (40 mg, 0.06 mmol) and CH$_2$Cl$_2$ (1.5 mL) was added HCl (2 M in Et$_2$O, 0.15 mL). The reaction mixture was allowed to stir at rt for 18 h giving a white solid. The solid was isolated via vacuum filtration and then washed with Et$_2$O to yield the title compound (18 mg, 63%). MS (ESI): mass calcd. for $C_{22}H_{23}ClF_3N_5O$, 465.15; m/z found, 466.2 [M+H]$^+$. $^1$H NMR (D$_2$O): 8.04 (d, J=8.3 Hz, 1H), 8.01 (br s, 1H), 7.85-7.80 (m, 1H), 7.53-7.44 (m, 5H), 6.46 (br s, 1H), 5.11-5.08 (m, 1H), 4.05-3.92 (m, 2H), 3.90-3.87 (m, 2H), 3.39 (t, J=5.8 Hz, 2H), 2.83 (s, 3H).

Example 164

(1R)-2-({6-[3-Chloro-4-(trifluoromethyl)phenyl]-2-methoxypyrimidin-4-yl}amino)-1-phenylethanol trifluoroacetic acid salt

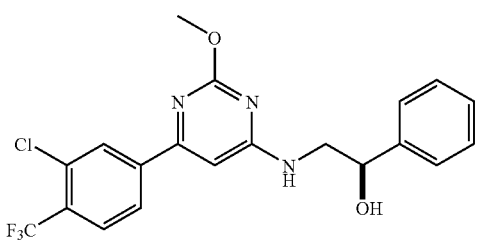 [SMILES: COc1nc(NC[C@H](O)c2ccccc2)cc(-c2ccc(C(F)(F)F)c(Cl)c2)n1]

A solution consisting of (1R)-2-({6-[3-chloro-4-(trifluoromethyl)phenyl]-2-(methylsulfonyl)pyrimidin-4-yl}amino)-1-phenylethanol (50.0 mg, 0.11 mmol) and NaOMe (25%, 0.75 mL) was heated in a sealed tube at 60° C. for 2 h. The reaction mixture was cooled to rt, filtered and washed with MeOH (0.75 mL). The filtrate was concentrated and purified via reverse phase chromatography to yield the title compound (38 mg, 66%). MS (ESI): mass calcd. for $C_{20}H_{17}ClF_3N_3O_2$, 423.09; m/z found, 424.1 [M+H]$^+$. $^1$H NMR (CD$_3$OD): 8.06 (s, 1H), 7.95 (d, J=8.6 Hz, 1H), 7.87 (d, J=8.3 Hz, 1H), 7.44 (d, J=7.6 Hz, 2H), 7.37-7.33 (m, 2H), 7.29-2.26 (m, 1H), 6.67 (s, 1H), 4.96-4.93 (m, 1H), 4.11 (s, 3H), 3.90-3.82 (m, 1H), 3.78-3.73 (m, 1H).

Example 165

(1R)-2-{[6-(3-Methyl-1,2-benzisoxazol-6-yl)pyrimidin-4-yl]amino}-1-phenylethanol

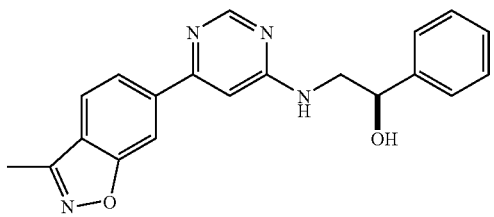 [SMILES: Cc1noc2cc(-c3cc(NC[C@H](O)c4ccccc4)ncn3)ccc12]

A mixture of 1-[2-fluoro-4-(6-{[(2R)-2-hydroxy-2-phenyl-ethyl]amino}-pyrimidin-4-yl)-phenyl]ethanone (88 mg, 0.25 mmol), hydroxylamine hydrochloride (41 mg, 0.60 mmol), KOH (85% aq., 0.158 mL), isopropanol (0.5 mL) and water (0.5 mL) was heated in a sealed tube at 90° C. for 10 h. An additional amount of KOH (85% aq., 2.38 mmol) was added and the temperature increased to 120° C. for an additional 21 h. The reaction mixture was diluted with water (5 mL) and extracted with DCM (5 mL×3). The combined extracts were dried (Na$_2$SO$_4$), concentrated, and the crude product purified (FCC) to yield the title compound (24 mg, 28%). MS (ESI): mass calcd. for $C_{20}H_{18}N_4O_2$, 346.14; m/z found, 347.2 [M+H]$^+$. $^1$H NMR (CDCl$_3$): 8.70 (d, J=0.8 Hz, 1H), 8.13 (dd, J=1.3, 0.8 Hz, 1H), 7.93 (dd, J=8.3, 1.3 Hz, 1H), 7.70 (dd, J=8.3, 0.8 Hz, 1H), 7.45-7.37 (m, 4H), 7.34-7.30 (m, 1H), 6.80 (d, J=1.0 Hz, 1H), 5.35-5.30 (m, 1H), 5.03-4.99 (m, 1H), 3.94-3.87 (m, 1H), 3.67-3.60 (m, 1H), 2.62 (s, 3H).

Example 166

1-({6-[3-Chloro-4-(trifluoromethyl)phenyl]pyrimidin-4-yl}amino)-2-Phenylpropan-2-ol

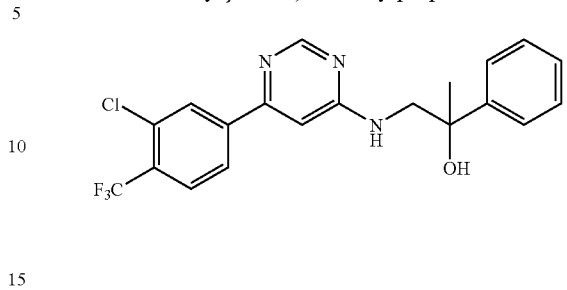

Title compound was prepared using analogous methods to those described in Example 106. MS (ESI): mass calcd. for $C_{20}H_{17}ClF_3N_3O$, 407.10; m/z found, 408.1 [M+H]$^+$. $^1$H NMR (CD$_3$OD): 8.45 (br s, 1H), 8.14 (s, 1H), 7.96 (d, J=8.2 Hz, 1H), 7.85 (d, J=8.2 Hz, 1H), 7.53 (d, J=7.7 Hz, 2H), 7.31 (d, J=7.7 Hz, 2H), 7.20 (t, J=6.6 Hz, 1H), 6.96 (br s, 1H), 3.88-3.80 (m, 1H), 3.73-3.70 (m, 1H), 1.58 (s, 3H).

Example 167

2-({6-[3-Chloro-4-(trifluoromethyl)phenyl]pyrimidin-4-yl}amino)-1-[4-(methylsulfanyl)phenyl]ethanol

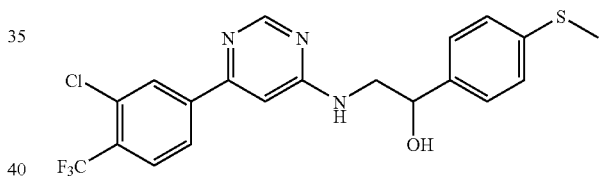

Step A: 2-Azido-1-(4-methylsulfanyl-phenyl)-ethanone. A solution consisting of 2-bromo-1-(4-methylsulfanyl-phenyl)-ethanone (2.00 g, 8.16 mmol) and DMF (7 mL) was cooled to 15° C. and treated portion-wise with sodium azide (583 mg, 8.98 mmol). Once addition was complete, the reaction mixture was stirred for 3 h with gradual warming to rt. The reaction mixture was then diluted with EtOAc (20 mL) and washed with water (25 mL×2), NaHCO$_3$ (satd., 25 mL×2), and brine. The combined organic phases were dried (Na$_2$SO$_4$) and concentrated to dryness to yield the title compound (1.69 g, 100%).

Step B: 2-Azido-1-(4-methylsulfanyl-phenyl)-ethanol. A solution consisting of 2-azido-1-(4-methylsulfanyl-phenyl)-ethanone (1.69 g, 8.15 mmol) and THF (8.15 mL) was cooled to 0° C. before slowly adding BH$_3$.THF (1.0 M solution, 8.15 ml) over 10 min. The resulting solution was stirred at 0° C. for 2 h. The reaction was quenched by slow addition of MeOH (10 mL) at 0° C., and then concentrating to dryness to yield the title compound (1.74 g, 100%).

Step C: 2-Amino-1-(4-methylsulfanyl-phenyl)-ethanol. To a stirred rt suspension consisting of 2-azido-1-(4-methylsulfanyl-phenyl)-ethanol (104.6 mg, 0.50 mmol), 10% Pd/C (100 mg, 0.10 mmol) and MeOH (25 mL) was added ammonium formate (316 mg, 5.0 mmol) under a $N_2$ atmosphere. The resulting mixture was heated at 64° C. for 2 h. After cooling to rt, the catalyst was removed by filtration through a pad of celite and the celite pad washed with MeOH. The filtrate was concentrated and purified (FCC) to yield the title compound (66 mg, 72%).

Step D: Title compound was prepared using methods analogous to those in Example 106, Step B. MS (ESI): mass calcd. for $C_{20}H_{17}ClF_3N_3OS$, 439.07; m/z found, 440.1 [M+H]$^+$. $^1$H NMR (CD$_3$OD): 8.49 (s, 1H), 8.16 (s, 1H), 7.99 (d, J=7.7 Hz, 1H), 7.88 (d, J=8.2 Hz, 1H), 7.38-7.30 (m, 2H), 7.25-7.23 (m, 2H), 6.96 (br s, 1H), 3.75-3.67 (m, 1H), 3.60 (dd, J=13.7, 7.7 Hz, 1H), 2.43 (s, 3H).

The compounds in Example 168-169 were prepared using methods analogous to those described in Example 167.

Example 168

2-({6-[3-Chloro-4-(trifluoromethyl)phenyl]pyrimidin-4-yl}amino)-1-thiophen-3-ylethanol

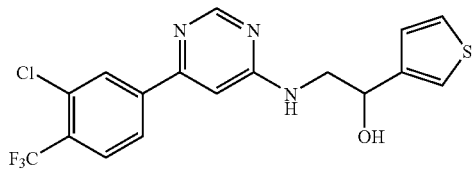 [SMILES: OC(CNc1cc(-c2ccc(C(F)(F)F)c(Cl)c2)ncn1)c1ccsc1]

MS (ESI): mass calcd. for $C_{17}H_{13}ClF_3N_3OS$, 399.04; m/z found, 400.1 [M+H]$^+$. $^1$H NMR (CD$_3$OD): 8.50 (s, 1H), 8.17 (s, 1H), 8.01 (d, J=8.8 Hz, 1H), 7.88 (d, J=8.3 Hz, 1H), 7.38 (dd, J=5.1, 3.0 Hz, 1H), 7.35-7.34 (m, 1H), 7.18 (dd, J=4.8, 1.3 Hz, 1H), 6.98 (s, 1H), 4.99 (dd, J=7.6, 4.8 Hz, 1H), 3.84-3.76 (m, 1H), 3.65 (dd, J=13.9, 7.6 Hz, 1H).

Example 169

2-({6-[3-Chloro-4-(trifluoromethyl)phenyl]pyrimidin-4-yl}amino)-1-(1,3-thiazol-2-yl)ethanol

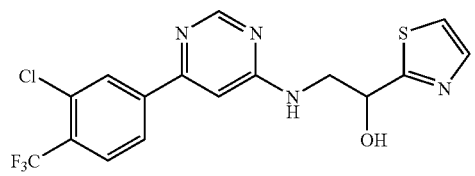 [SMILES: OC(CNc1cc(-c2ccc(C(F)(F)F)c(Cl)c2)ncn1)c1nccs1]

MS (ESI): mass calcd. for $C_{16}H_{12}ClF_3N_4OS$, 400.04; m/z found, 401.1 [M+H]$^+$. $^1$H NMR (CDCl$_3$): 8.68 (d, J=1.0 Hz, 1H), 8.12 (d, J=0.8 Hz, 1H), 7.92 (dq, J=8.1, 0.8 Hz, 1H), 7.78 (d, J=3.3 Hz, 1H), 7.77 (d, J=8.3 Hz, 1H), 7.32 (d, J=3.3 Hz, 1H), 6.78 (d, J=1.3 Hz, 1H), 5.49-5.44 (m, 1H), 5.27-5.24 (m, 1H), 4.20-4.14 (m, 1H), 4.01-3.95 (m, 1H).

Examples 170-172 were synthesized using methods analogous to those described in Example 20.

Example 170

(1R)-1-Phenyl-2-[(6-quinolin-6-ylpyrimidin-4-yl)amino]ethanol

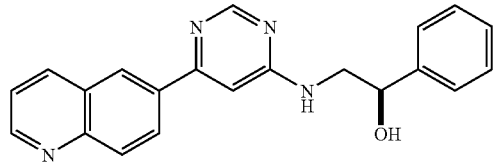 [SMILES: O[C@@H](CNc1cc(-c2ccc3ncccc3c2)ncn1)c1ccccc1]

MS (ESI): mass calcd. for $C_{21}H_{18}N_4O$, 342.15; m/z found, 343.2 [M+H]$^+$. $^1$H NMR (CD$_3$OD): 8.90 (dd, J=4.4, 1.6 Hz, 1H), 8.53 (d, J=2.2 Hz, 2H), 8.49 (d, J=8.2 Hz, 1H), 8.29 (dd, J=8.8, 2.2 Hz, 1H), 8.13 (d, J=8.8 Hz, 1H), 7.62-7.59 (m, 1H), 7.44 (d, J=7.7 Hz, 2H), 7.35 (t, J=7.7 Hz, 2H), 7.26 (t, J=7.1 Hz, 1H), 7.06 (s, 1H), 4.94-4.91 (m, 1H), 3.79-3.71 (m, 1H), 3.63 (dd, J=13.7, 7.7 Hz, 1H).

Example 171

N-tert-Butyl-4-(6-{[(2R)-2-hydroxy-2-phenylethyl]amino}pyrimidin-4-yl)benzenesulfonamide

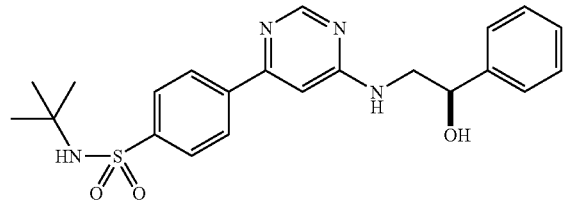 [SMILES: CC(C)(C)NS(=O)(=O)c1ccc(-c2cc(NC[C@H](O)c3ccccc3)ncn2)cc1]

MS (ESI): mass calcd. for $C_{22}H_{26}N_4O_3S$, 426.17; m/z found, 427.2 [M+H]$^+$. $^1$H NMR (CD$_3$OD): 8.22 (s, 1H), 7.82-7.73 (m, 2H), 7.73-7.68 (m, 2H), 7.21-7.13 (m, 2H), 7.11-7.04 (m, 2H), 7.03-6.94 (m, 1H), 6.73-6.62 (m, 1H), 4.67-4.61 (m, 1H), 3.56-3.42 (m, 1H), 3.34 (dd, J=13.7, 7.6 Hz, 1H), 0.94 (s, 9H).

Example 172

(1R)-1-Phenyl-2-({6-[4-(thiomorpholin-4-ylsulfonyl)phenyl]pyrimidin-4-yl}amino)ethanol

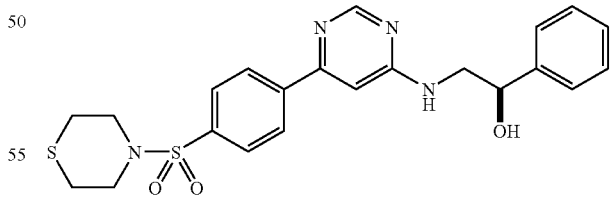

MS (ESI): mass calcd. for $C_{22}H_{24}N_4O_3S_2$, 456.13; m/z found, 457.4 [M+H]$^+$. $^1$H NMR (CD$_3$OD): 8.69-8.36 (m, 1H), 8.18-8.09 (m, 2H), 7.92-7.86 (m, 2H), 7.45 (d, J=7.4 Hz, 2H), 7.36 (t, J=7.6 Hz, 2H), 7.30-7.25 (m, 1H), 7.04-6.94 (m, 1H), 4.76-4.51 (m, 2H), 3.88-3.70 (m, 1H), 3.62 (dd, J=13.7, 7.8 Hz, 1H), 3.41-3.33 (m, 4H), 2.76-2.68 (m, 4H).

The compounds prepared in Example 173-182 were prepared using methods analogous to those described in Example 20.

Example 173

(1R)-1-(4-Fluorophenyl)-2-({6-[3-fluoro-4-(trifluoromethyl)phenyl]pyrimidin-4-yl}amino)ethanol

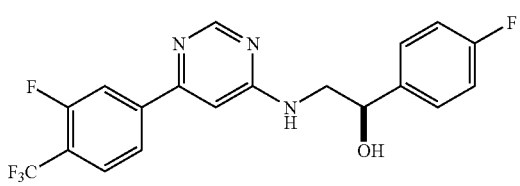 [SMILES: O[C@@H](CNc1cc(-c2ccc(C(F)(F)F)c(F)c2)ncn1)c1ccc(F)cc1]

MS (ESI): mass calcd. for $C_{19}H_{14}F_5N_3O$, 395.10; m/z found, 396.1 [M+H]$^+$. $^1$H NMR (CDCl$_3$): 8.68 (d, J=0.8 Hz, 1H), 7.85-7.81 (m, 2H), 7.71-7.67 (m, 1H), 7.40 (d, J=8.3 Hz, 1H), 7.39 (d, J=8.3 Hz, 1H), 7.07 (d, J=8.6 Hz, 1H), 7.06 (d, J=8.8 Hz, 1H), 6.74 (d, J=1.3 Hz, 1H), 5.35-5.30 (m, 1H), 5.01-4.98 (m, 1H), 3.91-3.85 (m, 1H), 3.62-3.56 (m, 1H).

Example 174

(1R)-1-(4-Fluorophenyl)-2-({6-[3-fluoro-4-(trifluoromethoxy)phenyl]pyrimidin-4-yl}amino)ethanol trifluoroacetic acid salt

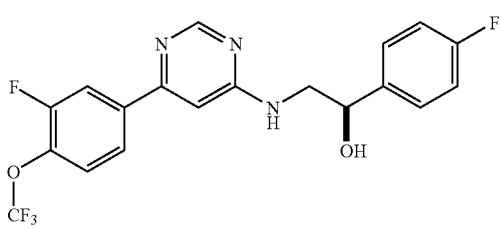 [SMILES: O[C@@H](CNc1cc(-c2ccc(OC(F)(F)F)c(F)c2)ncn1)c1ccc(F)cc1]

MS (ESI): mass calcd. for $C_{19}H_{14}F_5N_3O_2$, 411.10; m/z found, 412.1 [M+H]$^+$. $^1$H NMR (CD$_3$OD): 8.65 (s, 1H), 7.89-7.86 (m, 1H), 7.76-7.66 (m, 2H), 7.48-7.45 (m, 2H), 7.10-7.02 (m, 3H), 4.95-4.92 (m, 1H), 3.91-3.86 (m, 1H), 3.79-3.74 (m, 1H).

Example 175

(1R)-2-({6-[3-Chloro-4-(trifluoromethoxy)phenyl]pyrimidin-4-yl}amino)-1-(4-fluorophenyl)ethanol trifluoroacetic acid salt

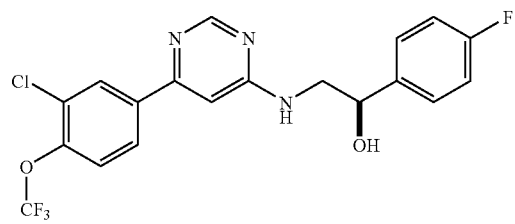 [SMILES: O[C@@H](CNc1cc(-c2ccc(OC(F)(F)F)c(Cl)c2)ncn1)c1ccc(F)cc1]

MS (ESI): mass calcd. for $C_{19}H_{14}ClF_4N_3O_2$, 427.07; m/z found, 428.1 [M+H]$^+$. $^1$H NMR (CD$_3$OD): 8.67 (s, 1H), 8.09 (s, 1H), 7.86 (d, J=8.6 Hz, 1H), 7.69 (d, J=8.6 Hz, 1H), 7.48-7.44 (m, 2H), 7.10-7.06 (m, 2H), 7.01 (s, 1H), 4.95-4.93 (m, 1H), 3.93-3.87 (m, 1H), 3.81-3.75 (m, 1H).

Example 176

(1R)-1-(4-fluorophenyl)-2-({6-[3-(pentafluoroethyl)-1,2-benzisoxazol-6-yl]pyrimidin-4-yl}amino)ethanol trifluoroacetic acid salt

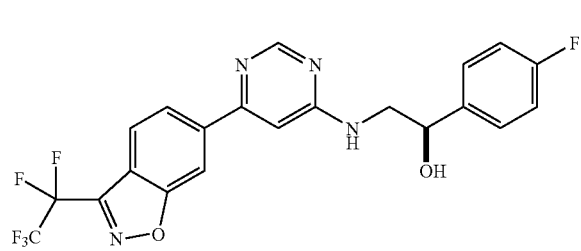 [SMILES: O[C@@H](CNc1cc(-c2ccc3c(C(F)(F)C(F)(F)F)noc3c2)ncn1)c1ccc(F)cc1]

Title compound was prepared using similar methods to those in Example 20. MS (ESI): mass calcd. for $C_{21}H_{14}F_6N_4O_2$, 468.10; m/z found, 469.1 [M+H]$^+$. $^1$H NMR (CD$_3$OD): 8.75 (s, 1H), 8.36 (s, 1H), 8.15 (d, J=8.4 Hz, 1H), 7.95 (d, J=8.4 Hz, 1H), 7.47 (dd, J=5.5, 8.3 Hz, 2H), 7.15 (s, 1H), 7.09 (t, J=8.7 Hz, 2H), 4.97-4.95 (m, 1H), 3.95-3.91 (m, 1H), 3.85-3.80 (m, 1H).

Example 177

(1R)-1-(4-Fluorophenyl)-2-({6-[3-(trifluoromethyl)-1,2-benzisoxazol-6-yl]pyrimidin-4-yl}amino)ethanol trifluoroacetic acid salt

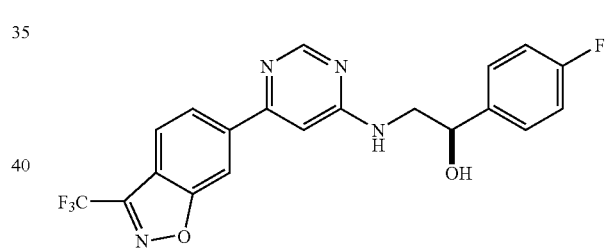

MS (ESI): mass calcd. for $C_{20}H_{14}F_4N_4O_2$, 418.10; m/z found, 419.2 [M+H]$^+$. $^1$H NMR (CD$_3$OD): 8.69 (br s, 1H), 8.36 (s, 1H), 8.13 (d, J=8.3 Hz, 1H), 7.99 (d, J=8.3 Hz, 1H), 7.49-7.45 (m, 2H), 7.13-7.07 (m, 3H), 4.97-4.94 (m, 1H), 3.92-3.86 (br hump, 1H), 3.80-3.75 (m, 1H).

Example 178

(1R)-2-({6-[3-Fluoro-4-(2,2,2-trifluoroethoxy)phenyl]pyrimidin-4-yl}amino)-1-phenylethanol trifluoroacetic acid salt

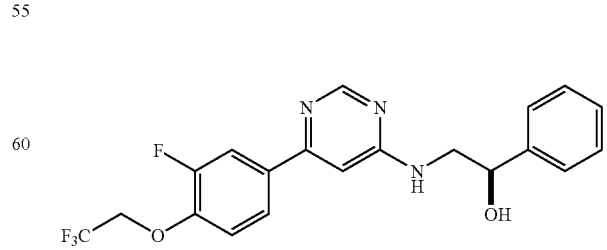

MS (ESI): mass calcd. for $C_{20}H_{17}F_4N_3O_2$, 407.13; m/z found, 408.2 [M+H]$^+$. $^1$H NMR (CD$_3$OD): 8.63 (s, 1H), 7.71

(dd, J=11.9, 1.8 Hz, 1H), 7.66-7.63 (m, 1H), 7.45-7.41 (m, 3H), 7.37-7.34 (m, 2H), 7.30-7.26 (m, 1H), 6.96 (s, 1H), 4.94 (dd, J=7.1, 5.1 Hz, 1H), 4.75 (q, J=8.3 Hz, 2H), 3.95-3.90 (m, 1H), 3.79 (dd, J=13.6, 7.6 Hz, 1H).

Example 179

(1R,2S)-2-({6-[3-chloro-4-(trifluoromethyl)phenyl]pyrimidin-4-ylamino}-1-phenylpropan-1-ol

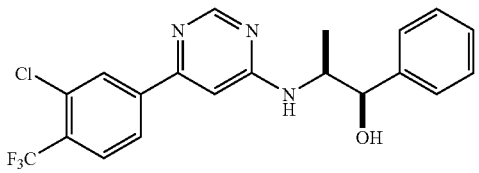 [SMILES: C[C@H](Nc1cc(-c2ccc(C(F)(F)F)c(Cl)c2)ncn1)[C@H](O)c1ccccc1]

MS (ESI): mass calcd. for $C_{20}H_{17}ClF_3N_3O$, 407.10; m/z found, 408.1 [M+H]$^+$. $^1$H NMR (CDCl$_3$): 8.69 (s, 1H), 8.12 (s, 1H), 7.93 (d, J=8.3 Hz, 1H), 7.78 (d, J=8.3 Hz, 1H), 7.37-7.36 (m, 4H), 7.33-7.28 (m, 1H), 6.72 (s, 1H), 5.02-4.97 (m, 2H), 4.56-4.47 (br hump, 1H), 1.17 (d, J=6.8 Hz, 3H).

Example 180

(1R)-1-Phenyl-2-[(6-{4-[(trifluoromethyl)sulfanyl]phenyl}pyrimidin-4-yl)amino]ethanol

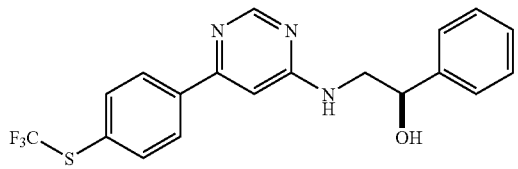 [SMILES: O[C@@H](CNc1cc(-c2ccc(SC(F)(F)F)cc2)ncn1)c1ccccc1]

MS (ESI): mass calcd. for $C_{19}H_{16}F_3N_3OS$, 391.10; m/z found, 392.4 [M+H]$^+$. $^1$H NMR (CDCl$_3$): 8.66 (s, 1H), 8.00 (d, J=8.5 Hz, 2H), 7.76 (d, J=8.2 Hz, 2H), 7.43-7.42 (m, 2H), 7.40-7.37 (m, 2H), 7.34-7.31 (m, 1H), 6.77 (s, 1H), 5.03-5.01 (m, 1H), 3.91-3.80 (br hump, 1H), 3.65-3.59 (m, 1H).

Example 181

(1R)-2-({6-[3-Chloro-4-(trifluoromethoxy)phenyl]pyrimidin-4-yl}amino)-1-phenylethanol

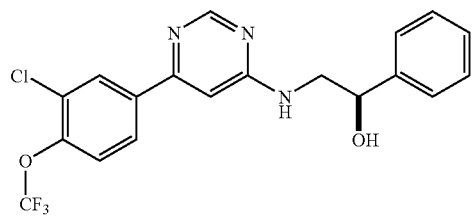 [SMILES: O[C@@H](CNc1cc(-c2ccc(OC(F)(F)F)c(Cl)c2)ncn1)c1ccccc1]

MS (ESI): mass calcd. for $C_{19}H_{15}ClF_3N_3O_2$, 409.08; m/z found, 410.4 [M+H]$^+$. $^1$H NMR (CDCl$_3$): 8.66 (s, 1H), 8.11 (d, J=1.9 Hz, 1H), 7.88 (dd, J=8.5, 2.2 Hz, 1H), 7.43-7.37 (m, 5H), 7.34-7.31 (m, 1H), 6.68 (s, 1H), 5.36-5.30 (br hump, 1H), 5.01-4.99 (m, 1H), 3.92-3.85 (br hump, 1H), 3.64-3.59 (m, 1H).

Example 182

(1R)-1-Phenyl-2-({6-[3-(trifluoromethyl)-1,2-benzisoxazol-6-yl]pyrimidin-4-yl}amino)ethanol

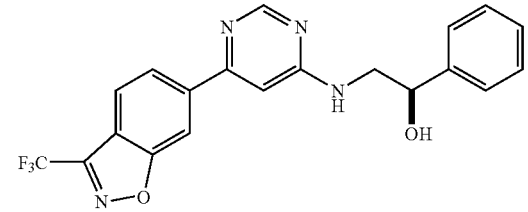 [SMILES: O[C@@H](CNc1cc(-c2ccc3c(C(F)(F)F)noc3c2)ncn1)c1ccccc1]

MS (ESI): mass calcd. for $C_{20}H_{15}F_3N_4O_2$, 400.11; m/z found, 401.4 [M+H]$^+$. $^1$H NMR (CDCl$_3$): 8.69 (s, 1H), 8.31 (s, 1H), 8.03 (dd, J=8.2, 1.1 Hz, 1H), 7.89 (d, J=8.2 Hz, 1H), 7.44-7.42 (m, 2H), 7.41-7.37 (m, 2H), 7.34-7.31 (m, 1H), 6.81 (s, 1H), 5.53-5.43 (br hump, 1H), 5.01 (dd, J=7.4, 3.3 Hz, 1H), 3.95-3.87 (br hump, 1H), 3.65-3.60 (m, 1H).

Example 183

(1R)-2-{[6-(2,2-Difluoro-1,3-benzodioxol-5-yl)pyrimidin-4-yl]amino}-1-phenylethanol

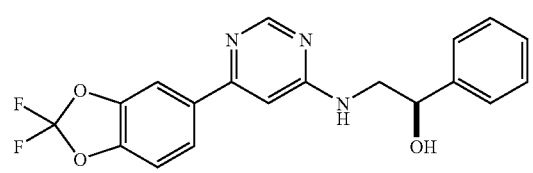 [SMILES: O[C@@H](CNc1cc(-c2ccc3c(c2)OC(F)(F)O3)ncn1)c1ccccc1]

Title compound was synthesized using methods analogous to those described in Example 20, with modifications to Step B as follows:

Step B. (1R)-2-[(6-Chloropyrimidin-4-yl)amino]-1-phenylethanol (75 mg, 0.30 mmol), 2,2-difluoro-5-(4,4,5,5-tetramethyl-[1,3,2]dioxaborolan-2-yl)-benzo[1,3]dioxole (85 mg, 0.30 mmol), Pd(OAc)$_2$ (1.3 mg, 0.006 mmol, 2 mol %), 2-dicyclohexylphosphino-2',6'-dimethoxy-1,1'-biphenyl (S-Phos) (4.9 mg, 0.012 mmol, 4 mol %) and K$_3$PO$_4$ (191 mg, 0.900 mmol) were dissolved in dioxane (1.0 mL), which had been degassed by bubbling N$_2$ into the solvent and water (0.1 mL) in a sealed tube. The tube was flushed with N$_2$ and heated at 100° C. for 16 h before cooling to rt and filtering through a pad of celite. The celite was washed with CH$_2$Cl$_2$ (5 mL) and the filtrate concentrated to dryness. The crude material was purified by (FCC) to yield the title compound (92 mg, 83%). MS (ESI): mass calcd. for $C_{19}H_{15}F_2N_3O_3$, 371.11; m/z found, 372.1 [M+H]$^+$. $^1$H NMR (CDCl$_3$): 8.64 (s, 1H), 7.73-7.71 (m, 2H), 7.43-7.37 (m, 4H), 7.34-7.30 (m, 1H), 7.14-7.12 (m, 1H), 6.65 (d, J=1.1 Hz, 1H), 5.31-5.25 (br hump, 1H), 5.01-4.99 (m, 1H), 3.91-3.85 (br hump, 1H), 3.64-3.59 (m, 1H).

Examples 184-187 were prepared using methods analogous to those described in Example 183.

Example 184

(1R)-1-Phenyl-2-({6-[5-(trifluoromethyl)-1-benzothiophen-2-yl]pyrimidin-4-yl}amino)ethanol trifluoroacetic acid salt

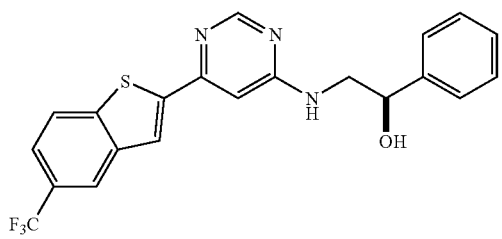 [SMILES: O[C@@H](CNc1cc(-c2cc3cc(C(F)(F)F)ccc3s2)ncn1)c1ccccc1]

MS (ESI): mass calcd. for $C_{21}H_{16}F_3N_3OS$, 415.10; m/z found, 416.4 [M+H]$^+$. $^1$H NMR (CD$_3$OD): 8.61 (s, 1H), 8.31 (s, 1H), 8.22, (s, 1H), 8.20 (d, J=8.5 Hz, 1H), 7.75 (d, J=8.5 Hz, 1H), 7.45 (d, J=8.0 Hz, 2H), 7.38-7.35 (m, 2H), 7.30-7.27 (m, 1H), 7.08 (s, 1H), 4.96-4.93 (m, 1H), 3.92-3.86 (m, 1H), 3.78-3.74 (m, 1H).

Example 185

(1R)-1-Phenyl-2-({6-[5-(trifluoromethoxy)-1-benzothiophen-2-yl]pyrimidin-4-yl}amino)ethanol trifluoroacetic acid salt

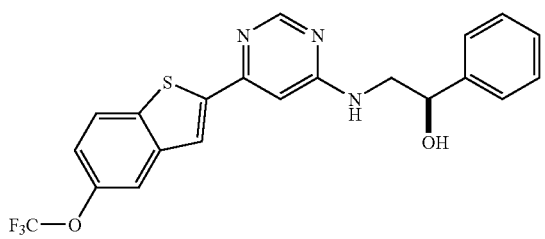 [SMILES: O[C@@H](CNc1cc(-c2cc3cc(OC(F)(F)F)ccc3s2)ncn1)c1ccccc1]

MS (ESI): mass calcd. for $C_{21}H_{16}F_3N_3O_2S$, 431.10; m/z found, 432.4 [M+H]$^+$. $^1$H NMR (CD$_3$OD): 8.57 (s, 1H), 8.13 (s, 1H), 8.08 (d, J=8.8 Hz, 1H), 7.89 (s, 1H), 7.46-7.41 (m, 3H), 7.38-7.34 (m, 2H), 7.29-7.26 (m, 1H), 7.05 (s, 1H), 4.95-4.92 (m, 1H), 3.90-3.83 (m, 1H), 3.78-3.72 (m, 1H).

Example 186

(1R)-1-Phenyl-2-({6-[6-(trifluoromethyl)-1-benzothiophen-2-yl]pyrimidin-4-yl}amino)ethanol trifluoroacetic acid salt

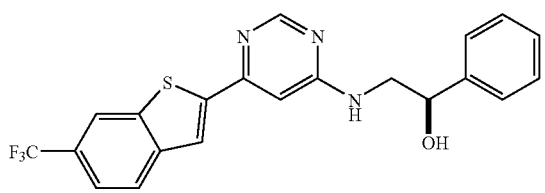 [SMILES: O[C@@H](CNc1cc(-c2cc3ccc(C(F)(F)F)cc3s2)ncn1)c1ccccc1]

MS (ESI): mass calcd. for $C_{21}H_{16}F_3N_3OS$, 415.10; m/z found, 416.4 [M+H]$^+$. $^1$H NMR (CD$_3$OD): 8.56 (s, 1H), 8.37 (d, J=0.8 Hz, 1H), 8.17 (s, 1H), 8.12 (d, J=8.3 Hz, 1H), 7.71 (dd, J=8.3, 1.5 Hz, 1H), 7.45 (d, J=7.3 Hz, 2H), 7.38-7.34 (m, 2H), 7.29-7.25 (m, 1H), 7.08 (s, 1H), 4.95-4.92 (m, 1H), 3.90-3.80 (m, 1H), 3.73 (dd, J=13.6, 7.6 Hz, 1H).

Example 187

(1R)-2-{[6-(5-Fluoro-1-benzothiophen-2-yl)pyrimidin-4-yl}amino]-1-Phenylethanol

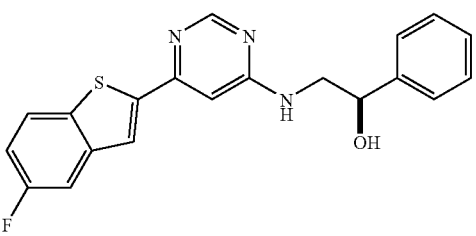 [SMILES: O[C@@H](CNc1cc(-c2cc3cc(F)ccc3s2)ncn1)c1ccccc1]

MS (ESI): mass calcd. for $C_{20}H_{16}FN_3OS$, 365.10; m/z found, 366.4 [M+H]$^+$. $^1$H NMR (CDCl$_3$): 8.62 (s, 1H), 7.85 (s, 1H), 7.79 (dd, J=8.8, 4.7 Hz, 1H), 7.47 (dd, J=9.3, 2.5 Hz, 1H), 7.44-7.38 (m, 4H), 7.34-7.31 (m, 1H), 7.14 (td, J=8.8, 2.5 Hz, 1H), 6.74 (d, J=1.1 Hz, 1H), 5.36-5.31 (br hump, 1H), 5.02-4.99 (m, 1H), 3.91-3.86 (m, 1H), 3.64-3.59 (m, 1H).

Example 188

(1R)-2-({6-[3-(pentafluoroethyl)-1,2-benzisoxazol-6-yl]pyrimidin-4-yl}amino)-1-phenylethanol trifluoroacetic acid salt

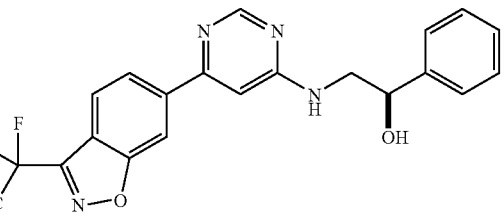

MS (ESI): mass calcd. for $C_{21}H_{15}F_5N_4O_2$, 450.11; m/z found, 451.2 [M+H]$^+$. $^1$H NMR (CD$_3$OD): 8.74 (s, 1H), 8.36 (s, 1H), 8.15 (d, J=8.4 Hz, 1H), 7.94 (dd, J=0.8, 8.4 Hz, 1H), 7.45 (d, J=7.4 Hz, 2H), 7.36 (t, J=7.3 Hz, 2H), 7.28 (t, J=7.1 Hz, 1H), 7.14 (s, 1H), 4.97-4.95 (m, 1H), 3.96-3.93 (m, 1H), 3.84-3.80 (m, 1H).

Example 189

2-({6-[3-Chloro-4-(trifluoromethyl)phenyl]pyrimidin-4-yl}amino)-1-[2-(difluoromethoxy)phenyl]ethanol

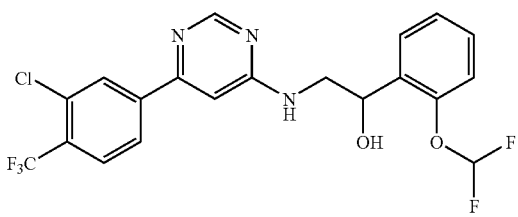 [SMILES: OC(CNc1cc(-c2ccc(C(F)(F)F)c(Cl)c2)ncn1)c1ccccc1OC(F)F]

Title compound was prepared using methods analogous to those described in Example 130. MS (ESI): mass calcd. for $C_{20}H_{15}ClF_5N_3O_2$, 459.08; m/z found, 460.1 [M+H]+. 1H NMR ((CD3)2CO): 8.53-8.48 (m, 1H), 8.28-8.18 (m, 1H), 8.11-8.03 (m, 1H), 8.00 (d, J=8.2 Hz, 1H), 7.73-7.56 (m, 2H), 7.41-7.30 (m, 1H), 7.28-7.24 (m, 1H), 7.16-7.12 (m, 2H), 5.65 (d, J=3.5 Hz, 1H), 5.14-5.08 (m, 1H), 3.76-3.56 (m, 1H), 3.57-3.45 (m, 1H).

Example 190

2-({6-[3-Chloro-4-(trifluoromethyl)phenyl]pyrimidin-4-yl}amino)-1-(4-fluorophenyl)ethanol

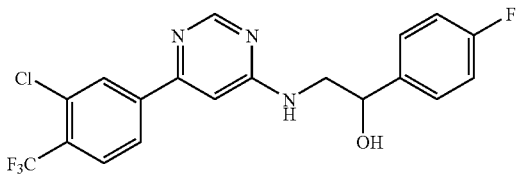 [SMILES: OC(CNc1cc(-c2ccc(C(F)(F)F)c(Cl)c2)ncn1)c1ccc(F)cc1]

Title compound was prepared using methods analogous to those described in Example 130 with modifications to Step A as follows:

Step A: 2-amino-1-(4-fluoro-phenyl)-ethanol. To a solution consisting of 2-amino-1-(4-fluoro-phenyl)-ethanone (150 mg, 0.9 mmol) and MeOH (5 mL) was added NaBH4 (97 mg, 2.6 mmol). The mixture was stirred at rt for 45 min and then concentrated to dryness. The residue was diluted with EtOAc and washed with a satd. NH4Cl solution before drying (Na2SO4), and concentrating to give 2-amino-1-(4-fluoro-phenyl)-ethanol (139 mg, 100%) which was used without further purification.

Step B. MS (ESI): mass calcd. for $C_{19}H_{14}ClF_4N_3O$, 411.08; m/z found, 412.4 [M+H]+. 1H NMR (CDCl3): 8.70 (s, 1H), 8.17-8.10 (m; 1H), 7.95 (d, J=8.2 Hz, 1H), 7.80 (d, J=8.2 Hz, 1H), 7.44-7.37 (m, 2H), 7.15-7.03 (m, 2H), 6.92-6.58 (m, 1H), 5.44-5.27 (m, 1H), 5.07-4.94 (m, 1H), 3.98-3.81 (m, 2H), 3.61 (ddd, J=14.0, 7.5, 5.2 Hz, 1H).

Example 191

4-[2-({6-[3-Chloro-4-(trifluoromethyl)phenyl]pyrimidin-4-yl}amino)-1-hydroxyethyl]benzonitrile

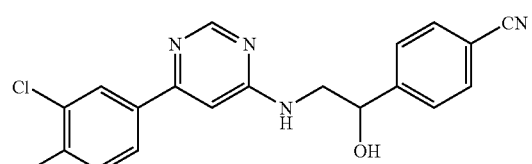

Title compound was prepared using methods analogous to those described in Example 130 with modifications to Step A as follows:

Step A. 4-(2-Amino-1-hydroxy-ethyl)-benzonitrile. To a solution consisting of 4-(2-bromo-acetyl)-benzonitrile (1 g, 4.5 mmol) and THF (17 mL) was added BH3.THF (1 M in THF, 5.4 mL) at 0° C. The solution was warmed to rt over 1 h. MeOH (4 mL) was added slowly to the reaction vessel and the reaction mixture stirred for an additional 30 min. The reaction mixture was then concentrated dryness and re-dissolved in MeOH (10 mL) before treating with NH4OH (10 mL). The mixture was stirred at rt for 12 h and then concentrated. The residue was dissolved in water and extracted with EtOAC. The organic layer was dried (Na2SO4), and concentrated. The crude residue was purified (FCC) to give the title compound (246 mg, 34%).

Step B. MS (ESI): mass calcd. for $C_{20}H_{14}ClF_3N_4O$, 418.08; m/z found, 419.1 [M+H]+. 1H NMR ((CD3)2CO): 8.69-8.39 (m, 2H), 8.29-8.19 (m, 1H), 8.14-8.05 (m, 1H), 8.00 Id, J=8.3 Hz, 1H), 7.81 (d, J=7.9 Hz, 1H), 7.71-7.55 (m, 2H), 7.19-7.06 (m, 1H), 5.94-5.75 (m, 1H), 4.98-4.76 (m, 1H), 3.77-3.55 (m, 1H), 3.54-3.44 (m, 1H).

Example 192

2-({6-[3-Chloro-4-(trifluoromethyl)phenyl]pyrimidin-4-yl}amino)-1-naphthalen-2-ylethanol

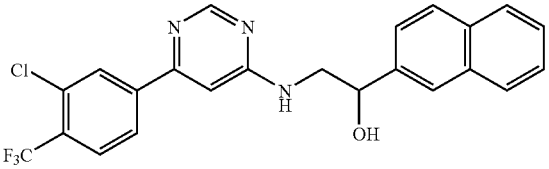 [SMILES: OC(CNc1cc(-c2ccc(C(F)(F)F)c(Cl)c2)ncn1)c1ccc2ccccc2c1]

Title compound was synthesized using procedures analogous to those described in Example 191. MS (ESI): mass calcd. for $C_{23}H_{17}ClF_3N_3O$, 443.10; m/z found, 444.1 [M+H]+. 1H NMR (CD3OD): 8.58-8.44 (m, 1H), 8.22-8.07 (m, 1H), 8.05-7.73 (m, 6H), 7.60 (dd, J=8.5, 1.66 Hz, 1H), 7.49-7.41 (m, 2H), 7.04-6.89 (m, 1H), 5.20-4.97 (m, 1H), 3.95-3.79 (m, 1H), 3.74 (dd, J=13.8, 7.4 Hz, 1H).

Example 193

2-({6-[3-Chloro-4-(trifluoromethyl)phenyl]pyrimidin-4-yl}amino)-1-(4-Pyridin-2-ylphenyl)ethanol

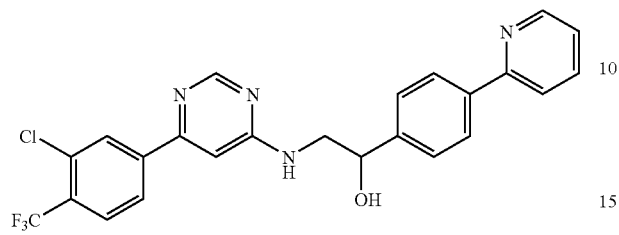

Step A: 2-Nitro-1-(4-pyridin-2-yl-phenyl)-ethanol. To a cooled (0° C.) solution consisting of 4-pyridin-2-yl-benzaldehyde (346 mg, 1.9 mmol) in THF (5 mL) and $NO_2CH_3$ (0.3 mL) and MeOH (2.5 mL) was added KOH (2.5 M, 1.13 mL). The reaction mixture was stirred at 0° C. for 30 min. and then quenched with a saturated $NH_4Cl$ solution. The aqueous mixture was extracted with EtOAC. The organic layer was dried ($Na_2SO_4$) and concentrated. The crude residue was purified (FCC) to give the title compound (257 mg, 60%).

Step B: 2-Amino-1-(4-pyridin-2-yl-phenyl)-ethanol. To a solution of consisting of 2-nitro-1-(4-pyridin-2-yl-phenyl)-ethanol (275 mg, 1.1 mmol) and acetone (5 mL) were added $NH_4Cl$ (900 mg, 16.9 mmol), Zn dust (1.10 g, 16.9 mmol), and water (1 mL). The reaction mixture was stirred for 2 h at rt and then filtered. The filtrate was washed with saturated $NaHCO_3$ and extracted with EtOAc. The organic layer was dried ($Na_2SO_4$) and concentrated. The crude residue was purified (FCC) to give the title compound (45 mg, 19%).

Step C: Title compound was prepared using methods analogous to those described in Example 130. MS (ESI): mass calcd. for $C_{24}H_{18}ClF_3N_4O$, 470.11; m/z found, 471.5 [M+H]+. 1H NMR (CDCl3): 8.70-8.69 (m, 1H), 8.12 (s, 1H), 8.01 (d, J=8.3 Hz, 2H), 7.92 (d, J=8.5 Hz, 1H), 7.78-7.70 (m, 3H), 7.53 (d, J=8.3 Hz, 2H), 7.26-7.22 (m, 2H), 6.73 (s, 1H), 5.36-5.26 (m, 1H), 5.11-5.06 (m, 1H), 4.02-3.93 (m, 1H), 3.70-3.64 (m, 1H).

Example 194

2-({6-[3-Chloro-4-(trifluoromethyl)phenyl]pyrimidin-4-yl}amino)-1-(4-thiophen-2-ylphenyl)ethanol

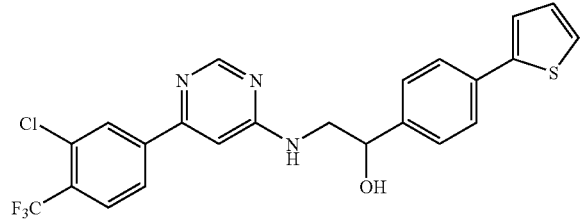 [SMILES: OC(CNc1cc(-c2ccc(C(F)(F)F)c(Cl)c2)ncn1)c1ccc(-c2cccs2)cc1]

Title compound was synthesized using methods analogous to those described in Example 193. MS (ESI): mass calcd. for $C_{23}H_{17}ClF_3N_3OS$, 475.07; m/z found, 476.4 [M+H]+. 1H NMR (CDCl3): 8.71 (s, 1H), 8.15-8.10 (m, 1H), 7.94 (d, J=8.6 Hz, 1H), 7.79 (d, J=8.3 Hz, 1H), 7.66-7.62 (m, 2H), 7.44 (d, J=8.2 Hz, 2H), 7.32 (ddd, J=6.2, 4.3, 1.1 Hz, 2H), 7.11 (dd, J=5.1, 3.6 Hz, 1H), 6.75 (s, 1H), 5.14-4.96 (m, 1H), 3.73-3.58 (m, 1H), 3.53-3.49 (m, 1H).

Example 195

1-Biphenyl-4-yl-2-({6-[3-chloro-4-(trifluoromethyl)phenyl]pyrimidin-4-yl}amino)ethanol

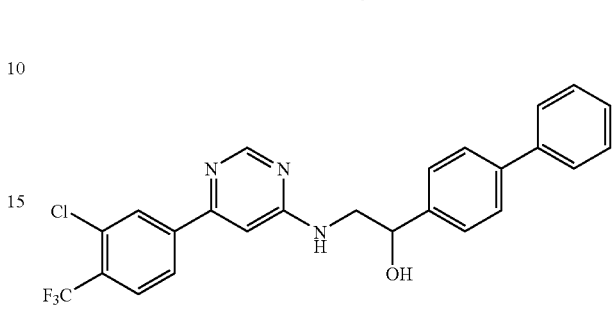

Title compound was prepared using methods analogous to those described in Example 130 with modifications to Step A as follows:

Step A: 2-Amino-1-biphenyl-4-yl-ethanol. To a solution consisting of 1-biphenyl-4-yl-2-bromo-ethanone (412 mg. 1.5 mmol) and EtOH (6 mL) was added $NaN_3$ (107 mg, 1.6 mmol) at rt. The mixture was stirred at rt for 2 h and then cooled to 0° C. $NaBH_4$ (61 mg, 1.6 mmol) was added and the mixture stirred for 45 min. A mixture (black slurry) of $CuSO_4.5H_2O$ (37 mg)/$NaBH_4$ (28 mg) in MeOH 2 mL) was prepared by adding the $NaBH_4$ to $CuSO_4.5H_2O$ in MeOH at 0° C. This slurry was poured into the reaction mixture. The reaction vessel was allowed to gradually warm to rt. An additional amount of $NaBH_4$ (28 mg) was added 30 min after the addition of the slurry. The reaction was stirred at rt for 2 h. The mixture was filtered through a pad of celite, adhered to silica gel (7-8 g) and purified (FCC) to give the title compound (256 mg, 80%).

Step B. MS (ESI): mass calcd. for $C_{25}H_{19}ClF_3N_3O$, 469.12; m/z found, 470.2 [M+H]+. 1H NMR (CDCl3): 8.69 (s, 1H), 8.15-8.08 (m, 1H), 7.92 (d, J=8.1 Hz, 1H), 7.77 (d, J=8.2 Hz, 1H), 7.61 (d, J=8.0 Hz, 2H), 7.58 (d, J=7.9 Hz, 2H), 7.49 (d, J=8.4 Hz, 2H), 7.45 (t, J=7.7 Hz, 2H), 7.39-7.33 (m, 1H), 6.74 (s, 1H), 5.52-5.29 (m, 1H), 5.11-4.96 (m, 1H), 4.03-3.82 (m, 1H), 3.70-3.63 (m, 1H).

Examples 196-218 were prepared using methods analogous to those described in Example 195.

Example 196

1-(1-Benzothiophen-2-yl)-2-({6-[3-chloro-4-(trifluoromethyl)phenyl]pyrimidin-4-yl}amino)ethanol

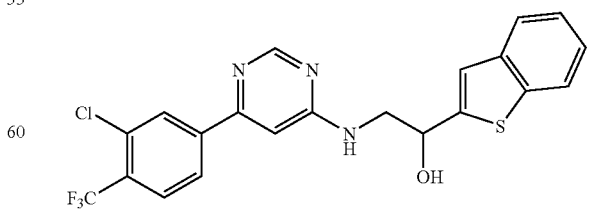

MS (ESI): mass calcd. for $C_{21}H_{15}ClF_3N_3OS$, 449.06; m/z found, 450.1 [M+H]+. 1H NMR (CDCl3): 8.70 (s, 1H), 8.11 (s, 1H), 7.93-7.90 (m, 1H), 7.82 (d, J=7.8 Hz, 1H), 7.77 (d, J=8.3 Hz, 1H), 7.75-7.72 (m, 1H), 7.40-7.27 (m, 3H), 6.76 (d, J=0.9 Hz, 1H), 5.45-5.16 (m, 2H), 4.20-3.91 (m, 1H), 3.86-3.75 (m, 1H).

Example 197

2-({6-[3-Chloro-4-(trifluoromethyl)phenyl]pyrimidin-4-yl}amino)-1-[3-fluoro-4-(trifluoromethyl)phenyl]ethanol

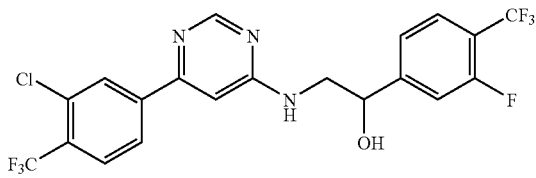 [SMILES: OC(CNc1cc(-c2ccc(C(F)(F)F)c(Cl)c2)ncn1)c1ccc(C(F)(F)F)c(F)c1]

MS (ESI): mass calcd. for $C_{20}H_{13}ClF_7N_3O$, 479.06; m/z found, 480.1 [M+H]$^+$. $^1$H NMR (CDCl$_3$): 8.72 (s, 1H), 8.13 (d, J=0.7 Hz, 1H), 7.94 (dd, J=8.3, 0.8 Hz, 1H), 7.79 (d, J=8.2 Hz, 1H), 7.61 (t, J=7.6 Hz, 1H), 7.33-7.27 (m, 2H), 6.78 (d, J=1.1 Hz, 1H), 5.43-5.16 (m, 1H), 5.12-5.04 (m, 1H), 4.05-3.86 (m, 1H), 3.62 (ddd, J=14.6, 6.8, 5.8 Hz, 1H).

Example 198

2-({6-[3-chloro-4-(trifluoromethyl)phenyl]pyrimidin-4-yl}amino)-1-[3-[(trifluoromethyl)sulfanyl]phenyl]ethanol

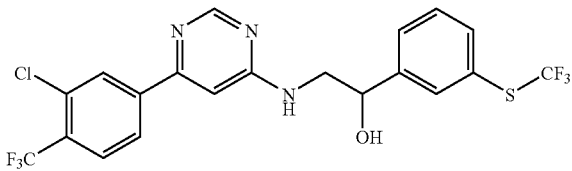

MS (ESI): mass calcd. for $C_{20}H_{14}ClF_6N_3OS$, 493.04; m/z found, 494.1 [M+H]$^+$. $^1$H NMR (CDCl$_3$): 8.69 (d, J=0.7 Hz, 1H), 8.11 (s, 1H), 7.92 (dd, J=8.2, 0.8 Hz, 1H), 7.78 (d, J=8.3 Hz, 1H), 7.72-7.69 (m, 1H), 7.63-7.57 (m, 1H), 7.56-7.52 (m, 1H), 7.44 (t, J=7.7 Hz, 1H), 6.74 (d, J=1.1 Hz, 1H), 5.42-5.19 (m, 1H), 5.04 (dd, J=7.2, 2.9 Hz, 1H), 4.02-3.81 (m, 1H), 3.62 (ddd, J=14.3, 7.2, 5.4 Hz, 1H).

Example 199

2-({6-[3-Chloro-4-(trifluoromethyl)phenyl]pyrimidin-4-yl}amino)-1-(2,3-dihydro-1,4-benzodioxin-6-yl)ethanol

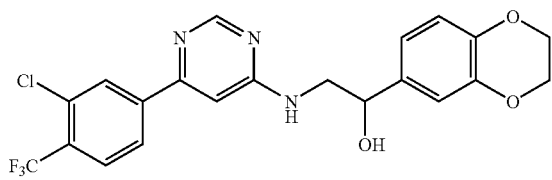 [SMILES: OC(CNc1cc(-c2ccc(C(F)(F)F)c(Cl)c2)ncn1)c1ccc2c(c1)OCCO2]

MS (ESI): mass calcd. for $C_{21}H_{17}ClF_3N_3O_3$, 451.09; m/z found, 452.1 [M+H]$^+$. $^1$H NMR (CDCl$_3$): 8.67 (s, 1H), 8.12 (s, 1H), 7.93 (d, J=7.9 Hz, 1H), 7.78 (d, J=8.2 Hz, 1H), 6.96-6.89 (m, 1H), 6.88-6.86 (m, 2H), 6.73-6.70 (m, 1H), 5.42-5.28 (m, 1H), 4.90-4.87 (m, 1H), 4.35-4.18 (m, 4H), 3.92-3.76 (m, 1H), 3.62-3.54 (m, 1H).

Example 200

2-({6-[3-Chloro-4-(trifluoromethyl)phenyl]pyrimidin-4-yl}amino)-1-[4-(1H-imidazol-1-yl)phenyl]ethanol

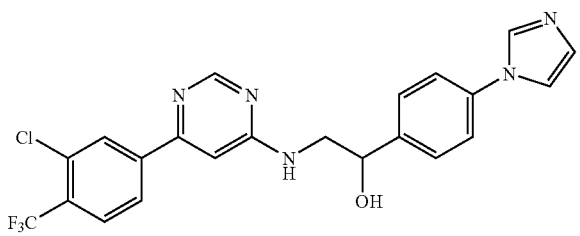 [SMILES: OC(CNc1cc(-c2ccc(C(F)(F)F)c(Cl)c2)ncn1)c1ccc(-n2ccnc2)cc1]

MS (ESI): mass calcd. for $C_{22}H_{17}ClF_3N_5O$, 459.11; m/z found, 460.1 [M+H]$^+$. $^1$H NMR (CDCl$_3$): 8.71 (s, 1H), 8.12 (s, 1H), 7.94 (d, J=8.5 Hz, 1H), 7.84 (s, 1H), 7.79 (d, J=8.3 Hz, 1H), 7.55 (d, J=8.3 Hz, 2H), 7.41 (d, J=8.5 Hz, 2H), 7.29-7.27 (m, 1H), 7.23-7.20 (m, 1H), 6.78-6.77 (m, 1H), 5.47-5.31 (m, 1H), 5.10-5.07 (m, 1H), 4.12-3.81 (m, 1H), 3.74-3.55 (m, 1H).

Example 201

1-(1-benzothiophen-3-yl)-2-({6-[3-chloro-4-(trifluoromethyl)phenyl]pyrimidin-4-yl}amino)ethanol

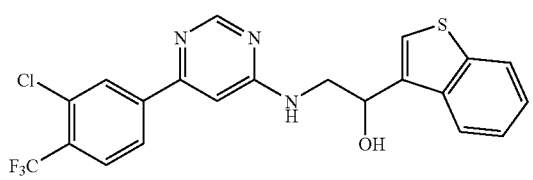 [SMILES: OC(CNc1cc(-c2ccc(C(F)(F)F)c(Cl)c2)ncn1)c1csc2ccccc12]

MS (ESI): mass calcd. for $C_{21}H_{15}ClF_3N_3OS$, 449.06; m/z found, 450.1 [M+H]$^+$. $^1$H NMR (CDCl$_3$): 8.70 (s, 1H), 8.08 (s, 1H), 7.93 (d, J=8.1 Hz, 1H), 7.90-7.82 (m, 2H), 7.76 (d, J=8.2 Hz, 1H), 7.52-7.47 (m, 1H), 7.46-7.35 (m, 2H), 6.68 (s, 1H), 5.47-5.34 (m, 2H), 4.21-4.01 (m, 1H), 3.77 (ddd, J=14.3, 7.0, 5.4 Hz, 1H).

Example 202

2-({6-[3-Chloro-4-(trifluoromethyl)phenyl]pyrimidin-4-yl}amino)-1-(3,4-dimethoxyphenyl)ethanol

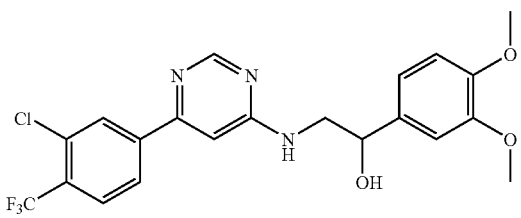

MS (ESI): mass calcd. for $C_{21}H_{19}ClF_3N_3O_3$, 453.11; m/z found, 454.2 [M+H]⁺. ¹H NMR (CDCl₃): 8.82-8.54 (m, 1H), 8.17-8.08 (m, 1H), 7.93 (d, J=8.4 Hz, 1H), 7.81-7.75 (m, 1H), 7.28-7.26 (m, 1H), 6.99-6.84 (m, 2H), 6.75-6.70 (m, 1H), 5.48-5.30 (m, 1H), 5.00-4.90 (m, 1H), 3.94-3.79 (m, 7H), 3.67-3.57 (m, 1H).

Example 203

1-(3-Chloro-4-methoxyphenyl)-2-({6-[3-chloro-4-(trifluoromethyl)phenyl]pyrimidin-4-yl}amino)ethanol

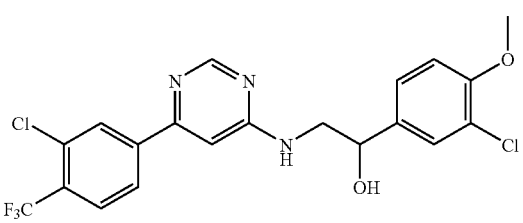 [SMILES: COc1ccc(C(O)CNc2cc(-c3ccc(C(F)(F)F)c(Cl)c3)ncn2)cc1Cl]

MS (ESI): mass calcd. for $C_{20}H_{16}Cl_2F_3N_3O_2$, 457.06; m/z found, 458.1 [M+H]⁺. ¹H NMR (CDCl₃): 8.68 (d, J=0.8 Hz, 1H), 8.12 (d, J=0.8 Hz, 1H), 7.93 (ddd, J=8.1, 1.5, 0.7 Hz, 1H), 7.78 (d, J=8.3 Hz, 1H), 7.44 (d, J=2.0 Hz, 1H), 7.28 (dd, J=2.2, 0.4 Hz, 1H), 6.93 (d, J=8.5 Hz, 1H), 6.74 (d, J=1.1 Hz, 1H), 5.45-5.17 (m, 1H), 4.97-4.87 (m, 1H), 3.90 (s, 3H), 3.87-3.82 (m, 1H), 3.59 (ddd, J=14.1, 7.4, 5.3 Hz, 1H).

Example 204

2-({6-[3-Chloro-4-(trifluoromethyl)phenyl]pyrimidin-4-yl}amino)-1-(3,4-dihydro-2H-1,5-benzodioxepin-7-yl)ethanol

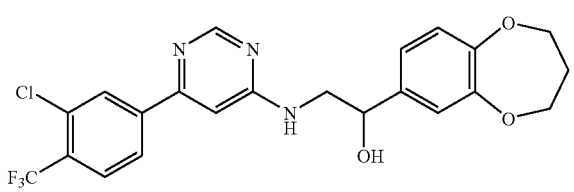 [SMILES: OC(CNc1cc(-c2ccc(C(F)(F)F)c(Cl)c2)ncn1)c1ccc2c(c1)OCCCO2]

MS (ESI): mass calcd. for $C_{22}H_{19}ClF_3N_3O_3$, 465.11; m/z found, 455.4 [M+H]⁺. ¹H NMR (CDCl₃): 8.67 (d, J=0.5 Hz, 1H), 8.12 (s, 1H), 7.92 (dd, J=8.3, 0.7 Hz, 1H), 7.77 (d, J=8.3 Hz, 1H), 7.06-7.01 (m, 1H), 6.98-6.95 (m, 2H), 6.72-6.70 (m, 1H), 5.50-5.11 (m, 1H), 4.92-4.87 (m, 1H), 4.28-4.10 (m, 4H), 3.91-3.78 (m, 1H), 3.58 (ddd, J=13.9, 7.5, 5.3 Hz, 1H), 2.23-2.16 (m, 2H).

Example 205

2-({6-[3-Chloro-4-(trifluoromethyl)phenyl]pyrimidin-4-yl}amino)-1-[2-fluoro-5-(trifluoromethyl)phenyl]ethanol

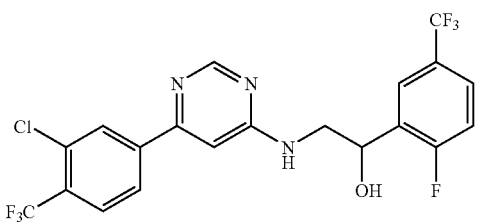 [SMILES: OC(CNc1cc(-c2ccc(C(F)(F)F)c(Cl)c2)ncn1)c1cc(C(F)(F)F)ccc1F]

MS (ESI): mass calcd. for $C_{20}H_{13}ClF_7N_3O$, 479.06; m/z found, 480.1 [M+H]⁺. ¹H NMR (CDCl₃): 8.71 (s, 1H), 8.15-8.10 (m, 1H), 7.96-7.90 (m, 2H), 7.79 (d, J=8.2 Hz, 1H), 7.60-7.53 (m, 1H), 7.17 (t, J=9.3 Hz, 1H), 6.79 (d, J=1.1 Hz, 1H), 5.42-5.16 (m, 3H), 4.02-3.84 (m, 1H), 3.80-3.71 (m, 1H).

Example 206

3-[2-({6-[3-Chloro-4-(trifluoromethyl)phenyl]pyrimidin-4-yl}amino)-1-hydroxyethyl]benzonitrile

MS (ESI): mass calcd. for $C_{20}H_{14}ClF_3N_4O$, 418.08; m/z found, 419.1 [M+H]⁺. ¹H NMR (CDCl₃): 8.76-8.66 (m, 1H), 8.15-8.10 (m, 1H), 7.94 (d, J=8.2 Hz, 1H), 7.79 (d, J=8.2 Hz, 1H), 7.76-7.74 (m, 1H), 7.67 (d, J=7.8 Hz, 1H), 7.62-7.59 (m, 1H), 7.52-7.47 (m, 1H), 6.78 (d, J=1.0 Hz, 1H), 5.40-5.17 (m, 1H), 5.09-5.04 (m, 1H), 4.03-3.83 (m, 1H), 3.63 (ddd, J=14.5, 7.0, 5.7 Hz, 1H).

Example 207

2-({6-[3-Chloro-4-(trifluoromethyl)phenyl]pyrimidin-4-yl}amino)-1-(3-phenylisoxazol-5-yl)ethanol

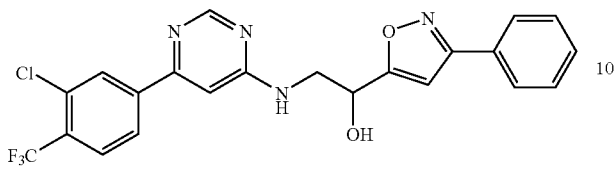

MS (ESI): mass calcd. for C$_{22}$H$_{16}$ClF$_3$N$_4$O$_2$, 460.09; m/z found, 461.1 [M+H]$^+$. $^1$H NMR (CDCl$_3$): 8.70 (d, J=0.8 Hz, 1H), 8.12 (d, J=0.8 Hz, 1H), 7.91 (dd, J=8.2, 0.9 Hz, 1H), 7.80-7.75 (m, 3H), 7.48-7.39 (m, 3H), 6.79 (d, J=1.2 Hz, 1H), 6.63 (d, J=0.9 Hz, 1H), 5.44-5.30 (m, 1H), 5.23-5.13 (m, 2H), 4.19-4.11 (m, 1H), 3.98-3.89 (m, 1H).

Example 208

2-({6-[3-Chloro-4-(trifluoromethyl)phenyl]pyrimidin-4-yl}amino)-1-(4-pyrrolidin-1-ylphenyl)ethanol

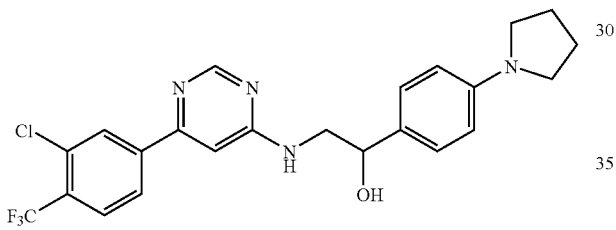

MS (ESI): mass calcd. for C$_{23}$H$_{22}$ClF$_3$N$_4$O, 462.14; m/z found, 463.2 [M+H]$^+$. $^1$H NMR (CDCl$_3$): 8.69-8.62 (m, 1H), 8.11 (s, 1H), 7.91 (d, J=7.7 Hz, 1H), 7.77 (d, J=8.3 Hz, 1H), 7.25-7.24 (m, 2H), 6.75-6.62 (m, 1H), 6.56 (d, J=8.6 Hz, 2H), 5.45-5.37 (m, 1H), 4.93-4.78 (m, 1H), 3.89-3.70 (m, 1H), 3.65-3.57 (m, 1H), 3.31-3.22 (m, 4H), 2.07-1.85 (m, 4H).

Example 209

2-({6-[3-Chloro-4-(trifluoromethyl)phenyl]pyrimidin-4-yl}amino)-1-(5-pyridin-2-ylthiophen-2-yl)ethanol

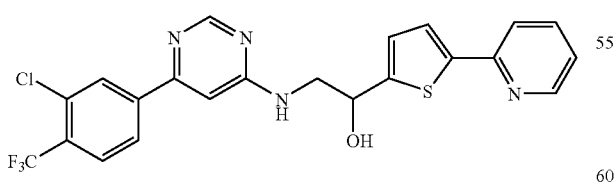

MS (ESI): mass calcd. for C$_{22}$H$_{16}$ClF$_3$N$_4$OS, 476.07; m/z found, 477.1 [M+H]$^+$. $^1$H NMR (CDCl$_3$): 8.68 (d, J=0.7 Hz, 1H), 8.55 (ddd, J=4.9, 1.7, 1.0 Hz, 1H), 8.14-8.10 (m, 1H), 7.92 (dd, J=8.2, 0.8 Hz, 1H), 7.75 (d, J=8.2 Hz, 1H), 7.71-7.66 (m, 1H), 7.63-7.60 (m, 1H), 7.45 (d, J=3.7 Hz, 1H), 7.15 (ddd, J=7.3, 4.9, 1.2 Hz, 1H), 7.05 (dd, J=3.7, 0.8 Hz, 1H), 6.76 (d, J=1.1 Hz, 1H), 5.50-5.34 (m, 1H), 5.29-5.21 (m, 1H), 4.15-3.93 (m, 1H), 3.77 (ddd, J=14.2, 6.4, 5.8 Hz, 1H).

Example 210

5-[2-({6-[3-Chloro-4-(trifluoromethyl)phenyl]pyrimidin-4-ylamino}-1-hydroxyethyl]-2-fluorobenzonitrile

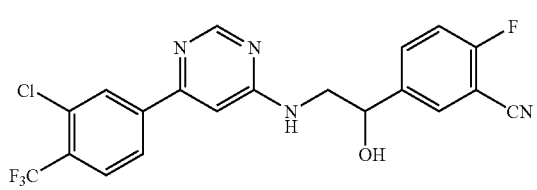 [SMILES: N#Cc1cc(C(O)CNc2cc(-c3ccc(C(F)(F)F)c(Cl)c3)ncn2)ccc1F]

MS (ESI): mass calcd. for C20H13ClF4N4O, 436.07; m/z found, 437.4 [M+H]$^+$. $^1$H NMR (CD$_3$OD): 8.52 (s, 1H), 8.22-8.16 (m, 1H), 8.02 (d, J=8.3 Hz, 1H), 7.9 (d, J=8.3 Hz, 1H), 7.86-7.76 (m, 2H), 7.35 (t, J=8.9 Hz, 1H), 7.00 (d, J=1.1 Hz, 1H), 5.00-4.95 (m, 1H), 4.95-4.91 (m, 1H), 3.86-3.69 (m, 1H), 3.64 (dd, J=13.9, 7.2 Hz, 1H).

Example 211

2-({6-[3-Chloro-4-(trifluoromethyl)phenyl]pyrimidin-4-yl}amino)-1-(2,6-difluorophenyl)ethanol

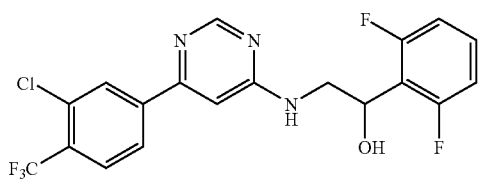 [SMILES: OC(CNc1cc(-c2ccc(C(F)(F)F)c(Cl)c2)ncn1)c1c(F)cccc1F]

MS (ESI): mass calcd. for C$_{19}$H$_{13}$ClF$_5$N$_3$O, 429.07; m/z found, 430.1 [M+H]$^+$. $^1$H NMR (CDCl$_3$): 8.68 (s, 1H), 8.15-8.10 (m, 1H), 7.94 (d, J=8.2 Hz, 1H), 7.79 (d, J=8.2 Hz, 1H), 7.30-7.26 (m, 1H), 6.92 (t, J=8.2 Hz, 2H), 6.80-6.78 (m, 1H), 5.50-5.40 (m, 1H), 5.33 (dt, J=7.7, 3.6 Hz, 1H), 4.08-3.93 (m, 1H), 3.90-3.81 (m, 1H).

Example 212

2-({6-[3-Chloro-4-(trifluoromethyl)phenyl]pyrimidin-4-yl}amino)-1-(2-fluorophenyl)ethanol

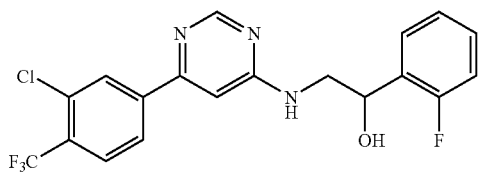

MS (ESI): mass calcd. for C$_{19}$H$_{14}$ClF$_4$N$_3$O, 411.08; m/z found, 412.1 [M+H]$^+$. $^1$H NMR (CDCl$_3$): 8.13 (s, 1H), 7.93 (d, J=8.3 Hz, 1H), 7.78 (d, J=8.3 Hz, 1H), 7.57 (dt, J=7.3, 1.4 Hz, 1H), 7.34-7.28 (m, 2H), 7.21-7.14 (m, 1H), 7.10-7.02 (m, 1H), 6.82-6.71 (m, 1H), 5.44-5.33 (m, 1H), 5.33-5.27 (m, 1H), 4.05-3.82 (m, 1H), 3.77-3.66 (m, 1H).

Example 213

2-[6-(3-Chloro-4-trifluoromethyl-phenyl)-pyrimidin-4-ylamino]-1-[3-(3,4-dichloro-phenyl)-isoxazol-5-yl]-ethanol

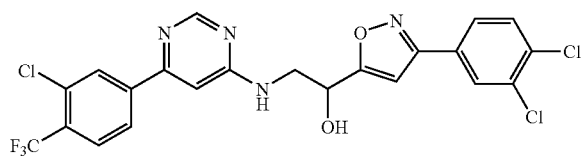 [SMILES: OC(CNc1cc(-c2ccc(C(F)(F)F)c(Cl)c2)ncn1)c1cc(-c2ccc(Cl)c(Cl)c2)no1]

MS (ESI): mass calcd. for $C_{22}H_{14}Cl_3F_3N_4O_2$, 528.01; m/z found, 531 [M+H]$^+$. $^1$H NMR (CDCl$_3$): 8.71 (s, 1H), 8.12 (s, 1H), 7.92 (dd, J=8.3, 0.7 Hz, 1H), 7.89 (d, J=2.0 Hz, 1H), 7.78 (d, J=8.3 Hz, 1H), 7.62 (dd, J=8.3, 2.0 Hz, 1H), 7.52 (d, J=8.4 Hz, 1H), 6.81 (d, J=1.1 Hz, 1H), 6.62 (d, J=0.9 Hz, 1H), 5.43-5.29 (m, 1H), 5.23-5.15 (m, 1H), 4.15 (ddd, J=14.8, 5.6, 2.3 Hz, 1H), 3.94 (td, J=14.8, 6.0 Hz, 1H).

Example 214

1-[3-(4-Chloro-phenyl)-isoxazol-5-yl]-2-[6-(3-chloro-4-trifluoromethyl-Phenyl)-pyrimidin-4-ylamino]-ethanol

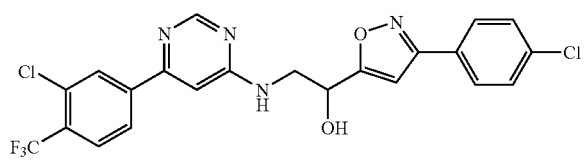

MS (ESI): mass calcd. for $C_{22}H_{15}Cl_2F_3N_4O_2$, 494.05; m/z found, 495.1 [M+H]$^+$. $^1$H NMR (CDCl$_3$): 8.71 (d, J=0.6 Hz, 1H), 8.16-8.06 (m, 1H), 7.91 (dd, J=8.2, 0.68 Hz, 1H), 7.78 (d, J=8.3 Hz, 1H), 7.74-7.71 (m, 2H), 7.46-7.38 (m, 2H), 6.80 (d, J=1.1 Hz, 1H), 6.62 (d, J=0.9 Hz, 1H), 5.44-5.31 (m, 1H), 5.21-5.15 (m, 1H), 4.18-4.11 (m, 1H), 3.99-3.88 (m, 1H).

Example 215

2-[6-(3-Chloro-4-trifluoromethyl-phenyl)-pyrimidin-4-ylamino]-1-[3-(2,4-dichloro-phenyl)-isoxazol-5-yl]-ethanol

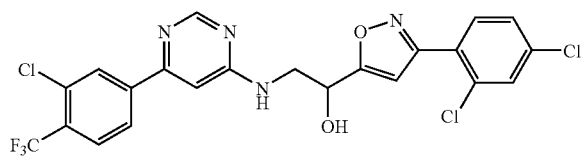 [SMILES: OC(CNc1cc(-c2ccc(C(F)(F)F)c(Cl)c2)ncn1)c1cc(-c2ccc(Cl)cc2Cl)no1]

MS (ESI): mass calcd. for $C_{22}H_{14}Cl_3F_3N_4O_2$, 528.01; m/z found, 531 [M+H]$^+$. $^1$H NMR (CDCl$_3$): 8.75-8.64 (m, 1H), 8.13 (s, 1H), 7.92 (d, J=8.0 Hz, 1H), 7.79 (d, J=8.3 Hz, 1H), 7.66 (d, J=8.4 Hz, 1H), 7.50 (d, J=2.1 Hz, 1H), 7.34 (dd, J=8.4, 2.1 Hz, 1H), 6.81 (d, J=1.1 Hz, 1H), 6.76 (d, J=0.8 Hz, 1H), 5.46-5.32 (m, 1H), 5.24-5.18 (m, 1H), 4.20-4.07 (m, 1H), 4.02-3.92 (m, 1H).

Example 216

1-Benzothiazol-2-yl-2-[6-(3-chloro-4-trifluoromethyl-phenyl)-pyrimidin-4-ylamino]-ethanol

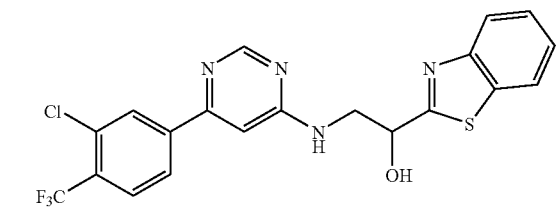

MS (ESI): mass calcd. for $C_{20}H_{14}ClF_3N_4OS$, 450.05; m/z found, 451.1 [M+H]$^+$. $^1$H NMR (CDCl$_3$): 8.71 (s, 1H), 8.10 (s, 1H), 7.99 (d, J=8.2 Hz, 1H), 7.90 (d, J=8.1 Hz, 2H), 7.76 (d, J=8.3 Hz, 1H), 7.49 (ddd, J=8.3, 7.3, 1.2 Hz, 1H), 7.42-7.37 (m, 1H), 6.77 (d, J=1.1 Hz, 1H), 5.54-5.40 (m, 1H), 5.35 (dt, J=5.3, 2.6 Hz, 1H), 4.37-4.19 (m, 1H), 4.09 (td, J=14.6, 5.8, Hz, 1H).

Example 217

1-[3,5-Bis(trifluoromethyl)phenyl]-2-({6-[3-chloro-4-(trifluoromethyl)phenyl]pyrimidin-4-yl}amino)ethanol

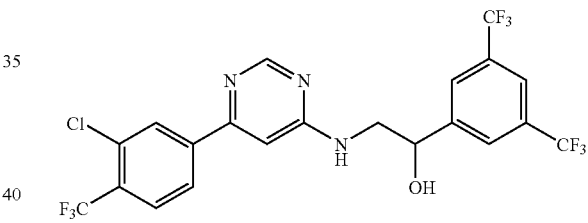

MS (ESI): mass calcd. for $C_{21}H_{13}ClF_9N_3O$, 529.06; m/z found, 530.1 [M+H]$^+$. $^1$H NMR (CDCl$_3$): 8.73 (s, 1H), 8.13 (s, 1H), 7.96-7.88 (m, 3H), 7.83-7.77 (m, 2H), 6.87-6.73 (m, 1H), 5.35-5.23 (m, 1H), 5.19-5.13 (m, 1H), 4.05-3.85 (m, 1H), 3.77-3.64 (m, 1H).

Example 218

1-(5-Bromo-1-benzothiophen-2-yl)-2-({6-[3-chloro-4-(trifluoromethyl)phenyl]pyrimidin-4-yl}amino)ethanol

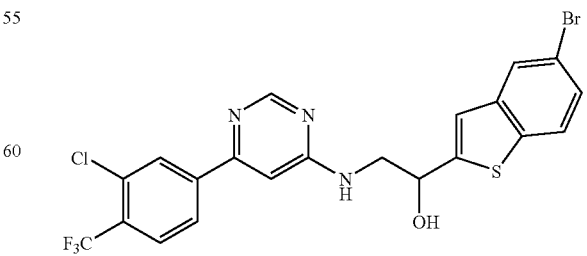

MS (ESI): mass calcd. for $C_{21}H_{14}BrClF_3N_3OS$, 526.97; m/z found, 530.0 [M+H]$^+$. $^1$H NMR (CDCl$_3$): 8.86-8.62 (m, 1H), 8.19-8.09 (m, 2H), 7.97-7.87 (m, 1H), 7.83-7.70 (m, 2H), 7.60-7.45 (m, 2H), 6.84-6.62 (m, 1H), 5.67-5.22 (m, 2H), 4.26-4.02 (m, 1H), 3.81-3.68 (m, 1H).

Examples 219-221 were prepared using methods analogous to those described in Example 20.

Example 219

(1R)-Phenyl-2-{6-[4-(1,2,2,2-tetrafluoro-1-trifluoromethyl-ethyl)-phenyl]-pyrimidin-4-ylamino}-ethanol

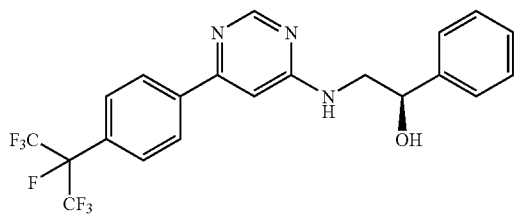 [SMILES: O[C@@H](CNc1cc(-c2ccc(C(F)(C(F)(F)F)C(F)(F)F)cc2)ncn1)c1ccccc1]

MS (ESI+): calcd for $C_{21}H_{16}F_7N_3O$ m/z 459.12. found 460.1 (M+H)+. 1H NMR (CD3OD): 8.50 (s, 1H), 8.24 (s, 1H), 8.14-8.09 (m, 1H), 7.77-7.69 (m, 2H), 7.43 (d, J=7.5 Hz, 2H), 7.34 (t, J=7.5 Hz, 2H), 7.25 (t, J=7.5 Hz, 1H), 6.96 (s, 1H), 4.92-4.90 (m, 1H), 3.74 (br s, 1H), 3.62-3.58 (m, 1H).

Example 220

(1R)-Phenyl-2-{6-[3-(1,2,2,2-tetrafluoro-1-trifluoromethyl-ethyl)-phenyl]-Pyrimidin-4-ylamino}-ethanol

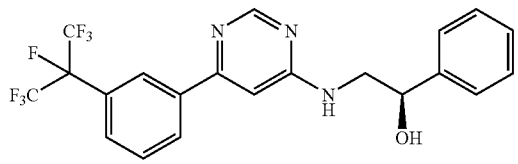 [SMILES: O[C@@H](CNc1cc(-c2cccc(C(F)(C(F)(F)F)C(F)(F)F)c2)ncn1)c1ccccc1]

MS (ESI+): calcd for $C_{21}H_{16}F_7N_3O$ m/z 459.12. found 460.2 (M+H)+. 1H NMR (CD3OD): 8.50 (s, 1H), 8.24 (s, 1H), 8.13 (d, J=7.5 Hz, 1H), 7.76 (d, J=8.0 Hz, 1H), 7.71 (t, J=7.5 Hz, 1H), 7.43 (d, J=7.5 Hz, 2H), 7.34 (t, J=7.5 Hz, 2H), 7.25 (t, J=7.5 Hz, 1H), 4.92-4.89 (m, 1H), 3.74 (brs, 1H), 3.62-3.58 (m, 1H).

Example 221

(1R)-Phenyl-2-[6-(3-trifluoromethyl-benzo[b]thiophen-6-yl)-pyrimidin-4-ethanol

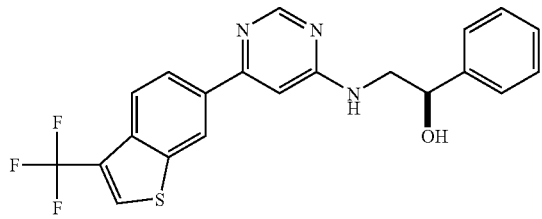 [SMILES: O[C@@H](CNc1cc(-c2ccc3c(C(F)(F)F)csc3c2)ncn1)c1ccccc1]

MS (ESI): mass calcd. for $C_{21}H_{16}F_3N_3OS$, 415.10; m/z found, 416.1 [M+H]+. 1H NMR (CD3OD): 8.70 (s, 1H), 8.52-8.51 (m, 2H), 8.13 (d, J=8.4 Hz, 1H), 7.90 (dd, J=1.7, 8.6 Hz, 1H), 7.45 (d, J=7.4 Hz, 2H), 7.36 (t, J=7.2 Hz, 2H), 7.30-7.26 (m, 1H), 7.12 (s, 1H), 4.98-4.95 (m, 1H), 3.95 (dd, J=4.2, 14 Hz, 1H), 3.85-3.80 (m, 1H).

Example 222 can be prepared using methods analogous to those described in Example 141.

Example 222

4-(3-Chloro-4-trifluoromethyl-phenyl)-6-(2-hydroxy-2-phenyl-(1R)-ethylamino)-pyrimidine-2-carbonitrile

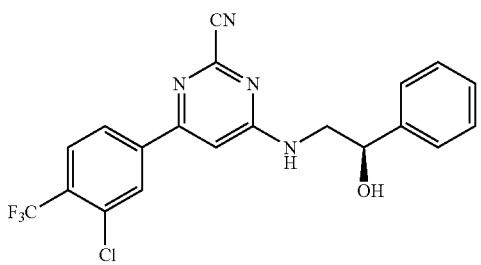 [SMILES: N#Cc1nc(NC[C@H](O)c2ccccc2)cc(-c2ccc(C(F)(F)F)c(Cl)c2)n1]

The compounds of the following Examples 223-245 were obtained by our employer from a third party as library compounds and therefore were known to us as compounds per se. We discovered that these compounds have FMH-modulating activity, and that they therefore have utility in the therapeutic compositions and methods according to the invention, as reflected by the assay results for these compounds shown in Table 1.

Example 223

2-{[6-(3,4-Dimethylphenyl)pyrimidin-4-yl]amino}-1-phenylethanol

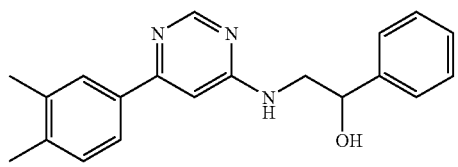 [SMILES: Cc1ccc(-c2cc(NCC(O)c3ccccc3)ncn2)cc1C]

Example 224

2-({6-[4-(1,1-Dimethylethyl)phenyl]pyrimidin-4-yl}amino)-1-phenylethanol

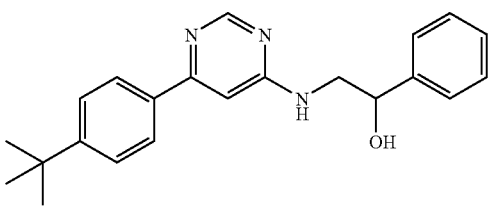 [SMILES: CC(C)(C)c1ccc(-c2cc(NCC(O)c3ccccc3)ncn2)cc1]

Example 225

2-[6-(4-Methylsulfanyl-phenyl)-Pyrimidin-4-ylamino]-1-phenyl-ethanol

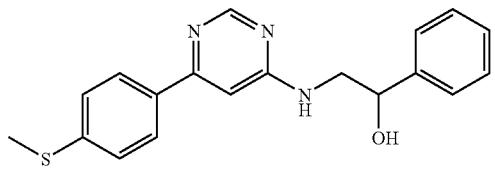

Example 226

4-{6-[(2-Hydroxy-2-phenylethyl)amino]pyrimidin-4-yl}benzonitrile

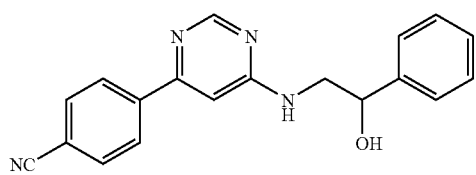

Example 227

2-(6-Benzo[b]thiophen-2-yl-pyrimidin-4-ylamino)-1-phenyl-ethanol

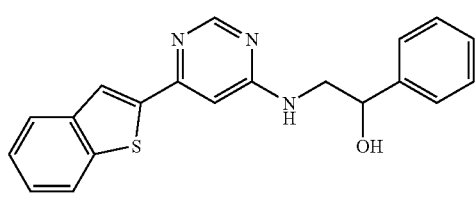 [SMILES: OC(CNc1cc(-c2cc3ccccc3s2)ncn1)c1ccccc1]

Example 228

1-(4-{6-[(2-Hydroxy-2-phenylethyl)amino]pyrimidin-4-yl}phenyl)ethanone

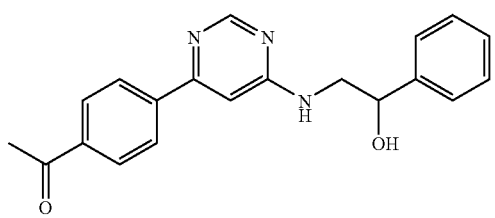 [SMILES: CC(=O)c1ccc(-c2cc(NCC(O)c3ccccc3)ncn2)cc1]

Example 229

2-[6-(3,4-Dimethoxy-phenyl)-pyrimidin-4-ylamino]-1-phenyl-ethanol

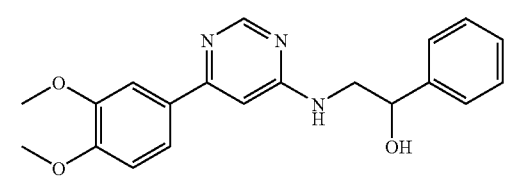 [SMILES: COc1ccc(-c2cc(NCC(O)c3ccccc3)ncn2)cc1OC]

Example 230

2-{[6-(4-Methylphenyl)pyrimidin-4-yl]amino}-1-phenylethanol

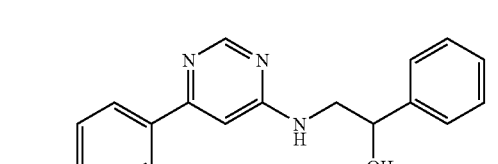

Example 231

1-Phenyl-2-[(6-{4-[(trifluoromethyl)oxy]phenyl}pyrimidin-4-yl)amino]ethanol trifluoroacetic acid salt

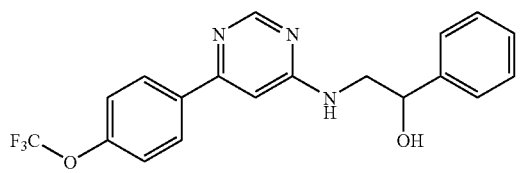

Example 232

2-(6-Benzo[1,3]dioxol-5-yl-pyrimidin-4-ylamino)-1-phenyl-ethanol

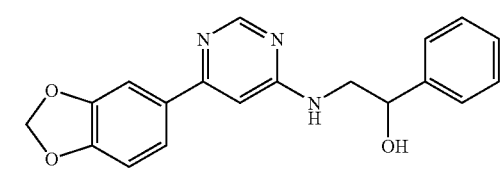 [SMILES: OC(CNc1cc(-c2ccc3c(c2)OCO3)ncn1)c1ccccc1]

Example 233

2-[6-(3-Methoxy-phenyl)-pyrimidin-4-ylamino]-1-phenyl-ethanol

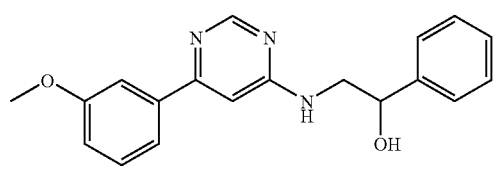 [SMILES: COc1cccc(-c2cc(NCC(O)c3ccccc3)ncn2)c1]

Example 234

2-[6-(3-Nitro-phenyl)-pyrimidin-4-ylamino]-1-phenyl-ethanol

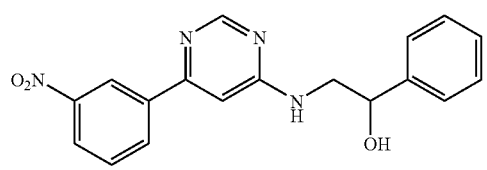 [SMILES: O=[N+]([O-])c1cccc(-c2cc(NCC(O)c3ccccc3)ncn2)c1]

Example 235

2-[(6-Naphthalen-2-ylpyrimidin-4-yl)amino]-1-phenylethanol

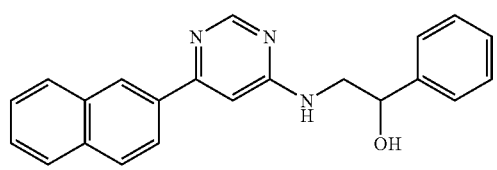 [SMILES: OC(CNc1cc(-c2ccc3ccccc3c2)ncn1)c1ccccc1]

Example 236

1-{5-[6-(2-Hydroxy-2-phenyl-ethylamino)-pyrimidin-4-yl]-thiophen-2-yl}-ethanone

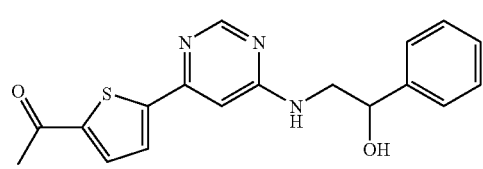 [SMILES: CC(=O)c1ccc(-c2cc(NCC(O)c3ccccc3)ncn2)s1]

Example 237

2-[6-(2,6-Difluoro-phenyl)-pyrimidin-4-ylamino]-1-phenyl-ethanol

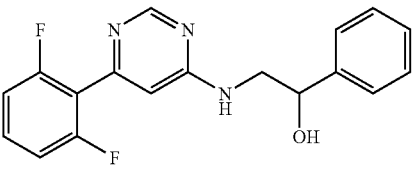 [SMILES: OC(CNc1cc(-c2c(F)cccc2F)ncn1)c1ccccc1]

Example 238

4-[6-(2-Hydroxy-2-phenyl-ethylamino)-pyrimidin-4-yl]-phenol

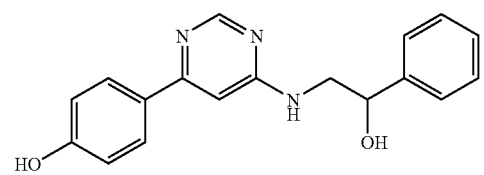

Example 239

2-[6-(3,5-Bis-trifluoromethyl-phenyl)-pyrimidin-4-ylamino]-1-phenyl-ethanol

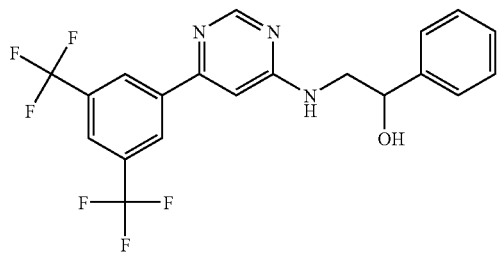 [SMILES: OC(CNc1cc(-c2cc(C(F)(F)F)cc(C(F)(F)F)c2)ncn1)c1ccccc1]

Example 240

2-[6-(3-Amino-phenyl)-pyrimidin-4-ylamino]-1-phenyl-ethanol

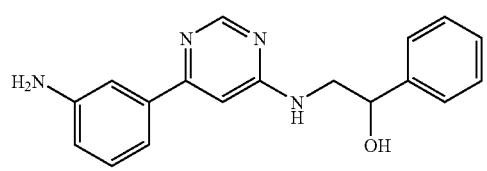

Example 241

2-[6-(4-Hydroxymethyl-phenyl)-Pyrimidin-4-ylamino]-1-phenyl-ethanol

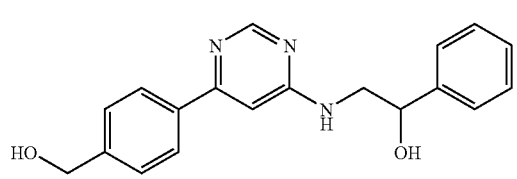 [SMILES: OCc1ccc(-c2cc(NCC(O)c3ccccc3)ncn2)cc1]

Example 242

N-{3-[6-(2-Hydroxy-2-phenyl-ethylamino)-pyrimidin-4-yl]-phenyl}-acetamide

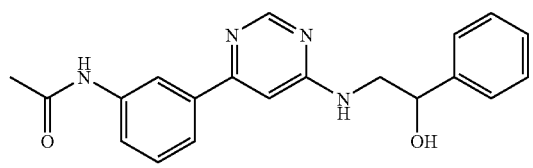 [SMILES: CC(=O)Nc1cccc(-c2cc(NCC(O)c3ccccc3)ncn2)c1]

Example 243

1-Phenyl-2-(6-phenyl-pyrimidin-4-ylamino)-ethanol

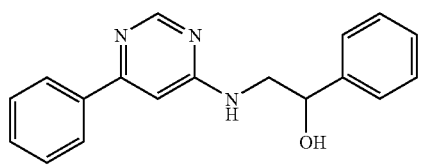 [SMILES: OC(CNc1cc(-c2ccccc2)ncn1)c1ccccc1]

Example 244

1-Phenyl-2-(6-thiophen-2-yl-pyrimidin-4-ylamino)-ethanol

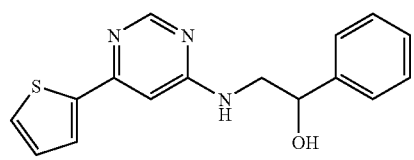 [SMILES: OC(CNc1cc(-c2cccs2)ncn1)c1ccccc1]

Example 245

1-Phenyl-2-(6-thiophen-3-yl-pyrimidin-4-ylamino)-ethanol

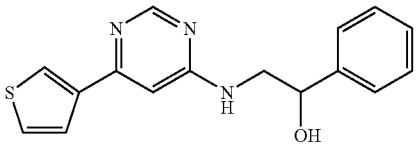 [SMILES: OC(CNc1cc(-c2ccsc2)ncn1)c1ccccc1]

Comparative Examples

The compounds of the following Comparative Examples 1-8 were also obtained by our employer from a third party as library compounds and therefore were known to us as compounds per se. The comparative assay results for these compounds are shown in Table 2.

Comparative Example 1

2-[6-(2,6-Bis-trifluoromethyl-phenyl)-pyrimidin-4-ylamino]-1-phenyl-ethanol

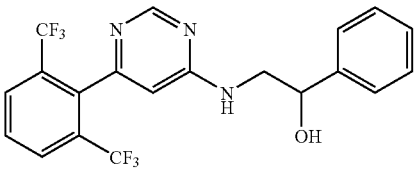 [SMILES: OC(CNc1cc(-c2c(C(F)(F)F)cccc2C(F)(F)F)ncn1)c1ccccc1]

Comparative Example 2

N-{3-[6-(2-Hydroxy-2-phenyl-ethylamino)-pyrimidin-4-yl]-phenyl}-acetamide

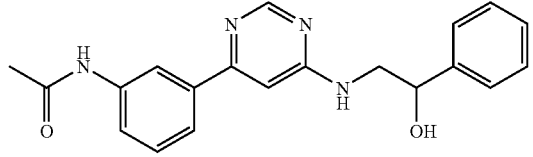 [SMILES: CC(=O)Nc1cccc(-c2cc(NCC(O)c3ccccc3)ncn2)c1]

Comparative Example 3

1-Phenyl-2-(6-phenyl-pyrimidin-4-ylamino)-ethanol

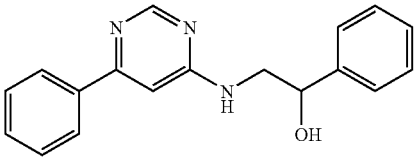 [SMILES: OC(CNc1cc(-c2ccccc2)ncn1)c1ccccc1]

Comparative Example 4

2-[6-(2,6-Difluoro-phenyl)-pyrimidin-4-ylamino]-1-phenyl-ethanol

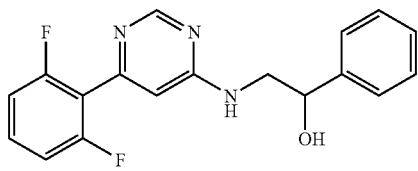 [SMILES: OC(CNc1cc(-c2c(F)cccc2F)ncn1)c1ccccc1]

Comparative Example 5

1-Phenyl-2-(6-thiophen-2-yl-pyrimidin-4-ylamino)-ethanol

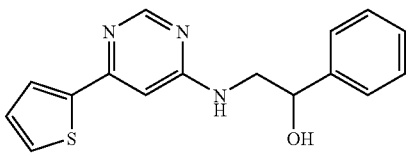 [SMILES: OC(CNc1cc(-c2cccs2)ncn1)c1ccccc1]

Comparative Example 6

4-[6-(2-Hydroxy-2-phenyl-ethylamino)-pyrimidin-4-yl]-phenol

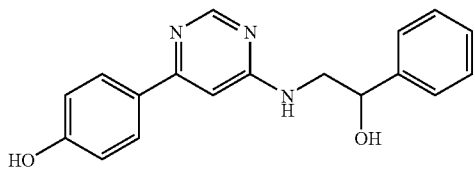 [SMILES: Oc1ccc(-c2cc(NCC(O)c3ccccc3)ncn2)cc1]

Comparative Example 7

1-Phenyl-2-(6-thiophen-3-yl-pyrimidin-4-ylamino)-ethanol

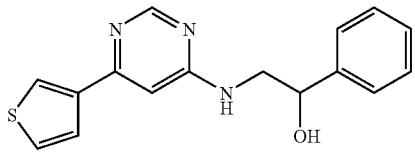 [SMILES: OC(CNc1cc(-c2ccsc2)ncn1)c1ccccc1]

Comparative Example 8

2-[6-(3-Amino-phenyl)-pyrimidin-4-ylamino]-1-phenyl-ethanol

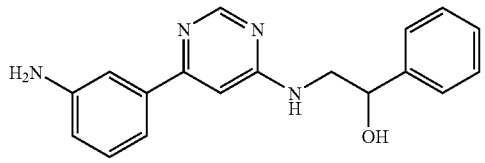

Biological Testing:

Assay Method 1

A. Transfection of Cells with Human FAAH

A 10-cm tissue culture dish with a confluent monolayer of SK-N-MC cells was split 2 days (d) prior to transfection. Using sterile technique, the media was removed and the cells were detached from the dish by the addition of trypsin. One fifth of the cells were then placed onto a new 10-cm dish. Cells were grown in a 37° C. incubator with 5% $CO_2$ in Minimal Essential Media Eagle with 10% Fetal Bovine Serum. After 2 d, cells were approximately 80% confluent. These cells were removed from the dish with trypsin and pelleted in a clinical centrifuge. The pellet was re-suspended in 400 μL complete media and transferred to an electroporation cuvette with a 0.4 cm gap between the electrodes. Supercoiled human FAAH cDNA (1 μg) was added to the cells and mixed. The voltage for the electroporation was set at 0.25 kV, and the capacitance was set at 960 μF. After electroporation, the cells were diluted into complete media (10 mL) and plated onto four 10-cm dishes. Because of the variability in the efficiency of electroporation, four different concentrations of cells were plated.

The ratios used were 1:20, 1:10, and 1:5, with the remainder of the cells being added to the fourth dish. The cells were allowed to recover for 24 h before adding the selection media (complete media with 600 μg/mL G418). After 10 d, dishes were analyzed for surviving colonies of cells. Dishes with well-isolated colonies were used. Cells from individual colonies were isolated and tested. The clones that showed the most FAAH activity, as measured by anandamide hydrolysis, were used for further study.

B. FMH Assay

T84 frozen cell pellets or transfected SK-N-MC cells (contents of 1×15 cm culture dishes) were homogenized in 50 mL of FAAH assay buffer (125 mM Tris, 1 mM EDTA, 0.2% Glycerol, 0.02% Triton X-100, 0.4 mM Hepes, pH 9). The assay mixture consisted of 50 μL of the cell homogenate, 10 μL of the test compound, and 40 μL of anandamide [1-$^3$H-ethanolamine] (3H-AEA, Perkin-Elmer, 10.3 $C_i$/mmol), which was added last, for a final tracer concentration of 80 nM. The reaction mixture was incubated at rt for 1 h. During the incubation, 96-well Multiscreen filter plates (catalog number MAFCNOB50; Millipore, Bedford, Mass., USA) were loaded with 25 μL of activated charcoal (Multiscreen column loader, catalog number MACL09625, Millipore) and washed once with 100 μL of MeOH. Also during the incubation, 96-well DYNEX MicroLite plates (catalog number NL510410) were loaded with 100 μL of MicroScint40 (catalog number 6013641, Packard Bioscience, Meriden, Conn., USA). After the 1 h incubation, 60 μL of the reaction mixture were transferred to the charcoal plates, which were then assembled on top of the DYNEX plates using Centrifuge Alignment Frames (catalog number MACF09604, Millipore). The unbound labeled ethanolamine was centrifuged through to the bottom plate (5 min at 2000 rpm), which was preloaded with the scintillant, as described above. The plates were sealed and left at rt for 1 h before counting on a Hewlett Packard TopCount.

Assay Method 2

A. Transfection of Cells with Rat FAAH-1

A 10-cm tissue culture dish with a confluent monolayer of SK-N-MC cells was split 2 days (d) prior to transfection. Using sterile technique, the media was removed and the cells were detached from the dish by the addition of trypsin. One fifth of the cells were then placed onto a new 10-cm dish. Cells were grown in a 37° C. incubator with 5% $CO_2$ in Minimal Essential Media Eagle with 10% Fetal Bovine Serum. After 2 d, cells were approximately 80% confluent. These cells were removed from the dish with trypsin and pelleted in a clinical centrifuge. The pellet was re-suspended in 400 μL complete media and transferred to an electroporation cuvette with a 0.4 cm-gap between the electrodes. Supercoiled rat FAAH cDNA (1 μg) was added to the cells and mixed. The voltage for the electroporation was set at 0.25 kV, and the capacitance was set at 960 μF. After electroporation, the cells were diluted into complete media (10 mL) and plated onto four 10-cm dishes. Because of the variability in the efficiency of electroporation, four different concentrations of cells were plated. The ratios used were 1:20, 1:10, and 1:5, with the remainder of the cells being added to the fourth dish. The cells were allowed to recover for 24 h before adding the selection media (complete media with 600 μg/mL G418). After 10 d, dishes were analyzed for surviving colonies of cells. Dishes with well-isolated colonies were used. Cells from individual colonies were isolated and tested. The clones that showed the most FAAH activity, as measured by anandamide hydrolysis, were used for further study.

B. Rat FMH-1 Assay

T84 frozen cell pellets or transfected SK-N-MC cells (contents of 1×15 cm culture dishes) were homogenized in 50 mL of FAAH assay buffer (125 mM Tris, 1 mM EDTA, 0.2% Glycerol, 0.02% Triton X-100, 0.4 mM Hepes, pH 9). The assay mixture consisted of 50 μL of the cell homogenate, 10 μL of the test compound, and 40 μL of anandamide [1-$^3$H-ethanolamine] ($^3$H-AEA, Perkin-Elmer, 10.3 C$_i$/mmol), which was added last, for a final tracer concentration of 80 nM. The reaction mixture was incubated at rt for 1 h. During the incubation, 96-well Multiscreen filter plates (catalog number MAFCNOB50; Millipore, Bedford, Mass., USA) were loaded with 25 μL of activated charcoal (Multiscreen column loader, catalog number MACL09625, Millipore) and washed once with 100 μL of MeOH. Also during the incubation, 96-well DYNEX MicroLite plates (catalog number NL510410) were loaded with 100 μL of MicroScint40 (catalog number 6013641, Packard Bioscience, Meriden, Conn., USA). After the 1 h incubation, 60 μL of the reaction mixture were transferred to the charcoal plates, which were then assembled on top of the DYNEX plates using Centrifuge Alignment Frames (catalog number MACF09604, Millipore). The unbound labeled ethanolamine was centrifuged through to the bottom plate (5 min at 2000 rpm), which was preloaded with the scintillant, as described above. The plates were sealed and left at rt for 1 h before counting on a Hewlett Packard TopCount.

Results for Example compounds tested in these assays are presented in Table 1. Results for Comparative Example compounds tested in these assays are presented in Table 2. Where activity is shown as greater than (>) a particular value, the value is the solubility limit of the compound in the assay medium or the highest concentration tested in the assay. Reference to the term "NT" in the tables means the compound was not tested.

TABLE 1

| Ex. | Assay 1 IC$_{50}$ (μM) | Assay 2 IC$_{50}$ (μM) |
| --- | --- | --- |
| 1 | 0.003 | 0.006 |
| 2 | 0.350 | 1.300 |
| 3 | 5.000 | >10 |
| 4 | 0.036 | 0.100 |
| 5 | 0.132 | 0.153 |
| 6 | 0.033 | 0.233 |
| 7 | 0.008 | 0.106 |
| 8 | 0.074 | 0.168 |
| 9 | 0.467 | 1.200 |
| 10 | 0.024 | 0.026 |
| 11 | 0.034 | 0.375 |
| 12 | 0.186 | 0.382 |
| 13 | 0.035 | 0.250 |
| 14 | 0.006 | 0.013 |
| 15 | 0.026 | 0.068 |
| 16 | 0.004 | 0.005 |
| 16A | 0.0057 | 0.0076 |
| 17 | 0.012 | 0.010 |
| 18 | 0.005 | 0.097 |
| 19 | 0.020 | 0.012 |
| 20 | 0.032 | 0.181 |
| 21 | 0.340 | 1.500 |
| 22 | 0.081 | 0.270 |
| 23 | 5.000 | 10.000 |
| 24 | 0.013 | 0.208 |
| 25 | 0.390 | 10.000 |
| 26 | 0.052 | 0.163 |
| 27 | 0.024 | 0.120 |
| 28 | 0.025 | 0.064 |
| 29 | 0.008 | 0.026 |
| 30 | 0.007 | 0.034 |
| 31 | 0.003 | 0.021 |
| 32 | 0.092 | 1.000 |
| 33 | 0.270 | 2.000 |
| 34 | 0.500 | 10.000 |
| 35 | 0.043 | 0.180 |
| 36 | 0.008 | 0.020 |
| 37 | 0.400 | 8.000 |
| 38 | 0.027 | 0.260 |
| 39 | 0.018 | 0.060 |
| 40 | 0.766 | >10 |
| 41 | 0.005 | 0.010 |
| 42 | 0.206 | 0.793 |
| 43 | 0.088 | 0.446 |
| 44 | 0.050 | 0.600 |
| 45 | 0.150 | 0.600 |
| 46 | 0.013 | 0.026 |
| 47 | 0.026 | 0.510 |
| 48 | 0.105 | 1.500 |
| 49 | 0.002 | 0.009 |
| 50 | 0.092 | 0.985 |
| 51 | 0.004 | 0.007 |
| 52 | 1.400 | 10.000 |
| 53 | 0.765 | >10 |
| 54 | 0.277 | 0.443 |
| 55 | 0.020 | 1.700 |
| 56 | 0.002 | 0.040 |
| 57 | 0.029 | 0.535 |
| 58 | 0.104 | 0.470 |
| 59 | 0.307 | 1.000 |
| 60 | 0.006 | 0.028 |
| 61 | 0.006 | 0.028 |
| 62 | 0.002 | 0.003 |
| 63 | 0.450 | 2.000 |
| 64 | 0.050 | 0.220 |
| 65 | 0.038 | 6.001 |
| 66 | 0.073 | 0.140 |
| 67 | 0.020 | 1.200 |
| 68 | 0.001 | 0.003 |
| 69 | 0.900 | >10 |
| 70 | 0.800 | >10 |
| 71 | 0.014 | 0.076 |
| 72 | 0.013 | 0.188 |
| 73 | 0.020 | 0.040 |
| 74 | 0.101 | 10.000 |
| 75 | 10.000 | >10 |
| 76 | 0.014 | 0.126 |
| 77 | 1.000 | 2.200 |
| 78 | 0.633 | >10 |
| 79 | 0.542 | 0.530 |
| 80 | 0.068 | 0.665 |
| 81 | 0.110 | 0.492 |
| 82 | 2.000 | 10.000 |
| 83 | 0.210 | 0.654 |

TABLE 1-continued

| Ex. | Assay 1 IC$_{50}$ (μM) | Assay 2 IC$_{50}$ (μM) |
|---|---|---|
| 84 | 0.044 | 0.965 |
| 85 | 0.018 | 5.000 |
| 86 | 0.095 | 1.200 |
| 87 | 0.042 | 1.400 |
| 88 | 0.065 | 0.033 |
| 89 | 1.600 | 1.400 |
| 90 | 0.004 | 0.675 |
| 91 | 0.003 | 0.057 |
| 92 | 0.110 | 0.850 |
| 93 | 0.183 | 0.152 |
| 94 | 0.060 | 0.270 |
| 95 | 0.018 | 0.066 |
| 96 | 0.001 | 0.014 |
| 97 | 0.580 | 8.000 |
| 98 | 0.850 | 8.000 |
| 99 | 10.000 | 10.000 |
| 100 | 0.043 | 1.400 |
| 101 | 0.032 | 0.080 |
| 102 | 0.017 | 0.050 |
| 103 | 0.305 | 0.350 |
| 104 | 0.130 | 0.058 |
| 105 | 0.190 | 1.000 |
| 106 | 0.016 | 0.041 |
| 107 | 0.240 | 0.320 |
| 108 | 0.110 | 0.150 |
| 109 | 0.150 | 0.042 |
| 110 | 5.000 | 10.000 |
| 111 | 0.122 | 0.220 |
| 112 | 0.524 | 0.760 |
| 113 | 0.018 | 0.041 |
| 114 | 0.046 | 0.043 |
| 115 | 0.140 | 0.205 |
| 116 | 0.090 | 0.110 |
| 117 | 0.032 | 0.022 |
| 118 | 0.093 | >10 |
| 119 | 0.017 | 0.055 |
| 120 | >10 | >10 |
| 121 | 0.580 | 3.000 |
| 122 | 0.013 | 0.019 |
| 123 | 0.700 | 10.000 |
| 124 | 0.800 | 4.000 |
| 125 | 0.890 | 5.000 |
| 126 | 1.200 | 1.000 |
| 127 | 0.122 | 0.112 |
| 128 | 1.200 | 5.000 |
| 129 | 0.016 | 0.120 |
| 130 | 0.120 | 0.015 |
| 131 | 0.024 | 0.015 |
| 132 | 0.012 | 0.015 |
| 133 | 0.030 | 0.015 |
| 134 | 0.027 | 0.019 |
| 135 | 0.100 | 0.016 |
| 136 | 0.084 | 0.340 |
| 137 | 0.920 | 5.000 |
| 138 | 0.371 | 10.000 |
| 139 | 2.000 | 10.000 |
| 140 | 0.127 | 0.265 |
| 141 | 0.012 | 0.005 |
| 142 | 0.009 | 0.060 |
| 143 | 6.00 | 4.00 |
| 144 | 0.015 | 0.003 |
| 145 | 7.00 | 2.00 |
| 146 | 0.026 | 0.004 |
| 147 | 0.205 | 1.600 |
| 148 | 3.000 | >10 |
| 149 | 0.412 | 10.000 |
| 150 | 1.500 | 5.000 |
| 151 | 10.000 | 10.000 |
| 152 | 4.000 | >10 |
| 153 | 0.303 | 10.000 |
| 154 | 0.065 | 1.200 |
| 155 | 0.060 | 0.270 |
| 156 | 0.018 | 0.066 |
| 157 | 2.000 | 4.000 |
| 158 | 3.464 | 0.110 |
| 159 | 0.020 | 0.007 |
| 160 | 0.150 | 0.290 |
| 161 | 10.000 | 0.580 |
| 162 | 0.570 | 0.130 |
| 163 | 2.000 | 2.000 |
| 164 | 0.015 | 0.014 |
| 165 | 0.004 | 0.019 |
| 166 | 3.000 | 10.000 |
| 167 | 0.060 | 0.020 |
| 168 | 0.066 | 0.042 |
| 169 | 6.001 | 8.000 |
| 170 | 0.081 | 4.000 |
| 171 | 1.600 | >10 |
| 172 | 8.000 | 1.500 |
| 173 | 0.002 | 0.011 |
| 174 | 0.002 | 0.005 |
| 175 | 0.002 | 0.003 |
| 176 | 0.009 | 0.010 |
| 177 | 0.003 | 0.003 |
| 178 | 0.008 | 0.070 |
| 179 | 0.009 | 0.040 |
| 180 | 0.001 | 0.011 |
| 181 | 0.007 | 0.020 |
| 182 | 0.010 | 0.004 |
| 183 | 0.036 | 0.089 |
| 184 | 0.031 | 0.160 |
| 185 | 0.020 | 0.090 |
| 186 | 7.071 | >10 |
| 187 | 0.020 | 0.400 |
| 188 | 0.024 | 0.035 |
| 189 | 0.170 | 0.150 |
| 190 | 0.007 | 0.012 |
| 191 | 0.019 | 0.007 |
| 192 | 0.047 | 0.006 |
| 193 | 0.040 | 0.850 |
| 194 | 0.011 | 0.210 |
| 195 | 0.010 | 0.400 |
| 196 | 0.108 | 0.043 |
| 197 | 0.100 | 0.034 |
| 198 | 0.092 | 0.025 |
| 199 | 0.500 | 0.120 |
| 200 | 0.165 | 1.600 |
| 201 | 0.170 | 0.170 |
| 202 | 0.225 | 0.100 |
| 203 | 0.270 | 0.200 |
| 204 | 0.548 | 0.082 |
| 205 | 0.080 | 0.014 |
| 206 | 0.025 | 0.015 |
| 207 | 0.067 | 0.111 |
| 208 | 0.028 | 0.500 |
| 209 | 0.012 | 0.036 |
| 210 | 0.020 | 0.020 |
| 211 | 0.056 | 0.050 |
| 212 | 0.065 | 0.039 |
| 213 | 0.022 | 0.400 |
| 214 | 0.036 | 0.160 |
| 215 | 0.240 | 1.000 |
| 216 | >10 | >10 |
| 217 | >10 | 8.000 |
| 218 | >10 | 1.000 |
| 219 | 2 | >10 |
| 220 | 0.042 | 0.69 |
| 221 | 0.019 | 0.48 |
| 223 | 0.144 | 0.707 |
| 224 | 0.028 | 0.538 |
| 225 | 0.011 | 0.128 |
| 226 | 0.341 | 0.663 |
| 227 | 0.033 | 0.216 |
| 228 | 0.026 | 0.066 |
| 229 | 0.408 | 10.00 |
| 230 | 0.575 | 3.464 |
| 231 | 0.031 | 0.201 |
| 232 | 0.150 | 1.00 |
| 233 | 2.00 | NT |
| 234 | >10 | >10 |
| 235 | 0.021 | 0.324 |
| 236 | 0.700 | 4.00 |
| 237 | >10 | >10 |
| 238 | 7 | >10 |

TABLE 1-continued

| Ex. | Assay 1 IC$_{50}$ (μM) | Assay 2 IC$_{50}$ (μM) |
| --- | --- | --- |
| 239 | >10 | >10 |
| 240 | >10 | >10 |
| 241 | NT | NT |
| 242 | >10 | >10 |
| 243 | >10 | >10 |
| 244 | >10 | >10 |
| 245 | >10 | >10 |

TABLE 2

| Ex. | Assay 1 IC$_{50}$ (μM) | Assay 2 IC$_{50}$ (μM) |
| --- | --- | --- |
| CE1 | >10 | >10 |
| CE2 | >10 | >10 |
| CE3 | >10 | >10 |
| CE4 | >10 | >10 |
| CE5 | >10 | >10 |
| CE6 | 7.00 | >10 |
| CE7 | >10 | >10 |
| CE8 | >10 | >10 |

While the invention has been illustrated by reference to exemplary and preferred embodiments, it will be understood that the invention is intended not to be limited to the foregoing detailed description, but to be defined by the appended claims as properly construed under principles of patent law.

What is claimed is:

1. A compound of Formula (I-A):

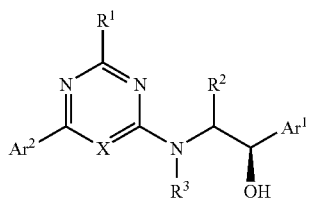

(I-A)

wherein:

$R^1$ is —H, —C$_{1-4}$alkyl, —OC$_{1-4}$alkyl, —S(O)$_{0-2}$C$_{1-4}$alkyl, —CN, —CF$_3$, —N(R$^a$)R$^b$, or a monocyclic cycloalkyl group,
where R$^a$ and R$^b$ are each independently —H, —C$_{1-4}$alkyl optionally substituted with —OH, N(R$^m$)R$^n$, where R$^m$ and R$^n$ are —H, C$_{1-4}$alkyl; or taken together with the nitrogen of attachment R$^a$ and R$^b$ form a 4-7 membered heterocycloalkyl ring;

Ar$^1$ is a phenyl, napthyl, a 5 or 6 membered monocyclic heteroaryl group with carbon at the point of attachment, or a 9 or 10 membered bicyclic heteroaryl group with carbon at the point of attachment, each unsubstituted or substituted with:
(i) one, two, or three R$^c$ moieties,
where each R$^c$ moiety is independently —C$_{1-4}$alkyl, —C$_{1-4}$alkyl-OH, —C$_{1-4}$alkyl-CN, —CF$_3$, —OH, —OC$_{1-4}$alkyl, —OCF$_3$, —OCHF$_2$, —OCH$_2$CF$_3$, —S(O)$_{0-2}$C$_{1-4}$alkyl, —SCF$_3$, —SO$_2$CF$_3$, —CHO, —COC$_{1-4}$alkyl, —CO$_2$C$_{1-4}$alkyl, —CO$_2$H, —N(R$^d$)R$^e$, —SO$_2$NR$^d$R$^e$, —NR$^d$SO$_2$R$^e$, —C(O)NR$^d$R$^e$, —NO$_2$, —CN, phenyl, pyridyl, or halo, where R$^d$ and R$^e$ are each independently —H or —C$_{1-4}$alkyl, or taken together R$^d$ and R$^e$ with the nitrogen of attachment form a 4-7 membered heterocycloalkyl ring; or
(ii) two or three R$^c$ moieties where two R$^c$ moieties are adjacent to each other and together form —O(CH$_2$)$_{1-3}$O— unsubstituted or substituted with one or two fluoro groups, and the third R$^c$ moiety, when present, is —C$_{1-4}$alkyl, —CF$_3$, —OH, —OCF$_3$, —OCHF$_2$, —OCH$_2$CF$_3$, —S(O)$_{0-2}$C$_{1-4}$alkyl, —SCF$_3$, —SO$_2$CF$_3$, —CHO, —COC$_{1-4}$alkyl, —CO$_2$C$_{1-4}$alkyl, —CO$_2$H, —N(R$^d$)R$^e$, —SO$_2$NR$^d$R$^e$, —NR$^d$SO$_2$R$^e$, —C(O)NR$^d$R$^e$, —NO$_2$, —CN, or halo,
where R$^d$ and R$^e$ are each independently —H or —C$_{1-4}$alkyl;

X is C(R$^f$),
where R$^f$ is —H or methyl;

Ar$^2$ is:
(i) a phenyl group substituted with: (a) one, two, or three R$^g$ moieties each at a meta or para position, and optionally with one or two additional R$^g$ moieties at an ortho position;
where each R$^g$ moiety is independently —C$_{1-4}$alkyl, —C$_{1-4}$alkyl-OH, C$_{1-4}$alkyl-CN, perhaloalkyl, perhaloalkoxy, —OC$_{1-4}$alkyl, —OC$_{1-4}$alkyl-(monocyclic cycloalkyl), —S(O)$_{0-2}$C$_{1-4}$alkyl, —SCF$_3$, —SO$_2$CF$_3$, —CHO, —COC$_{1-4}$alkyl, —CO$_2$C$_{1-4}$alkyl, —CO$_2$H, —N(R$^h$)R$^i$, —SO$_2$NR$^j$R$^k$, —NR$^h$SO$_2$R$^i$, —C(O)NR$^j$R$^k$, —NO$_2$, —CN, or halo; or a phenoxy, benzyl, phenethyl, or benzoyl group unsubstituted or substituted with —C$_{1-4}$alkyl, —OC$_{1-4}$alkyl, perhaloalkyl, perhaloalkoxy, —NO$_2$, —CN, or halo;

where R$^h$ is —H or —C$_{1-4}$alkyl;
R$^i$ is —C$_{1-4}$alkyl or monoyclic cycloalkyl group;
or R$^h$ and R$^i$ taken together with the atoms to which they are attached form a monocyclic heterocycloalkyl ring;
R$^j$ is —H or —C$_{1-4}$alkyl; and
R$^k$ is —H, —C$_{1-4}$alkyl or monoyclic cycloalkyl group;
or R$^j$ and R$^k$ taken together with the atoms to which they are attached form a monocyclic heterocycloalkyl ring; or
(b) two adjacent R$^g$ moieties together form —O(CH$_2$)$_{1-2}$O— unsubstituted or substituted with one or two fluoro groups;
(ii) a monocyclic heteroaryl group substituted with one, two, or three R$^g$ moieties, where each R$^g$ moiety is independently or two adjacent R$^g$ moieties together form —O(CH$_2$)$_{1-2}$O— unsubstituted or substituted with one or two fluoro groups; or
(iii) a naphthyl or bicyclic heteroaryl group unsubstituted or substituted with one, two, or three R$^l$ moieties;
where each R$^l$ moiety is independently —C$_{1-4}$alkyl, —OC$_{1-4}$alkyl, perhaloalkyl, perhaloalkoxy, —NO$_2$, —CN, or halo;

R$^2$ is —H or methyl; and
R$^3$ is —H or methyl;
provided, however, that Ar$^2$ is not —CHO or para substituted —OCF$_3$ when Ar$^1$ is unsubstituted phenyl;
or a pharmaceutically acceptable salt.

2. A compound as defined in claim 1, wherein R¹ is —H, methyl, isopropyl, trifluoromethyl, methylsulfanyl, methylsulfinyl, methanesulfonyl, amino, methylamino, dimethylamino, or cyclopropyl.

3. A compound as defined in claim 1, wherein R¹ is —H.

4. A compound as defined in claim 1, wherein Ar¹ is a phenyl group, unsubstituted or substituted with one, two, or three R$^e$ moieties.

5. A compound as defined in claim 1, wherein R$^f$ is —H.

6. A compound as defined in claim 1, wherein Ar² is a phenyl substituted with one, two or three R$^g$ moieties each at a meta or para position.

7. A compound as defined in claim 1, wherein Ar² is a thiophenyl, pyridinyl, pyrimidinyl, or pyrazolyl group, each substituted with one, two, or three R$^g$ moieties.

8. A compound as defined in claim 1, wherein Ar² is a naphthyl, benzoxadiazolyl, indolyl, benzothiophenyl, quinolinyl, or indazolyl, each unsubstituted or substituted with one, two, or three R$^i$ moieties.

9. A compound as defined in claim 1, wherein R² is —H.

10. A compound as defined in claim 1, wherein R³ is —H.

11. A compound selected from the group consisting of:
  (1R)-2-({6-[4-(Ethyloxy)-3-(trifluoromethyl)phenyl]pyrimidin-4-yl}amino)-1-phenylethanol;
  (1R)-1-Phenyl-2-({6-[4-(trifluoromethyl)phenyl]pyrimidin-4-yl}amino)ethanol;
  (1R)-2-({6-[3-Chloro-4-(trifluoromethyl)phenyl]pyrimidin-4-yl}amino)-1-phenylethanol;
  (1R)-2-({6-[3-Chloro-4-(trifluoromethyl)phenyl]pyrimidin-4-yl}amino)-1-phenylethanol hydrochloride salt;
  (1R)-2-({6-[4-(1-Methylethyl)phenyl]pyrimidin-4-yl}amino)-1-phenylethanol;
  (1R)-2-[(6-{3-Chloro-4-[(1-methylethyl)oxy]phenyl}pyrimidin-4-yl)amino]-1-phenylethanol;
  (1R)-2-{[6-(3-Fluoro-4-methylphenyl)pyrimidin-4-yl]amino}-1-phenylethanol;
  (1R)-2-({6-[4-(Hydroxymethyl)phenyl]pyrimidin-4-yl}amino)-1-phenylethanol;
  4-(6-{[(2R)-2-Hydroxy-2-phenylethyl]amino}pyrimidin-4-yl)benzaldehyde;
  3-(6-{[(2R)-2-Hydroxy-2-phenylethyl]amino}pyrimidin-4-yl)benzaldehyde;
  (1R)-1-Phenyl-2-[(6-{4-[(2,2,2-trifluoroethyl)oxy]phenyl}pyrimidin-4-yl)amino]ethanol;
  (1R)-1-Phenyl-2-[(6-{3-[(2,2,2-trifluoroethyl)oxy]phenyl}pyrimidin-4-yl)amino]ethanol;
  (1R)-2-{[6-(4-Chloro-3-methylphenyl)pyrimidin-4-yl]amino}-1-phenylethanol;
  (1R)-2-{[6-(4-Chloro-3-fluorophenyl)pyrimidin-4-yl]amino}-1-phenylethanol;
  (1R)-2-({6-[4-Chloro-3-(trifluoromethyl)phenyl]pyrimidin-4-yl}amino)-1-phenylethanol;
  (1R)-2-({6-[3-Fluoro-4-(trifluoromethoxy)phenyl]pyrimidin-4-yl}amino)-1-phenylethanol;
  (1R)-2-{[6-(4-Ethoxy-3-fluorophenyl)pyrimidin-4-yl]amino}-1-phenylethanol;
  (1R)-2-{[6-(4-Ethoxy-3-methylphenyl)pyrimidin-4-yl]amino}-1-phenylethanol;
  (1R)-2-({6-[4-(Cyclopropylmethoxy)phenyl]pyrimidin-4-yl}amino)-1-phenylethanol;
  (1R)-2-{[6-(4-Butoxy-3-fluorophenyl)pyrimidin-4-yl]amino}-1-phenylethanol;
  (1R)-2-{[6-(4-Butoxyphenyl)pyrimidin-4-yl]amino}-1-phenylethanol;
  (1R)-2-{[6-(3-Fluoro-4-propoxyphenyl)pyrimidin-4-yl]amino}-1-phenylethanol;
  (1R)-2-({6-[3-Fluoro-4-(1-methylethoxy)phenyl]pyrimidin-4-yl}amino)-1-phenylethanol;
  (1R)-2-({6-[4-(2-Methylpropoxy)phenyl]pyrimidin-4-yl}amino)-1-phenylethanol;
  (1R)-2-{[6-(4-Methoxy-3-methylphenyl)pyrimidin-4-yl]amino}-1-phenylethanol;
  (1R)-2-{[6-(3-Chloro-4-methylphenyl)pyrimidin-4-yl]amino}-1-phenylethanol;
  (1R)-2-{[6-(3,5-Dimethylphenyl)pyrimidin-4-yl]amino}-1-phenylethanol;
  (1R)-2-({6-[3-Fluoro-4-(trifluoromethyl)phenyl]pyrimidin-4-yl}amino)-1-phenylethanol;
  (1R)-2-({6-[3-Fluoro-5-(trifluoromethyl)phenyl]pyrimidin-4-yl}amino)-1-phenylethanol;
  (1R)-2-{[6-(3-Chloro-5-fluorophenyl)pyrimidin-4-yl]amino}-1-phenylethanol;
  (1R)-1-Phenyl-2-{[6-(4-propoxyphenyl)pyrimidin-4-yl]amino}ethanol;
  (1R)-2-{[6-(2,1,3-Benzoxadiazol-5-yl)pyrimidin-4-yl]amino}-1-phenylethanol;
  (1R)-2-({6-[3-Methyl-4-(1-methylethoxy)phenyl]pyrimidin-4-yl}amino)-1-phenylethanol;
  (1R)-2-({6-[3-Chloro-4-(trifluoromethyl)phenyl]-5-methylpyrimidin-4-yl}amino)-1-phenylethanol;
  (1R)-2-({6-[3-Fluoro-4-(trifluoromethyl)phenyl]-5-methylpyrimidin-4-yl}amino)-1-phenylethanol;
  (1R)-2-({6-[4-(Difluoromethoxy)-3,5-difluorophenyl]pyrimidin-4-yl}amino)-1-phenylethanol;
  2-[4-(6-{[(2R)-2-Hydroxy-2-phenylethyl]amino}pyrimidin-4-yl)phenyl]-2-methylpropanenitrile;
  1-[2-Fluoro-4-(6-{[(2R)-2-hydroxy-2-phenylethyl]amino}pyrimidin-4-yl)phenyl]ethanone;
  (1R)-2-({6-[3,5-Dimethyl-4-(1-methylethoxy)phenyl]pyrimidin-4-yl}amino)-1-phenylethanol;
  (1R)-2-{[6-(1H-Indo)-6-yl)pyrimidin-4-yl]amino}-1-phenylethanol;
  (1R)-1-Phenyl-2-{[6-(3,4,5-trifluorophenyl)pyrimidin-4-yl]amino}ethanol;
  (1R)-2-{[6-(1-Methyl-1H-indol-2-yl)pyrimidin-4-yl]amino}-1-phenylethanol;
  (1R)-2-{[6-(5-Methyl-1-benzothiophen-2-yl)pyrimidin-4-yl]amino}-1-phenylethanol;
  [4-(6-{[(2R)-2-Hydroxy-2-phenylethyl]amino}pyrimidin-4-yl)phenyl]methanone;
  (1R)-2-{[6-(3,5-Difluorophenyl)pyrimidin-4-yl]amino}-1-phenylethanol;
  (1R)-2-{[6-(3,4-Difluorophenyl)pyrimidin-4-yl]amino}-1-phenylethanol;
  (1R)-2-({6-[3-Chloro-4-(trifluoromethyl)phenyl]-2-(methylsulfanyl)pyrimidin-4-yl}amino)-1-phenylethanol;
  (1R)-2-({2-Amino-6-[3-chloro-4-(trifluoromethyl)phenyl]pyrimidin-4-yl}amino)-1-phenylethanol;
  (1R)-2-({6-[3-Chloro-4-(trifluoromethyl)phenyl]pyrimidin-4-yl}amino)-1-(4-fluorophenyl)ethanol;
  (1R)-2-{[6-(6-Methoxypyridin-3-yl)pyrimidin-4-yl]amino}-1-phenylethanol;
  (1R)-2-{[6-(6-Ethoxypyridin-3-yl)pyrimidin-4-yl]amino}-1-phenylethanol;
  (1R)-2-({6-[4-(Dimethylamino)phenyl]pyrimidin-4-yl}amino)-1-phenylethanol;
  (1R)-2-({6-[4-(Methylsulfonyl)phenyl]pyrimidin-4-yl}amino)-1-phenylethanol;
  N-Cyclopropyl-4-(6-{[(2R)-2-hydroxy-2-phenylethyl]amino}pyrimidin-4-yl)benzenesulfonamide;
  (1R)-2-{[6-(3-Chloro-4-ethoxyphenyl)pyrimidin-4-yl]amino}-1-phenylethanol;

(1R)-2-[(2'-Morpholin-4-yl-4,5'-bipyrimidin-6-yl)amino]-1-phenylethanol;
(1R)-2-{[6-(6-Morpholin-4-ylpyridin-3-yl)pyrimidin-4-yl]amino}-1-phenylethanol;
(1R)-2-{[6-(3-Fluoro-4-methoxyphenyl)pyrimidin-4-yl]amino}-1-phenylethanol;
(1R)-2-{[6-(2,3-Dihydro-1,4-benzodioxin-6-yl)pyrimidin-4-yl]amino}-1-phenylethanol;
(1R)-2-({6-[3-Chloro-4-(trifluoromethyl)phenyl]-2-methylpyrimidin-4-yl}amino)-1-phenylethanol;
(1R)-2-{[6-(1-Benzyl-1H-pyrazol-4-yl)pyrimidin-4-yl]amino}-1-phenylethanol;
(1R)-2-{[6-(6-Fluoro-5-methylpyridin-3-yl)pyrimidin-4-yl]amino}-1-phenylethanol;
4-(6-{[(2R)-2-Hydroxy-2-phenylethyl]amino}pyrimidin-4-yl)-N,N-dimethylbenzenesulfonamide;
5-(6-{[(2R)-2-Hydroxy-2-phenylethyl]amino}pyrimidin-4-yl)pyridine-2-carbonitrile;
(1R)-2-({6-[6-(Dimethylamino)pyridin-3-yl]pyrimidin-4-yl}amino)-1-phenylethanol;
(1R)-1-Phenyl-2-({6-[4-(piperidin-1-ylsulfonyl)phenyl]pyrimidin-4-yl}amino)ethanol;
(1R)-1-Phenyl-2-({6-[4-(pyrrolidin-1-ylsulfonyl)phenyl]pyrimidin-4-yl}amino)ethanol;
4-(6-{[(2R)-2-Hydroxy-2-phenylethyl]amino}pyrimidin-4-yl)benzenesulfonamide;
(1R)-2-{[6-(4-Fluorophenyl)pyrimidin-4-yl]amino}-1-phenylethanol;
(1R)-2-{[6-(3-Chloro-4-fluorophenyl)pyrimidin-4-yl]amino}-1-phenylethanol;
(1R)-2-({6-[3-(Methylsulfanyl)phenyl]pyrimidin-4-yl}amino)-1-phenylethanol;
(1R)-2-{[6-(1H-Indo-5-yl)pyrimidin-4-yl]amino}-1-phenylethanol;
(1R)-1-Phenyl-2-[(6-quinolin-3-ylpyrimidin-4-yl)amino]ethanol;
(1R)-2-{[6-(1-Benzothiophen-3-yl)pyrimidin-4-yl]amino}-1-phenylethanol;
2-Fluoro-4-(6-{[(2R)-2-hydroxy-2-phenylethyl]amino}pyrimidin-4-yl)benzonitrile;
2-Fluoro-5-(6-{[(2R)-2-hydroxy-2-phenylethyl]amino}pyrimidin-4-yl)benzonitrile;
(1R)-2-{[6-(1-Methyl-1H-indol-5-yl)pyrimidin-4-yl]amino}-1-phenylethanol;
(1R)-2-[6-{4-[(1-Methylethyl)sulfanyl]phenyl}pyrimidin-4-yl)amino]-1-phenylethanol;
[4-(6-{[(2R)-2-Hydroxy-2-phenylethyl]amino}pyrimidin-4-yl)phenyl]acetonitrile;
(1R)-2-({6-[3-Chloro-4-(trifluoromethyl)phenyl]-2-(trifluoromethyl)pyrimidin-4-yl}amino)-1-phenylethanol;
(1R)-2-{[6-(3,4-Dichlorophenyl)-2-methylpyrimidin-4-yl]amino}-1-phenylethanol;
(1R)-2-{[6-(3,4-Dichlorophenyl)-pyrimidin-4-yl]amino}-1-phenylethanol;
(1R)-2-({6-[4-(Ethylsulfanyl)phenyl]pyrimidin-4-yl}amino)-1-phenylethanol;
(1R)-2-{[6-(3-Ethoxyphenyl)pyrimidin-4-yl]amino}-1-phenylethanol;
(1R)-1-Phenyl-2-{[6-(3-propoxyphenyl)pyrimidin-4-yl]amino}ethanol;
(1R)-2-{[6-(3-Butoxyphenyl)pyrimidin-4-yl]amino}-1-phenylethanol;
(1R)-2-{[6-(1-Benzothiophen-5-yl)pyrimidin-4-yl]amino}-1-phenylethanol;
(1R)-2-({6-[3-Chloro-4-(trifluoromethyl)phenyl]-2-(dimethylamino)pyrimidin-4-yl}amino)-1-phenylethanol;
(1R)-2-({6-[3-Fluoro-4-(trifluoromethyl)phenyl]-2-(methylsulfanyl)pyrimidin-4-yl}amino)-1-phenylethanol;
(1R)-1-Phenyl-2-({6-[3-(trifluoromethyl)phenyl]pyrimidin-4-yl}amino)ethanol;
(1R,2S)-1-Phenyl-2-[(6-{4-[(trifluoromethyl)oxy]phenyl}pyrimidin-4-yl)amino]propan-1-ol;
(1R,2R)-2-[Methyl(6-{4-[(trifluoromethyl)oxy]phenyl}pyrimidin-4-yl)amino]-1-phenylpropan-1-ol;
(1R,2S)-2-[Methyl(6-{4-[(trifluoromethyl)oxy]phenyl}pyrimidin-4-yl)amino]-1-phenylpropan-1-ol;
(1R)-2-({6-[3-Fluoro-4-(1-hydroxyethyl)phenyl]pyrimidin-4-yl}amino)-1-phenylethanol;
(1R)-2-{[2-Cyclopropyl-6-(3,4-dichlorophenyl)pyrimidin-4-yl]amino}-1-phenylethanol;
(1R)-2-{[6-(3,4-Dichlorophenyl)-2-(1-methylethyl)pyrimidin-4-yl]amino}-1-phenylethanol;
(1R)-2-({6-[3-Chloro-4-(trifluoromethyl)phenyl]-2-(methylsulfonyl)pyrimidin-4-yl}amino)-1-phenylethanol;
(1R)-2-({6-[3-Chloro-4-(trifluoromethyl)phenyl]-2-(methylsulfinyl)pyrimidin-4-yl}amino)-1-phenylethanol;
(1R)-2-{[6-(3-Methyl-1H-indazol-6-yl)pyrimidin-4-yl]amino}-1-phenylethanol;
(1R)-2-({6-[3-Chloro-4-(trifluoromethyl)phenyl]-2-(methylamino)pyrimidin-4-yl}amino)-1-phenylethanol;
(1R)-2-{[6-(4-Iodophenyl)pyrimidin-4-yl]amino}-1-phenylethanol;
(1R)-2-[6-(3-Chloro-4-trifluoromethyl-phenyl)-pyrimidin-4-ylamino]-1-(3,4-difluoro-phenyl)-ethanol;
(1R)-1-(4-Chloro-3-fluoro-phenyl)-2-[6-(3-chloro-4-trifluoromethyl-phenyl)-pyrimidin-4-ylamino]-ethanol;
(1R)-2-({6-[2,4-Bis(trifluoromethyl)phenyl]pyrimidin-4-yl}amino)-1-phenylethanol;
(1R)-2-({6-[2-Methoxy-4-(trifluoromethoxy)phenyl]pyrimidin-4-yl}amino)-1-phenylethanol;
(1R)-2-{[6-(4-Ethoxy-2-methylphenyl)pyrimidin-4-yl]amino}-1-phenylethanol;
(1R)-2-{[6-(3,4-Dichlorophenyl)-2-methylpyrimidin-4-yl]amino}-1-phenylethanol;
(1R)-2-{[6-(3,4-Dichlorophenyl)-pyrimidin-4-yl]amino}-1-phenylethanol;
(1R)-2-({2-[(2-Aminoethyl)amino]-6-[3-chloro-4-(trifluoromethyl)phenyl]pyrimidin-4-yl}amino)-1-phenylethanol;
(1R)-2-[(6-[3-Chloro-4-(trifluoromethyl)phenyl]-2-{[2-(dimethylamino)ethyl]amino}pyrimidin-4-yl)amino]-1-phenylethanol;
(1R)-2-({6-[3-Chloro-4-(trifluoromethyl)phenyl]-2-(ethylamino)pyrimidin-4-yl}amino)-1-phenylethanol;
(1R)-2-({6-[3-Chloro-4-(trifluoromethyl)phenyl]-2-[(2-hydroxyethyl)amino]pyrimidin-4-yl}amino)-1-phenylethanol;
(1R)-2-({2-Azetidin-1-yl-6-[3-chloro-4-(trifluoromethyl)phenyl]pyrimidin-4-yl}amino)-1-phenylethanol;
(1R)-2-({6-[3-Chloro-4-(trifluoromethyl)phenyl]-2-(cyclopropylamino)pyrimidin-4-yl}amino)-1-phenylethanol;
(1R)-2-[(6-[3-Chloro-4-(trifluoromethyl)phenyl]-2-{[2-(methylamino)ethyl]amino}pyrimidin-4-yl)amino]-1-phenylethanol;
(1R)-2-({6-[3-Chloro-4-(trifluoromethyl)phenyl]-2-methoxypyrimidin-4-yl}amino)-1-phenylethanol;
(1R)-2-{[6-(3-Methyl-1,2-benzisoxazol-6-yl)pyrimidin-4-yl]amino}-1-phenylethanol;
(1R)-1-Phenyl-2-[(6-quinolin-6-ylpyrimidin-4-yl)amino]ethanol;
N-tert-Butyl-4-(6-{[(2R)-2-hydroxy-2-phenylethyl]amino}pyrimidin-4-yl)benzenesulfonamide;

(1R)-1-Phenyl-2-({6-[4-(thiomorpholin-4-ylsulfonyl) phenyl]pyrimidin-4-yl}amino)ethanol;
(1R)-1-(4-Fluorophenyl)-2-({6-[3-fluoro-4-(trifluoromethyl)phenyl]pyrimidin-4-yl}amino)ethanol;
(1R)-1-(4-Fluorophenyl)-2-({6-[3-fluoro-4-(trifluoromethoxy)phenyl]pyrimidin-4-yl}amino)ethanol;
(1R)-2-({6-[3-Chloro-4-(trifluoromethoxy)phenyl]pyrimidin-4-yl}amino)-1-(4-fluorophenyl)ethanol;
(1R)-1-(4-fluorophenyl)-2-({6-[3-(pentafluoroethyl)-1,2-benzisoxazol-6-yl]pyrimidin-4-yl}amino)ethanol;
(1R)-1-(4-Fluorophenyl)-2-({6-[3-(trifluoromethyl)-1,2-benzisoxazol-6-yl]pyrimidin-4-yl}amino)ethanol;
(1R)-2-({6-[3-Fluoro-4-(2,2,2-trifluoroethoxy)phenyl] pyrimidin-4-yl}amino)-1-phenylethanol;
(1R,2S)-2-({6-[3-chloro-4-(trifluoromethyl)phenyl]pyrimidin-4-yl}amino)-1-phenylpropan-1-ol;
(1R)-1-Phenyl-2-[(6-{4-[(trifluoromethyl)sulfanyl] phenyl}pyrimidin-4-yl)amino]ethanol;
(1R)-2-({6-[3-Chloro-4-(trifluoromethoxy)phenyl]pyrimidin-4-yl}amino)-1-phenylethanol;
(1R)-1-Phenyl-2-({6-[3-(trifluoromethyl)-1,2-benzisoxazol-6-yl]pyrimidin-4-yl}amino)ethanol;
(1R)-2-{[6-(2,2-Difluoro-1,3-benzodioxol-5-yl)pyrimidin-4-yl]amino}-1-phenylethanol;
(1R)-1-Phenyl-2-({6-[5-(trifluoromethyl)-1-benzothiophen-2-yl]pyrimidin-4-yl}amino)ethanol;
(1R)-1-Phenyl-2-({6-[5-(trifluoromethoxy)-1-benzothiophen-2-yl]pyrimidin-4-yl}amino)ethanol;
(1R)-1-Phenyl-2-({6-[6-(trifluoromethyl)-1-benzothiophen-2-yl]pyrimidin-4-yl}amino)ethanol;
(1R)-2-{[6-(5-Fluoro-1-benzothiophen-2-yl)pyrimidin-4-yl]amino}-1-phenylethanol;
(1R)-2-({6-[3-(pentafluoroethyl)-1,2-benzisoxazol-6-yl] pyrimidin-4-yl}amino)-1-phenylethanol;
(1R)-Phenyl-2-{6-[4-(1,2,2,2-tetrafluoro-1-trifluoromethyl-ethyl)-phenyl]-pyrimidin-4-ylamino}-ethanol; and
(1R)-Phenyl-2-{6-[3-(1,2,2,2-tetrafluoro-1-trifluoromethyl-ethyl)-phenyl]-pyrimidin-4-ylamino}-ethanol;
(1R)-Phenyl-2-[6-(3-trifluoromethyl-benzo[b]thiophen-6-yl)-pyrimidin-4-ethanol; and
4-(3-Chloro-4-trifluoromethyl-phenyl)-6-(2-hydroxy-2-phenyl-(1R)-ethylamino)-pyrimidine-2-carbonitrile;
or a pharmaceutically acceptable salt.

12. A compound of Formula (I-B):

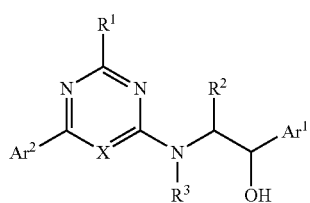

(I-B)

wherein:
$R^1$ is —$C_{1-4}$alkyl, —$OC_{1-4}$alkyl, —$S(O)_{0-2}C_{1-4}$alkyl, —CN, —$CF_3$, —N($R^a$)$R^b$, or a monocyclic cycloalkyl group,
where $R^a$ and $R^b$ are each independently —H, —$C_{1-4}$alkyl optionally substituted with —OH, N($R^m$)$R^n$, where $R^m$ and $R^n$ are —H, $C_{1-4}$alkyl; or taken together with the nitrogen of attachment $R^a$ and $R^b$ form a 4-7 membered heterocycloalkyl ring;

$Ar^1$ is a phenyl, napthyl, a 5 or 6 membered monocyclic heteroaryl group with carbon at the point of attachment, or a 9 or 10 membered bicyclic heteroaryl group with carbon at the point of attachment, each unsubstituted or substituted with;
(i) one, two, or three $R^c$ moieties,
where each $R^c$ moiety is independently —$C_{1-4}$alkyl, —$C_{1-4}$alkyl-OH, —$C_{1-4}$alkyl-CN, —$CF_3$, —OH, —$OC_{1-4}$alkyl, —$OCF_3$, —$OCHF_2$, —$OCH_2CF_3$, —$S(O)_{0-2}C_{1-4}$alkyl, —$SCF_3$, —$SO_2CF_3$, —CHO, —$COC_{1-4}$alkyl, —$CO_2C_{1-4}$alkyl, —$CO_2H$, —N($R^d$)$R^e$, —$SO_2NR^dR^e$, —$NR^dSO_2R^e$, —C(O)$NR^dR^e$, —$NO_2$, —CN, phenyl, pyridyl, or halo,
where $R^d$ and $R^e$ are each independently —H or —$C_{1-4}$alkyl, or taken together $R^d$ and $R^e$ with the nitrogen of attachment form a 4-7 membered heterocycloalkyl ring; or
(ii) two or three $R^c$ moieties where two $R^c$ moieties are adjacent to each other and together form —O(CH$_2$)$_{1-3}$O— unsubstituted or substituted with one or two fluoro groups, and the third $R^c$ moiety, when present, is —$C_{1-4}$alkyl, —$C_{1-4}$alkyl-OH, —$C_{1-4}$alkyl-CN, —$CF_3$, —OH, —$OC_{1-4}$alkyl, —$OCF_3$, —$OCHF_2$, —$OCH_2CF_3$, —$S(O)_{0-2}C_{1-4}$alkyl, —$SCF_3$, —$SO_2CF_3$, —CHO, —$COC_{1-4}$alkyl, —$CO_2C_{1-4}$alkyl, —$CO_2H$, —N($R^d$)$R^e$, —$SO_2NR^dR^e$, —$NR^dSO_2R^e$, —C(O)$NR^dR^e$, —$NO_2$, —CN, or halo,
where $R^d$ and $R^e$ are each independently —H or —$C_{1-4}$alkyl;
X is C($R^f$),
where $R^f$ is —H or methyl;
$Ar^2$ is:
(i) a phenyl group substituted with: (a) one, two, or three $R^g$ moieties each at a meta or para position, and optionally with one or two additional $R^g$ moieties at an ortho position;
where each $R^g$ moiety is independently —$C_{1-4}$alkyl, —$C_{1-4}$alkyl-OH, —$C_{1-4}$alkyl-CN, perhaloalkyl, perhaloalkoxy, —$OC_{1-4}$alkyl, —$OC_{1-4}$alkyl-(monocyclic cycloalkyl), —$S(O)_{0-2}C_{1-4}$alkyl, —$SCF_3$, —$SO_2CF_3$, —CHO, —$COC_{1-4}$alkyl, —$CO_2C_{1-4}$alkyl, —$CO_2H$, —N($R^h$)$R^i$, —$SO_2NR^hR^k$, —$NR^hSO_2R^i$, —C(O)$NR^hR^k$, —$NO_2$, —CN, or halo; or a phenoxy, benzyl, phenethyl, or benzoyl group unsubstituted or substituted with —$C_{1-4}$alkyl, perhaloalkyl, perhaloalkoxy, —$NO_2$, —CN, or halo;
where $R^h$ is —H or —$C_{1-4}$alkyl;
$R^i$ is —$C_{1-4}$alkyl or monoyclic cycloalkyl group;
or $R^h$ and $R^i$ taken together with the atoms to which they are attached form a monocyclic heterocycloalkyl ring;
$R^j$ is —H or —$C_{1-4}$alkyl; and
$R^k$ is —H, —$C_{1-4}$alkyl or monoyclic cycloalkyl group;
or $R^j$ and $R^k$ taken together with the atoms to which they are attached form a monocyclic heterocycloalkyl ring; or
(b) two adjacent $R^g$ moieties together form —O(CH$_2$)$_{1-2}$O— unsubstituted or substituted with one or two fluoro groups;
(ii) a monocyclic heteroaryl group substituted with one, two, or three $R^g$ moieties, where each $R^g$ moiety is independent or two adjacent $R^g$ moieties together form —O(CH$_2$)$_{1-2}$O— unsubstituted or substituted with one or two fluoro groups; or (iii) a naphthyl or bicyclic heteroaryl group unsubstituted or substituted with one, two, or three $R^i$ moieties;
where each $R^i$ moiety is independently —$C_{1-4}$alkyl, perhaloalkyl, perhaloalkoxy, —$NO_2$, —CN, or halo;
$R^2$ is —H or methyl; and
$R^3$ is —H or methyl;
or a pharmaceutically acceptable salt.

13. A compound as defined in claim 12, wherein $R^1$ is methyl, isopropyl, trifluoromethyl, methylsulfanyl, methylsulfinyl, methanesulfonyl, amino, methylamino, dimethylamino, or cyclopropyl.

14. A compound as defined in claim 12, wherein $Ar^1$ is a phenyl group, each unsubstituted or substituted with one, two, or three $R^c$ moieties.

15. A compound as defined in claim 12, wherein $R^f$ is —H.

16. A compound as defined in claim 12, wherein $Ar^2$ is a phenyl substituted with one, two or three $R^g$ moieties each at a meta or para position.

17. A compound as defined in claim 12, wherein $Ar^2$ is a thiophenyl, pyridinyl, pyrimidinyl, or pyrazolyl group, each substituted with one, two, or three $R^g$ moieties.

18. A compound as defined in claim 12, wherein $Ar^2$ is a naphthyl, benzoxadiazolyl, indolyl, benzothiophenyl, quinolinyl, or indazolyl, each unsubstituted or substituted with one, two, or three $R^i$ moieties.

19. A compound as defined in claim 12, wherein each $R^i$ moiety is independently methyl.

20. A compound as defined in claim 12, wherein $R^2$ is —H.

21. A compound as defined in claim 12, wherein $R^3$ is —H.

22. A compound as defined in claim 12, wherein the secondary hydroxyl group adjacent to $Ar^1$ is in the configuration as shown below:

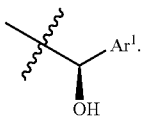

23. A compound selected from the group consisting of:
(1R)-2-({6-[3-Chloro-4-(trifluoromethyl)phenyl]-2-(methylsulfanyl)pyrimidin-4-yl}amino)-1-phenylethanol;
(1R)-2-({2-Amino-6-[3-chloro-4-(trifluoromethyl)phenyl]pyrimidin-4-yl}amino)-1-phenylethanol;
(1R)-2-({6-[3-Chloro-4-(trifluoromethyl)phenyl]-2-methylpyrimidin-4-yl}amino)-1-phenylethanol;
(1R)-2-({6-[3-Chloro-4-(trifluoromethyl)phenyl]-2-(trifluoromethyl)pyrimidin-4-yl}amino)-1-phenylethanol;
(1R)-2-{[6-(3,4-Dichlorophenyl)-2-methylpyrimidin-4-yl]amino}-1-phenylethanol;
(1R)-2-({6-[3-Chloro-4-(trifluoromethyl)phenyl]-2-(dimethylamino)pyrimidin-4-yl}amino)-1-phenylethanol;
(1R)-2-({6-[3-Fluoro-4-(trifluoromethyl)phenyl]-2-(methylsulfanyl)pyrimidin-4-yl}amino)-1-phenylethanol;
(1R)-2-{[2-Cyclopropyl-6-(3,4-dichlorophenyl)pyrimidin-4-yl]amino}-1-phenylethanol;
(1R)-2-{[6-(3,4-Dichlorophenyl)-2-(1-methylethyl)pyrimidin-4-yl]amino}-1-phenylethanol;
(1R)-2-({6-[3-Chloro-4-(trifluoromethyl)phenyl]-2-(methylsulfonyl)pyrimidin-4-yl}amino)-1-phenylethanol;
(1R)-2-({6-[3-Chloro-4-(trifluoromethyl)phenyl]-2-(methylsulfinyl)pyrimidin-4-yl}amino)-1-phenylethanol;
(1R)-2-({6-[3-Chloro-4-(trifluoromethyl)phenyl]-2-(methylamino)pyrimidin-4-yl}amino)-1-phenylethanol;
(1R)-2-{[6-(3,4-Dichlorophenyl)-2-methylpyrimidin-4-yl]amino}-1-phenylethanol;
(1R)-2-({2-[(2-Aminoethyl)amino]-6-[3-chloro-4-(trifluoromethyl)phenyl]pyrimidin-4-yl}amino)-1-phenylethanol;
(1R)-2-[(6-[3-Chloro-4-(trifluoromethyl)phenyl]-2-{[2-(dimethylamino)ethyl]amino}pyrimidin-4-yl)amino]-1-phenylethanol;
(1R)-2-({6-[3-Chloro-4-(trifluoromethyl)phenyl]-2-(ethylamino)pyrimidin-4-yl}amino)-1-phenylethanol;
(1R)-2-({6-[3-Chloro-4-(trifluoromethyl)phenyl]-2-[(2-hydroxyethyl)amino]pyrimidin-4-yl}amino)-1-phenylethanol;
(1R)-2-({2-Azetidin-1-yl-6-[3-chloro-4-(trifluoromethyl)phenyl]pyrimidin-4-yl}amino)-1-phenylethanol;
(1R)-2-({6-[3-Chloro-4-(trifluoromethyl)phenyl]-2-(cyclopropylamino)pyrimidin-4-yl}amino)-1-phenylethanol;
(1R)-2-[(6-[3-Chloro-4-(trifluoromethyl)phenyl]-2-{[2-(methylamino)ethyl]amino}pyrimidin-4-yl)amino]-1-phenylethanol;
(1R)-2-({6-[3-Chloro-4-(trifluoromethyl)phenyl]-2-methoxypyrimidin-4-yl}amino)-1-phenylethanol; and
4-(3-Chloro-4-trifluoromethyl-phenyl)-6-(2-hydroxy-2-phenyl-(1R)-ethylamino)-pyrimidine-2-carbonitrile;
or a pharmaceutically acceptable salt.

24. A compound of Formula (I-C):

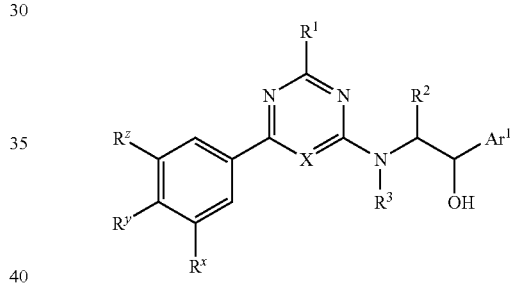

wherein:
$R^1$ is —H, —$C_{1-4}$alkyl, —$OC_{1-4}$alkyl, —$S(O)_{0-2}C_{1-4}$alkyl, —CN, —$CF_3$, —$N(R^a)R^b$, or a monocyclic cycloalkyl group,
where $R^a$ and $R^b$ are each independently —H, —$C_{1-4}$alkyl optionally substituted with —OH, $N(R^m)R^n$, where $R^m$ and $R^n$ are —H, $C_{1-4}$alkyl; or taken together with the nitrogen of attachment $R^a$ and $R^b$ form a 4-7 membered heterocycloalkyl ring;
$Ar^1$ is a phenyl, napthyl, a 5 or 6 membered monocyclic heteroaryl group with carbon a the point of attachment, or a 9 or 10 membered bicyclic heteroaryl group with carbon at the point of attachment, each unsubstituted or substituted with;
(i) one, two, or three $R^c$ moieties,
where each $R^c$ moiety is independently —$C_{1-4}$alkyl, —$C_{1-4}$alkyl-OH, —$C_{1-4}$alkyl-ON, —$CF_3$, —OH, —$OC_{1-4}$alkyl, —$OCF_3$, —$OCHF_2$, —$OCH_2CF_3$, —$S(O)_{0-2}C_{1-4}$alkyl, —$SCF_3$, —$SO_2CF_3$, —CHO, —$CO_2C_{1-4}$alkyl, —$CO_2C_{1-4}$alkyl, —$CO_2H$, —$N(R^d)R^e$, —$SO_2NR^dR^e$, —$NR^dSO_2R^e$, —C(O)$NR^dR^e$, —$NO_2$, —CN, phenyl, pyridyl, or halo,
where $R^d$ and $R^e$ are each independently —H or —$C_{1-4}$alkyl, or taken together $R^d$ and $R^e$ with the nitrogen of attachment form a 4-7 membered heterocycloalkyl; or (ii) two or three $R^c$ moieties where two $R^c$ moieties are adjacent to each other and together form —O(CH$_2$)$_{1-3}$O— unsubstituted or substituted with one or two fluoro groups, and the third $R^c$ moiety, when present, is —C$_{1-4}$alkyl, —C$_{1-4}$alkyl-OH, —C$_{1-4}$alkyl-CN, —CF$_3$, —OH, —OC$_{1-4}$alkyl, —OCF$_3$, —OCHF$_2$, —OCH$_2$CF$_3$, —S(O)$_{0-2}$C$_{1-4}$ alkyl, —SCF$_3$, —SO$_2$CF$_3$, —CHO, —COC$_{1-4}$alkyl, —CO$_2$C$_{1-4}$alkyl, —CO$_2$H, —N(R$^d$)R$^e$, —SO$_2$NR$^d$R$^e$, —NR$^d$SO$_2$R$^e$, —C(O)NR$^d$R$^e$, —NO$_2$, —CN, or halo,
where $R^d$ and $R^e$ are each independently —H or —C$_{1-4}$alkyl;
X is C(R$^f$),
where R$^f$ is —H or methyl;
$R^x$, $R^y$, and $R^z$ are each independently a)-c):
a) $R^x$ and $R^z$ are each —H, and $R^y$ is —NO$_2$, —C$_{2-3}$alkyl, —OC$_{2-4}$alkyl, or phenoxy;
b) $R^x$ and $R^z$ are each —H, $R^y$ is —OCF$_3$, and Ar$^1$ is a substituted phenyl group or an unsubstituted or substituted pyridyl group; or
c) one of $R^x$, $R^y$, and $R^z$ is —Cl, —F, or —CF$_3$, and the other two are: (i) independently —H or an R$^g$ moiety, provided that when $R^y$ is —H then $R^x$ and $R^z$ are not CF$_3$;
where each R$^g$ moiety is —C$_{1-4}$alkyl, —C$_{1-4}$alkyl-OH, —C$_{1-4}$alkyl-CN, perhaloalkyl, perhaloalkoxy, —OC$_{1-4}$alkyl, —OC$_{1-4}$alkyl-(monocyclic cycloalkyl), —S(O)$_{0-2}$C$_{1-4}$alkyl, —SCF$_3$, —SO$_2$CF$_3$, —CHO, —COC$_{1-4}$alkyl, —CO$_2$C$_{1-4}$ alkyl, —CO$_2$H, —N(R$^h$)R$^i$, —SO$_2$NR$^j$R$^k$, —NR$^h$SO$_2$R$^i$, —C(O)NR$^j$R$^k$, —NO$_2$, —CN, or halo; or a phenoxy, benzyl, phenethyl, or benzoyl group unsubstituted or substituted with —C$_{1-4}$alkyl, —OC$_{1-4}$alkyl, perhaloalkyl, perhaloalkoxy, —NO$_2$, —CN, or halo;
where R$^h$ is —H or —C$_{1-4}$alkyl;
R$^i$ is —C$_{1-4}$alkyl or monoyclic cycloalkyl group;
or R$^h$ and R$^i$ taken together with the atoms to which they are attached form a monocyclic heterocycloalkyl ring;
R$^j$ is —H or —C$_{1-4}$alkyl; and
R$^k$ is —H, —C$_{1-4}$alkyl or monoyclic cycloalkyl group; or
R$^j$ and R$^k$ taken together with the atoms to which they are attached form a monocyclic heterocycloalkyl ring; or
(ii) two adjacent R$^g$ moieties together form —O(CH$_2$)$_{1-2}$O— unsubstituted or substituted with one or two fluoro groups; or
(iii) a naphthyl or bicyclic heteroaryl group unsubstituted or substituted with one, two, or three R$^l$ moieties;
where each R$^l$ moiety is independently —C$_{1-4}$alkyl, —OC$_{1-4}$alkyl, perhaloalkyl, perhaloalkoxy, —NO$_2$, —CN, or halo;
$R^2$ is —H or methyl; and
$R^3$ is —H or methyl;
or a pharmaceutically acceptable salt.

25. A compound as defined in claim 24, wherein R$^1$ is —H, methyl, isopropyl, trifluoromethyl, methylsulfanyl, methylsulfinyl, methanesulfonyl, amino, methylamino, dimethylamino, or cyclopropyl.

26. A compound as defined in claim 24, wherein R$^1$ is —H.

27. A compound as defined in claim 24, wherein Ar$^1$ is a phenyl group, each unsubstituted or substituted with one, two, or three R$^c$ moieties.

28. A compound as defined in claim 24, wherein R$^f$ is —H.

29. A compound as defined in claim 24, wherein $R^x$ is —Cl or —F, $R^z$ is —H, and $R^y$ is —H or R$^g$.

30. A compound as defined in claim 24, wherein $R^x$ is —Cl or —F, $R^z$ is —H, and $R^y$ is —C$_{1-4}$alkyl, —CF$_3$, —OC$_{1-4}$alkyl, —OCF$_3$, or halo.

31. A compound as defined in claim 24, wherein $R^2$ is —H.

32. A compound as defined in claim 24, wherein $R^3$ is —H.

33. A compound as defined in claim 24, wherein the secondary hydroxyl group adjacent to Ar$^1$ is in the configuration as shown below:

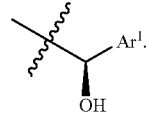

34. A compound selected from the group consisting of:
(1R)-2-({6-[4-(Ethyloxy)-3-(trifluoromethyl)phenyl]pyrimidin-4-yl}amino)-1-phenylethanol;
2-{[6-(4-Chlorophenyl)pyrimidin-4-yl]amino}-1-phenylethanol;
2-{[6-(4-Fluorophenyl)pyrimidin-4-yl]amino}-1-phenylethanol;
1-Phenyl-2-({6-[4-(trifluoromethyl)phenyl]pyrimidin-4-yl}amino)ethanol;
2-{[6-(4-Nitrophenyl)pyrimidin-4-yl]amino}-1-phenylethanol;
2-{[6-(4-Ethylphenyl)pyrimidin-4-yl]amino}-1-phenylethanol;
2-({6-[4-(1-Methylethyl)phenyl]pyrimidin-4-yl}amino)-1-phenylethanol;
2-{[6-(3,4-Dichlorophenyl)pyrimidin-4-yl]amino}-1-phenylethanol;
2-{[6-(3-Chlorophenyl)pyrimidin-4-yl]amino}-1-phenylethanol;
2-({6-[3-Chloro-4-(trifluoromethyl)phenyl]pyrimidin-4-yl}amino)-1-phenylethanol;
2-({6-[4-(Ethyloxy)phenyl]pyrimidin-4-yl}amino)-1-phenylethanol;
2-[(6-{4-[(1-Methylethyl)oxy]phenyl}pyrimidin-4-yl)amino]-1-phenylethanol;
1-Phenyl-2-({6-[4-(phenyloxy)phenyl]pyrimidin-4-yl}amino)ethanol;
2-({6-[3-Chloro-4-(ethyloxy)phenyl]pyrimidin-4-yl}amino)-1-phenylethanol;
(1R)-1-Phenyl-2-({6-[4-(trifluoromethyl)phenyl]pyrimidin-4-yl}amino)ethanol;
(1R)-2-({6-[3-Chloro-4-(trifluoromethyl)phenyl]pyrimidin-4-yl}amino)-1-phenylethanol;
(1R)-2-({6-[3-Chloro-4-(trifluoromethyl)phenyl]pyrimidin-4-yl}amino)-1-phenylethanol hydrochloride salt;
(1R)-2-({6-[4-(1-Methylethyl)phenyl]pyrimidin-4-yl}amino)-1-phenylethanol;
(1R)-2-[(6-{3-Chloro-4-[(1-methylethyl)oxy]phenyl}pyrimidin-4-yl)amino]-1-phenylethanol;
(1R)-2-{[6-(3-Fluoro-4-methylphenyl)pyrimidin-4-yl]amino}-1-phenylethanol;
(1R)-2-{[6-(4-Chloro-3-methylphenyl)pyrimidin-4-yl]amino}-1-phenylethanol;
(1R)-2-{[6-(4-Chloro-3-fluorophenyl)pyrimidin-4-yl]amino}-1-phenylethanol;
(1R)-2-({6-[4-Chloro-3-(trifluoromethyl)phenyl]pyrimidin-4-yl}amino)-1-phenylethanol;
(1R)-2-({6-[3-Fluoro-4-(trifluoromethoxy)phenyl]pyrimidin-4-yl}amino)-1-phenylethanol;

(1R)-2-{[6-(4-Ethoxy-3-fluorophenyl)pyrimidin-4-yl]amino}-1-phenylethanol;
(1R)-2-{[6-(4-Butoxy-3-fluorophenyl)pyrimidin-4-yl]amino}-1-phenylethanol;
(1R)-2-{[6-(4-Butoxyphenyl)pyrimidin-4-yl]amino}-1-phenylethanol;
(1R)-2-{[6-(3-Fluoro-4-propoxyphenyl)pyrimidin-4-yl]amino}-1-phenylethanol;
(1R)-2-({6-[3-Fluoro-4-(1-methylethoxy)phenyl]pyrimidin-4-yl}amino)-1-phenylethanol;
(1R)-2-({6-[4-(2-Methylpropoxy)phenyl]pyrimidin-4-yl}amino)-1-phenylethanol;
(1R)-2-{[6-(3-Chloro-4-methylphenyl)pyrimidin-4-yl]amino}-1-phenylethanol;
(1R)-2-({6-[3-Fluoro-4-(trifluoromethyl)phenyl]pyrimidin-4-yl}amino)-1-phenylethanol;
(1R)-2-({6-[3-Fluoro-5-(trifluoromethyl)phenyl]pyrimidin-4-yl}amino)-1-phenylethanol;
(1R)-2-{[6-(3-Chloro-5-fluorophenyl)pyrimidin-4-yl]amino}-1-phenylethanol;
(1R)-1-Phenyl-2-{[6-(4-propoxyphenyl)pyrimidin-4-yl]amino}ethanol;
(1R)-2-({6-[3-Chloro-4-(trifluoromethyl)phenyl]-5-methylpyrimidin-4-yl}amino)-1-phenylethanol;
(1R)-2-({6-[3-Fluoro-4-(trifluoromethyl)phenyl]-5-methylpyrimidin-4-yl}amino)-1-phenylethanol;
(1R)-2-({6-[4-(Difluoromethoxy)-3,5-difluorophenyl]pyrimidin-4-yl}amino)-1-phenylethanol;
1-[2-Fluoro-4-(6-{[(2R)-2-hydroxy-2-phenylethyl]amino}pyrimidin-4-yl)phenyl]ethanone;
(1R)-1-Phenyl-2-{[6-(3,4,5-trifluorophenyl)pyrimidin-4-yl]amino}ethanol;
(1R)-2-{[6-(3,5-Difluorophenyl)pyrimidin-4-yl]amino}-1-phenylethanol;
(1R)-2-{[6-(3,4-Difluorophenyl)pyrimidin-4-yl]amino}-1-phenylethanol;
(1R)-2-({6-[3-Chloro-4-(trifluoromethyl)phenyl]-2-(methylsulfanyl)pyrimidin-4-yl}amino)-1-phenylethanol;
(1R)-2-({2-Amino-6-[3-chloro-4-(trifluoromethyl)phenyl]pyrimidin-4-yl}amino)-1-phenylethanol;
(1R)-2-({6-[3-Chloro-4-(trifluoromethyl)phenyl]pyrimidin-4-yl}amino)-1-(4-fluorophenyl)ethanol;
(1R)-2-{[6-(3-Chloro-4-ethoxyphenyl)pyrimidin-4-yl]amino}-1-phenylethanol;
(1R)-2-{[6-(3-Fluoro-4-methoxyphenyl)pyrimidin-4-yl]amino}-1-phenylethanol;
(1R)-2-({6-[3-Chloro-4-(trifluoromethyl)phenyl]-2-methylpyrimidin-4-yl}amino)-1-phenylethanol;
(1R)-2-{[6-(4-Fluorophenyl)pyrimidin-4-yl]amino}-1-phenylethanol;
(1R)-2-{[6-(3-Chloro-4-fluorophenyl)pyrimidin-4-yl]amino}-1-phenylethanol;
2-Fluoro-4-(6-{[(2R)-2-hydroxy-2-phenylethyl]amino}pyrimidin-4-yl)benzonitrile;
2-Fluoro-5-(6-{[(2R)-2-hydroxy-2-phenylethyl]amino}pyrimidin-4-yl)benzonitrile;
(1R)-2-({6-[3-Chloro-4-(trifluoromethyl)phenyl]-2-(trifluoromethyl)pyrimidin-4-yl}amino)-1-phenylethanol;
(1R)-2-{[6-(3,4-Dichlorophenyl)-2-methylpyrimidin-4-yl]amino}-1-phenylethanol;
(1R)-2-{[6-(3,4-Dichlorophenyl)-pyrimidin-4-yl]amino}-1-phenylethanol;
(1R)-2-({6-[3-Chloro-4-(trifluoromethyl)phenyl]-2-(dimethylamino)pyrimidin-4-yl}amino)-1-phenylethanol;
(1R)-2-({6-[3-Fluoro-4-(trifluoromethyl)phenyl]-2-(methylsulfanyl)pyrimidin-4-yl}amino)-1-phenylethanol;
(1R)-1-Phenyl-2-({6-[3-(trifluoromethyl)phenyl]pyrimidin-4-yl}amino)ethanol;
1-(4-Nitrophenyl)-2-[(6-{4-[(trifluoromethyl)oxy]phenyl}pyrimidin-4-yl)amino]ethanol;
2-[(6-{4-[(Trifluoromethyl)oxy]phenyl}pyrimidin-4-yl)amino]-1-[4-(trifluoromethyl)phenyl]ethanol;
1-(4-Chlorophenyl)-2-[(6-{4-[(trifluoromethyl)oxy]phenyl}pyrimidin-4-yl)amino]ethanol;
4-{1-Hydroxy-2-[(6-{4-[(trifluoromethyl)oxy]phenyl}pyrimidin-4-yl)amino]ethyl}phenol;
1-[4-(Methyloxy)phenyl]-2-[(6-{4-[(trifluoromethyl)oxy]phenyl}-pyrimidin-4-yl)amino]ethanol;
4-{1-Hydroxy-2-[(6-{4-[(trifluoromethyl)oxy]phenyl}pyrimidin-4-yl)amino]ethyl}-2-(methyloxy)phenol;
1-(4-Fluorophenyl)-2-[(6-{4-[(trifluoromethyl)oxy]phenyl}pyrimidin-4-yl)amino]ethanol;
1-(3,4-Dichlorophenyl)-2-[(6-{4-[(trifluoromethyl)oxy]phenyl}-pyrimidin-4-yl)amino]ethanol;
1-(2-Chlorophenyl)-2-[(6-{4-[(trifluoromethyl)oxy]phenyl}pyrimidin-4-yl)amino]ethanol;
1-(3-Chlorophenyl)-2-[(6-{4-[(trifluoromethyl)oxy]phenyl}pyrimidin-4-yl)amino]ethanol;
1-[3-(Methyloxy)phenyl]-2-[(6-{4-[(trifluoromethyl)oxy]phenyl}-pyrimidin-4-yl)amino]ethanol;
1-[2-(Methyloxy)phenyl]-2-[(6-{4-[(trifluoromethyl)oxy]phenyl}-pyrimidin-4-yl)amino]ethanol;
1-(2,2-Difluoro-1,3-benzodioxol-5-yl)-2-[(6-{4-[(trifluoromethyl)oxy]phenyl}pyrimidin-4-yl)amino]ethanol;
1-Pyridin-2-yl-2-[(6-{4-[(trifluoromethyl)oxy]phenyl}pyrimidin-4-yl)amino]ethanol;
1-Pyridin-3-yl-2-[(6-{4-[(trifluoromethyl)oxy]phenyl}pyrimidin-4-yl)amino]ethanol;
1-Pyridin-4-yl-2-[(6-{4-[(trifluoromethyl)oxy]phenyl}pyrimidin-4-yl)amino]ethanol;
1-(3,5-Dichlorophenyl)-2-[(6-{4-[(trifluoromethyl)oxy]phenyl}-pyrimidin-4-yl)amino]ethanol;
1-(1,3-Benzodioxol-5-yl)-2-[(6-{4-[(trifluoromethyl)oxy]phenyl}-pyrimidin-4-yl)amino]ethanol;
(1S)-2-({6-[3-Chloro-4-(trifluoromethyl)phenyl]pyrimidin-4-yl}amino)-1-phenylethanol;
(1R)-2-({6-[3-Fluoro-4-(1-hydroxyethyl)phenyl]pyrimidin-4-yl}amino)-1-phenylethanol;
2-({6-[3-Chloro-4-(trifluoromethyl)phenyl]pyrimidin-4-yl}amino)-1-[3-(trifluoromethoxy)phenyl]ethanol;
2-({6-[3-Chloro-4-(trifluoromethyl)phenyl]pyrimidin-4-yl}amino)-1-(3-fluorophenyl)ethanol;
2-[6-(3-Chloro-4-trifluoromethyl-phenyl)-pyrimidin-4-ylamino]-1-(3,4-difluoro-phenyl)-ethanol;
1-(4-Chloro-3-fluoro-phenyl)-2-({6-[3-chloro-4-(trifluoromethyl)phenyl]pyrimidin-4-yl}amino)ethanol;
1-(3-Chloro-4-fluorophenyl)-2-({6-[3-chloro-4-(trifluoromethyl)phenyl]pyrimidin-4-yl}amino)ethanol;
2-({6-[3-Chloro-4-(trifluoromethyl)phenyl]pyrimidin-4-yl}amino)-1-[3-(trifluoromethyl)phenyl]ethanol;
(1R)-2-{[2-Cyclopropyl-6-(3,4-dichlorophenyl)pyrimidin-4-yl]amino}-1-phenylethanol;
(1R)-2-{[6-(3,4-Dichlorophenyl)-2-(1-methylethyl)pyrimidin-4-yl]amino}-1-phenylethanol;
(1R)-2-({6-[3-Chloro-4-(trifluoromethyl)phenyl]-2-(methylsulfonyl)pyrimidin-4-yl}amino)-1-phenylethanol;
(1R)-2-({6-[3-Chloro-4-(trifluoromethyl)phenyl]-2-(methylsulfinyl)pyrimidin-4-yl}amino)-1-phenylethanol;
(1R)-2-({6-[3-Chloro-4-(trifluoromethyl)phenyl]-2-(methylamino)pyrimidin-4-yl}amino)-1-phenylethanol;
(1S)-2-[6-(3-Chloro-4-trifluoromethyl-phenyl)-pyrimidin-4-ylamino]-1-(3,4-difluoro-phenyl)-ethanol;

(1R)-2-[6-(3-Chloro-4-trifluoromethyl-phenyl)-pyrimidin-4-ylamino]-1-(3,4-difluoro-phenyl)-ethanol;
(1S)-1-(4-Chloro-3-fluoro-phenyl)-2-[6-(3-chloro-4-trifluoromethyl-phenyl)-pyrimidin-4-ylamino]-ethanol;
(1R)-1-(4-Chloro-3-fluoro-phenyl)-2-[6-(3-chloro-4-trifluoromethyl-phenyl)-pyrimidin-4-ylamino]-ethanol;
(1R)-2-{[6-(3,4-Dichlorophenyl)-2-methylpyrimidin-4-yl]amino}-1-phenylethanol;
(1R)-2-{[6-(3,4-Dichlorophenyl)-pyrimidin-4-yl]amino}-1-phenylethanol;
(1R)-2-({2-[(2-Aminoethyl)amino]-6-[3-chloro-4-(trifluoromethyl)phenyl]pyrimidin-4-yl}amino)-1-phenylethanol;
(1R)-2-[(6-[3-Chloro-4-(trifluoromethyl)phenyl]-2-{[2-(dimethylamino)ethyl]amino}pyrimidin-4-yl)amino]-1-phenylethanol;
(1R)-2-({6-[3-Chloro-4-(trifluoromethyl)phenyl]-2-(ethylamino)pyrimidin-4-yl}amino)-1-phenylethanol;
(1R)-2-({6-[3-Chloro-4-(trifluoromethyl)phenyl]-2-[(2-hydroxyethyl)amino]pyrimidin-4-yl}amino)-1-phenylethanol;
(1R)-2-({2-Azetidin-1-yl-6-[3-chloro-4-(trifluoromethyl)phenyl]pyrimidin-4-yl}amino)-1-phenylethanol;
(1R)-2-({6-[3-Chloro-4-(trifluoromethyl)phenyl]-2-(cyclopropylamino)pyrimidin-4-yl}amino)-1-phenylethanol;
(1R)-2-[(6-[3-Chloro-4-(trifluoromethyl)phenyl]-2-{[2-(methylamino)ethyl]amino}pyrimidin-4-yl)amino]-1-phenylethanol;
(1R)-2-({6-[3-Chloro-4-(trifluoromethyl)phenyl]-2-methoxypyrimidin-4-yl}amino)-1-phenylethanol;
1-({6-[3-Chloro-4-(trifluoromethyl)phenyl]pyrimidin-4-yl}amino)-2-phenylpropan-2-ol,
2-({6-[3-Chloro-4-(trifluoromethyl)phenyl]pyrimidin-4-yl}amino)-1-[4-(methylsulfanyl)phenyl]ethanol;
2-({6-[3-Chloro-4-(trifluoromethyl)phenyl]pyrimidin-4-yl}amino)-1-thiophen-3-ylethanol;
2-({6-[3-Chloro-4-(trifluoromethyl)phenyl]pyrimidin-4-yl}amino)-1-(1,3-thiazol-2-yl)ethanol;
(1R)-1-(4-Fluorophenyl)-2-({6-[3-fluoro-4-(trifluoromethyl)phenyl]pyrimidin-4-yl}amino)ethanol;
(1R)-1-(4-Fluorophenyl)-2-({6-[3-fluoro-4-(trifluoromethoxy)phenyl]pyrimidin-4-yl}amino)ethanol;
(1R)-2-({6-[3-Chloro-4-(trifluoromethoxy)phenyl]pyrimidin-4-yl}amino)-1-(4-fluorophenyl)ethanol;
(1R)-2-({6-[3-Fluoro-4-(2,2,2-trifluoroethoxy)phenyl]pyrimidin-4-yl}amino)-1-phenylethanol;
(1R,2S)-2-({6-[3-chloro-4-(trifluoromethyl)phenyl]pyrimidin-4-yl}amino)-1-phenylpropan-1-ol;
(1R)-2-({6-[3-Chloro-4-(trifluoromethoxy)phenyl]pyrimidin-4-yl}amino)-1-phenylethanol;
2-({6-[3-Chloro-4-(trifluoromethyl)phenyl]pyrimidin-4-yl}amino)-1-[2-(difluoromethoxy)phenyl]ethanol;
2-({6-[3-Chloro-4-(trifluoromethyl)phenyl]pyrimidin-4-yl}amino)-1-(4-fluorophenyl)ethanol;
4-[2-({6-[3-Chloro-4-(trifluoromethyl)phenyl]pyrimidin-4-yl}amino)-1-hydroxyethyl]benzonitrile;
2-({6-[3-Chloro-4-(trifluoromethyl)phenyl]pyrimidin-4-yl}amino)-1-naphthalen-2-ylethanol;
2-({6-[3-Chloro-4-(trifluoromethyl)phenyl]pyrimidin-4-yl}amino)-1-(4-pyridin-2-ylphenyl)ethanol;
2-({6-[3-Chloro-4-(trifluoromethyl)phenyl]pyrimidin-4-yl}amino)-1-(4-thiophen-2-ylphenyl)ethanol;
1-Biphenyl-4-yl-2-({6-[3-chloro-4-(trifluoromethyl)phenyl]pyrimidin-4-yl}amino)ethanol;
1-(1-Benzothiophen-2-yl)-2-({6-[3-chloro-4-(trifluoromethyl)phenyl]pyrimidin-4-yl}amino)ethanol;
2-({6-[3-Chloro-4-(trifluoromethyl)phenyl]pyrimidin-4-yl}amino)-1-[3-fluoro-4-(trifluoromethyl)phenyl]ethanol;
2-({6-[3-chloro-4-(trifluoromethyl)phenyl]pyrimidin-4-yl}amino)-1-{3-[(trifluoromethyl)sulfanyl]phenyl}ethanol;
2-({6-[3-Chloro-4-(trifluoromethyl)phenyl]pyrimidin-4-yl}amino)-1-(2,3-dihydro-1,4-benzodioxin-6-yl)ethanol;
2-({6-[3-Chloro-4-(trifluoromethyl)phenyl]pyrimidin-4-yl}amino)-1-[4-(1H-imidazol-1-yl)phenyl]ethanol;
1-(1-benzothiophen-3-yl)-2-({6-[3-chloro-4-(trifluoromethyl)phenyl]pyrimidin-4-yl}amino)ethanol;
2-({6-[3-Chloro-4-(trifluoromethyl)phenyl]pyrimidin-4-yl}amino)-1-(3,4-dimethoxyphenyl)ethanol;
1-(3-Chloro-4-methoxyphenyl)-2-({6-[3-chloro-4-(trifluoromethyl)phenyl]pyrimidin-4-yl}amino)ethanol;
2-({6-[3-Chloro-4-(trifluoromethyl)phenyl]pyrimidin-4-yl}amino)-1-(3,4-dihydro-2H-1,5-benzodioxepin-7-yl)ethanol;
2-({6-[3-Chloro-4-(trifluoromethyl)phenyl]pyrimidin-4-yl}amino)-1-[2-fluoro-5-(trifluoromethyl)phenyl]ethanol;
3-[2-({6-[3-Chloro-4-(trifluoromethyl)phenyl]pyrimidin-4-yl}amino)-1-hydroxyethyl]benzonitrile;
2-({6-[3-Chloro-4-(trifluoromethyl)phenyl]pyrimidin-4-yl}amino)-1-(3-phenylisoxazol-5-yl)ethanol;
2-({6-[3-Chloro-4-(trifluoromethyl)phenyl]pyrimidin-4-yl}amino)-1-(4-pyrrolidin-1-ylphenyl)ethanol;
2-({6-[3-Chloro-4-(trifluoromethyl)phenyl]pyrimidin-4-yl}amino)-1-(5-pyridin-2-ylthiophen-2-yl)ethanol;
5-[2-({6-[3-Chloro-4-(trifluoromethyl)phenyl]pyrimidin-4-yl}amino)-1-hydroxyethyl]-2-fluorobenzonitrile;
2-({6-[3-Chloro-4-(trifluoromethyl)phenyl]pyrimidin-4-yl}amino)-1-(2,6-difluorophenyl)ethanol;
2-({6-[3-Chloro-4-(trifluoromethyl)phenyl]pyrimidin-4-yl}amino)-1-(2-fluorophenyl)ethanol;
2-[6-(3-Chloro-4-trifluoromethyl-phenyl)-pyrimidin-4-ylamino]-1-[3-(3,4-dichloro-phenyl)-isoxazol-5-yl]-ethanol;
1-[3-(4-Chloro-phenyl)-isoxazol-5-yl]-2-[6-(3-chloro-4-trifluoromethyl-phenyl)-pyrimidin-4-ylamino]-ethanol;
2-[6-(3-Chloro-4-trifluoromethyl-phenyl)-pyrimidin-4-ylamino]-1-[3-(2,4-dichloro-phenyl)-isoxazol-5-yl]-ethanol;
1-Benzothiazol-2-yl-2-[6-(3-chloro-4-trifluoromethyl-phenyl)-pyrimidin-4-ylamino]-ethanol;
1-[3,5-Bis(trifluoromethyl)phenyl]-2-({6-[3-chloro-4-(trifluoromethyl)phenyl]pyrimidin-4-yl}amino)ethanol;
1-(5-Bromo-1-benzothiophen-2-yl)-2-({6-[3-chloro-4-(trifluoromethyl)phenyl]pyrimidin-4-yl}amino)ethanol; and
4-(3-Chloro-4-trifluoromethyl-phenyl)-6-(2-hydroxy-2-phenyl-(1R)-ethylamino)-pyrimidine-2-carbonitrile;
or a pharmaceutically acceptable salt.

35. A compound selected from the group consisting of:
2-({6-[4-(Methyloxy)phenyl]pyrimidin-4-yl}amino)-1-phenylethanol
2-{[6-(3-Methylphenyl)pyrimidin-4-yl]amino}-1-phenylethanol
1-Phenyl-2-[(6-{3-[(trifluoromethyl)oxy]phenyl}pyrimidin-4-yl)amino]ethanol
(1R,2R)-1-Phenyl-2-[(6-{4-[(trifluoromethyl)oxy]phenyl}pyrimidin-4-yl)amino]propan-1-ol (1S)-1-Phenyl-2-[(6-{4-[(trifluoromethyl)oxy]
  phenyl}pyrimidin-4-yl)amino]ethanol
1-[4-(6-{[(2R)-2-Hydroxy-2-phenylethyl]
  amino}pyrimidin-4-yl)phenyl]ethanone; and
(1R)-1-Phenyl-2-[(6-{4-[(trifluoromethyl)oxy]
  phenyl}pyrimidin-4-yl)amino]ethanol;
or a pharmaceutically acceptable salt.

36. A pharmaceutical composition comprising:
(a) an effective amount of at least one compound selected from the group consisting of compounds of Formula (I):

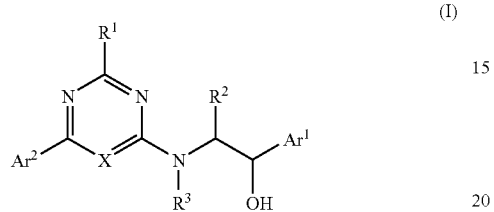

(I)

wherein:
$R^1$ is —H, —$C_{1-4}$alkyl, —$OC_{1-4}$alkyl, —$S(O)_{0-2}C_{1-4}$alkyl, —CN, —$CF_3$, —$N(R^a)R^b$, or a monocyclic cycloalkyl group,
  where $R^a$ and $R^b$ are each independently —H, —$C_{1-4}$alkyl optionally substituted with —OH, $N(R^m)R^n$, where $R^m$ and $R^n$ are —H, $C_{1-4}$alkyl; or taken together with the nitrogen of attachment $R^a$ and $R^b$ form a 4-7 membered heterocycloalkyl ring;
$Ar^1$ is a phenyl, napthyl, a 5 or 6 membered monocyclic heteroaryl group with carbon at the point of attachment, or a 9 or 10 membered bicyclic heteroaryl group with carbon at the point of attachment, each unsubstituted or substituted with;
(i) one, two, or three $R^c$ moieties,
  where each $R^c$ moiety is independently —$C_{1-4}$alkyl, —$C_{1-4}$alkyl-OH, —$C_{1-4}$alkyl-CN, —$CF_3$, —OH, —$OC_{1-4}$alkyl, —$OCF_3$, —$OCHF_2$, —$OCH_2CF_3$, —$S(O)_{0-2}C_{1-4}$alkyl, —$SCF_3$, —$SO_2CF_3$, —CHO, —$COC_{1-4}$alkyl, —$CO_2C_{1-4}$alkyl, —$CO_2H$, —$N(R^d)R^e$, —$SO_2NR^dR^e$, —$NR^dSO_2R^e$, —$C(O)NR^dR^e$, —$NO_2$, —CN, phenyl, pyridyl, or halo,
  where $R^d$ and $R^e$ are each independently —H or —$C_{1-4}$alkyl, or taken together $R^d$ and $R^e$ with the nitrogen of attachment form a 4-7 membered heterocycloalkyl ring; or
(ii) two or three $R^c$ moieties where two $R^c$ moieties are adjacent to each other and together form —$O(CH_2)_{1-3}O$— unsubstituted or substituted with one or two fluoro groups, and the third $R^c$ moiety, when present, is —$C_{1-4}$alkyl, —$C_{1-4}$alkyl-OH, —$C_{1-4}$alkyl-CN, —$CF_3$, —OH, —$OC_{1-4}$alkyl, —$OCF_3$, —$OCHF_2$, —$OCH_2CF_3$, —$S(O)_{0-2}C_{1-4}$alkyl, —$SCF_3$, —$SO_2CF_3$, —CHO, —$COC_{1-4}$alkyl, —$CO_2C_{1-4}$alkyl, —$CO_2H$, —$N(R^d)R^e$, —$SO_2NR^dR^e$, —$NR^dSO_2R^e$, —$C(O)NR^dR^e$, —$NO_2$, —CN, or halo,
  where $R^d$ and $R^e$ are each independently —H or —$C_{1-4}$alkyl;
X is $C(R^f)$,
  where $R^f$ is —H or methyl;
$Ar^2$ is:
(i) a phenyl group substituted with: (a) one, two, or three $R^g$ moieties each at a meta or para position, and optionally with one or two additional $R^g$ moieties at an ortho position;
  where each $R^g$ moiety is independently —$C_{1-4}$alkyl, —$C_{1-4}$alkyl-OH, —$C_{1-4}$alkyl-CN, perhaloalkyl, perhaloalkoxy, —$OC_{1-4}$alkyl, —$OC_{1-4}$alkyl-(monocyclic cycloalkyl), —$S(O)_{0-2}C_{1-4}$alkyl, —$SCF_3$, —$SO_2CF_3$, —CHO, —$COC_{1-4}$alkyl, —$CO_2C_{1-4}$alkyl, —$CO_2H$, —$N(R^h)R^i$, —$SO_2NR^jR^k$, —$NR^hSO_2R^i$, —$C(O)NR^jR^k$, —$NO_2$, —CN, or halo; or a phenoxy, benzyl, phenethyl, or benzoyl group unsubstituted or substituted with —$C_{1-4}$alkyl, —$OC_{1-4}$alkyl, perhaloalkyl, perhaloalkoxy, —$NO_2$, —CN, or halo;
  where $R^h$ is —H or —$C_{1-4}$alkyl;
  $R^i$ is —$C_{1-4}$alkyl or monoyclic cycloalkyl group;
  or $R^h$ and $R^i$ taken together with the atoms to which they are attached form a monocyclic heterocycloalkyl ring;
  $R^j$ is —H or —$C_{1-4}$alkyl; and
  $R^k$ is —H, —$C_{1-4}$alkyl or monoyclic cycloalkyl group;
  or $R^j$ and $R^k$ taken together with the atoms to which they are attached form a monocyclic heterocycloalkyl ring; or
(b) two adjacent $R^g$ moieties together form —$O(CH_2)_{1-2}O$— unsubstituted or substituted with one or two fluoro groups;
(ii) a monocyclic heteroaryl group substituted with one, two, or three $R^g$ moieties, where each $R^g$ moiety is independent or two adjacent $R^g$ moieties together form —$O(CH_2)_{1-2}O$— unsubstituted or substituted with one or two fluoro groups; or
(iii) a naphthyl or bicyclic heteroaryl group unsubstituted or substituted with one, two, or three $R^l$ moieties;
  where each $R^l$ moiety is independently —$C_{1-4}$alkyl, —$OC_{1-4}$alkyl, perhaloalkyl, perhaloalkoxy, —$NO_2$, —CN, or halo;
$R^2$ is —H or methyl; and
$R^3$ is —H or methyl;
and pharmaceutically acceptable salts; and
(b) a pharmaceutically acceptable excipient.

* * * * *